(12) United States Patent
Cassayre et al.

(10) Patent No.: US 8,957,058 B2
(45) Date of Patent: Feb. 17, 2015

(54) INSECTICIDAL PYRROLIDIN-YL-ARYL-CARBOXAMIDES

(75) Inventors: Jerome Yves Cassayre, Stein (CH); Peter Renold, Stein (CH); Myriem El Qacemi, Stein (CH); Guillaume Berthon, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 13/878,118

(22) PCT Filed: Oct. 3, 2011

(86) PCT No.: PCT/EP2011/067224
§ 371 (c)(1),
(2), (4) Date: Apr. 5, 2013

(87) PCT Pub. No.: WO2012/045700
PCT Pub. Date: Apr. 12, 2012

(65) Prior Publication Data
US 2014/0128358 A1  May 8, 2014

(30) Foreign Application Priority Data

Oct. 5, 2010 (EP) .................................. 10186477
Jul. 8, 2011 (EP) .................................. 11173297

(51) Int. Cl.
| | | |
|---|---|---|
| *A61K 31/43* | (2006.01) | |
| *C07D 207/00* | (2006.01) | |
| *C07D 295/00* | (2006.01) | |
| *A01N 43/78* | (2006.01) | |
| *C07D 207/08* | (2006.01) | |
| *C07D 401/04* | (2006.01) | |
| *C07D 409/10* | (2006.01) | |
| *C07D 409/14* | (2006.01) | |
| *A01N 43/36* | (2006.01) | |
| *A01N 43/40* | (2006.01) | |
| *A01N 43/50* | (2006.01) | |
| *A01N 43/60* | (2006.01) | |

(52) U.S. Cl.
CPC .............. *A01N 43/78* (2013.01); *C07D 207/08* (2013.01); *C07D 401/04* (2013.01); *C07D 409/10* (2013.01); *C07D 409/14* (2013.01); *A01N 43/36* (2013.01); *A01N 43/40* (2013.01); *A01N 43/50* (2013.01); *A01N 43/60* (2013.01)
USPC ............................ 514/195; 548/518; 548/543

(58) Field of Classification Search
None
See application file for complete search history.

(56) References Cited

FOREIGN PATENT DOCUMENTS

| | | |
|---|---|---|
| WO | 2008/128711 | 10/2008 |
| WO | 2009/080250 | 7/2009 |
| WO | 2010/020522 | 2/2010 |
| WO | 2010/043315 | 4/2010 |
| WO | WO2012035011 A1 * | 3/2012 |

OTHER PUBLICATIONS

International Search Report, International Application No. PCT/EP2011/067224, completion date: Nov. 3, 2011.

* cited by examiner

*Primary Examiner* — Heidi Reese
(74) *Attorney, Agent, or Firm* — James Cueva

(57) ABSTRACT

The invention relates to compounds of formula (I): where $A^1$, $A^2$, $A^3$, $A^4$, $G^1$, $R^1$, $R^2$, $R^3$ and $R^4$ are as defined in claim 1; or a salt or N-oxide thereof. Furthermore, the present invention relates to processes and intermediates for preparing compounds of formula (I), to insecticidal, acaricidal, nematicidal and molluscicidal compositions comprising the compounds of formula (I) and to methods of using the compounds of formula (I) to control insect, acarine, nematode and mollusc pests.

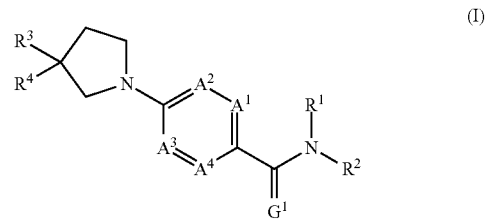

(I)

17 Claims, No Drawings

INSECTICIDAL PYRROLIDIN-YL-ARYL-CARBOXAMIDES

This application is a 371 of International Application No. PCT/EP2011/067224 filed Oct. 3, 2011, which claims priority to EP 10186477.5 filed Oct. 5, 2010, and EP 11173297.0 filed Jul. 8, 2011, the contents of which are incorporated herein by reference.

The present invention relates to certain pyrrolidine derivatives with a four-membered ring as terminal group, to processes and intermediates for preparing these derivatives, to insecticidal, acaricidal, nematicidal and molluscicidal compositions comprising these derivatives and to methods of using these derivatives to control insect, acarine, nematode and mollusc pests.

Certain pyrrolidine derivatives with insecticidal properties are disclosed in, for example, JP2008110971 and WO08128711.

It has now surprisingly been found that pyrrolidine derivatives with a four-membered ring as terminal group have advantageous properties as insecticidal compounds.

The present invention therefore provides a compound of formula (I)

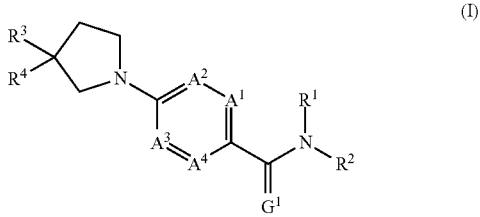

(I)

where
$A^1$, $A^2$, $A^3$ and $A^4$ are independently of each other C—H, C—$R^5$ or nitrogen;
$G^1$ is oxygen or sulfur;
$R^1$ is hydrogen, $C_1$-$C_8$alkyl, $C_1$-$C_8$alkoxy-, $C_1$-$C_8$alkylcarbonyl-, $C_1$-$C_8$alkoxycarbonyl- or $C_1$-$C_8$haloalkoxycarbonyl-;
$R^2$ is a group of formula (II)

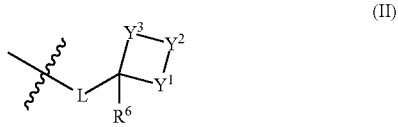

(II)

where
L is a single bond or $C_1$-$C_6$alkylene; and
$Y^1$, $Y^2$ and $Y^3$ are independently of another $CR^8R^9$, C=O, C=N—$OR^{10}$, N—$R^{10}$, S, SO, $SO_2$, S=N—$R^{10}$ or SO=N—$R^{10}$, provided that at least one of $Y^1$, $Y^2$ or $Y^3$ is not $CR^8R^9$, C=O or C=N—$OR^{10}$;
$R^3$ is $C_1$-$C_8$haloalkyl;
$R^4$ is aryl or aryl substituted by one to five $R^7$, or heteroaryl or heteroaryl substituted by one to five $R^7$;
each $R^5$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_1$-$C_8$alkoxy-, $C_1$-$C_8$haloalkoxy-, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl- or $C_1$-$C_8$haloalkylsulfonyl-, or two $R^5$ on adjacent carbon atoms together form a —CH=CH—CH=CH— bridge;
$R^6$ is hydrogen, $C_1$-$C_8$haloalkyl or $C_1$-$C_8$alkyl;
each $R^7$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy-, $C_1$-$C_8$haloalkoxy-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, $C_1$-$C_8$alkylcarbonyl-, $C_1$-$C_8$alkoxycarbonyl-, aryl or aryl substituted by one to five $R^{11}$, or heterocyclyl or heterocyclyl substituted by one to five $R^{11}$;
each $R^8$ and $R^9$ is independently hydrogen, halogen, $C_1$-$C_8$alkyl or $C_1$-$C_8$haloalkyl;
each $R^{10}$ is independently hydrogen, cyano, $C_1$-$C_8$alkyl, $C_1$-$C_8$haloalkyl, $C_1$-$C_8$alkylcarbonyl-, $C_1$-$C_8$haloalkylcarbonyl-, $C_1$-$C_8$alkoxycarbonyl-, $C_1$-$C_8$haloalkoxycarbonyl-, $C_1$-$C_8$alkylsulfonyl-, $C_1$-$C_8$haloalkylsulfonyl-, aryl-$C_1$-$C_4$alkylene- or aryl-$C_1$-$C_4$alkylene- where the aryl moiety is substituted by one to three $R^{12}$, or heteroaryl-$C_1$-$C_4$alkylene- or heteroaryl-$C_1$-$C_4$alkylene- where the heteroaryl moiety is substituted by one to three $R^{12}$;
each $R^{11}$ and $R^{12}$ is independently halogen, cyano, nitro, $C_1$-$C_8$alkyl, $C_1$-$C_8$haloalkyl, $C_1$-$C_8$alkoxy-, $C_1$-$C_8$haloalkoxy- or $C_1$-$C_8$alkoxycarbonyl-;
or a salt or N-oxide thereof.

The compounds of formula (I) may exist in different geometric or optical isomers or tautomeric forms. This invention covers all such isomers and tautomers and mixtures thereof in all proportions as well as isotopic forms such as deuterated compounds.

The compounds of the invention may contain one or more asymmetric carbon atoms, for example, at the —$CR^3R^4$— group, and may exist as enantiomers (or as pairs of diastereoisomers) or as mixtures of such.

Alkyl groups (either alone or as part of a larger group, such as alkoxy-, alkylthio-, alkylsulfinyl-, alkylsulfonyl-, alkylcarbonyl- or alkoxycarbonyl-) can be in the form of a straight or branched chain and are, for example, methyl, ethyl, propyl, prop-2-yl, butyl, but-2-yl, 2-methyl-prop-1-yl or 2-methyl-prop-2-yl. The alkyl groups are, unless indicated to the contrary, preferably $C_1$-$C_6$, more preferably $C_1$-$C_4$, most preferably $C_1$-$C_3$ alkyl groups.

Alkylene groups can be in the form of a straight or branched chain and are, for example, —$CH_2$—, —$CH_2$—$CH_2$—, —$CH(CH_3)$—, —$CH_2$—$CH_2$—$CH_2$—, —$CH(CH_3)$—$CH_2$—, or —$CH(CH_2CH_3)$—. The alkylene groups are, unless indicated to the contrary, preferably $C_1$-$C_3$, more preferably $C_1$-$C_2$, most preferably $C_1$ alkylene groups.

Alkenyl groups can be in the form of straight or branched chains, and can be, where appropriate, of either the (E)- or (Z)-configuration. Examples are vinyl and allyl. The alkenyl groups are, unless indicated to the contrary, preferably $C_2$-$C_6$, more preferably $C_2$-$C_4$, most preferably $C_2$-$C_3$ alkenyl groups.

Alkynyl groups can be in the form of straight or branched chains. Examples are ethynyl and propargyl. The alkynyl groups are, unless indicated to the contrary, preferably $C_2$-$C_6$, more preferably $C_2$-$C_4$, most preferably $C_2$-$C_3$ alkynyl groups.

Halogen is fluorine, chlorine, bromine or iodine.

Haloalkyl groups (either alone or as part of a larger group, such as haloalkoxy-, haloalkylthio-, haloalkylsulfinyl-, haloalkylsulfonyl-, haloalkylcarbonyl- or haloalkoxycarbonyl-) are alkyl groups which are substituted by one or more of the same or different halogen atoms and are, for example, difluoromethyl, trifluoromethyl, chlorodifluoromethyl or 2,2,2-trifluoro-ethyl.

Haloalkenyl groups are alkenyl groups which are substituted by one or more of the same or different halogen atoms and are, for example, 2,2-difluoro-vinyl or 1,2-dichloro-2-fluoro-vinyl.

Haloalkynyl groups are alkynyl groups which are substituted by one or more of the same or different halogen atoms and are, for example, 1-chloro-prop-2-ynyl.

Cycloalkyl groups can be in mono- or bi-cyclic form and are, for example, cyclopropyl, cyclobutyl, cyclohexyl and bicyclo[2.2.1]heptan-2-yl. The cycloalkyl groups are, unless indicated to the contrary, preferably $C_3$-$C_8$, more preferably $C_3$-$C_6$ cycloalkyl groups.

Aryl groups are aromatic ring systems which can be in mono-, bi- or tricyclic form. Examples of such rings include phenyl, naphthyl, anthracenyl, indenyl or phenanthrenyl. Preferred aryl groups are phenyl and naphthyl, phenyl being most preferred. Where an aryl moiety is said to be substituted, the aryl moiety is, unless indicated to the contrary, preferably substituted by one to four substituents, most preferably by one to three substituents.

Heteroaryl groups are aromatic ring system containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of monocyclic groups include pyridyl, pyridazinyl, pyrimidinyl, pyrazinyl, pyrrolyl, pyrazolyl, imidazolyl, triazolyl, furanyl, thiophenyl, oxazolyl, isoxazolyl, oxadiazolyl, thiazolyl, isothiazolyl and thiadiazolyl. Examples of bicyclic groups include quinolinyl, cinnolinyl, quinoxalinyl, indolyl, indazolyl, benzimidazolyl, benzothiophenyl and benzothiazolyl. Monocyclic heteroaryl groups are preferred, pyridyl being most preferred. Where a heteroaryl moiety is said to be substituted, the heteroaryl moiety is, unless indicated to the contrary, preferably substituted by one to four substituents, most preferably by one to three substituents.

Heterocyclyl groups are defined to include heteroaryl groups and in addition their unsaturated or partially unsaturated analogues. Examples of monocyclic groups include thietanyl, pyrrolidinyl, tetrahydrofuranyl, [1,3]dioxolanyl, piperidinyl, piperazinyl, [1,4]dioxanyl, and morpholinyl or their oxidised versions such as 1-oxo-thietanyl and 1,1-dioxo-thietanyl. Examples of bicyclic groups include 2,3-dihydro-benzofuranyl, benzo[1,3]dioxolanyl, and 2,3-dihydro-benzo-[1,4]dioxinyl. Where a heterocyclyl moiety is said to be substituted, the heterocyclyl moiety is, unless indicated to the contrary, preferably substituted by one to four substituents, most preferably by one to three substituents.

Preferred values of $A^1, A^2, A^3, A^4, G, R^1, R^2, R^3, R^4, L, Y^1, Y^2, Y^3, R^5, R^6, R^7, R^8, R^9, R^{10}, R^{11}, R^{12}, R^{13}$ and m are, in any combination, as set out below.

Preferably no more than two of $A^1$, $A^2$, $A^3$ and $A^4$ are nitrogen.

Preferably $A^1$ is C—H or C—$R^5$, most preferably $A^1$ is C—$R^5$.

Preferably $A^2$ is C—H or C—$R^5$, most preferably $A^2$ is C—H.

Preferably $A^3$ is C—H or C—$R^5$, most preferably $A^3$ is C—H.

Preferably $A^4$ is C—H or C—$R^5$, most preferably $A^4$ is C—H.

In one preferred group of compounds $A^1, A^2, A^3$ and $A^4$ are independently of each other C—H or C—$R^5$.

In one preferred group of compounds $A^1$ is C—$R^5$, $A^2$ is C—H, $A^3$ is C—H or nitrogen and $A^4$ is C—H or nitrogen.

In another preferred group of compounds $A^1$ is C—$R^5$, $A^2$ is C—H, $A^3$ is C—H or nitrogen and $A^4$ is C—H.

In a further preferred group of compounds $A^1$ is C—$R^5$, $A^2$ is C—H, $A^3$ is C—H and $A^4$ is C—H.

In a further preferred group of compounds $A^1$ is C—$R^5$, $A^2$ is C—$R^{5'}$, CH or nitrogen; $A^3$ and $A^4$ are independently CH or nitrogen; wherein no more than two of $A^2$, $A^3$ and $A^4$ are nitrogen and wherein $A^3$ and $A^4$ are not both nitrogen;

In a further preferred group of compounds $A^1$ is C—$R^5$ and $A^2$, $A^3$ and $A^4$ are selected from the following combinations $A^2$ is CH, $A^3$ is CH, $A^4$ is CH; $A^2$ is N, $A^3$ is CH, $A^4$ is CH; $A^2$ is N, $A^3$ is N, $A^4$ is CH; $A^2$ is CH, $A^3$ is N, $A^4$ is CH; and $A^2$ is CH, $A^3$ is CH, $A^4$ is N. Preferably $G^1$ is oxygen.

Preferably $R^1$ is hydrogen, methyl, ethyl, methylcarbonyl- or methoxycarbonyl-, more preferably hydrogen, methyl or ethyl, most preferably hydrogen.

Preferably $R^2$ is a group of formula (IIa)

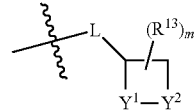

(IIa)

where
L is a single bond, methylene, ethylene or propylene,
$R^{13}$ is $C_1$-$C_8$alkyl,
m is 0, 1, 2, 3, 4, or 5, and
one of $Y^1$ and $Y^2$ is S, SO, $SO_2$, S=N—$R^{10}$, SO=N—$R^{10}$ or C=N—$OR^{10}$, e.g. S, SO, $SO_2$, S=N—$R^{10}$ or SO=N—$R^{10}$, e.g. S, SO, $SO_2$ or C=N—$OR^{10}$, e.g. S, SO or $SO_2$, and the other is $CH_2$ in which each H may be replaced by $R^{13}$.

More preferably $R^2$ is a group of formula (IIb)

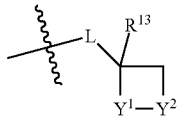

(IIb)

where
L is a single bond, methylene, ethylene or propylene,
$R^{13}$ is hydrogen or $C_1$-$C_8$alkyl, e.g. $C_1$-$C_8$alkyl, and
one of $Y^1$ and $Y^2$ is S, SO, $SO_2$, SO=N—$R^{10}$ or C=N—$OR^{10}$, e.g. S, SO, $SO_2$, S=N—$R^{10}$ or SO=N—$R^{10}$, e.g. S, SO, $SO_2$ or C=N—$OR^{10}$, e.g. S, SO or $SO_2$, and the other is $CH_2$.

More preferably $R^2$ is a group of formula (IIc)

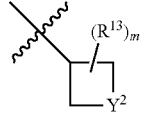

(IIc)

where
$R^{13}$ is $C_1$-$C_8$alkyl, preferably methyl,
m is 0, 1, 2, 3, 4, or 5, and
$Y^2$ is S, SO, $SO_2$, SO=N—$R^{10}$ or C=N—$OR^{10}$, e.g. S, SO, $SO_2$ or C=N—$OR^{10}$, e.g. S, SO or $SO_2$.

Even more preferably $R^2$ is a group of formula (IId)

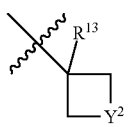
(IId)

where
$R^{13}$ is hydrogen or $C_1$-$C_8$alkyl, e.g. hydrogen or methyl, and
$Y^2$ is S, SO, SO$_2$, SO=N—$R^{10}$ or C=N—OR$^{10}$, e.g. S, SO, SO$_2$ or C=N—OR$^{10}$, e.g. S, SO or SO$_2$, Most preferably $R^2$ is thietan-3-yl-, 1-oxo-thietan-3-yl-, 1,1-dioxo-thietan-3-yl- or 3-methyl-thietan-3-yl-, more preferably thietan-3-yl-, 1-oxo-thietan-3-yl-, or 1,1-dioxo-thietan-3-yl-.

In another preferred group of compounds $R^2$ is a group of formula (IIc')

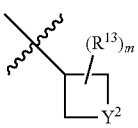
(IIc')

where
$R^{13}$ is $C_1$-$C_8$alkyl,
m is 0, 1, 2, 3, 4, or 5, and
$Y^2$ is S, SO, SO$_2$, S=N—$R^{10}$ or SO=N—$R^{10}$.

In another group of preferred compounds $R^2$ is a group of formula (IId')

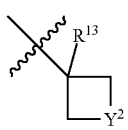
(IId')

where
$R^{13}$ is hydrogen or $C_1$-$C_8$alkyl, and
$Y^2$ is S, SO, SO$_2$, S=N—$R^{10}$ or SO=N—$R^{10}$.

In another preferred group of compounds $R^2$ is a group of formula II wherein L is a bond, methylene or ethylene, one of $Y^1$ and $Y^2$ is S, SO or SO$_2$ and the other is $CR^8R^9$, and $Y^3$ is $CR^8R^9$; preferably L is a bond, methylene or ethylene, one of $Y^1$ and $Y^2$ is S, SO or SO$_2$ and the other is CH$_2$, and $Y^3$ is CH$_2$; most preferably L is a bond, $Y^2$ is S, SO or SO$_2$ and $Y^1$ and $Y^3$ is CH$_2$.

In another preferred group of compounds $R^2$ is thietan-3-yl-, 1-oxo-thietan-3-yl-, 1,1-Dioxo-thietan-3-yl-, 2,2-dimethylthietan-3-yl-, 2,2-dimethyl-1-oxo-thietan-3-yl-, 2,2-dimethyl-1,1-Dioxo-thietan-3-yl-, 3-Methyl-thietan-3-yl-, 3-Methyl-1-oxo-thietan-3-yl-, 3-Methyl-1,1-Dioxo-thietan-3-yl-, thietan-3-ylmethyl-, 1-oxo-thietan-3-ylmethyl-, 1,1-Dioxo-thietan-3-ylmethyl-, thietan-2-ylmethyl-, (1-oxothietan-2-yl)methyl-, (1,1-dioxothietan-2-yl)methyl-, 2-(thietan-3-yl)ethanyl, 2-(1,1-dioxothietan-3-yl)ethanyl, or 2-(1-oxothietan-3-yl)ethanyl more preferably $R^2$ is 2-(thietan-3-yl)ethanyl, 2-(1,1-dioxothietan-3-yl)ethanyl, 2-(1-oxothietan-3-yl)ethanyl, thietan-3-ylmethyl-, 1-oxo-thietan-3-ylmethyl-, 1,1-Dioxo-thietan-3-ylmethyl-, thietan-3-yl-, 1-oxo-thietan-3-yl-, or 1,1-Dioxo-thietan-3-yl-, most preferably thietan-3-yl-, 1-oxo-thietan-3-yl-, 1,1-Dioxo-thietan-3-yl-.

Preferably $R^3$ is chlorodifluoromethyl or trifluoromethyl, most preferably trifluoromethyl.

Preferably $R^4$ is phenyl or phenyl substituted by one to five $R^7$, more preferably phenyl substituted by one to three $R^7$, even more preferably $R^4$ is 3-chloro-5-trifluoromethyl-phenyl-, 3,5-dichloro-phenyl-, 3,5-bis-(trifluoromethyl)-phenyl-, 3,5-dichloro-4-fluoro-phenyl-, 3,4,5-trichloro-phenyl- or 3-trifluoromethyl-phenyl-, most preferably 3,5-dichlorophenyl.

Preferably L is a single bond, methylene, ethylene or propylene.

More preferably L is methylene or a single bond.
Even more preferably L is a single bond.
Preferably $Y^1$ is $CR^8R^9$, more preferably CH$_2$.
Preferably $Y^2$ is S, SO, SO$_2$, S=N—$R^{10}$, SO=N—$R^{10}$, or C=N—OR$^{10}$, e.g. S, SO, SO$_2$, S=N—$R^{10}$ or SO=N—$R^{10}$, more preferably S, SO, SO$_2$, S=N—C=N, SO=NH, SO=N—C=N or C=N—OR$^{10}$ e.g. S, SO, SO$_2$, S=N—C=N, SO=NH or SO=N—C=N, most preferably S, SO, SO$_2$ or C=N—OR$^{10}$, e.g. S, SO or SO$_2$.
Preferably $Y^3$ is $CR^8R^9$, more preferably CH$_2$.
Preferably each $R^5$ is independently halogen, $C_1$-$C_8$alkyl, $C_1$-$C_8$haloalkyl or $C_1$-$C_8$alkenyl, or two $R^5$ on adjacent carbon atoms together form a —CH=CH—CH=CH— bridge, more preferably each $R^5$ is independently bromo, chloro, fluoro, methyl, trifluoromethyl or vinyl, or two $R^5$ on adjacent carbon atoms, preferably $R^5$ on $A^1$ and $A^2$, together form a —CH=CH—CH=CH— bridge, most preferably each $R^5$ is independently methyl.

In another preferred group of compounds each $R^5$ is independently hydrogen, chloro, bromo, fluoro, trifluoromethyl, methyl, ethyl, methoxy, nitro, trifluoromethoxy, cyano, cyclopropyl, more preferably each $R^5$ is independently hydrogen, chloro, bromo, fluoro, trifluoromethyl, methyl, ethyl, nitro, cyano, cyclopropyl, even more preferably each $R^5$ is independently chloro, bromo, fluoro, methyl, trifluoromethyl.

Preferably each $R^7$ is independently halogen, cyano, $C_1$-$C_8$alkyl, $C_1$-$C_8$haloalkyl or $C_1$-$C_8$alkoxy-, more preferably bromo, chloro, fluoro, cyano, methyl, trifluoromethyl, methoxy or trifluoromethoxy, preferably bromo, chloro, fluoro or trifluoromethyl, most preferably bromo or chloro.

Preferably each $R^8$ is independently hydrogen or $C_1$-$C_8$alkyl, more preferably hydrogen or methyl, most preferably hydrogen.

Preferably each $R^9$ is independently hydrogen or $C_1$-$C_8$alkyl, more preferably hydrogen or methyl, most preferably hydrogen.

Preferably each $R^{10}$ is independently hydrogen, cyano, $C_1$-$C_8$alkyl, $C_1$-$C_8$haloalkyl, phenyl-$C_1$-$C_4$alkylene- or phenyl-$C_1$-$C_4$alkylene- where the phenyl moiety is substituted by one to three $R^{12}$, more preferably hydrogen, cyano, $C_1$-$C_4$alkyl, $C_1$-$C_4$haloalkyl, or benzyl-, even more preferably methyl, hydrogen, 2,2,2-trifluoro-ethyl or cyano.

Preferably each $R^{11}$ is independently bromo, chloro, fluoro, cyano, nitro, methyl, ethyl, trifluoromethyl, methoxy, difluoromethoxy or trifluoromethoxy, more preferably bromo, chloro, fluoro, nitro or methyl, most preferably chloro, fluoro or methyl.

Preferably each $R^{12}$ is independently bromo, chloro, fluoro, cyano, nitro, methyl, ethyl, trifluoromethyl, methoxy, difluoromethoxy or trifluoromethoxy, more preferably bromo, chloro, fluoro, nitro or methyl, most preferably chloro, fluoro or methyl.

Preferably each $R^{13}$ is independently methyl.

Preferably m is 0 or 1, most preferably 0.

A group of preferred compounds are those wherein $A^1$, $A^2$, $A^3$ and $A^4$ are independently of each other C—H or C—$R^5$, preferably $A^1$ is C—$R^5$, $A^2$ is C—H, $A^3$ is C—H or nitrogen and $A^4$ is C—H or nitrogen;

$G^1$ is oxygen;

$R^1$ is hydrogen, methyl, ethyl, methylcarbonyl- or methoxycarbonyl-;

$R^2$ is a group of formula (IIa)

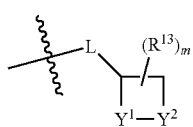

(IIa)

where
L is a single bond, methylene methylene, ethylene or propylene,
m is 0, 1, 2, 3, 4, or 5, and
one of $Y^1$ and $Y^2$ is S, SO, $SO_2$, S=N—$R^{10}$, SO=N—$R^{10}$ or C=N—$OR^{10}$, and the other is $CH_2$ in which each H may be replaced by $R^{13}$;
$R^3$ is $C_1$-$C_8$ haloalkyl;
$R^4$ is phenyl substituted by one to three $R^7$;
each $R^5$ is independently halogen, $C_1$-$C_8$alkyl, $C_1$-$C_8$haloalkyl or $C_1$-$C_8$alkenyl, or two $R^5$ on adjacent carbon atoms together form a —CH=CH—CH=CH— bridge;
each $R^7$ is independently halogen, cyano, $C_1$-$C_8$alkyl, $C_1$-$C_8$haloalkyl or $C_1$-$C_8$alkoxy-;
each $R^{10}$ is independently methyl, hydrogen, 2,2,2-trifluoro-ethyl or cyano;
$R^{13}$ is $C_1$-$C_8$alkyl.

Another group of preferred compounds are those wherein $A^1$, $A^2$, $A^3$ and $A^4$ are independently of each other C—H or C—$R^5$, preferably $A^1$ is C—$R^5$, $A^2$ is C—H, $A^3$ is C—H and $A^4$ is C—H;
$G^1$ is oxygen;
$R^1$ is hydrogen, methyl or ethyl;
$R^2$ is a group of formula (IIb)

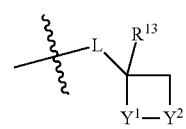

(IIb)

where
L is a single bond, methylene, ethylene or propylene;
one of $Y^1$ and $Y^2$ is S, SO, $SO_2$, SO=N—$R^{10}$ or C=N—$OR^{10}$ and the other is $CH_2$;
$R^3$ is chlorodifluoromethyl or trifluoromethyl;
$R^4$ is 3-chloro-5-trifluoromethyl-phenyl-, 3,5-dichlorophenyl-, 3,5-bis-(trifluoromethyl)-phenyl-, 3,5-dichloro-4-fluoro-phenyl-, 3,4,5-trichloro-phenyl- or 3-trifluoromethyl-phenyl-;
each $R^5$ is independently bromo, chloro, fluoro, methyl, trifluoromethyl or vinyl, or two $R^5$ on adjacent carbon atoms together form a —CH=CH—CH=CH— bridge;
each $R^{10}$ is independently methyl, 2,2,2-trifluoro-ethyl or hydrogen;
$R^{13}$ is hydrogen or $C_1$-$C_8$alkyl.

Yet another group of preferred compounds are those wherein
$A^1$, $A^2$, $A^3$ and $A^4$ are independently of each other C—H or C—$R^5$, preferably $A^1$ is C—$R^5$, $A^2$ is C—H, $A^3$ is C—H and $A^4$ is C—H;
$G^1$ is oxygen;
$R^1$ is hydrogen;
$R^2$ is a group of formula (IIc)

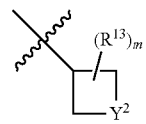

(IIc)

where
m is 0, 1, 2, 3, 4, or 5, and
$Y^2$ is S, SO, $SO_2$, or C=N—$OR^{10}$;
$R^3$ is chlorodifluoromethyl or trifluoromethyl;
$R^4$ is 3-chloro-5-trifluoromethyl-phenyl-, 3,5-dichlorophenyl-, 3,5-bis-(trifluoromethyl)-phenyl-, 3,5-dichloro-4-fluoro-phenyl-, 3,4,5-trichloro-phenyl- or 3-trifluoromethyl-phenyl-;
each $R^5$ is independently bromo, chloro, fluoro, methyl, trifluoromethyl or vinyl, or two $R^5$ on adjacent carbon atoms together form a —CH=CH—CH=CH— bridge;
each $R^{10}$ is independently methyl, 2,2,2-trifluoro-ethyl or hydrogen;
$R^{13}$ is methyl.

A further group of preferred compounds are those wherein $A^1$ is C—$R^5$, $A^2$ is C—H, $A^3$ is C—H and $A^4$ is C—H;
$G^1$ is oxygen;
$R^1$ is hydrogen;
$R^2$ is a group of formula (IId)

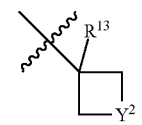

(IId)

where
$Y^2$ is S, SO, $SO_2$;
$R^3$ is trifluoromethyl;
$R^4$ is 3,5-dichloro-phenyl;
each $R^5$ is independently methyl;
$R^{13}$ is hydrogen or methyl.

In one preferred embodiment there is provided a compound of formula (IA)

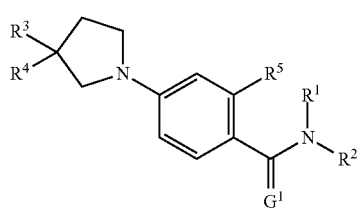

(IA)

where $G^1$, $R^1$, $R^2$, $R^3$, $R^4$ and $R^5$ are as defined for a compound of formula (I); or a salt or N-oxide thereof. The preferred values of $G^1$, $R^1$, $R^2$, $R^3$, $R^4$ and $R^5$ are as defined for a compound of formula (I).

In one preferred embodiment there is provided a compound of formula (IB)

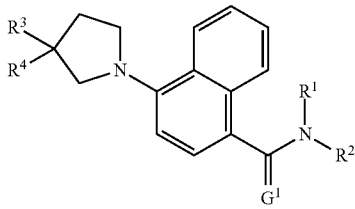

where G, $R^1$, $R^2$, $R^3$ and $R^4$ are as defined for a compound of formula (I); or a salt or N-oxide thereof. The preferred values of G, $R^1$, $R^2$, $R^3$ and $R^4$ are as defined for a compound of formula (I).

In one preferred embodiment there is provided a compound of formula (IC)

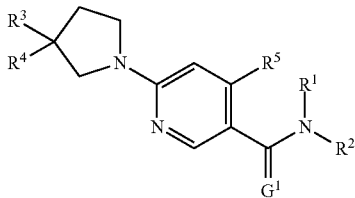

where $G^1$, $R^1$, $R^2$, $R^3$, $R^4$ and $R^5$ are as defined for a compound of formula (I); or a salt or N-oxide thereof. The preferred values of $G^1$, $R^1$, $R^2$, $R^3$, $R^4$ and $R^5$ are as defined for a compound of formula (I).

In one preferred embodiment there is provided a compound of formula (ID)

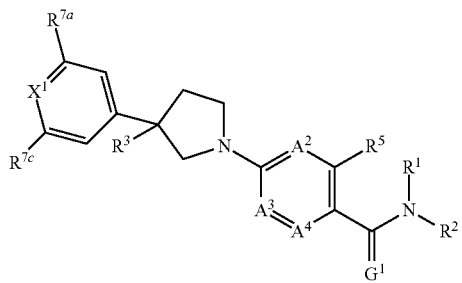

wherein
$A^2$ is C—$R^5$, CH or nitrogen;
$A^3$ and $A^4$ are independently CH or nitrogen;
wherein no more than two of $A^2$, $A^3$ and $A^4$ are nitrogen and wherein $A^3$ and $A^4$ are not both nitrogen;
$G^1$ is oxygen;
$R^1$ is hydrogen;
$R^2$ is a group of formula II;
L is a bond, methylene or ethylene;
one of $Y^1$ and $Y^2$ is S, SO or $SO_2$ and the other is $CR^8R^9$;
$Y^3$ is $CR^8R^9$;
$R^3$ is trifluoromethyl, difluoromethyl or chlorodifluoromethyl;

$R^5$ is hydrogen, halogen, cyano, nitro, $NH_2$, $C_1$-$C_2$alkyl, $C_1$-$C_2$haloalkyl, $C_3$-$C_5$cycloalkyl, $C_3$-$C_5$halocycloalkyl, $C_1$-$C_2$alkoxy or $C_1$-$C_2$haloalkoxy;
$R^{5'}$ when present together with $R^5$ forms a —CH=CH—CH=CH— bridge;
$R^6$ is hydrogen or methyl;
$X^1$ is C—$R^{7b}$ or nitrogen.
$R^{7a}$, $R^{7b}$ and $R^{7c}$ are independently hydrogen, halogen or trihalomethyl, wherein at least two or $R^{7a}$, $R^{7b}$, and $R^{7c}$ are not hydrogen;
each $R^8$ and $R^9$ is independently hydrogen or methyl.
Preferably $R^{7a}$, $R^{7b}$ and $R^{7c}$ are independently hydrogen, chloro, bromo or trifluoromethyl, wherein at least two of $R^{7a}$, $R^{7b}$ and $R^{7c}$ are not hydrogen. Preferably at least two of $R^{7a}$, $R^{7b}$ and $R^{7c}$ are chloro, bromo or trifluoromethyl.
Preferably $X^1$ is C—$R^{7b}$;
Preferably $R^{7a}$ is chloro, $X^1$ is CH, $R^{7c}$ is chloro, or $R^{7a}$ is chloro, $X^1$ is C—F, $R^{7c}$ is hydrogen, or $R^{7a}$ is fluoro, $X^1$ is C—Cl, $R^{7c}$ is hydrogen, or $R^{7a}$ is chloro, $X^1$ is C—Cl, $R^{7c}$ is hydrogen, or $R^{7a}$ is chloro, $X^1$ is C—Br, $R^{7c}$ is chloro, or $R^{7a}$ is chloro, $X^1$ is C—F, $R^{7c}$ is chloro, or $R^{7a}$ is chloro, $X^1$ is C—Cl, $R^{7c}$ is chloro, or $R^{7a}$ is chloro, $X^1$ is C—I, $R^{7c}$ is chloro, or $R^{7a}$ is fluoro, $X^1$ is C—F, $R^{7c}$ is fluoro, or $R^{7a}$ is chloro, $X^1$ is CH, $R^{7c}$ is bromo, or $R^{7a}$ is chloro, $X^1$ is CH, $R^{7c}$ is fluoro, or $R^{7a}$ is chloro, $X^1$ is CH, $R^{7c}$ is trifluoromethyl, or $R^{7a}$ is chloro, $X^1$ is C—Cl, $R^{7c}$ is trifluoromethyl, or $R^{7a}$ is trifluoromethyl, $X^1$ is CH, $R^{7c}$ is trifluoromethyl, or $R^{7a}$ is trifluoromethyl, $X^1$ is C—Cl, $R^{7c}$ is trifluoromethyl, or $R^{7a}$ is trifluoromethyl, $X^1$ is CH, $R^{7c}$ is hydrogen, or $R^{7a}$ is chloro, $X^1$ is N, $R^{7c}$ is chloro, or $R^{7a}$ is trifluoromethyl, $X^1$ is N, $R^{7c}$ is trifluoromethyl. Most preferably $X^1$ is chloro, $X^1$ is CH, $R^{7c}$ is chloro.

In one group of compounds of formula ID $A^2$ is C—$R^{5'}$ and $R^{5'}$ together with $R^5$ forms a —CH=CH—CH=CH— bridge.

In one group of compounds of formula ID $X^1$ is C—$R^{7b}$, $A^2$, $A^3$ and $A^4$ are C—H, and $R^5$ is chloro, bromo, methyl or trifluoromethyl.

In one group of compounds of formula ID $X^1$ is C—$R^{7b}$, $A^2$, $A^3$ and $A^4$ are C—H, $G^1$ is oxygen, $Y^1$ is $CH_2$, $Y^2$ is S, SO or $SO_2$, $Y^3$ is $CH_2$, L is a bond, $R^5$ is chloro, bromo, methyl or trifluoromethyl and $R^6$ is hydrogen.

In another group of compounds of formula ID $R^3$ is trifluoromethyl, $X^1$ is C—$R^{7b}$, $A^2$, $A^3$ and $A^4$ are C—H, $G^1$ is oxygen, $Y^1$ is $CH_2$, $Y^2$ is S, SO or $SO_2$, $Y^3$ is $CH_2$, L is a bond, $R^5$ is chloro, bromo, methyl or trifluoromethyl and $R^6$ is hydrogen.

In another group of compounds of formula ID $R^3$ is trifluoromethyl, $X^1$ is C—$R^{7b}$, $A^2$, $A^3$ and $A^4$ are C—H, $G^1$ is oxygen, $Y^1$ is $CH_2$, $Y^2$ is S, SO or $SO_2$, $Y^3$ is $CH_2$, L is a bond, $R^5$ is chloro, bromo, methyl or trifluoromethyl, $R^6$ is hydrogen, $R^{7a}$ is chloro, $R^{7b}$ is hydrogen and $R^{7c}$ is chloro.

Certain intermediates are novel and as such form a further aspect of the invention.

A group of novel intermediates are compounds of formula (Int-1)

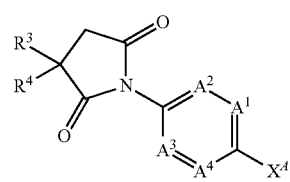

wherein $A^1$, $A^2$, $A^3$, $A^4$, $R^3$ and $R^4$ are as defined for a compound of formula (I); and $X^4$ is a leaving group such as a halogen atom, preferably bromine or chlorine, more preferably bromine. The preferences for $A^1$, $A^2$, $A^3$, $A^4$, $R^3$ and $R^4$ are the same as the preferences set out for the corresponding substituents of a compound of formula (I).

A further group of novel intermediates are compounds of formula (Int-II)

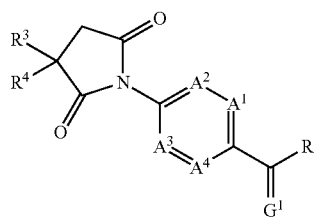

(Int-II)

wherein $A^1$, $A^2$, $A^3$, $A^4$, $G^1$, $R^3$ and $R^4$ are as defined for a compound of formula (I); R is OH, $C_1$-$C_6$alkoxy or a halogen atom, preferably bromine or chlorine, more preferably chlorine. The preferences for $A^1$, $A^2$, $A^3$, $A^4$, $G^1$, $R^3$ and $R^4$ are the same as the preferences set out for the corresponding substituents of a compound of formula (I).

A further group of novel intermediates are compounds of formula (Int-III)

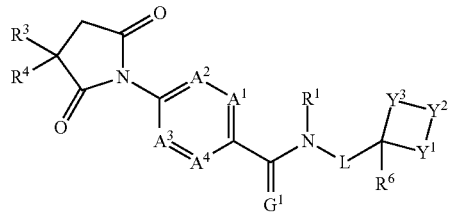

(Int-III)

wherein $A^1$, $A^2$, $A^3$, $A^4$, $G^1$, L, $R^1$, $R^3$, $R^4$, $R^6$, $Y^1$, $Y^2$ and $Y^3$ are as defined for a compound of formula (I). The preferences for $A^1$, $A^2$, $A^3$, $A^4$, $G^1$, L, $R^3$, $R^4$, $R^6$, $Y^1$, $Y^2$ and $Y^3$ are the same as the preferences set out for the corresponding substituents of a compound of formula (I).

A further group of novel intermediates are compounds of formula (Int-IV)

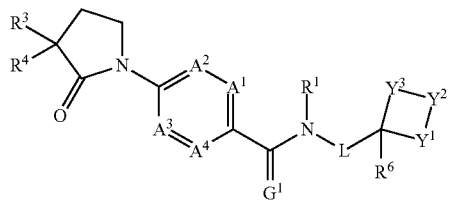

(Int-IV)

wherein $A^1$, $A^2$, $A^3$, $A^4$, $G^1$, L, $R^1$, $R^3$, $R^4$, $R^6$, $Y^1$, $Y^2$ and $Y^3$ are as defined for a compound of formula (I). The preferences for $A^1$, $A^2$, $A^3$, $A^4$, $G^1$, L, $R^3$, $R^4$, $R^6$, $Y^1$, $Y^2$ and $Y^3$ are the same as the preferences set out for the corresponding substituents of a compound of formula (I).

A further group of novel intermediates are compounds of formula (Int-V)

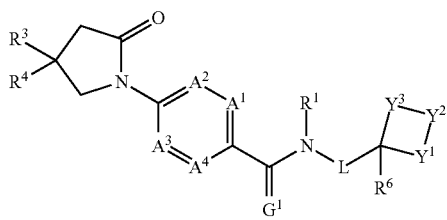

(Int-V)

wherein $A^1$, $A^2$, $A^3$, $A^4$, $G^1$, L, $R^1$, $R^3$, $R^4$, $R^6$, $Y^1$, $Y^2$ and $Y^3$ are as defined for a compound of formula (I). The preferences for $A^1$, $A^2$, $A^3$, $A^4$, $G^1$, L, $R^3$, $R^4$, $R^6$, $Y^1$, $Y^2$ and $Y^3$ are the same as the preferences set out for the corresponding substituents of a compound of formula (I).

A further group of novel intermediates are compounds of formula (Int-VI)

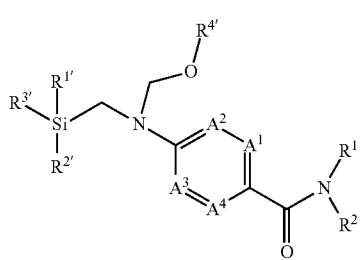

(Int-VI)

wherein $A^1$, $A^2$, $A^3$, $A^4$, $R^1$ and $R^2$ are as defined for a compound of formula (I), $R^{1'}$, $R^{2'}$ and $R^{3'}$ are each independently optionally substituted alkyl or optionally substituted phenyl, preferably $C_1$-$C_8$ alkyl, $C_1$-$C_8$ haloalkyl, phenyl or phenyl optionally substituted with one to five groups independently selected from halogen and $C_1$-$C_8$ alkyl, $R^{4'}$ is optionally substituted alkyl or optionally substituted phenyl, e.g. phenyl optionally substituted with one to five groups independently selected from halogen and $C_1$-$C_8$ alkyl, preferably $C_1$-$C_8$ alkyl or $C_1$-$C_8$ haloalkyl. The preferences for $A^1$, $A^2$, $A^3$, $A^4$, $R^1$ and $R^2$ are the same as the preferences set out for the corresponding substituents of a compound of formula (I).

A further group of novel intermediates are compounds of formula (Int-VII)

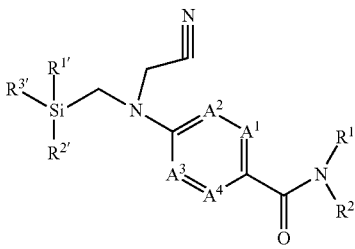

(Int-VII)

wherein $A^1$, $A^2$, $A^3$, $A^4$, $R^1$ and $R^2$ are as defined for a compound of formula (I), $R^{1'}$, $R^{2'}$ and $R^{3'}$ are each independently optionally substituted alkyl or optionally substituted phenyl, preferably $C_1$-$C_8$ alkyl, $C_1$-$C_8$ haloalkyl, phenyl or phenyl optionally substituted with one to five groups independently selected from halogen and $C_1$-$C_8$ alkyl. The preferences for $A^1$, $A^2$, $A^3$, $A^4$, $R^1$ and $R^2$ are the same as the preferences set out for the corresponding substituents of a compound of formula (I).

A group of novel intermediates are compounds of formula (Int-VIII)

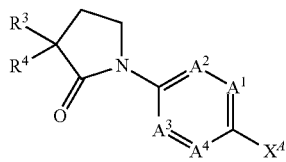

(Int-VIII)

wherein $A^1$, $A^2$, $A^3$, $A^4$, $R^3$ and $R^4$ are as defined for a compound of formula (I); and $X^A$ is a leaving group such as a halogen atom, preferably bromine or chlorine, more preferably bromine. The preferences for $A^1$, $A^2$, $A^3$, $A^4$, $R^3$ and $R^4$ are the same as the preferences set out for the corresponding substituents of a compound of formula (I).

A further group of novel intermediates are compounds of formula (Int-IX)

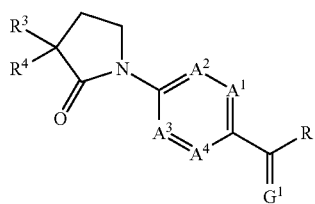

(Int-IX)

wherein $A^1$, $A^2$, $A^3$, $A^4$, $G^1$, $R^3$ and $R^4$ are as defined for a compound of formula (I); R is OH, $C_1$-$C_6$alkoxy or a halogen atom, preferably bromine or chlorine, more preferably chlorine. The preferences for $A^1$, $A^2$, $A^3$, $A^4$, $G^1$, $R^3$ and $R^4$ are the same as the preferences set out for the corresponding substituents of a compound of formula (I).

A group of novel intermediates are compounds of formula (Int-X)

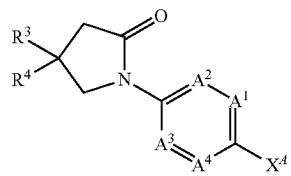

(Int-X)

wherein $A^1$, $A^2$, $A^3$, $A^4$, $R^3$ and $R^4$ are as defined for a compound of formula (I); and $X^A$ is a leaving group such as a halogen atom, preferably bromine or chlorine, more preferably bromine. The preferences for $A^1$, $A^2$, $A^3$, $A^4$, $R^3$ and $R^4$ are the same as the preferences set out for the corresponding substituents of a compound of formula (I).

A further group of novel intermediates are compounds of formula (Int-XI)

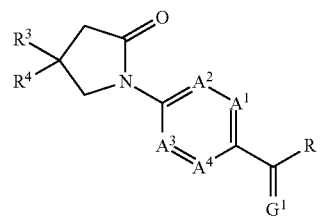

(Int-XI)

wherein $A^1$, $A^2$, $A^3$, $A^4$, $G^1$, $R^3$ and $R^4$ areas defined for a compound of formula (I); R is OH, $C_1$-$C_6$alkoxy or a halogen atom, preferably bromine or chlorine, more preferably chlorine. The preferences for $A^1$, $A^2$, $A^3$, $A^4$, $G^1$, $R^3$ and $R^4$ are the same as the preferences set out for the corresponding substituents of a compound of formula (I).

The compounds in Table 1 to Table 59 below illustrate the compounds of the invention.

TABLE 1

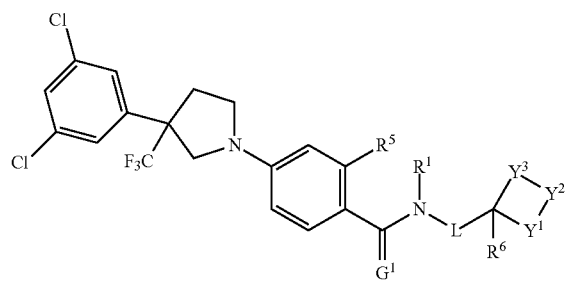

(I-A)

| Compound numbers | $R^6$ | L | $Y^1$ | $Y^3$ | $Y^2$ | $R^5$ |
|---|---|---|---|---|---|---|
| 1.0001 | H | Single bond | $CH_2$ | $CH_2$ | C=O | bromo |
| 1.0002 | H | Single bond | CH(Me) | $CH_2$ | C=O | bromo |
| 1.0003 | H | Single bond | $C(Me)_2$ | $CH_2$ | C=O | bromo |
| 1.0004 | H | Single bond | $C(Me)_2$ | $C(Me)_2$ | C=O | bromo |
| 1.0005 | Me | Single bond | $CH_2$ | $CH_2$ | C=O | bromo |
| 1.0006 | Me | Single bond | CH(Me) | $CH_2$ | C=O | bromo |
| 1.0007 | Me | Single bond | $C(Me)_2$ | $CH_2$ | C=O | bromo |
| 1.0008 | Me | Single bond | $C(Me)_2$ | $C(Me)_2$ | C=O | bromo |
| 1.0009 | H | $CH_2$ | $CH_2$ | $CH_2$ | C=O | bromo |
| 1.0010 | H | $CH_2$ | CH(Me) | $CH_2$ | C=O | bromo |

TABLE 1-continued (I-A)

| Compound numbers | R⁶ | L | Y¹ | Y³ | Y² | R⁵ |
|---|---|---|---|---|---|---|
| 1.0011 | H | CH₂ | C(Me)₂ | CH₂ | C=O | bromo |
| 1.0012 | H | CH₂ | C(Me)₂ | C(Me)₂ | C=O | bromo |
| 1.0013 | Me | CH₂ | CH₂ | CH₂ | C=O | bromo |
| 1.0014 | Me | CH₂ | CH(Me) | CH₂ | C=O | bromo |
| 1.0015 | Me | CH₂ | C(Me)₂ | CH₂ | C=O | bromo |
| 1.0016 | Me | CH₂ | C(Me)₂ | C(Me)₂ | C=O | bromo |
| 1.0017 | H | Single bond | CH2 | CH2 | C=N—OMe | bromo |
| 1.0018 | H | Single bond | CH(Me) | CH2 | C=N—OMe | bromo |
| 1.0019 | H | Single bond | C(Me)2 | CH2 | C=N—OMe | bromo |
| 1.0020 | H | Single bond | C(Me)2 | C(Me)2 | C=N—OMe | bromo |
| 1.0021 | Me | Single bond | CH2 | CH2 | C=N—OMe | bromo |
| 1.0022 | Me | Single bond | CH(Me) | CH2 | C=N—OMe | bromo |
| 1.0023 | Me | Single bond | C(Me)2 | CH2 | C=N—OMe | bromo |
| 1.0024 | Me | Single bond | C(Me)2 | C(Me)2 | C=N—OMe | bromo |
| 1.0025 | H | CH2 | CH2 | CH2 | C=N—OMe | bromo |
| 1.0026 | H | CH2 | CH(Me) | CH2 | C=N—OMe | bromo |
| 1.0027 | H | CH2 | C(Me)2 | CH2 | C=N—OMe | bromo |
| 1.0028 | H | CH2 | C(Me)2 | C(Me)2 | C=N—OMe | bromo |
| 1.0029 | Me | CH2 | CH2 | CH2 | C=N—OMe | bromo |
| 1.0030 | Me | CH2 | CH(Me) | CH2 | C=N—OMe | bromo |
| 1.0031 | Me | CH2 | C(Me)2 | CH2 | C=N—OMe | bromo |
| 1.0032 | Me | CH2 | C(Me)2 | C(Me)2 | C=N—OMe | bromo |
| 1.0033 | H | Single bond | CH2 | CH2 | N—Me | bromo |
| 1.0034 | H | Single bond | CH(Me) | CH2 | N—Me | bromo |
| 1.0035 | H | Single bond | C(Me)2 | CH2 | N—Me | bromo |
| 1.0036 | H | Single bond | C(Me)2 | C(Me)2 | N—Me | bromo |
| 1.0037 | Me | Single bond | CH2 | CH2 | N—Me | bromo |
| 1.0038 | Me | Single bond | CH(Me) | CH2 | N—Me | bromo |
| 1.0039 | Me | Single bond | C(Me)2 | CH2 | N—Me | bromo |
| 1.0040 | Me | Single bond | C(Me)2 | C(Me)2 | N—Me | bromo |
| 1.0041 | H | CH2 | CH2 | CH2 | N—Me | bromo |
| 1.0042 | H | CH2 | CH(Me) | CH2 | N—Me | bromo |
| 1.0043 | H | CH2 | C(Me)2 | CH2 | N—Me | bromo |
| 1.0044 | H | CH2 | C(Me)2 | C(Me)2 | N—Me | bromo |
| 1.0045 | Me | CH2 | CH2 | CH2 | N—Me | bromo |
| 1.0046 | Me | CH2 | CH(Me) | CH2 | N—Me | bromo |
| 1.0047 | Me | CH2 | C(Me)2 | CH2 | N—Me | bromo |
| 1.0048 | Me | CH2 | C(Me)2 | C(Me)2 | N—Me | bromo |
| 1.0049 | H | Single bond | CH2 | CH2 | N—CH₂—C₆H₅ | bromo |
| 1.0050 | H | Single bond | CH(Me) | CH2 | N—CH₂—C₆H₅ | bromo |
| 1.0051 | H | Single bond | C(Me)2 | CH2 | N—CH₂—C₆H₅ | bromo |
| 1.0052 | H | Single bond | C(Me)2 | C(Me)2 | N—CH₂—C₆H₅ | bromo |
| 1.0053 | Me | Single bond | CH2 | CH2 | N—CH₂—C₆H₅ | bromo |
| 1.0054 | Me | Single bond | CH(Me) | CH2 | N—CH₂—C₆H₅ | bromo |
| 1.0055 | Me | Single bond | C(Me)2 | CH2 | N—CH₂—C₆H₅ | bromo |
| 1.0056 | Me | Single bond | C(Me)2 | C(Me)2 | N—CH₂—C₆H₅ | bromo |
| 1.0057 | H | CH2 | CH2 | CH2 | N—CH₂—C₆H₅ | bromo |
| 1.0058 | H | CH2 | CH(Me) | CH2 | N—CH₂—C₆H₅ | bromo |
| 1.0059 | H | CH2 | C(Me)2 | CH2 | N—CH₂—C₆H₅ | bromo |
| 1.0060 | H | CH2 | C(Me)2 | C(Me)2 | N—CH₂—C₆H₅ | bromo |
| 1.0061 | Me | CH2 | CH2 | CH2 | N—CH₂—C₆H₅ | bromo |
| 1.0062 | Me | CH2 | CH(Me) | CH2 | N—CH₂—C₆H₅ | bromo |
| 1.0063 | Me | CH2 | C(Me)2 | CH2 | N—CH₂—C₆H₅ | bromo |
| 1.0064 | Me | CH2 | C(Me)2 | C(Me)2 | N—CH₂—C₆H₅ | bromo |
| 1.0065 | H | Single bond | CH2 | CH2 | S | bromo |
| 1.0066 | H | Single bond | CH(Me) | CH2 | S | bromo |
| 1.0067 | H | Single bond | C(Me)2 | CH2 | S | bromo |
| 1.0068 | H | Single bond | C(Me)2 | C(Me)2 | S | bromo |
| 1.0069 | Me | Single bond | CH2 | CH2 | S | bromo |
| 1.0070 | Me | Single bond | CH(Me) | CH2 | S | bromo |
| 1.0071 | Me | Single bond | C(Me)2 | CH2 | S | bromo |
| 1.0072 | Me | Single bond | C(Me)2 | C(Me)2 | S | bromo |

TABLE 1-continued

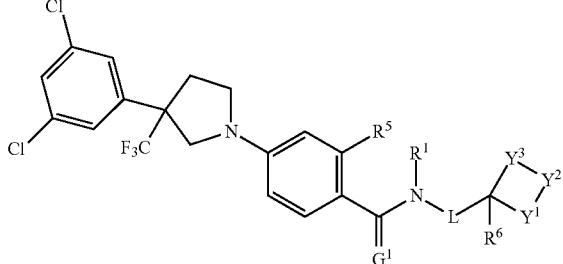

(I-A)

| Compound numbers | R⁶ | L | Y¹ | Y³ | Y² | R⁵ |
|---|---|---|---|---|---|---|
| 1.0073 | H | CH2 | CH2 | CH2 | S | bromo |
| 1.0074 | H | CH2 | CH(Me) | CH2 | S | bromo |
| 1.0075 | H | CH2 | C(Me)2 | CH2 | S | bromo |
| 1.0076 | H | CH2 | C(Me)2 | C(Me)2 | S | bromo |
| 1.0077 | Me | CH2 | CH2 | CH2 | S | bromo |
| 1.0078 | Me | CH2 | CH(Me) | CH2 | S | bromo |
| 1.0079 | Me | CH2 | C(Me)2 | CH2 | S | bromo |
| 1.0080 | Me | CH2 | C(Me)2 | C(Me)2 | S | bromo |
| 1.0081 | H | CH2CH2 | CH2 | CH2 | S | bromo |
| 1.0082 | H | CH2CH2 | CH(Me) | CH2 | S | bromo |
| 1.0083 | H | CH2CH2 | C(Me)2 | CH2 | S | bromo |
| 1.0084 | H | CH2CH2 | C(Me)2 | C(Me)2 | S | bromo |
| 1.0085 | Me | CH2CH2 | CH2 | CH2 | S | bromo |
| 1.0086 | Me | CH2CH2 | CH(Me) | CH2 | S | bromo |
| 1.0087 | Me | CH2CH2 | C(Me)2 | CH2 | S | bromo |
| 1.0088 | Me | CH2CH2 | C(Me)2 | C(Me)2 | S | bromo |
| 1.0089 | H | Single bond | CH2 | CH2 | SO | bromo |
| 1.0090 | H | Single bond | CH(Me) | CH2 | SO | bromo |
| 1.0091 | H | Single bond | C(Me)2 | CH2 | SO | bromo |
| 1.0092 | H | Single bond | C(Me)2 | C(Me)2 | SO | bromo |
| 1.0093 | Me | Single bond | CH2 | CH2 | SO | bromo |
| 1.0094 | Me | Single bond | CH(Me) | CH2 | SO | bromo |
| 1.0095 | Me | Single bond | C(Me)2 | CH2 | SO | bromo |
| 1.0096 | Me | Single bond | C(Me)2 | C(Me)2 | SO | bromo |
| 1.0097 | H | CH2 | CH2 | CH2 | SO | bromo |
| 1.0098 | H | CH2 | CH(Me) | CH2 | SO | bromo |
| 1.0099 | H | CH2 | C(Me)2 | CH2 | SO | bromo |
| 1.0100 | H | CH2 | C(Me)2 | C(Me)2 | SO | bromo |
| 1.0101 | Me | CH2 | CH2 | CH2 | SO | bromo |
| 1.0102 | Me | CH2 | CH(Me) | CH2 | SO | bromo |
| 1.0103 | Me | CH2 | C(Me)2 | CH2 | SO | bromo |
| 1.0104 | Me | CH2 | C(Me)2 | C(Me)2 | SO | bromo |
| 1.0105 | H | Single bond | CH2 | CH2 | SO$_2$ | bromo |
| 1.0106 | H | Single bond | CH(Me) | CH2 | SO$_2$ | bromo |
| 1.0107 | H | Single bond | C(Me)2 | CH2 | SO$_2$ | bromo |
| 1.0108 | H | Single bond | C(Me)2 | C(Me)2 | SO$_2$ | bromo |
| 1.0109 | Me | Single bond | CH2 | CH2 | SO$_2$ | bromo |
| 1.0110 | Me | Single bond | CH(Me) | CH2 | SO$_2$ | bromo |
| 1.0111 | Me | Single bond | C(Me)2 | CH2 | SO$_2$ | bromo |
| 1.0112 | Me | Single bond | C(Me)2 | C(Me)2 | SO$_2$ | bromo |
| 1.0113 | H | CH2 | CH2 | CH2 | SO$_2$ | bromo |
| 1.0114 | H | CH2 | CH(Me) | CH2 | SO$_2$ | bromo |
| 1.0115 | H | CH2 | C(Me)2 | CH2 | SO$_2$ | bromo |
| 1.0116 | H | CH2 | C(Me)2 | C(Me)2 | SO$_2$ | bromo |
| 1.0117 | Me | CH2 | CH2 | CH2 | SO$_2$ | bromo |
| 1.0118 | Me | CH2 | CH(Me) | CH2 | SO$_2$ | bromo |
| 1.0119 | Me | CH2 | C(Me)2 | CH2 | SO$_2$ | bromo |
| 1.0120 | Me | CH2 | C(Me)2 | C(Me)2 | SO$_2$ | bromo |
| 1.0121 | H | Single bond | CH2 | CH2 | SONH | bromo |
| 1.0122 | H | Single bond | CH(Me) | CH2 | SONH | bromo |
| 1.0123 | H | Single bond | C(Me)2 | CH2 | SONH | bromo |
| 1.0124 | H | Single bond | C(Me)2 | C(Me)2 | SONH | bromo |
| 1.0125 | Me | Single bond | CH2 | CH2 | SONH | bromo |
| 1.0126 | Me | Single bond | CH(Me) | CH2 | SONH | bromo |
| 1.0127 | Me | Single bond | C(Me)2 | CH2 | SONH | bromo |
| 1.0128 | Me | Single bond | C(Me)2 | C(Me)2 | SONH | bromo |
| 1.0129 | H | CH2 | CH2 | CH2 | SONH | bromo |
| 1.0130 | H | CH2 | CH(Me) | CH2 | SONH | bromo |
| 1.0131 | H | CH2 | C(Me)2 | CH2 | SONH | bromo |
| 1.0132 | H | CH2 | C(Me)2 | C(Me)2 | SONH | bromo |
| 1.0133 | Me | CH2 | CH2 | CH2 | SONH | bromo |
| 1.0134 | Me | CH2 | CH(Me) | CH2 | SONH | bromo |

TABLE 1-continued

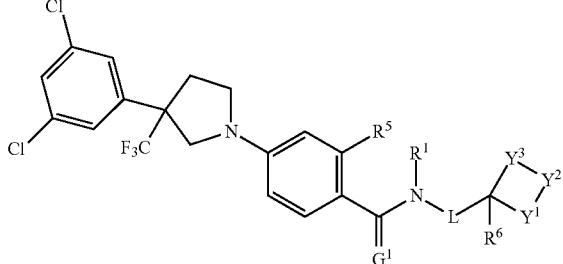

(I-A)

| Compound numbers | R⁶ | L | Y¹ | Y³ | Y² | R⁵ |
|---|---|---|---|---|---|---|
| 1.0135 | Me | CH2 | C(Me)2 | CH2 | SONH | bromo |
| 1.0136 | Me | CH2 | C(Me)2 | C(Me)2 | SONH | bromo |
| 1.0137 | H | Single bond | CH2 | CH2 | C=N—OCH₂CF₃ | bromo |
| 1.0138 | H | Single bond | CH(Me) | CH2 | C=N—OCH₂CF₃ | bromo |
| 1.0139 | H | Single bond | C(Me)2 | CH2 | C=N—OCH₂CF₃ | bromo |
| 1.0140 | H | Single bond | C(Me)2 | C(Me)2 | C=N—OCH₂CF₃ | bromo |
| 1.0141 | Me | Single bond | CH2 | CH2 | C=N—OCH₂CF₃ | bromo |
| 1.0142 | Me | Single bond | CH(Me) | CH2 | C=N—OCH₂CF₃ | bromo |
| 1.0143 | Me | Single bond | C(Me)2 | CH2 | C=N—OCH₂CF₃ | bromo |
| 1.0144 | Me | Single bond | C(Me)2 | C(Me)2 | C=N—OCH₂CF₃ | bromo |
| 1.0145 | H | CH2 | CH2 | CH2 | C=N—OCH₂CF₃ | bromo |
| 1.0146 | H | CH2 | CH(Me) | CH2 | C=N—OCH₂CF₃ | bromo |
| 1.0147 | H | CH2 | C(Me)2 | CH2 | C=N—OCH₂CF₃ | bromo |
| 1.0148 | H | CH2 | C(Me)2 | C(Me)2 | C=N—OCH₂CF₃ | bromo |
| 1.0149 | Me | CH2 | CH2 | CH2 | C=N—OCH₂CF₃ | bromo |
| 1.0150 | Me | CH2 | CH(Me) | CH2 | C=N—OCH₂CF₃ | bromo |
| 1.0151 | Me | CH2 | C(Me)2 | CH2 | C=N—OCH₂CF₃ | bromo |
| 1.0152 | Me | CH2 | C(Me)2 | C(Me)2 | C=N—OCH₂CF₃ | bromo |
| 1.0153 | H | CH2 | S | CH2 | CH2 | bromo |
| 1.0154 | H | CH2 | S | CH2 | CH(Me) | bromo |
| 1.0155 | H | CH2 | S | CH2 | C(Me)2 | bromo |
| 1.0156 | H | CH2 | S | CH(Me) | CH2 | bromo |
| 1.0157 | H | CH2 | S | CH(Me) | CH(Me) | bromo |
| 1.0158 | H | CH2 | S | CH(Me) | C(Me)2 | bromo |
| 1.0159 | H | CH2 | S | C(Me)2 | C(Me)2 | bromo |
| 1.0160 | H | CH2 | S | C(Me)2 | CH(Me) | bromo |
| 1.0161 | H | CH2 | S | C(Me)2 | CH2 | bromo |
| 1.0162 | Me | CH2 | S | CH2 | CH2 | bromo |
| 1.0163 | Me | CH2 | S | CH2 | CH(Me) | bromo |
| 1.0164 | Me | CH2 | S | CH2 | C(Me)2 | bromo |
| 1.0165 | Me | CH2 | S | CH(Me) | CH2 | bromo |
| 1.0166 | Me | CH2 | S | CH(Me) | CH(Me) | bromo |
| 1.0167 | Me | CH2 | S | CH(Me) | C(Me)2 | bromo |
| 1.0168 | Me | CH2 | S | C(Me)2 | C(Me)2 | bromo |
| 1.0169 | Me | CH2 | S | C(Me)2 | CH(Me) | bromo |
| 1.0170 | Me | CH2 | S | C(Me)2 | CH2 | bromo |
| 1.0171 | H | CH2 | SO | CH2 | CH2 | bromo |
| 1.0172 | H | CH2 | SO | CH2 | CH(Me) | bromo |
| 1.0173 | H | CH2 | SO | CH2 | C(Me)2 | bromo |
| 1.0174 | H | CH2 | SO | CH(Me) | CH2 | bromo |
| 1.0175 | H | CH2 | SO | CH(Me) | CH(Me) | bromo |
| 1.0176 | H | CH2 | SO | CH(Me) | C(Me)2 | bromo |
| 1.0177 | H | CH2 | SO | C(Me)2 | C(Me)2 | bromo |
| 1.0178 | H | CH2 | SO | C(Me)2 | CH(Me) | bromo |
| 1.0179 | H | CH2 | SO | C(Me)2 | CH2 | bromo |
| 1.0180 | Me | CH2 | SO | CH2 | CH2 | bromo |
| 1.0181 | Me | CH2 | SO | CH2 | CH(Me) | bromo |
| 1.0182 | Me | CH2 | SO | CH2 | C(Me)2 | bromo |
| 1.0183 | Me | CH2 | SO | CH(Me) | CH2 | bromo |
| 1.0184 | Me | CH2 | SO | CH(Me) | CH(Me) | bromo |
| 1.0185 | Me | CH2 | SO | CH(Me) | C(Me)2 | bromo |
| 1.0186 | Me | CH2 | SO | C(Me)2 | C(Me)2 | bromo |
| 1.0187 | Me | CH2 | SO | C(Me)2 | CH(Me) | bromo |
| 1.0188 | Me | CH2 | SO | C(Me)2 | CH2 | bromo |
| 1.0189 | H | CH2 | SO₂ | CH2 | CH2 | bromo |
| 1.0190 | H | CH2 | SO₂ | CH2 | CH(Me) | bromo |
| 1.0191 | H | CH2 | SO₂ | CH2 | C(Me)2 | bromo |
| 1.0192 | H | CH2 | SO₂ | CH(Me) | CH2 | bromo |
| 1.0193 | H | CH2 | SO₂ | CH(Me) | CH(Me) | bromo |
| 1.0194 | H | CH2 | SO₂ | CH(Me) | C(Me)2 | bromo |
| 1.0195 | H | CH2 | SO₂ | C(Me)2 | C(Me)2 | bromo |
| 1.0196 | H | CH2 | SO₂ | C(Me)2 | CH(Me) | bromo |

TABLE 1-continued

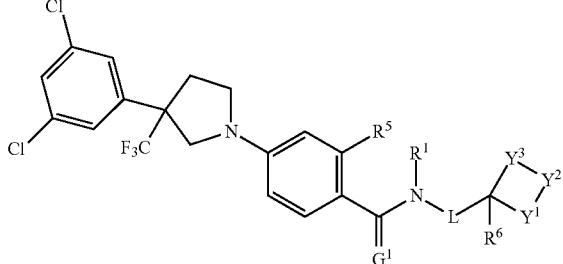

(I-A)

| Compound numbers | R⁶ | L | Y¹ | Y³ | Y² | R⁵ |
|---|---|---|---|---|---|---|
| 1.0197 | H | CH2 | SO₂ | C(Me)2 | CH2 | bromo |
| 1.0198 | Me | CH2 | SO₂ | CH2 | CH2 | bromo |
| 1.0199 | Me | CH2 | SO₂ | CH2 | CH(Me) | bromo |
| 1.0200 | Me | CH2 | SO₂ | CH2 | C(Me)2 | bromo |
| 1.0201 | Me | CH2 | SO₂ | CH(Me) | CH2 | bromo |
| 1.0202 | Me | CH2 | SO₂ | CH(Me) | CH(Me) | bromo |
| 1.0203 | Me | CH2 | SO₂ | CH(Me) | C(Me)2 | bromo |
| 1.0204 | Me | CH2 | SO₂ | C(Me)2 | C(Me)2 | bromo |
| 1.0205 | Me | CH2 | SO₂ | C(Me)2 | CH(Me) | bromo |
| 1.0206 | Me | CH2 | SO₂ | C(Me)2 | CH2 | bromo |
| 1.0207 | H | Single bond | CH2 | CH2 | C=O | cyano |
| 1.0208 | H | Single bond | CH(Me) | CH2 | C=O | cyano |
| 1.0209 | H | Single bond | C(Me)2 | CH2 | C=O | cyano |
| 1.0210 | H | Single bond | C(Me)2 | C(Me)2 | C=O | cyano |
| 1.0211 | Me | Single bond | CH2 | CH2 | C=O | cyano |
| 1.0212 | Me | Single bond | CH(Me) | CH2 | C=O | cyano |
| 1.0213 | Me | Single bond | C(Me)2 | CH2 | C=O | cyano |
| 1.0214 | Me | Single bond | C(Me)2 | C(Me)2 | C=O | cyano |
| 1.0215 | H | CH2 | CH2 | CH2 | C=O | cyano |
| 1.0216 | H | CH2 | CH(Me) | CH2 | C=O | cyano |
| 1.0217 | H | CH2 | C(Me)2 | CH2 | C=O | cyano |
| 1.0218 | H | CH2 | C(Me)2 | C(Me)2 | C=O | cyano |
| 1.0219 | Me | CH2 | CH2 | CH2 | C=O | cyano |
| 1.0220 | Me | CH2 | CH(Me) | CH2 | C=O | cyano |
| 1.0221 | Me | CH2 | C(Me)2 | CH2 | C=O | cyano |
| 1.0222 | Me | CH2 | C(Me)2 | C(Me)2 | C=O | cyano |
| 1.0223 | H | Single bond | CH2 | CH2 | C=N—OMe | cyano |
| 1.0224 | H | Single bond | CH(Me) | CH2 | C=N—OMe | cyano |
| 1.0225 | H | Single bond | C(Me)2 | CH2 | C=N—OMe | cyano |
| 1.0226 | H | Single bond | C(Me)2 | C(Me)2 | C=N—OMe | cyano |
| 1.0227 | Me | Single bond | CH2 | CH2 | C=N—OMe | cyano |
| 1.0228 | Me | Single bond | CH(Me) | CH2 | C=N—OMe | cyano |
| 1.0229 | Me | Single bond | C(Me)2 | CH2 | C=N—OMe | cyano |
| 1.0230 | Me | Single bond | C(Me)2 | C(Me)2 | C=N—OMe | cyano |
| 1.0231 | H | CH2 | CH2 | CH2 | C=N—OMe | cyano |
| 1.0232 | H | CH2 | CH(Me) | CH2 | C=N—OMe | cyano |
| 1.0233 | H | CH2 | C(Me)2 | CH2 | C=N—OMe | cyano |
| 1.0234 | H | CH2 | C(Me)2 | C(Me)2 | C=N—OMe | cyano |
| 1.0235 | Me | CH2 | CH2 | CH2 | C=N—OMe | cyano |
| 1.0236 | Me | CH2 | CH(Me) | CH2 | C=N—OMe | cyano |
| 1.0237 | Me | CH2 | C(Me)2 | CH2 | C=N—OMe | cyano |
| 1.0238 | Me | CH2 | C(Me)2 | C(Me)2 | C=N—OMe | cyano |
| 1.0239 | H | Single bond | CH2 | CH2 | N—Me | cyano |
| 1.0240 | H | Single bond | CH(Me) | CH2 | N—Me | cyano |
| 1.0241 | H | Single bond | C(Me)2 | CH2 | N—Me | cyano |
| 1.0242 | H | Single bond | C(Me)2 | C(Me)2 | N—Me | cyano |
| 1.0243 | Me | Single bond | CH2 | CH2 | N—Me | cyano |
| 1.0244 | Me | Single bond | CH(Me) | CH2 | N—Me | cyano |
| 1.0245 | Me | Single bond | C(Me)2 | CH2 | N—Me | cyano |
| 1.0246 | Me | Single bond | C(Me)2 | C(Me)2 | N—Me | cyano |
| 1.0247 | H | CH2 | CH2 | CH2 | N—Me | cyano |
| 1.0248 | H | CH2 | CH(Me) | CH2 | N—Me | cyano |
| 1.0249 | H | CH2 | C(Me)2 | CH2 | N—Me | cyano |
| 1.0250 | H | CH2 | C(Me)2 | C(Me)2 | N—Me | cyano |
| 1.0251 | Me | CH2 | CH2 | CH2 | N—Me | cyano |
| 1.0252 | Me | CH2 | CH(Me) | CH2 | N—Me | cyano |
| 1.0253 | Me | CH2 | C(Me)2 | CH2 | N—Me | cyano |
| 1.0254 | Me | CH2 | C(Me)2 | C(Me)2 | N—Me | cyano |
| 1.0255 | H | Single bond | CH2 | CH2 | N—CH2—C6H5 | cyano |
| 1.0256 | H | Single bond | CH(Me) | CH2 | N—CH2—C6H5 | cyano |
| 1.0257 | H | Single bond | C(Me)2 | CH2 | N—CH2—C6H5 | cyano |
| 1.0258 | H | Single bond | C(Me)2 | C(Me)2 | N—CH2—C6H5 | cyano |

TABLE 1-continued (I-A)

| Compound numbers | R⁶ | L | Y¹ | Y³ | Y² | R⁵ |
|---|---|---|---|---|---|---|
| 1.0259 | Me | Single bond | CH2 | CH2 | N—CH2—C6H5 | cyano |
| 1.0260 | Me | Single bond | CH(Me) | CH2 | N—CH2—C6H5 | cyano |
| 1.0261 | Me | Single bond | C(Me)2 | CH2 | N—CH2—C6H5 | cyano |
| 1.0262 | Me | Single bond | C(Me)2 | C(Me)2 | N—CH2—C6H5 | cyano |
| 1.0263 | H | CH2 | CH2 | CH2 | N—CH2—C6H5 | cyano |
| 1.0264 | H | CH2 | CH(Me) | CH2 | N—CH2—C6H5 | cyano |
| 1.0265 | H | CH2 | C(Me)2 | CH2 | N—CH2—C6H5 | cyano |
| 1.0266 | H | CH2 | C(Me)2 | C(Me)2 | N—CH2—C6H5 | cyano |
| 1.0267 | Me | CH2 | CH2 | CH2 | N—CH2—C6H5 | cyano |
| 1.0268 | Me | CH2 | CH(Me) | CH2 | N—CH2—C6H5 | cyano |
| 1.0269 | Me | CH2 | C(Me)2 | CH2 | N—CH2—C6H5 | cyano |
| 1.0270 | Me | CH2 | C(Me)2 | C(Me)2 | N—CH2—C6H5 | cyano |
| 1.0271 | H | Single bond | CH2 | CH2 | S | cyano |
| 1.0272 | H | Single bond | CH(Me) | CH2 | S | cyano |
| 1.0273 | H | Single bond | C(Me)2 | CH2 | S | cyano |
| 1.0274 | H | Single bond | C(Me)2 | C(Me)2 | S | cyano |
| 1.0275 | Me | Single bond | CH2 | CH2 | S | cyano |
| 1.0276 | Me | Single bond | CH(Me) | CH2 | S | cyano |
| 1.0277 | Me | Single bond | C(Me)2 | CH2 | S | cyano |
| 1.0278 | Me | Single bond | C(Me)2 | C(Me)2 | S | cyano |
| 1.0279 | H | CH2 | CH2 | CH2 | S | cyano |
| 1.0280 | H | CH2 | CH(Me) | CH2 | S | cyano |
| 1.0281 | H | CH2 | C(Me)2 | CH2 | S | cyano |
| 1.0282 | H | CH2 | C(Me)2 | C(Me)2 | S | cyano |
| 1.0283 | Me | CH2 | CH2 | CH2 | S | cyano |
| 1.0284 | Me | CH2 | CH(Me) | CH2 | S | cyano |
| 1.0285 | Me | CH2 | C(Me)2 | CH2 | S | cyano |
| 1.0286 | Me | CH2 | C(Me)2 | C(Me)2 | S | cyano |
| 1.0287 | H | Single bond | CH2 | CH2 | SO | cyano |
| 1.0288 | H | Single bond | CH(Me) | CH2 | SO | cyano |
| 1.0289 | H | Single bond | C(Me)2 | CH2 | SO | cyano |
| 1.0290 | H | Single bond | C(Me)2 | C(Me)2 | SO | cyano |
| 1.0291 | Me | Single bond | CH2 | CH2 | SO | cyano |
| 1.0292 | Me | Single bond | CH(Me) | CH2 | SO | cyano |
| 1.0293 | Me | Single bond | C(Me)2 | CH2 | SO | cyano |
| 1.0294 | Me | Single bond | C(Me)2 | C(Me)2 | SO | cyano |
| 1.0295 | H | CH2 | CH2 | CH2 | SO | cyano |
| 1.0296 | H | CH2 | CH(Me) | CH2 | SO | cyano |
| 1.0297 | H | CH2 | C(Me)2 | CH2 | SO | cyano |
| 1.0298 | H | CH2 | C(Me)2 | C(Me)2 | SO | cyano |
| 1.0299 | Me | CH2 | CH2 | CH2 | SO | cyano |
| 1.0300 | Me | CH2 | CH(Me) | CH2 | SO | cyano |
| 1.0301 | Me | CH2 | C(Me)2 | CH2 | SO | cyano |
| 1.0302 | Me | CH2 | C(Me)2 | C(Me)2 | SO | cyano |
| 1.0303 | H | Single bond | CH2 | CH2 | SO | cyano |
| 1.0304 | H | Single bond | CH(Me) | CH2 | SO2 | cyano |
| 1.0305 | H | Single bond | C(Me)2 | CH2 | SO2 | cyano |
| 1.0306 | H | Single bond | C(Me)2 | C(Me)2 | SO2 | cyano |
| 1.0307 | Me | Single bond | CH2 | CH2 | SO2 | cyano |
| 1.0308 | Me | Single bond | CH(Me) | CH2 | SO2 | cyano |
| 1.0309 | Me | Single bond | C(Me)2 | CH2 | SO2 | cyano |
| 1.0310 | Me | Single bond | C(Me)2 | C(Me)2 | SO2 | cyano |
| 1.0311 | H | CH2 | CH2 | CH2 | SO2 | cyano |
| 1.0312 | H | CH2 | CH(Me) | CH2 | SO2 | cyano |
| 1.0313 | H | CH2 | C(Me)2 | CH2 | SO2 | cyano |
| 1.0314 | H | CH2 | C(Me)2 | C(Me)2 | SO2 | cyano |
| 1.0315 | Me | CH2 | CH2 | CH2 | SO2 | cyano |
| 1.0316 | Me | CH2 | CH(Me) | CH2 | SO2 | cyano |
| 1.0317 | Me | CH2 | C(Me)2 | CH2 | SO2 | cyano |
| 1.0318 | Me | CH2 | C(Me)2 | C(Me)2 | SO2 | cyano |
| 1.0319 | H | Single bond | CH2 | CH2 | SONH | cyano |
| 1.0320 | H | Single bond | CH(Me) | CH2 | SONH | cyano |

TABLE 1-continued

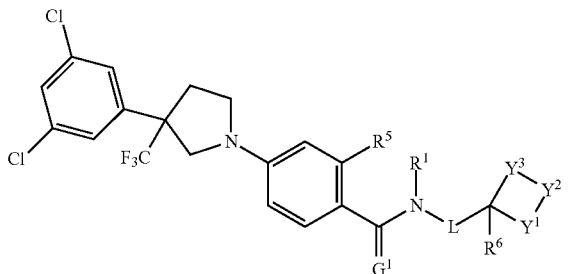

(I-A)

| Compound numbers | R6 | L | Y1 | Y3 | Y2 | R5 |
|---|---|---|---|---|---|---|
| 1.0321 | H | Single bond | C(Me)2 | CH2 | SONH | cyano |
| 1.0322 | H | Single bond | C(Me)2 | C(Me)2 | SONH | cyano |
| 1.0323 | Me | Single bond | CH2 | CH2 | SONH | cyano |
| 1.0324 | Me | Single bond | CH(Me) | CH2 | SONH | cyano |
| 1.0325 | Me | Single bond | C(Me)2 | CH2 | SONH | cyano |
| 1.0326 | Me | Single bond | C(Me)2 | C(Me)2 | SONH | cyano |
| 1.0327 | H | CH2 | CH2 | CH2 | SONH | cyano |
| 1.0328 | H | CH2 | CH(Me) | CH2 | SONH | cyano |
| 1.0329 | H | CH2 | C(Me)2 | CH2 | SONH | cyano |
| 1.0330 | H | CH2 | C(Me)2 | C(Me)2 | SONH | cyano |
| 1.0331 | Me | CH2 | CH2 | CH2 | SONH | cyano |
| 1.0332 | Me | CH2 | CH(Me) | CH2 | SONH | cyano |
| 1.0333 | Me | CH2 | C(Me)2 | CH2 | SONH | cyano |
| 1.0334 | Me | CH2 | C(Me)2 | C(Me)2 | SONH | cyano |
| 1.0335 | H | Single bond | CH2 | CH2 | C=N—OCH2CF3 | cyano |
| 1.0336 | H | Single bond | CH(Me) | CH2 | C=N—OCH2CF3 | cyano |
| 1.0337 | H | Single bond | C(Me)2 | CH2 | C=N—OCH2CF3 | cyano |
| 1.0338 | H | Single bond | C(Me)2 | C(Me)2 | C=N—OCH2CF3 | cyano |
| 1.0339 | Me | Single bond | CH2 | CH2 | C=N—OCH2CF3 | cyano |
| 1.0340 | Me | Single bond | CH(Me) | CH2 | C=N—OCH2CF3 | cyano |
| 1.0341 | Me | Single bond | C(Me)2 | CH2 | C=N—OCH2CF3 | cyano |
| 1.0342 | Me | Single bond | C(Me)2 | C(Me)2 | C=N—OCH2CF3 | cyano |
| 1.0343 | H | CH2 | CH2 | CH2 | C=N—OCH2CF3 | cyano |
| 1.0344 | H | CH2 | CH(Me) | CH2 | C=N—OCH2CF3 | cyano |
| 1.0345 | H | CH2 | C(Me)2 | CH2 | C=N—OCH2CF3 | cyano |
| 1.0346 | H | CH2 | C(Me)2 | C(Me)2 | C=N—OCH2CF3 | cyano |
| 1.0347 | Me | CH2 | CH2 | CH2 | C=N—OCH2CF3 | cyano |
| 1.0348 | Me | CH2 | CH(Me) | CH2 | C=N—OCH2CF3 | cyano |
| 1.0349 | Me | CH2 | C(Me)2 | CH2 | C=N—OCH2CF3 | cyano |
| 1.0350 | Me | CH2 | C(Me)2 | C(Me)2 | C=N—OCH2CF3 | cyano |
| 1.0351 | H | CH2 | S | CH2 | CH2 | cyano |
| 1.0352 | H | CH2 | S | CH2 | CH(Me) | cyano |
| 1.0353 | H | CH2 | S | CH2 | C(Me)2 | cyano |
| 1.0354 | H | CH2 | S | CH(Me) | CH2 | cyano |
| 1.0355 | H | CH2 | S | CH(Me) | CH(Me) | cyano |
| 1.0356 | H | CH2 | S | CH(Me) | C(Me)2 | cyano |
| 1.0357 | H | CH2 | S | C(Me)2 | C(Me)2 | cyano |
| 1.0358 | H | CH2 | S | C(Me)2 | CH(Me) | cyano |
| 1.0359 | H | CH2 | S | C(Me)2 | CH2 | cyano |
| 1.0360 | Me | CH2 | S | CH2 | CH2 | cyano |
| 1.0361 | Me | CH2 | S | CH2 | CH(Me) | cyano |
| 1.0362 | Me | CH2 | S | CH2 | C(Me)2 | cyano |
| 1.0363 | Me | CH2 | S | CH(Me) | CH2 | cyano |
| 1.0364 | Me | CH2 | S | CH(Me) | CH(Me) | cyano |
| 1.0365 | Me | CH2 | S | CH(Me) | C(Me)2 | cyano |
| 1.0366 | Me | CH2 | S | C(Me)2 | C(Me)2 | cyano |
| 1.0367 | Me | CH2 | S | C(Me)2 | CH(Me) | cyano |
| 1.0368 | Me | CH2 | S | C(Me)2 | CH2 | cyano |
| 1.0369 | H | CH2 | SO | CH2 | CH2 | cyano |
| 1.0370 | H | CH2 | SO | CH2 | CH(Me) | cyano |
| 1.0371 | H | CH2 | SO | CH2 | C(Me)2 | cyano |
| 1.0372 | H | CH2 | SO | CH(Me) | CH2 | cyano |
| 1.0373 | H | CH2 | SO | CH(Me) | CH(Me) | cyano |
| 1.0374 | H | CH2 | SO | CH(Me) | C(Me)2 | cyano |
| 1.0375 | H | CH2 | SO | C(Me)2 | C(Me)2 | cyano |
| 1.0376 | H | CH2 | SO | C(Me)2 | CH(Me) | cyano |
| 1.0377 | H | CH2 | SO | C(Me)2 | CH2 | cyano |
| 1.0378 | Me | CH2 | SO | CH2 | CH2 | cyano |
| 1.0379 | Me | CH2 | SO | CH2 | CH(Me) | cyano |
| 1.0380 | Me | CH2 | SO | CH2 | C(Me)2 | cyano |
| 1.0381 | Me | CH2 | SO | CH(Me) | CH2 | cyano |
| 1.0382 | Me | CH2 | SO | CH(Me) | CH(Me) | cyano |

TABLE 1-continued

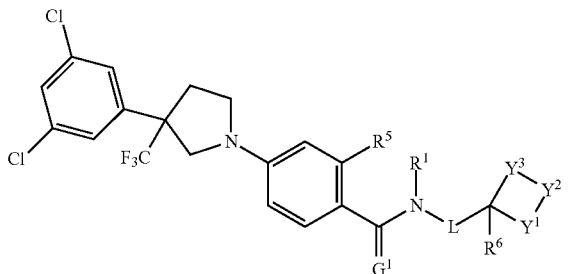

(I-A)

| Compound numbers | R⁶ | L | Y¹ | Y³ | Y² | R⁵ |
|---|---|---|---|---|---|---|
| 1.0383 | Me | CH2 | SO | CH(Me) | C(Me)2 | cyano |
| 1.0384 | Me | CH2 | SO | C(Me)2 | C(Me)2 | cyano |
| 1.0385 | Me | CH2 | SO | C(Me)2 | CH(Me) | cyano |
| 1.0386 | Me | CH2 | SO | C(Me)2 | CH2 | cyano |
| 1.0387 | H | CH2 | SO2 | CH2 | CH2 | cyano |
| 1.0388 | H | CH2 | SO2 | CH2 | CH(Me) | cyano |
| 1.0389 | H | CH2 | SO2 | CH2 | C(Me)2 | cyano |
| 1.0390 | H | CH2 | SO2 | CH(Me) | CH2 | cyano |
| 1.0391 | H | CH2 | SO2 | CH(Me) | CH(Me) | cyano |
| 1.0392 | H | CH2 | SO2 | CH(Me) | C(Me)2 | cyano |
| 1.0393 | H | CH2 | SO2 | C(Me)2 | C(Me)2 | cyano |
| 1.0394 | H | CH2 | SO2 | C(Me)2 | CH(Me) | cyano |
| 1.0395 | H | CH2 | SO2 | C(Me)2 | CH2 | cyano |
| 1.0396 | Me | CH2 | SO2 | CH2 | CH2 | cyano |
| 1.0397 | Me | CH2 | SO2 | CH2 | CH(Me) | cyano |
| 1.0398 | Me | CH2 | SO2 | CH2 | C(Me)2 | cyano |
| 1.0399 | Me | CH2 | SO2 | CH(Me) | CH2 | cyano |
| 1.0400 | Me | CH2 | SO2 | CH(Me) | CH(Me) | cyano |
| 1.0401 | Me | CH2 | SO2 | CH(Me) | C(Me)2 | cyano |
| 1.0402 | Me | CH2 | SO2 | C(Me)2 | C(Me)2 | cyano |
| 1.0403 | Me | CH2 | SO2 | C(Me)2 | CH(Me) | cyano |
| 1.0404 | Me | CH2 | SO2 | C(Me)2 | CH2 | cyano |
| 1.0405 | H | Single bond | CH2 | CH2 | C=O | methyl |
| 1.0406 | H | Single bond | CH(Me) | CH2 | C=O | methyl |
| 1.0407 | H | Single bond | C(Me)2 | CH2 | C=O | methyl |
| 1.0408 | H | Single bond | C(Me)2 | C(Me)2 | C=O | methyl |
| 1.0409 | Me | Single bond | CH2 | CH2 | C=O | methyl |
| 1.0410 | Me | Single bond | CH(Me) | CH2 | C=O | methyl |
| 1.0411 | Me | Single bond | C(Me)2 | CH2 | C=O | methyl |
| 1.0412 | Me | Single bond | C(Me)2 | C(Me)2 | C=O | methyl |
| 1.0413 | H | CH2 | CH2 | CH2 | C=O | methyl |
| 1.0414 | H | CH2 | CH(Me) | CH2 | C=O | methyl |
| 1.0415 | H | CH2 | C(Me)2 | CH2 | C=O | methyl |
| 1.0416 | H | CH2 | C(Me)2 | C(Me)2 | C=O | methyl |
| 1.0417 | Me | CH2 | CH2 | CH2 | C=O | methyl |
| 1.0418 | Me | CH2 | CH(Me) | CH2 | C=O | methyl |
| 1.0419 | Me | CH2 | C(Me)2 | CH2 | C=O | methyl |
| 1.0420 | Me | CH2 | C(Me)2 | C(Me)2 | C=O | methyl |
| 1.0421 | H | Single bond | CH2 | CH2 | C=N—OMe | methyl |
| 1.0422 | H | Single bond | CH(Me) | CH2 | C=N—OMe | methyl |
| 1.0423 | H | Single bond | C(Me)2 | CH2 | C=N—OMe | methyl |
| 1.0424 | H | Single bond | C(Me)2 | C(Me)2 | C=N—OMe | methyl |
| 1.0425 | Me | Single bond | CH2 | CH2 | C=N—OMe | methyl |
| 1.0426 | Me | Single bond | CH(Me) | CH2 | C=N—OMe | methyl |
| 1.0427 | Me | Single bond | C(Me)2 | CH2 | C=N—OMe | methyl |
| 1.0428 | Me | Single bond | C(Me)2 | C(Me)2 | C=N—OMe | methyl |
| 1.0429 | H | CH2 | CH2 | CH2 | C=N—OMe | methyl |
| 1.0430 | H | CH2 | CH(Me) | CH2 | C=N—OMe | methyl |
| 1.0431 | H | CH2 | C(Me)2 | CH2 | C=N—OMe | methyl |
| 1.0432 | H | CH2 | C(Me)2 | C(Me)2 | C=N—OMe | methyl |
| 1.0433 | Me | CH2 | CH2 | CH2 | C=N—OMe | methyl |
| 1.0434 | Me | CH2 | CH(Me) | CH2 | C=N—OMe | methyl |
| 1.0435 | Me | CH2 | C(Me)2 | CH2 | C=N—OMe | methyl |
| 1.0436 | Me | CH2 | C(Me)2 | C(Me)2 | C=N—OMe | methyl |
| 1.0437 | H | Single bond | CH2 | CH2 | N—Me | methyl |
| 1.0438 | H | Single bond | CH(Me) | CH2 | N—Me | methyl |
| 1.0439 | H | Single bond | C(Me)2 | CH2 | N—Me | methyl |
| 1.0440 | H | Single bond | C(Me)2 | C(Me)2 | N—Me | methyl |
| 1.0441 | Me | Single bond | CH2 | CH2 | N—Me | methyl |
| 1.0442 | Me | Single bond | CH(Me) | CH2 | N—Me | methyl |
| 1.0443 | Me | Single bond | C(Me)2 | CH2 | N—Me | methyl |
| 1.0444 | Me | Single bond | C(Me)2 | C(Me)2 | N—Me | methyl |

TABLE 1-continued (I-A)

| Compound numbers | R6 | L | Y1 | Y3 | Y2 | R5 |
|---|---|---|---|---|---|---|
| 1.0445 | H | CH2 | CH2 | CH2 | N—Me | methyl |
| 1.0446 | H | CH2 | CH(Me) | CH2 | N—Me | methyl |
| 1.0447 | H | CH2 | C(Me)2 | CH2 | N—Me | methyl |
| 1.0448 | H | CH2 | C(Me)2 | C(Me)2 | N—Me | methyl |
| 1.0449 | Me | CH2 | CH2 | CH2 | N—Me | methyl |
| 1.0450 | Me | CH2 | CH(Me) | CH2 | N—Me | methyl |
| 1.0451 | Me | CH2 | C(Me)2 | CH2 | N—Me | methyl |
| 1.0452 | Me | CH2 | C(Me)2 | C(Me)2 | N—Me | methyl |
| 1.0453 | H | Single bond | CH2 | CH2 | N—CH2—C6H5 | methyl |
| 1.0454 | H | Single bond | CH(Me) | CH2 | N—CH2—C6H5 | methyl |
| 1.0455 | H | Single bond | C(Me)2 | CH2 | N—CH2—C6H5 | methyl |
| 1.0456 | H | Single bond | C(Me)2 | C(Me)2 | N—CH2—C6H5 | methyl |
| 1.0457 | Me | Single bond | CH2 | CH2 | N—CH2—C6H5 | methyl |
| 1.0458 | Me | Single bond | CH(Me) | CH2 | N—CH2—C6H5 | methyl |
| 1.0459 | Me | Single bond | C(Me)2 | CH2 | N—CH2—C6H5 | methyl |
| 1.0460 | Me | Single bond | C(Me)2 | C(Me)2 | N—CH2—C6H5 | methyl |
| 1.0461 | H | CH2 | CH2 | CH2 | N—CH2—C6H5 | methyl |
| 1.0462 | H | CH2 | CH(Me) | CH2 | N—CH2—C6H5 | methyl |
| 1.0463 | H | CH2 | C(Me)2 | CH2 | N—CH2—C6H5 | methyl |
| 1.0464 | H | CH2 | C(Me)2 | C(Me)2 | N—CH2—C6H5 | methyl |
| 1.0465 | Me | CH2 | CH2 | CH2 | N—CH2—C6H5 | methyl |
| 1.0466 | Me | CH2 | CH(Me) | CH2 | N—CH2—C6H5 | methyl |
| 1.0467 | Me | CH2 | C(Me)2 | CH2 | N—CH2—C6H5 | methyl |
| 1.0468 | Me | CH2 | C(Me)2 | C(Me)2 | N—CH2—C6H5 | methyl |
| 1.0469 | H | Single bond | CH2 | CH2 | S | methyl |
| 1.0470 | H | Single bond | CH(Me) | CH2 | S | methyl |
| 1.0471 | H | Single bond | C(Me)2 | CH2 | S | methyl |
| 1.0472 | H | Single bond | C(Me)2 | C(Me)2 | S | methyl |
| 1.0473 | Me | Single bond | CH2 | CH2 | S | methyl |
| 1.0474 | Me | Single bond | CH(Me) | CH2 | S | methyl |
| 1.0475 | Me | Single bond | C(Me)2 | CH2 | S | methyl |
| 1.0476 | Me | Single bond | C(Me)2 | C(Me)2 | S | methyl |
| 1.0477 | H | CH2 | CH2 | CH2 | S | methyl |
| 1.0478 | H | CH2 | CH(Me) | CH2 | S | methyl |
| 1.0479 | H | CH2 | C(Me)2 | CH2 | S | methyl |
| 1.0480 | H | CH2 | C(Me)2 | C(Me)2 | S | methyl |
| 1.0481 | Me | CH2 | CH2 | CH2 | S | methyl |
| 1.0482 | Me | CH2 | CH(Me) | CH2 | S | methyl |
| 1.0483 | Me | CH2 | C(Me)2 | CH2 | S | methyl |
| 1.0484 | Me | CH2 | C(Me)2 | C(Me)2 | S | methyl |
| 1.0485 | H | Single bond | CH2 | CH2 | SO | methyl |
| 1.0486 | H | Single bond | CH(Me) | CH2 | SO | methyl |
| 1.0487 | H | Single bond | C(Me)2 | CH2 | SO | methyl |
| 1.0488 | H | Single bond | C(Me)2 | C(Me)2 | SO | methyl |
| 1.0489 | Me | Single bond | CH2 | CH2 | SO | methyl |
| 1.0490 | Me | Single bond | CH(Me) | CH2 | SO | methyl |
| 1.0491 | Me | Single bond | C(Me)2 | CH2 | SO | methyl |
| 1.0492 | Me | Single bond | C(Me)2 | C(Me)2 | SO | methyl |
| 1.0493 | H | CH2 | CH2 | CH2 | SO | methyl |
| 1.0494 | H | CH2 | CH(Me) | CH2 | SO | methyl |
| 1.0495 | H | CH2 | C(Me)2 | CH2 | SO | methyl |
| 1.0496 | H | CH2 | C(Me)2 | C(Me)2 | SO | methyl |
| 1.0497 | Me | CH2 | CH2 | CH2 | SO | methyl |
| 1.0498 | Me | CH2 | CH(Me) | CH2 | SO | methyl |
| 1.0499 | Me | CH2 | C(Me)2 | CH2 | SO | methyl |
| 1.0500 | Me | CH2 | C(Me)2 | C(Me)2 | SO | methyl |
| 1.0501 | H | Single bond | CH2 | CH2 | SO2 | methyl |
| 1.0502 | H | Single bond | CH(Me) | CH2 | SO2 | methyl |
| 1.0503 | H | Single bond | C(Me)2 | CH2 | SO2 | methyl |
| 1.0504 | H | Single bond | C(Me)2 | C(Me)2 | SO2 | methyl |
| 1.0505 | Me | Single bond | CH2 | CH2 | SO2 | methyl |
| 1.0506 | Me | Single bond | CH(Me) | CH2 | SO2 | methyl |

TABLE 1-continued

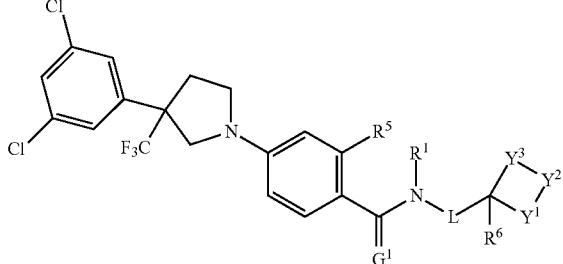

(I-A)

| Compound numbers | R⁶ | L | Y¹ | Y³ | Y² | R⁵ |
|---|---|---|---|---|---|---|
| 1.0507 | Me | Single bond | C(Me)2 | CH2 | SO2 | methyl |
| 1.0508 | Me | Single bond | C(Me)2 | C(Me)2 | SO2 | methyl |
| 1.0509 | H | CH2 | CH2 | CH2 | SO2 | methyl |
| 1.0510 | H | CH2 | CH(Me) | CH2 | SO2 | methyl |
| 1.0511 | H | CH2 | C(Me)2 | CH2 | SO2 | methyl |
| 1.0512 | H | CH2 | C(Me)2 | C(Me)2 | SO2 | methyl |
| 1.0513 | Me | CH2 | CH2 | CH2 | SO2 | methyl |
| 1.0514 | Me | CH2 | CH(Me) | CH2 | SO2 | methyl |
| 1.0515 | Me | CH2 | C(Me)2 | CH2 | SO2 | methyl |
| 1.0516 | Me | CH2 | C(Me)2 | C(Me)2 | SO2 | methyl |
| 1.0517 | H | Single bond | CH2 | CH2 | SONH | methyl |
| 1.0518 | H | Single bond | CH(Me) | CH2 | SONH | methyl |
| 1.0519 | H | Single bond | C(Me)2 | CH2 | SONH | methyl |
| 1.0520 | H | Single bond | C(Me)2 | C(Me)2 | SONH | methyl |
| 1.0521 | Me | Single bond | CH2 | CH2 | SONH | methyl |
| 1.0522 | Me | Single bond | CH(Me) | CH2 | SONH | methyl |
| 1.0523 | Me | Single bond | C(Me)2 | CH2 | SONH | methyl |
| 1.0524 | Me | Single bond | C(Me)2 | C(Me)2 | SONH | methyl |
| 1.0525 | H | CH2 | CH2 | CH2 | SONH | methyl |
| 1.0526 | H | CH2 | CH(Me) | CH2 | SONH | methyl |
| 1.0527 | H | CH2 | C(Me)2 | CH2 | SONH | methyl |
| 1.0528 | H | CH2 | C(Me)2 | C(Me)2 | SONH | methyl |
| 1.0529 | Me | CH2 | CH2 | CH2 | SONH | methyl |
| 1.0530 | Me | CH2 | CH(Me) | CH2 | SONH | methyl |
| 1.0531 | Me | CH2 | C(Me)2 | CH2 | SONH | methyl |
| 1.0532 | Me | CH2 | C(Me)2 | C(Me)2 | SONH | methyl |
| 1.0533 | H | Single bond | CH2 | CH2 | C=N—OCH2CF3 | methyl |
| 1.0534 | H | Single bond | CH(Me) | CH2 | C=N—OCH2CF3 | methyl |
| 1.0535 | H | Single bond | C(Me)2 | CH2 | C=N—OCH2CF3 | methyl |
| 1.0536 | H | Single bond | C(Me)2 | C(Me)2 | C=N—OCH2CF3 | methyl |
| 1.0537 | Me | Single bond | CH2 | CH2 | C=N—OCH2CF3 | methyl |
| 1.0538 | Me | Single bond | CH(Me) | CH2 | C=N—OCH2CF3 | methyl |
| 1.0539 | Me | Single bond | C(Me)2 | CH2 | C=N—OCH2CF3 | methyl |
| 1.0540 | Me | Single bond | C(Me)2 | C(Me)2 | C=N—OCH2CF3 | methyl |
| 1.0541 | H | CH2 | CH2 | CH2 | C=N—OCH2CF3 | methyl |
| 1.0542 | H | CH2 | CH(Me) | CH2 | C=N—OCH2CF3 | methyl |
| 1.0543 | H | CH2 | C(Me)2 | CH2 | C=N—OCH2CF3 | methyl |
| 1.0544 | H | CH2 | C(Me)2 | C(Me)2 | C=N—OCH2CF3 | methyl |
| 1.0545 | Me | CH2 | CH2 | CH2 | C=N—OCH2CF3 | methyl |
| 1.0546 | Me | CH2 | CH(Me) | CH2 | C=N—OCH2CF3 | methyl |
| 1.0547 | Me | CH2 | C(Me)2 | CH2 | C=N—OCH2CF3 | methyl |
| 1.0548 | Me | CH2 | C(Me)2 | C(Me)2 | C=N—OCH2CF3 | methyl |
| 1.0549 | H | CH2 | S | CH2 | CH2 | methyl |
| 1.0550 | H | CH2 | S | CH2 | CH(Me) | methyl |
| 1.0551 | H | CH2 | S | CH2 | C(Me)2 | methyl |
| 1.0552 | H | CH2 | S | CH(Me) | CH2 | methyl |
| 1.0553 | H | CH2 | S | CH(Me) | CH(Me) | methyl |
| 1.0554 | H | CH2 | S | CH(Me) | C(Me)2 | methyl |
| 1.0555 | H | CH2 | S | C(Me)2 | C(Me)2 | methyl |
| 1.0556 | H | CH2 | S | C(Me)2 | CH(Me) | methyl |
| 1.0557 | H | CH2 | S | C(Me)2 | CH2 | methyl |
| 1.0558 | Me | CH2 | S | CH2 | CH2 | methyl |
| 1.0559 | Me | CH2 | S | CH2 | CH(Me) | methyl |
| 1.0560 | Me | CH2 | S | CH2 | C(Me)2 | methyl |
| 1.0561 | Me | CH2 | S | CH(Me) | CH2 | methyl |
| 1.0562 | Me | CH2 | S | CH(Me) | CH(Me) | methyl |
| 1.0563 | Me | CH2 | S | CH(Me) | C(Me)2 | methyl |
| 1.0564 | Me | CH2 | S | C(Me)2 | C(Me)2 | methyl |
| 1.0565 | Me | CH2 | S | C(Me)2 | CH(Me) | methyl |
| 1.0566 | Me | CH2 | S | C(Me)2 | CH2 | methyl |
| 1.0567 | H | CH2 | SO | CH2 | CH2 | methyl |
| 1.0568 | H | CH2 | SO | CH2 | CH(Me) | methyl |

TABLE 1-continued

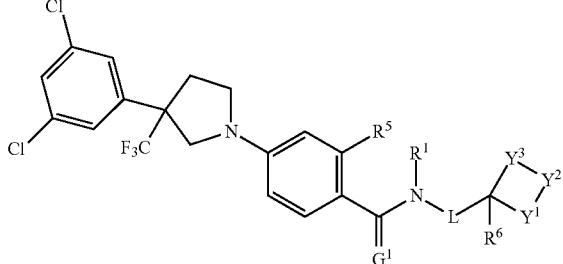

(I-A)

| Compound numbers | R⁶ | L | Y¹ | Y³ | Y² | R⁵ |
|---|---|---|---|---|---|---|
| 1.0569 | H | CH2 | SO | CH2 | C(Me)2 | methyl |
| 1.0570 | H | CH2 | SO | CH(Me) | CH2 | methyl |
| 1.0571 | H | CH2 | SO | CH(Me) | CH(Me) | methyl |
| 1.0572 | H | CH2 | SO | CH(Me) | C(Me)2 | methyl |
| 1.0573 | H | CH2 | SO | C(Me)2 | C(Me)2 | methyl |
| 1.0574 | H | CH2 | SO | C(Me)2 | CH(Me) | methyl |
| 1.0575 | H | CH2 | SO | C(Me)2 | CH2 | methyl |
| 1.0576 | Me | CH2 | SO | CH2 | CH2 | methyl |
| 1.0577 | Me | CH2 | SO | CH2 | CH(Me) | methyl |
| 1.0578 | Me | CH2 | SO | CH2 | C(Me)2 | methyl |
| 1.0579 | Me | CH2 | SO | CH(Me) | CH2 | methyl |
| 1.0580 | Me | CH2 | SO | CH(Me) | CH(Me) | methyl |
| 1.0581 | Me | CH2 | SO | CH(Me) | C(Me)2 | methyl |
| 1.0582 | Me | CH2 | SO | C(Me)2 | C(Me)2 | methyl |
| 1.0583 | Me | CH2 | SO | C(Me)2 | CH(Me) | methyl |
| 1.0584 | Me | CH2 | SO | C(Me)2 | CH2 | methyl |
| 1.0585 | H | CH2 | SO2 | CH2 | CH2 | methyl |
| 1.0586 | H | CH2 | SO2 | CH2 | CH(Me) | methyl |
| 1.0587 | H | CH2 | SO2 | CH2 | C(Me)2 | methyl |
| 1.0588 | H | CH2 | SO2 | CH(Me) | CH2 | methyl |
| 1.0589 | H | CH2 | SO2 | CH(Me) | CH(Me) | methyl |
| 1.0590 | H | CH2 | SO2 | CH(Me) | C(Me)2 | methyl |
| 1.0591 | H | CH2 | SO2 | C(Me)2 | C(Me)2 | methyl |
| 1.0592 | H | CH2 | SO2 | C(Me)2 | CH(Me) | methyl |
| 1.0593 | H | CH2 | SO2 | C(Me)2 | CH2 | methyl |
| 1.0594 | Me | CH2 | SO2 | CH2 | CH2 | methyl |
| 1.0595 | Me | CH2 | SO2 | CH2 | CH(Me) | methyl |
| 1.0596 | Me | CH2 | SO2 | CH2 | C(Me)2 | methyl |
| 1.0597 | Me | CH2 | SO2 | CH(Me) | CH2 | methyl |
| 1.0598 | Me | CH2 | SO2 | CH(Me) | CH(Me) | methyl |
| 1.0599 | Me | CH2 | SO2 | CH(Me) | C(Me)2 | methyl |
| 1.0600 | Me | CH2 | SO2 | C(Me)2 | C(Me)2 | methyl |
| 1.0601 | Me | CH2 | SO2 | C(Me)2 | CH(Me) | methyl |
| 1.0602 | Me | CH2 | SO2 | C(Me)2 | CH2 | methyl |
| 1.0603 | H | Single bond | CH2 | CH2 | C=O | chloro |
| 1.0604 | H | Single bond | CH(Me) | CH2 | C=O | chloro |
| 1.0605 | H | Single bond | C(Me)2 | CH2 | C=O | chloro |
| 1.0606 | H | Single bond | C(Me)2 | C(Me)2 | C=O | chloro |
| 1.0607 | Me | Single bond | CH2 | CH2 | C=O | chloro |
| 1.0608 | Me | Single bond | CH(Me) | CH2 | C=O | chloro |
| 1.0609 | Me | Single bond | C(Me)2 | CH2 | C=O | chloro |
| 1.0610 | Me | Single bond | C(Me)2 | C(Me)2 | C=O | chloro |
| 1.0611 | H | CH2 | CH2 | CH2 | C=O | chloro |
| 1.0612 | H | CH2 | CH(Me) | CH2 | C=O | chloro |
| 1.0613 | H | CH2 | C(Me)2 | CH2 | C=O | chloro |
| 1.0614 | H | CH2 | C(Me)2 | C(Me)2 | C=O | chloro |
| 1.0615 | Me | CH2 | CH2 | CH2 | C=O | chloro |
| 1.0616 | Me | CH2 | CH(Me) | CH2 | C=O | chloro |
| 1.0617 | Me | CH2 | C(Me)2 | CH2 | C=O | chloro |
| 1.0618 | Me | CH2 | C(Me)2 | C(Me)2 | C=O | chloro |
| 1.0619 | H | Single bond | CH2 | CH2 | C=N—OMe | chloro |
| 1.0620 | H | Single bond | CH(Me) | CH2 | C=N—OMe | chloro |
| 1.0621 | H | Single bond | C(Me)2 | CH2 | C=N—OMe | chloro |
| 1.0622 | H | Single bond | C(Me)2 | C(Me)2 | C=N—OMe | chloro |
| 1.0623 | Me | Single bond | CH2 | CH2 | C=N—OMe | chloro |
| 1.0624 | Me | Single bond | CH(Me) | CH2 | C=N—OMe | chloro |
| 1.0625 | Me | Single bond | C(Me)2 | CH2 | C=N—OMe | chloro |
| 1.0626 | Me | Single bond | C(Me)2 | C(Me)2 | C=N—OMe | chloro |
| 1.0627 | H | CH2 | CH2 | CH2 | C=N—OMe | chloro |
| 1.0628 | H | CH2 | CH(Me) | CH2 | C=N—OMe | chloro |
| 1.0629 | H | CH2 | C(Me)2 | CH2 | C=N—OMe | chloro |
| 1.0630 | H | CH2 | C(Me)2 | C(Me)2 | C=N—OMe | chloro |

TABLE 1-continued (I-A)

| Compound numbers | R⁶ | L | Y¹ | Y³ | Y² | R⁵ |
|---|---|---|---|---|---|---|
| 1.0631 | Me | CH2 | CH2 | CH2 | C=N—OMe | chloro |
| 1.0632 | Me | CH2 | CH(Me) | CH2 | C=N—OMe | chloro |
| 1.0633 | Me | CH2 | C(Me)2 | CH2 | C=N—OMe | chloro |
| 1.0634 | Me | CH2 | C(Me)2 | C(Me)2 | C=N—OMe | chloro |
| 1.0635 | H | Single bond | CH2 | CH2 | N—Me | chloro |
| 1.0636 | H | Single bond | CH(Me) | CH2 | N—Me | chloro |
| 1.0637 | H | Single bond | C(Me)2 | CH2 | N—Me | chloro |
| 1.0638 | H | Single bond | C(Me)2 | C(Me)2 | N—Me | chloro |
| 1.0639 | Me | Single bond | CH2 | CH2 | N—Me | chloro |
| 1.0640 | Me | Single bond | CH(Me) | CH2 | N—Me | chloro |
| 1.0641 | Me | Single bond | C(Me)2 | CH2 | N—Me | chloro |
| 1.0642 | Me | Single bond | C(Me)2 | C(Me)2 | N—Me | chloro |
| 1.0643 | H | CH2 | CH2 | CH2 | N—Me | chloro |
| 1.0644 | H | CH2 | CH(Me) | CH2 | N—Me | chloro |
| 1.0645 | H | CH2 | C(Me)2 | CH2 | N—Me | chloro |
| 1.0646 | H | CH2 | C(Me)2 | C(Me)2 | N—Me | chloro |
| 1.0647 | Me | CH2 | CH2 | CH2 | N—Me | chloro |
| 1.0648 | Me | CH2 | CH(Me) | CH2 | N—Me | chloro |
| 1.0649 | Me | CH2 | C(Me)2 | CH2 | N—Me | chloro |
| 1.0650 | Me | CH2 | C(Me)2 | C(Me)2 | N—Me | chloro |
| 1.0651 | H | Single bond | CH2 | CH2 | N—CH2—C6H5 | chloro |
| 1.0652 | H | Single bond | CH(Me) | CH2 | N—CH2—C6H5 | chloro |
| 1.0653 | H | Single bond | C(Me)2 | CH2 | N—CH2—C6H5 | chloro |
| 1.0654 | H | Single bond | C(Me)2 | C(Me)2 | N—CH2—C6H5 | chloro |
| 1.0655 | Me | Single bond | CH2 | CH2 | N—CH2—C6H5 | chloro |
| 1.0656 | Me | Single bond | CH(Me) | CH2 | N—CH2—C6H5 | chloro |
| 1.0657 | Me | Single bond | C(Me)2 | CH2 | N—CH2—C6H5 | chloro |
| 1.0658 | Me | Single bond | C(Me)2 | C(Me)2 | N—CH2—C6H5 | chloro |
| 1.0659 | H | CH2 | CH2 | CH2 | N—CH2—C6H5 | chloro |
| 1.0660 | H | CH2 | CH(Me) | CH2 | N—CH2—C6H5 | chloro |
| 1.0661 | H | CH2 | C(Me)2 | CH2 | N—CH2—C6H5 | chloro |
| 1.0662 | H | CH2 | C(Me)2 | C(Me)2 | N—CH2—C6H5 | chloro |
| 1.0663 | Me | CH2 | CH2 | CH2 | N—CH2—C6H5 | chloro |
| 1.0664 | Me | CH2 | CH(Me) | CH2 | N—CH2—C6H5 | chloro |
| 1.0665 | Me | CH2 | C(Me)2 | CH2 | N—CH2—C6H5 | chloro |
| 1.0666 | Me | CH2 | C(Me)2 | C(Me)2 | N—CH2—C6H5 | chloro |
| 1.0667 | H | Single bond | CH2 | CH2 | S | chloro |
| 1.0668 | H | Single bond | CH(Me) | CH2 | S | chloro |
| 1.0669 | H | Single bond | C(Me)2 | CH2 | S | chloro |
| 1.0670 | H | Single bond | C(Me)2 | C(Me)2 | S | chloro |
| 1.0671 | Me | Single bond | CH2 | CH2 | S | chloro |
| 1.0672 | Me | Single bond | CH(Me) | CH2 | S | chloro |
| 1.0673 | Me | Single bond | C(Me)2 | CH2 | S | chloro |
| 1.0674 | Me | Single bond | C(Me)2 | C(Me)2 | S | chloro |
| 1.0675 | H | CH2 | CH2 | CH2 | S | chloro |
| 1.0676 | H | CH2 | CH(Me) | CH2 | S | chloro |
| 1.0677 | H | CH2 | C(Me)2 | CH2 | S | chloro |
| 1.0678 | H | CH2 | C(Me)2 | C(Me)2 | S | chloro |
| 1.0679 | Me | CH2 | CH2 | CH2 | S | chloro |
| 1.0680 | Me | CH2 | CH(Me) | CH2 | S | chloro |
| 1.0681 | Me | CH2 | C(Me)2 | CH2 | S | chloro |
| 1.0682 | Me | CH2 | C(Me)2 | C(Me)2 | S | chloro |
| 1.0683 | H | Single bond | CH2 | CH2 | SO | chloro |
| 1.0684 | H | Single bond | CH(Me) | CH2 | SO | chloro |
| 1.0685 | H | Single bond | C(Me)2 | CH2 | SO | chloro |
| 1.0686 | H | Single bond | C(Me)2 | C(Me)2 | SO | chloro |
| 1.0687 | Me | Single bond | CH2 | CH2 | SO | chloro |
| 1.0688 | Me | Single bond | CH(Me) | CH2 | SO | chloro |
| 1.0689 | Me | Single bond | C(Me)2 | CH2 | SO | chloro |
| 1.0690 | Me | Single bond | C(Me)2 | C(Me)2 | SO | chloro |
| 1.0691 | H | CH2 | CH2 | CH2 | SO | chloro |
| 1.0692 | H | CH2 | CH(Me) | CH2 | SO | chloro |

TABLE 1-continued

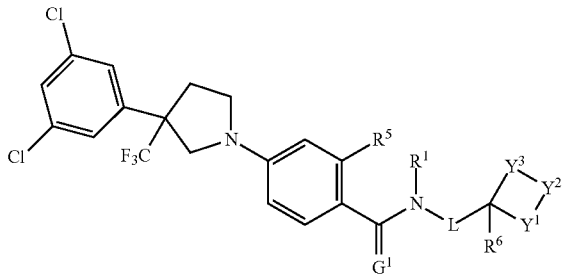

(I-A)

| Compound numbers | R6 | L | Y1 | Y3 | Y2 | R5 |
|---|---|---|---|---|---|---|
| 1.0693 | H | CH2 | C(Me)2 | CH2 | SO | chloro |
| 1.0694 | H | CH2 | C(Me)2 | C(Me)2 | SO | chloro |
| 1.0695 | Me | CH2 | CH2 | CH2 | SO | chloro |
| 1.0696 | Me | CH2 | CH(Me) | CH2 | SO | chloro |
| 1.0697 | Me | CH2 | C(Me)2 | CH2 | SO | chloro |
| 1.0698 | Me | CH2 | C(Me)2 | C(Me)2 | SO | chloro |
| 1.0699 | H | Single bond | CH2 | CH2 | SO2 | chloro |
| 1.0700 | H | Single bond | CH(Me) | CH2 | SO2 | chloro |
| 1.0701 | H | Single bond | C(Me)2 | CH2 | SO2 | chloro |
| 1.0702 | H | Single bond | C(Me)2 | C(Me)2 | SO2 | chloro |
| 1.0703 | Me | Single bond | CH2 | CH2 | SO2 | chloro |
| 1.0704 | Me | Single bond | CH(Me) | CH2 | SO2 | chloro |
| 1.0705 | Me | Single bond | C(Me)2 | CH2 | SO2 | chloro |
| 1.0706 | Me | Single bond | C(Me)2 | C(Me)2 | SO2 | chloro |
| 1.0707 | H | CH2 | CH2 | CH2 | SO2 | chloro |
| 1.0708 | H | CH2 | CH(Me) | CH2 | SO2 | chloro |
| 1.0709 | H | CH2 | C(Me)2 | CH2 | SO2 | chloro |
| 1.0710 | H | CH2 | C(Me)2 | C(Me)2 | SO2 | chloro |
| 1.0711 | Me | CH2 | CH2 | CH2 | SO2 | chloro |
| 1.0712 | Me | CH2 | CH(Me) | CH2 | SO2 | chloro |
| 1.0713 | Me | CH2 | C(Me)2 | CH2 | SO2 | chloro |
| 1.0714 | Me | CH2 | C(Me)2 | C(Me)2 | SO2 | chloro |
| 1.0715 | H | Single bond | CH2 | CH2 | SONH | chloro |
| 1.0716 | H | Single bond | CH(Me) | CH2 | SONH | chloro |
| 1.0717 | H | Single bond | C(Me)2 | CH2 | SONH | chloro |
| 1.0718 | H | Single bond | C(Me)2 | C(Me)2 | SONH | chloro |
| 1.0719 | Me | Single bond | CH2 | CH2 | SONH | chloro |
| 1.0720 | Me | Single bond | CH(Me) | CH2 | SONH | chloro |
| 1.0721 | Me | Single bond | C(Me)2 | CH2 | SONH | chloro |
| 1.0722 | Me | Single bond | C(Me)2 | C(Me)2 | SONH | chloro |
| 1.0723 | H | CH2 | CH2 | CH2 | SONH | chloro |
| 1.0724 | H | CH2 | CH(Me) | CH2 | SONH | chloro |
| 1.0725 | H | CH2 | C(Me)2 | CH2 | SONH | chloro |
| 1.0726 | H | CH2 | C(Me)2 | C(Me)2 | SONH | chloro |
| 1.0727 | Me | CH2 | CH2 | CH2 | SONH | chloro |
| 1.0728 | Me | CH2 | CH(Me) | CH2 | SONH | chloro |
| 1.0729 | Me | CH2 | C(Me)2 | CH2 | SONH | chloro |
| 1.0730 | Me | CH2 | C(Me)2 | C(Me)2 | SONH | chloro |
| 1.0731 | H | Single bond | CH2 | CH2 | C=N—OCH2CF3 | chloro |
| 1.0732 | H | Single bond | CH(Me) | CH2 | C=N—OCH2CF3 | chloro |
| 1.0733 | H | Single bond | C(Me)2 | CH2 | C=N—OCH2CF3 | chloro |
| 1.0734 | H | Single bond | C(Me)2 | C(Me)2 | C=N—OCH2CF3 | chloro |
| 1.0735 | Me | Single bond | CH2 | CH2 | C=N—OCH2CF3 | chloro |
| 1.0736 | Me | Single bond | CH(Me) | CH2 | C=N—OCH2CF3 | chloro |
| 1.0737 | Me | Single bond | C(Me)2 | CH2 | C=N—OCH2CF3 | chloro |
| 1.0738 | Me | Single bond | C(Me)2 | C(Me)2 | C=N—OCH2CF3 | chloro |
| 1.0739 | H | CH2 | CH2 | CH2 | C=N—OCH2CF3 | chloro |
| 1.0740 | H | CH2 | CH(Me) | CH2 | C=N—OCH2CF3 | chloro |
| 1.0741 | H | CH2 | C(Me)2 | CH2 | C=N—OCH2CF3 | chloro |
| 1.0742 | H | CH2 | C(Me)2 | C(Me)2 | C=N—OCH2CF3 | chloro |
| 1.0743 | Me | CH2 | CH2 | CH2 | C=N—OCH2CF3 | chloro |
| 1.0744 | Me | CH2 | CH(Me) | CH2 | C=N—OCH2CF3 | chloro |
| 1.0745 | Me | CH2 | C(Me)2 | CH2 | C=N—OCH2CF3 | Chloro |
| 1.0746 | Me | CH2 | C(Me)2 | C(Me)2 | C=N—OCH2CF3 | chloro |
| 1.0747 | H | CH2 | S | CH2 | CH2 | chloro |
| 1.0748 | H | CH2 | S | CH2 | CH(Me) | chloro |
| 1.0749 | H | CH2 | S | CH2 | C(Me)2 | chloro |
| 1.0750 | H | CH2 | S | CH(Me) | CH2 | chloro |
| 1.0751 | H | CH2 | S | CH(Me) | CH(Me) | chloro |
| 1.0752 | H | CH2 | S | CH(Me) | C(Me)2 | chloro |
| 1.0753 | H | CH2 | S | C(Me)2 | C(Me)2 | chloro |
| 1.0754 | H | CH2 | S | C(Me)2 | CH(Me) | chloro |

TABLE 1-continued

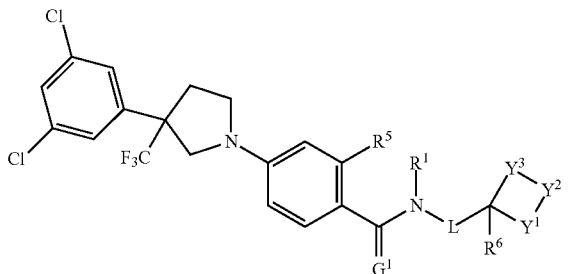

(I-A)

| Compound numbers | R⁶ | L | Y¹ | Y³ | Y² | R⁵ |
|---|---|---|---|---|---|---|
| 1.0755 | H | CH2 | S | C(Me)2 | CH2 | chloro |
| 1.0756 | Me | CH2 | S | CH2 | CH2 | chloro |
| 1.0757 | Me | CH2 | S | CH2 | CH(Me) | chloro |
| 1.0758 | Me | CH2 | S | CH2 | C(Me)2 | chloro |
| 1.0759 | Me | CH2 | S | CH(Me) | CH2 | chloro |
| 1.0760 | Me | CH2 | S | CH(Me) | CH(Me) | chloro |
| 1.0761 | Me | CH2 | S | CH(Me) | C(Me)2 | chloro |
| 1.0762 | Me | CH2 | S | C(Me)2 | C(Me)2 | chloro |
| 1.0763 | Me | CH2 | S | C(Me)2 | CH(Me) | chloro |
| 1.0764 | Me | CH2 | S | C(Me)2 | CH2 | chloro |
| 1.0765 | H | CH2 | SO | CH2 | CH2 | chloro |
| 1.0766 | H | CH2 | SO | CH2 | CH(Me) | chloro |
| 1.0767 | H | CH2 | SO | CH2 | C(Me)2 | chloro |
| 1.0768 | H | CH2 | SO | CH(Me) | CH2 | chloro |
| 1.0769 | H | CH2 | SO | CH(Me) | CH(Me) | chloro |
| 1.0770 | H | CH2 | SO | CH(Me) | C(Me)2 | chloro |
| 1.0771 | H | CH2 | SO | C(Me)2 | C(Me)2 | chloro |
| 1.0772 | H | CH2 | SO | C(Me)2 | CH(Me) | chloro |
| 1.0773 | H | CH2 | SO | C(Me)2 | CH2 | chloro |
| 1.0774 | Me | CH2 | SO | CH2 | CH2 | chloro |
| 1.0775 | Me | CH2 | SO | CH2 | CH(Me) | chloro |
| 1.0776 | Me | CH2 | SO | CH2 | C(Me)2 | chloro |
| 1.0777 | Me | CH2 | SO | CH(Me) | CH2 | chloro |
| 1.0778 | Me | CH2 | SO | CH(Me) | CH(Me) | chloro |
| 1.0779 | Me | CH2 | SO | CH(Me) | C(Me)2 | chloro |
| 1.0780 | Me | CH2 | SO | C(Me)2 | C(Me)2 | chloro |
| 1.0781 | Me | CH2 | SO | C(Me)2 | CH(Me) | chloro |
| 1.0782 | Me | CH2 | SO | C(Me)2 | CH2 | chloro |
| 1.0783 | H | CH2 | SO2 | CH2 | CH2 | chloro |
| 1.0784 | H | CH2 | SO2 | CH2 | CH(Me) | chloro |
| 1.0785 | H | CH2 | SO2 | CH2 | C(Me)2 | chloro |
| 1.0786 | H | CH2 | SO2 | CH(Me) | CH2 | chloro |
| 1.0787 | H | CH2 | SO2 | CH(Me) | CH(Me) | chloro |
| 1.0788 | H | CH2 | SO2 | CH(Me) | C(Me)2 | chloro |
| 1.0789 | H | CH2 | SO2 | C(Me)2 | C(Me)2 | chloro |
| 1.0790 | H | CH2 | SO2 | C(Me)2 | CH(Me) | chloro |
| 1.0791 | H | CH2 | SO2 | C(Me)2 | CH2 | chloro |
| 1.0792 | Me | CH2 | SO2 | CH2 | CH2 | chloro |
| 1.0793 | Me | CH2 | SO2 | CH2 | CH(Me) | chloro |
| 1.0794 | Me | CH2 | SO2 | CH2 | C(Me)2 | chloro |
| 1.0795 | Me | CH2 | SO2 | CH(Me) | CH2 | chloro |
| 1.0796 | Me | CH2 | SO2 | CH(Me) | CH(Me) | chloro |
| 1.0797 | Me | CH2 | SO2 | CH(Me) | C(Me)2 | chloro |
| 1.0798 | Me | CH2 | SO2 | C(Me)2 | C(Me)2 | chloro |
| 1.0799 | Me | CH2 | SO2 | C(Me)2 | CH(Me) | chloro |
| 1.0800 | Me | CH2 | SO2 | C(Me)2 | CH2 | chloro |
| 1.0801 | H | Single bond | CH2 | CH2 | C=O | trifluoromethyl |
| 1.0802 | H | Single bond | CH(Me) | CH2 | C=O | trifluoromethyl |
| 1.0803 | H | Single bond | C(Me)2 | CH2 | C=O | trifluoromethyl |
| 1.0804 | H | Single bond | C(Me)2 | C(Me)2 | C=O | trifluoromethyl |
| 1.0805 | Me | Single bond | CH2 | CH2 | C=O | trifluoromethyl |
| 1.0806 | Me | Single bond | CH(Me) | CH2 | C=O | trifluoromethyl |
| 1.0807 | Me | Single bond | C(Me)2 | CH2 | C=O | trifluoromethyl |
| 1.0808 | Me | Single bond | C(Me)2 | C(Me)2 | C=O | trifluoromethyl |
| 1.0809 | H | CH2 | CH2 | CH2 | C=O | trifluoromethyl |
| 1.0810 | H | CH2 | CH(Me) | CH2 | C=O | trifluoromethyl |
| 1.0811 | H | CH2 | C(Me)2 | CH2 | C=O | trifluoromethyl |
| 1.0812 | H | CH2 | C(Me)2 | C(Me)2 | C=O | trifluoromethyl |
| 1.0813 | Me | CH2 | CH2 | CH2 | C=O | trifluoromethyl |
| 1.0814 | Me | CH2 | CH(Me) | CH2 | C=O | trifluoromethyl |
| 1.0815 | Me | CH2 | C(Me)2 | CH2 | C=O | trifluoromethyl |
| 1.0816 | Me | CH2 | C(Me)2 | C(Me)2 | C=O | trifluoromethyl |

TABLE 1-continued

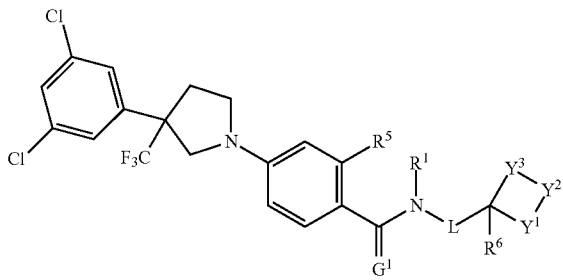

(I-A)

| Compound numbers | R6 | L | Y1 | Y3 | Y2 | R5 |
|---|---|---|---|---|---|---|
| 1.0817 | H | Single bond | CH2 | CH2 | C=N—OMe | trifluoromethyl |
| 1.0818 | H | Single bond | CH(Me) | CH2 | C=N—OMe | trifluoromethyl |
| 1.0819 | H | Single bond | C(Me)2 | CH2 | C=N—OMe | trifluoromethyl |
| 1.0820 | H | Single bond | C(Me)2 | C(Me)2 | C=N—OMe | trifluoromethyl |
| 1.0821 | Me | Single bond | CH2 | CH2 | C=N—OMe | trifluoromethyl |
| 1.0822 | Me | Single bond | CH(Me) | CH2 | C=N—OMe | trifluoromethyl |
| 1.0823 | Me | Single bond | C(Me)2 | CH2 | C=N—OMe | trifluoromethyl |
| 1.0824 | Me | Single bond | C(Me)2 | C(Me)2 | C=N—OMe | trifluoromethyl |
| 1.0825 | H | CH2 | CH2 | CH2 | C=N—OMe | trifluoromethyl |
| 1.0826 | H | CH2 | CH(Me) | CH2 | C=N—OMe | trifluoromethyl |
| 1.0827 | H | CH2 | C(Me)2 | CH2 | C=N—OMe | trifluoromethyl |
| 1.0828 | H | CH2 | C(Me)2 | C(Me)2 | C=N—OMe | trifluoromethyl |
| 1.0829 | Me | CH2 | CH2 | CH2 | C=N—OMe | trifluoromethyl |
| 1.0830 | Me | CH2 | CH(Me) | CH2 | C=N—OMe | trifluoromethyl |
| 1.0831 | Me | CH2 | C(Me)2 | CH2 | C=N—OMe | trifluoromethyl |
| 1.0832 | Me | CH2 | C(Me)2 | C(Me)2 | C=N—OMe | trifluoromethyl |
| 1.0833 | H | Single bond | CH2 | CH2 | N—Me | trifluoromethyl |
| 1.0834 | H | Single bond | CH(Me) | CH2 | N—Me | trifluoromethyl |
| 1.0835 | H | Single bond | C(Me)2 | CH2 | N—Me | trifluoromethyl |
| 1.0836 | H | Single bond | C(Me)2 | C(Me)2 | N—Me | trifluoromethyl |
| 1.0837 | Me | Single bond | CH2 | CH2 | N—Me | trifluoromethyl |
| 1.0838 | Me | Single bond | CH(Me) | CH2 | N—Me | trifluoromethyl |
| 1.0839 | Me | Single bond | C(Me)2 | CH2 | N—Me | trifluoromethyl |
| 1.0840 | Me | Single bond | C(Me)2 | C(Me)2 | N—Me | trifluoromethyl |
| 1.0841 | H | CH2 | CH2 | CH2 | N—Me | trifluoromethyl |
| 1.0842 | H | CH2 | CH(Me) | CH2 | N—Me | trifluoromethyl |
| 1.0843 | H | CH2 | C(Me)2 | CH2 | N—Me | trifluoromethyl |
| 1.0844 | H | CH2 | C(Me)2 | C(Me)2 | N—Me | trifluoromethyl |
| 1.0845 | Me | CH2 | CH2 | CH2 | N—Me | trifluoromethyl |
| 1.0846 | Me | CH2 | CH(Me) | CH2 | N—Me | trifluoromethyl |
| 1.0847 | Me | CH2 | C(Me)2 | CH2 | N—Me | trifluoromethyl |
| 1.0848 | Me | CH2 | C(Me)2 | C(Me)2 | N—Me | trifluoromethyl |
| 1.0849 | H | Single bond | CH2 | CH2 | N—CH2—C6H5 | trifluoromethyl |
| 1.0850 | H | Single bond | CH(Me) | CH2 | N—CH2—C6H5 | trifluoromethyl |
| 1.0851 | H | Single bond | C(Me)2 | CH2 | N—CH2—C6H5 | trifluoromethyl |
| 1.0852 | H | Single bond | C(Me)2 | C(Me)2 | N—CH2—C6H5 | trifluoromethyl |
| 1.0853 | Me | Single bond | CH2 | CH2 | N—CH2—C6H5 | trifluoromethyl |
| 1.0854 | Me | Single bond | CH(Me) | CH2 | N—CH2—C6H5 | trifluoromethyl |
| 1.0855 | Me | Single bond | C(Me)2 | CH2 | N—CH2—C6H5 | trifluoromethyl |
| 1.0856 | Me | Single bond | C(Me)2 | C(Me)2 | N—CH2—C6H5 | trifluoromethyl |
| 1.0857 | H | CH2 | CH2 | CH2 | N—CH2—C6H5 | trifluoromethyl |
| 1.0858 | H | CH2 | CH(Me) | CH2 | N—CH2—C6H5 | trifluoromethyl |
| 1.0859 | H | CH2 | C(Me)2 | CH2 | N—CH2—C6H5 | trifluoromethyl |
| 1.0860 | H | CH2 | C(Me)2 | C(Me)2 | N—CH2—C6H5 | trifluoromethyl |
| 1.0861 | Me | CH2 | CH2 | CH2 | N—CH2—C6H5 | trifluoromethyl |
| 1.0862 | Me | CH2 | CH(Me) | CH2 | N—CH2—C6H5 | trifluoromethyl |
| 1.0863 | Me | CH2 | C(Me)2 | CH2 | N—CH2—C6H5 | trifluoromethyl |
| 1.0864 | Me | CH2 | C(Me)2 | C(Me)2 | N—CH2—C6H5 | trifluoromethyl |
| 1.0865 | H | Single bond | CH2 | CH2 | S | trifluoromethyl |
| 1.0866 | H | Single bond | CH(Me) | CH2 | S | trifluoromethyl |
| 1.0867 | H | Single bond | C(Me)2 | CH2 | S | trifluoromethyl |
| 1.0868 | H | Single bond | C(Me)2 | C(Me)2 | S | trifluoromethyl |
| 1.0869 | Me | Single bond | CH2 | CH2 | S | trifluoromethyl |
| 1.0870 | Me | Single bond | CH(Me) | CH2 | S | trifluoromethyl |
| 1.0871 | Me | Single bond | C(Me)2 | CH2 | S | trifluoromethyl |
| 1.0872 | Me | Single bond | C(Me)2 | C(Me)2 | S | trifluoromethyl |
| 1.0873 | H | CH2 | CH2 | CH2 | S | trifluoromethyl |
| 1.0874 | H | CH2 | CH(Me) | CH2 | S | trifluoromethyl |
| 1.0875 | H | CH2 | C(Me)2 | CH2 | S | trifluoromethyl |
| 1.0876 | H | CH2 | C(Me)2 | C(Me)2 | S | trifluoromethyl |
| 1.0877 | Me | CH2 | CH2 | CH2 | S | trifluoromethyl |
| 1.0878 | Me | CH2 | CH(Me) | CH2 | S | trifluoromethyl |

TABLE 1-continued

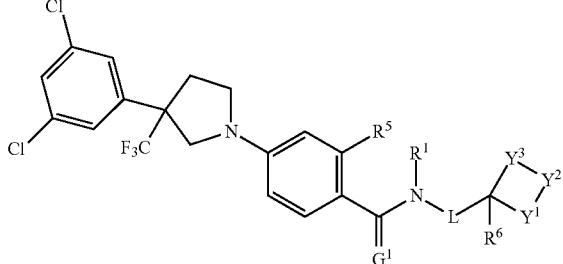

(I-A)

| Compound numbers | R6 | L | Y1 | Y3 | Y2 | R5 |
|---|---|---|---|---|---|---|
| 1.0879 | Me | CH2 | C(Me)2 | CH2 | S | trifluoromethyl |
| 1.0880 | Me | CH2 | C(Me)2 | C(Me)2 | S | trifluoromethyl |
| 1.0881 | H | Single bond | CH2 | CH2 | SO | trifluoromethyl |
| 1.0882 | H | Single bond | CH(Me) | CH2 | SO | trifluoromethyl |
| 1.0883 | H | Single bond | C(Me)2 | CH2 | SO | trifluoromethyl |
| 1.0884 | H | Single bond | C(Me)2 | C(Me)2 | SO | trifluoromethyl |
| 1.0885 | Me | Single bond | CH2 | CH2 | SO | trifluoromethyl |
| 1.0886 | Me | Single bond | CH(Me) | CH2 | SO | trifluoromethyl |
| 1.0887 | Me | Single bond | C(Me)2 | CH2 | SO | trifluoromethyl |
| 1.0888 | Me | Single bond | C(Me)2 | C(Me)2 | SO | trifluoromethyl |
| 1.0889 | H | CH2 | CH2 | CH2 | SO | trifluoromethyl |
| 1.0890 | H | CH2 | CH(Me) | CH2 | SO | trifluoromethyl |
| 1.0891 | H | CH2 | C(Me)2 | CH2 | SO | trifluoromethyl |
| 1.0892 | H | CH2 | C(Me)2 | C(Me)2 | SO | trifluoromethyl |
| 1.0893 | Me | CH2 | CH2 | CH2 | SO | trifluoromethyl |
| 1.0894 | Me | CH2 | CH(Me) | CH2 | SO | trifluoromethyl |
| 1.0895 | Me | CH2 | C(Me)2 | CH2 | SO | trifluoromethyl |
| 1.0896 | Me | CH2 | C(Me)2 | C(Me)2 | SO | trifluoromethyl |
| 1.0897 | H | Single bond | CH2 | CH2 | SO2 | trifluoromethyl |
| 1.0898 | H | Single bond | CH(Me) | CH2 | SO2 | trifluoromethyl |
| 1.0899 | H | Single bond | C(Me)2 | CH2 | SO2 | trifluoromethyl |
| 1.0900 | H | Single bond | C(Me)2 | C(Me)2 | SO2 | trifluoromethyl |
| 1.0901 | Me | Single bond | CH2 | CH2 | SO2 | trifluoromethyl |
| 1.0902 | Me | Single bond | CH(Me) | CH2 | SO2 | trifluoromethyl |
| 1.0903 | Me | Single bond | C(Me)2 | CH2 | SO2 | trifluoromethyl |
| 1.0904 | Me | Single bond | C(Me)2 | C(Me)2 | SO2 | trifluoromethyl |
| 1.0905 | H | CH2 | CH2 | CH2 | SO2 | trifluoromethyl |
| 1.0906 | H | CH2 | CH(Me) | CH2 | SO2 | trifluoromethyl |
| 1.0907 | H | CH2 | C(Me)2 | CH2 | SO2 | trifluoromethyl |
| 1.0908 | H | CH2 | C(Me)2 | C(Me)2 | SO2 | trifluoromethyl |
| 1.0909 | Me | CH2 | CH2 | CH2 | SO2 | trifluoromethyl |
| 1.0910 | Me | CH2 | CH(Me) | CH2 | SO2 | trifluoromethyl |
| 1.0911 | Me | CH2 | C(Me)2 | CH2 | SO2 | trifluoromethyl |
| 1.0912 | Me | CH2 | C(Me)2 | C(Me)2 | SO2 | trifluoromethyl |
| 1.0913 | H | Single bond | CH2 | CH2 | SONH | trifluoromethyl |
| 1.0914 | H | Single bond | CH(Me) | CH2 | SONH | trifluoromethyl |
| 1.0915 | H | Single bond | C(Me)2 | CH2 | SONH | trifluoromethyl |
| 1.0916 | H | Single bond | C(Me)2 | C(Me)2 | SONH | trifluoromethyl |
| 1.0917 | Me | Single bond | CH2 | CH2 | SONH | trifluoromethyl |
| 1.0918 | Me | Single bond | CH(Me) | CH2 | SONH | trifluoromethyl |
| 1.0919 | Me | Single bond | C(Me)2 | CH2 | SONH | trifluoromethyl |
| 1.0920 | Me | Single bond | C(Me)2 | C(Me)2 | SONH | trifluoromethyl |
| 1.0921 | H | CH2 | CH2 | CH2 | SONH | trifluoromethyl |
| 1.0922 | H | CH2 | CH(Me) | CH2 | SONH | trifluoromethyl |
| 1.0923 | H | CH2 | C(Me)2 | CH2 | SONH | trifluoromethyl |
| 1.0924 | H | CH2 | C(Me)2 | C(Me)2 | SONH | trifluoromethyl |
| 1.0925 | Me | CH2 | CH2 | CH2 | SONH | trifluoromethyl |
| 1.0926 | Me | CH2 | CH(Me) | CH2 | SONH | trifluoromethyl |
| 1.0927 | Me | CH2 | C(Me)2 | CH2 | SONH | trifluoromethyl |
| 1.0928 | Me | CH2 | C(Me)2 | C(Me)2 | SONH | trifluoromethyl |
| 1.0929 | H | Single bond | CH2 | CH2 | C=N—OCH2CF3 | trifluoromethyl |
| 1.0930 | H | Single bond | CH(Me) | CH2 | C=N—OCH2CF3 | trifluoromethyl |
| 1.0931 | H | Single bond | C(Me)2 | CH2 | C=N—OCH2CF3 | trifluoromethyl |
| 1.0932 | H | Single bond | C(Me)2 | C(Me)2 | C=N—OCH2CF3 | trifluoromethyl |
| 1.0933 | Me | Single bond | CH2 | CH2 | C=N—OCH2CF3 | trifluoromethyl |
| 1.0934 | Me | Single bond | CH(Me) | CH2 | C=N—OCH2CF3 | trifluoromethyl |
| 1.0935 | Me | Single bond | C(Me)2 | CH2 | C=N—OCH2CF3 | trifluoromethyl |
| 1.0936 | Me | Single bond | C(Me)2 | C(Me)2 | C=N—OCH2CF3 | trifluoromethyl |
| 1.0937 | H | CH2 | CH2 | CH2 | C=N—OCH2CF3 | trifluoromethyl |
| 1.0938 | H | CH2 | CH(Me) | CH2 | C=N—OCH2CF3 | trifluoromethyl |
| 1.0939 | H | CH2 | C(Me)2 | CH2 | C=N—OCH2CF3 | trifluoromethyl |
| 1.0940 | H | CH2 | C(Me)2 | C(Me)2 | C=N—OCH2CF3 | trifluoromethyl |

TABLE 1-continued

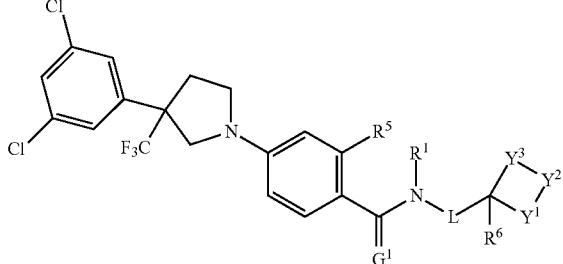

(I-A)

| Compound numbers | $R^6$ | L | $Y^1$ | $Y^3$ | $Y^2$ | $R^5$ |
|---|---|---|---|---|---|---|
| 1.0941 | Me | CH2 | CH2 | CH2 | C=N—OCH2CF3 | trifluoromethyl |
| 1.0942 | Me | CH2 | CH(Me) | CH2 | C=N—OCH2CF3 | trifluoromethyl |
| 1.0943 | Me | CH2 | C(Me)2 | CH2 | C=N—OCH2CF3 | trifluoromethyl |
| 1.0944 | Me | CH2 | C(Me)2 | C(Me)2 | C=N—OCH2CF3 | trifluoromethyl |
| 1.0945 | H | CH2 | S | CH2 | CH2 | trifluoromethyl |
| 1.0946 | H | CH2 | S | CH2 | CH(Me) | trifluoromethyl |
| 1.0947 | H | CH2 | S | CH2 | C(Me)2 | trifluoromethyl |
| 1.0948 | H | CH2 | S | CH(Me) | CH2 | trifluoromethyl |
| 1.0949 | H | CH2 | S | CH(Me) | CH(Me) | trifluoromethyl |
| 1.0950 | H | CH2 | S | CH(Me) | C(Me)2 | trifluoromethyl |
| 1.0951 | H | CH2 | S | C(Me)2 | C(Me)2 | trifluoromethyl |
| 1.0952 | H | CH2 | S | C(Me)2 | CH(Me) | trifluoromethyl |
| 1.0953 | H | CH2 | S | C(Me)2 | CH2 | trifluoromethyl |
| 1.0954 | Me | CH2 | S | CH2 | CH2 | trifluoromethyl |
| 1.0955 | Me | CH2 | S | CH2 | CH(Me) | trifluoromethyl |
| 1.0956 | Me | CH2 | S | CH2 | C(Me)2 | trifluoromethyl |
| 1.0957 | Me | CH2 | S | CH(Me) | CH2 | trifluoromethyl |
| 1.0958 | Me | CH2 | S | CH(Me) | CH(Me) | trifluoromethyl |
| 1.0959 | Me | CH2 | S | CH(Me) | C(Me)2 | trifluoromethyl |
| 1.0960 | Me | CH2 | S | C(Me)2 | C(Me)2 | trifluoromethyl |
| 1.0961 | Me | CH2 | S | C(Me)2 | CH(Me) | trifluoromethyl |
| 1.0962 | Me | CH2 | S | C(Me)2 | CH2 | trifluoromethyl |
| 1.0963 | H | CH2 | SO | CH2 | CH2 | trifluoromethyl |
| 1.0964 | H | CH2 | SO | CH2 | CH(Me) | trifluoromethyl |
| 1.0965 | H | CH2 | SO | CH2 | C(Me)2 | trifluoromethyl |
| 1.0966 | H | CH2 | SO | CH(Me) | CH2 | trifluoromethyl |
| 1.0967 | H | CH2 | SO | CH(Me) | CH(Me) | trifluoromethyl |
| 1.0968 | H | CH2 | SO | CH(Me) | C(Me)2 | trifluoromethyl |
| 1.0969 | H | CH2 | SO | C(Me)2 | C(Me)2 | trifluoromethyl |
| 1.0970 | H | CH2 | SO | C(Me)2 | CH(Me) | trifluoromethyl |
| 1.0971 | H | CH2 | SO | C(Me)2 | CH2 | trifluoromethyl |
| 1.0972 | Me | CH2 | SO | CH2 | CH2 | trifluoromethyl |
| 1.0973 | Me | CH2 | SO | CH2 | CH(Me) | trifluoromethyl |
| 1.0974 | Me | CH2 | SO | CH2 | C(Me)2 | trifluoromethyl |
| 1.0975 | Me | CH2 | SO | CH(Me) | CH2 | trifluoromethyl |
| 1.0976 | Me | CH2 | SO | CH(Me) | CH(Me) | trifluoromethyl |
| 1.0977 | Me | CH2 | SO | CH(Me) | C(Me)2 | trifluoromethyl |
| 1.0978 | Me | CH2 | SO | C(Me)2 | C(Me)2 | trifluoromethyl |
| 1.0979 | Me | CH2 | SO | C(Me)2 | CH(Me) | trifluoromethyl |
| 1.0980 | Me | CH2 | SO | C(Me)2 | CH2 | trifluoromethyl |
| 1.0981 | H | CH2 | SO2 | CH2 | CH2 | trifluoromethyl |
| 1.0982 | H | CH2 | SO2 | CH2 | CH(Me) | trifluoromethyl |
| 1.0983 | H | CH2 | SO2 | CH2 | C(Me)2 | trifluoromethyl |
| 1.0984 | H | CH2 | SO2 | CH(Me) | CH2 | trifluoromethyl |
| 1.0985 | H | CH2 | SO2 | CH(Me) | CH(Me) | trifluoromethyl |
| 1.0986 | H | CH2 | SO2 | CH(Me) | C(Me)2 | trifluoromethyl |
| 1.0987 | H | CH2 | SO2 | C(Me)2 | C(Me)2 | trifluoromethyl |
| 1.0988 | H | CH2 | SO2 | C(Me)2 | CH(Me) | trifluoromethyl |
| 1.0989 | H | CH2 | SO2 | C(Me)2 | CH2 | trifluoromethyl |
| 1.0990 | Me | CH2 | SO2 | CH2 | CH2 | trifluoromethyl |
| 1.0991 | Me | CH2 | SO2 | CH2 | CH(Me) | trifluoromethyl |
| 1.0992 | Me | CH2 | SO2 | CH2 | C(Me)2 | trifluoromethyl |
| 1.0993 | Me | CH2 | SO2 | CH(Me) | CH2 | trifluoromethyl |
| 1.0994 | Me | CH2 | SO2 | CH(Me) | CH(Me) | trifluoromethyl |
| 1.0995 | Me | CH2 | SO2 | CH(Me) | C(Me)2 | trifluoromethyl |
| 1.0996 | Me | CH2 | SO2 | C(Me)2 | C(Me)2 | trifluoromethyl |
| 1.0997 | Me | CH2 | SO2 | C(Me)2 | CH(Me) | trifluoromethyl |
| 1.0998 | Me | CH2 | SO2 | C(Me)2 | CH2 | trifluoromethyl |
| 1.0999 | H | Single bond | CH2 | CH2 | C=O | fluoro |
| 1.1000 | H | Single bond | CH(Me) | CH2 | C=O | fluoro |
| 1.1001 | H | Single bond | C(Me)2 | CH2 | C=O | fluoro |
| 1.1002 | H | Single bond | C(Me)2 | C(Me)2 | C=O | fluoro |

TABLE 1-continued (I-A)

| Compound numbers | R⁶ | L | Y¹ | Y³ | Y² | R⁵ |
|---|---|---|---|---|---|---|
| 1.1003 | Me | Single bond | CH2 | CH2 | C=O | fluoro |
| 1.1004 | Me | Single bond | CH(Me) | CH2 | C=O | fluoro |
| 1.1005 | Me | Single bond | C(Me)2 | CH2 | C=O | fluoro |
| 1.1006 | Me | Single bond | C(Me)2 | C(Me)2 | C=O | fluoro |
| 1.1007 | H | CH2 | CH2 | CH2 | C=O | fluoro |
| 1.1008 | H | CH2 | CH(Me) | CH2 | C=O | fluoro |
| 1.1009 | H | CH2 | C(Me)2 | CH2 | C=O | fluoro |
| 1.1010 | H | CH2 | C(Me)2 | C(Me)2 | C=O | fluoro |
| 1.1011 | Me | CH2 | CH2 | CH2 | C=O | fluoro |
| 1.1012 | Me | CH2 | CH(Me) | CH2 | C=O | fluoro |
| 1.1013 | Me | CH2 | C(Me)2 | CH2 | C=O | fluoro |
| 1.1014 | Me | CH2 | C(Me)2 | C(Me)2 | C=O | fluoro |
| 1.1015 | H | Single bond | CH2 | CH2 | C=N—OMe | fluoro |
| 1.1016 | H | Single bond | CH(Me) | CH2 | C=N—OMe | fluoro |
| 1.1017 | H | Single bond | C(Me)2 | CH2 | C=N—OMe | fluoro |
| 1.1018 | H | Single bond | C(Me)2 | C(Me)2 | C=N—OMe | fluoro |
| 1.1019 | Me | Single bond | CH2 | CH2 | C=N—OMe | fluoro |
| 1.1020 | Me | Single bond | CH(Me) | CH2 | C=N—OMe | fluoro |
| 1.1021 | Me | Single bond | C(Me)2 | CH2 | C=N—OMe | fluoro |
| 1.1022 | Me | Single bond | C(Me)2 | C(Me)2 | C=N—OMe | fluoro |
| 1.1023 | H | CH2 | CH2 | CH2 | C=N—OMe | fluoro |
| 1.1024 | H | CH2 | CH(Me) | CH2 | C=N—OMe | fluoro |
| 1.1025 | H | CH2 | C(Me)2 | CH2 | C=N—OMe | fluoro |
| 1.1026 | H | CH2 | C(Me)2 | C(Me)2 | C=N—OMe | fluoro |
| 1.1027 | Me | CH2 | CH2 | CH2 | C=N—OMe | fluoro |
| 1.1028 | Me | CH2 | CH(Me) | CH2 | C=N—OMe | fluoro |
| 1.1029 | Me | CH2 | C(Me)2 | CH2 | C=N—OMe | fluoro |
| 1.1030 | Me | CH2 | C(Me)2 | C(Me)2 | C=N—OMe | fluoro |
| 1.1031 | H | Single bond | CH2 | CH2 | N—Me | fluoro |
| 1.1032 | H | Single bond | CH(Me) | CH2 | N—Me | fluoro |
| 1.1033 | H | Single bond | C(Me)2 | CH2 | N—Me | fluoro |
| 1.1034 | H | Single bond | C(Me)2 | C(Me)2 | N—Me | fluoro |
| 1.1035 | Me | Single bond | CH2 | CH2 | N—Me | fluoro |
| 1.1036 | Me | Single bond | CH(Me) | CH2 | N—Me | fluoro |
| 1.1037 | Me | Single bond | C(Me)2 | CH2 | N—Me | fluoro |
| 1.1038 | Me | Single bond | C(Me)2 | C(Me)2 | N—Me | fluoro |
| 1.1039 | H | CH2 | CH2 | CH2 | N—Me | fluoro |
| 1.1040 | H | CH2 | CH(Me) | CH2 | N—Me | fluoro |
| 1.1041 | H | CH2 | C(Me)2 | CH2 | N—Me | fluoro |
| 1.1042 | H | CH2 | C(Me)2 | C(Me)2 | N—Me | fluoro |
| 1.1043 | Me | CH2 | CH2 | CH2 | N—Me | fluoro |
| 1.1044 | Me | CH2 | CH(Me) | CH2 | N—Me | fluoro |
| 1.1045 | Me | CH2 | C(Me)2 | CH2 | N—Me | fluoro |
| 1.1046 | Me | CH2 | C(Me)2 | C(Me)2 | N—Me | fluoro |
| 1.1047 | H | Single bond | CH2 | CH2 | N—CH2—C6H5 | fluoro |
| 1.1048 | H | Single bond | CH(Me) | CH2 | N—CH2—C6H5 | fluoro |
| 1.1049 | H | Single bond | C(Me)2 | CH2 | N—CH2—C6H5 | fluoro |
| 1.1050 | H | Single bond | C(Me)2 | C(Me)2 | N—CH2—C6H5 | fluoro |
| 1.1051 | Me | Single bond | CH2 | CH2 | N—CH2—C6H5 | fluoro |
| 1.1052 | Me | Single bond | CH(Me) | CH2 | N—CH2—C6H5 | fluoro |
| 1.1053 | Me | Single bond | C(Me)2 | CH2 | N—CH2—C6H5 | fluoro |
| 1.1054 | Me | Single bond | C(Me)2 | C(Me)2 | N—CH2—C6H5 | fluoro |
| 1.1055 | H | CH2 | CH2 | CH2 | N—CH2—C6H5 | fluoro |
| 1.1056 | H | CH2 | CH(Me) | CH2 | N—CH2—C6H5 | fluoro |
| 1.1057 | H | CH2 | C(Me)2 | CH2 | N—CH2—C6H5 | fluoro |
| 1.1058 | H | CH2 | C(Me)2 | C(Me)2 | N—CH2—C6H5 | fluoro |
| 1.1059 | Me | CH2 | CH2 | CH2 | N—CH2—C6H5 | fluoro |
| 1.1060 | Me | CH2 | CH(Me) | CH2 | N—CH2—C6H5 | fluoro |
| 1.1061 | Me | CH2 | C(Me)2 | CH2 | N—CH2—C6H5 | fluoro |
| 1.1062 | Me | CH2 | C(Me)2 | C(Me)2 | N—CH2—C6H5 | fluoro |
| 1.1063 | H | Single bond | CH2 | CH2 | S | fluoro |
| 1.1064 | H | Single bond | CH(Me) | CH2 | S | fluoro |

TABLE 1-continued (I-A)

A structure showing a 3,5-dichlorophenyl group and CF₃ attached to a pyrrolidine, connected via N to a phenyl ring bearing R⁵ and a C(=G¹)-N(R¹)-L-C(R⁶)(Y¹)(Y³-Y²) side chain.

| Compound numbers | R⁶ | L | Y¹ | Y³ | Y² | R⁵ |
|---|---|---|---|---|---|---|
| 1.1065 | H | Single bond | C(Me)2 | CH2 | S | fluoro |
| 1.1066 | H | Single bond | C(Me)2 | C(Me)2 | S | fluoro |
| 1.1067 | Me | Single bond | CH2 | CH2 | S | fluoro |
| 1.1068 | Me | Single bond | CH(Me) | CH2 | S | fluoro |
| 1.1069 | Me | Single bond | C(Me)2 | CH2 | S | fluoro |
| 1.1070 | Me | Single bond | C(Me)2 | C(Me)2 | S | fluoro |
| 1.1071 | H | CH2 | CH2 | CH2 | S | fluoro |
| 1.1072 | H | CH2 | CH(Me) | CH2 | S | fluoro |
| 1.1073 | H | CH2 | C(Me)2 | CH2 | S | fluoro |
| 1.1074 | H | CH2 | C(Me)2 | C(Me)2 | S | fluoro |
| 1.1075 | Me | CH2 | CH2 | CH2 | S | fluoro |
| 1.1076 | Me | CH2 | CH(Me) | CH2 | S | fluoro |
| 1.1077 | Me | CH2 | C(Me)2 | CH2 | S | fluoro |
| 1.1078 | Me | CH2 | C(Me)2 | C(Me)2 | S | fluoro |
| 1.1079 | H | Single bond | CH2 | CH2 | SO | fluoro |
| 1.1080 | H | Single bond | CH(Me) | CH2 | SO | fluoro |
| 1.1081 | H | Single bond | C(Me)2 | CH2 | SO | fluoro |
| 1.1082 | H | Single bond | C(Me)2 | C(Me)2 | SO | fluoro |
| 1.1083 | Me | Single bond | CH2 | CH2 | SO | fluoro |
| 1.1084 | Me | Single bond | CH(Me) | CH2 | SO | fluoro |
| 1.1085 | Me | Single bond | C(Me)2 | CH2 | SO | fluoro |
| 1.1086 | Me | Single bond | C(Me)2 | C(Me)2 | SO | fluoro |
| 1.1087 | H | CH2 | CH2 | CH2 | SO | fluoro |
| 1.1088 | H | CH2 | CH(Me) | CH2 | SO | fluoro |
| 1.1089 | H | CH2 | C(Me)2 | CH2 | SO | fluoro |
| 1.1090 | H | CH2 | C(Me)2 | C(Me)2 | SO | fluoro |
| 1.1091 | Me | CH2 | CH2 | CH2 | SO | fluoro |
| 1.1092 | Me | CH2 | CH(Me) | CH2 | SO | fluoro |
| 1.1093 | Me | CH2 | C(Me)2 | CH2 | SO | fluoro |
| 1.1094 | Me | CH2 | C(Me)2 | C(Me)2 | SO | fluoro |
| 1.1095 | H | Single bond | CH2 | CH2 | SO2 | fluoro |
| 1.1096 | H | Single bond | CH(Me) | CH2 | SO2 | fluoro |
| 1.1097 | H | Single bond | C(Me)2 | CH2 | SO2 | fluoro |
| 1.1098 | H | Single bond | C(Me)2 | C(Me)2 | SO2 | fluoro |
| 1.1099 | Me | Single bond | CH2 | CH2 | SO2 | fluoro |
| 1.1100 | Me | Single bond | CH(Me) | CH2 | SO2 | fluoro |
| 1.1101 | Me | Single bond | C(Me)2 | CH2 | SO2 | fluoro |
| 1.1102 | Me | Single bond | C(Me)2 | C(Me)2 | SO2 | fluoro |
| 1.1103 | H | CH2 | CH2 | CH2 | SO2 | fluoro |
| 1.1104 | H | CH2 | CH(Me) | CH2 | SO2 | fluoro |
| 1.1105 | H | CH2 | C(Me)2 | CH2 | SO2 | fluoro |
| 1.1106 | H | CH2 | C(Me)2 | C(Me)2 | SO2 | fluoro |
| 1.1107 | Me | CH2 | CH2 | CH2 | SO2 | fluoro |
| 1.1108 | Me | CH2 | CH(Me) | CH2 | SO2 | fluoro |
| 1.1109 | Me | CH2 | C(Me)2 | CH2 | SO2 | fluoro |
| 1.1110 | Me | CH2 | C(Me)2 | C(Me)2 | SO2 | fluoro |
| 1.1111 | H | Single bond | CH2 | CH2 | SONH | fluoro |
| 1.1112 | H | Single bond | CH(Me) | CH2 | SONH | fluoro |
| 1.1113 | H | Single bond | C(Me)2 | CH2 | SONH | fluoro |
| 1.1114 | H | Single bond | C(Me)2 | C(Me)2 | SONH | fluoro |
| 1.1115 | Me | Single bond | CH2 | CH2 | SONH | fluoro |
| 1.1116 | Me | Single bond | CH(Me) | CH2 | SONH | fluoro |
| 1.1117 | Me | Single bond | C(Me)2 | CH2 | SONH | fluoro |
| 1.1118 | Me | Single bond | C(Me)2 | C(Me)2 | SONH | fluoro |
| 1.1119 | H | CH2 | CH2 | CH2 | SONH | fluoro |
| 1.1120 | H | CH2 | CH(Me) | CH2 | SONH | fluoro |
| 1.1121 | H | CH2 | C(Me)2 | CH2 | SONH | fluoro |
| 1.1122 | H | CH2 | C(Me)2 | C(Me)2 | SONH | fluoro |
| 1.1123 | Me | CH2 | CH2 | CH2 | SONH | fluoro |
| 1.1124 | Me | CH2 | CH(Me) | CH2 | SONH | fluoro |
| 1.1125 | Me | CH2 | C(Me)2 | CH2 | SONH | fluoro |
| 1.1126 | Me | CH2 | C(Me)2 | C(Me)2 | SONH | fluoro |

TABLE 1-continued (I-A)

| Compound numbers | R⁶ | L | Y¹ | Y³ | Y² | R⁵ |
|---|---|---|---|---|---|---|
| 1.1127 | H | Single bond | CH2 | CH2 | C=N—OCH2CF3 | fluoro |
| 1.1128 | H | Single bond | CH(Me) | CH2 | C=N—OCH2CF3 | fluoro |
| 1.1129 | H | Single bond | C(Me)2 | CH2 | C=N—OCH2CF3 | fluoro |
| 1.1130 | H | Single bond | C(Me)2 | C(Me)2 | C=N—OCH2CF3 | fluoro |
| 1.1131 | Me | Single bond | CH2 | CH2 | C=N—OCH2CF3 | fluoro |
| 1.1132 | Me | Single bond | CH(Me) | CH2 | C=N—OCH2CF3 | fluoro |
| 1.1133 | Me | Single bond | C(Me)2 | CH2 | C=N—OCH2CF3 | fluoro |
| 1.1134 | Me | Single bond | C(Me)2 | C(Me)2 | C=N—OCH2CF3 | fluoro |
| 1.1135 | H | CH2 | CH2 | CH2 | C=N—OCH2CF3 | fluoro |
| 1.1136 | H | CH2 | CH(Me) | CH2 | C=N—OCH2CF3 | fluoro |
| 1.1137 | H | CH2 | C(Me)2 | CH2 | C=N—OCH2CF3 | fluoro |
| 1.1138 | H | CH2 | C(Me)2 | C(Me)2 | C=N—OCH2CF3 | fluoro |
| 1.1139 | Me | CH2 | CH2 | CH2 | C=N—OCH2CF3 | fluoro |
| 1.1140 | Me | CH2 | CH(Me) | CH2 | C=N—OCH2CF3 | fluoro |
| 1.1141 | Me | CH2 | C(Me)2 | CH2 | C=N—OCH2CF3 | fluoro |
| 1.1142 | Me | CH2 | C(Me)2 | C(Me)2 | C=N—OCH2CF3 | fluoro |
| 1.1143 | H | CH2 | S | CH2 | CH2 | fluoro |
| 1.1144 | H | CH2 | S | CH2 | CH(Me) | fluoro |
| 1.1145 | H | CH2 | S | CH2 | C(Me)2 | fluoro |
| 1.1146 | H | CH2 | S | CH(Me) | CH2 | fluoro |
| 1.1147 | H | CH2 | S | CH(Me) | CH(Me) | fluoro |
| 1.1148 | H | CH2 | S | CH(Me) | C(Me)2 | fluoro |
| 1.1149 | H | CH2 | S | C(Me)2 | C(Me)2 | fluoro |
| 1.1150 | H | CH2 | S | C(Me)2 | CH(Me) | fluoro |
| 1.1151 | H | CH2 | S | C(Me)2 | CH2 | fluoro |
| 1.1152 | Me | CH2 | S | CH2 | CH2 | fluoro |
| 1.1153 | Me | CH2 | S | CH2 | CH(Me) | fluoro |
| 1.1154 | Me | CH2 | S | CH2 | C(Me)2 | fluoro |
| 1.1155 | Me | CH2 | S | CH(Me) | CH2 | fluoro |
| 1.1156 | Me | CH2 | S | CH(Me) | CH(Me) | fluoro |
| 1.1157 | Me | CH2 | S | CH(Me) | C(Me)2 | fluoro |
| 1.1158 | Me | CH2 | S | C(Me)2 | C(Me)2 | fluoro |
| 1.1159 | Me | CH2 | S | C(Me)2 | CH(Me) | fluoro |
| 1.1160 | Me | CH2 | S | C(Me)2 | CH2 | fluoro |
| 1.1161 | H | CH2 | SO | CH2 | CH2 | fluoro |
| 1.1162 | H | CH2 | SO | CH2 | CH(Me) | fluoro |
| 1.1163 | H | CH2 | SO | CH2 | C(Me)2 | fluoro |
| 1.1164 | H | CH2 | SO | CH(Me) | CH2 | fluoro |
| 1.1165 | H | CH2 | SO | CH(Me) | CH(Me) | fluoro |
| 1.1166 | H | CH2 | SO | CH(Me) | C(Me)2 | fluoro |
| 1.1167 | H | CH2 | SO | C(Me)2 | C(Me)2 | fluoro |
| 1.1168 | H | CH2 | SO | C(Me)2 | CH(Me) | fluoro |
| 1.1169 | H | CH2 | SO | C(Me)2 | CH2 | fluoro |
| 1.1170 | Me | CH2 | SO | CH2 | CH2 | fluoro |
| 1.1171 | Me | CH2 | SO | CH2 | CH(Me) | fluoro |
| 1.1172 | Me | CH2 | SO | CH2 | C(Me)2 | fluoro |
| 1.1173 | Me | CH2 | SO | CH(Me) | CH2 | fluoro |
| 1.1174 | Me | CH2 | SO | CH(Me) | CH(Me) | fluoro |
| 1.1175 | Me | CH2 | SO | CH(Me) | C(Me)2 | fluoro |
| 1.1176 | Me | CH2 | SO | C(Me)2 | C(Me)2 | fluoro |
| 1.1177 | Me | CH2 | SO | C(Me)2 | CH(Me) | fluoro |
| 1.1178 | Me | CH2 | SO | C(Me)2 | CH2 | fluoro |
| 1.1179 | H | CH2 | SO2 | CH2 | CH2 | fluoro |
| 1.1180 | H | CH2 | SO2 | CH2 | CH(Me) | fluoro |
| 1.1181 | H | CH2 | SO2 | CH2 | C(Me)2 | fluoro |
| 1.1182 | H | CH2 | SO2 | CH(Me) | CH2 | fluoro |
| 1.1183 | H | CH2 | SO2 | CH(Me) | CH(Me) | fluoro |
| 1.1184 | H | CH2 | SO2 | CH(Me) | C(Me)2 | fluoro |
| 1.1185 | H | CH2 | SO2 | C(Me)2 | C(Me)2 | fluoro |
| 1.1186 | H | CH2 | SO2 | C(Me)2 | CH(Me) | fluoro |
| 1.1187 | H | CH2 | SO2 | C(Me)2 | CH2 | fluoro |
| 1.1188 | Me | CH2 | SO2 | CH2 | CH2 | fluoro |

TABLE 1-continued (I-A)

| Compound numbers | R⁶ | L | Y¹ | Y³ | Y² | R⁵ |
|---|---|---|---|---|---|---|
| 1.1189 | Me | CH2 | SO2 | CH2 | CH(Me) | fluoro |
| 1.1190 | Me | CH2 | SO2 | CH2 | C(Me)2 | fluoro |
| 1.1191 | Me | CH2 | SO2 | CH(Me) | CH2 | fluoro |
| 1.1192 | Me | CH2 | SO2 | CH(Me) | CH(Me) | fluoro |
| 1.1193 | Me | CH2 | SO2 | CH(Me) | C(Me)2 | fluoro |
| 1.1194 | Me | CH2 | SO2 | C(Me)2 | C(Me)2 | fluoro |
| 1.1195 | Me | CH2 | SO2 | C(Me)2 | CH(Me) | fluoro |
| 1.1196 | Me | CH2 | SO2 | C(Me)2 | CH2 | fluoro |
| 1.1197 | H | CH2CH2 | CH2 | CH2 | S | bromo |
| 1.1198 | H | CH2CH2 | CH(Me) | CH2 | S | bromo |
| 1.1199 | H | CH2CH2 | C(Me)2 | CH2 | S | bromo |
| 1.1200 | H | CH2CH2 | C(Me)2 | C(Me)2 | S | bromo |
| 1.1201 | Me | CH2CH2 | CH2 | CH2 | S | bromo |
| 1.1202 | Me | CH2CH2 | CH(Me) | CH2 | S | bromo |
| 1.1203 | Me | CH2CH2 | C(Me)2 | CH2 | S | bromo |
| 1.1204 | Me | CH2CH2 | C(Me)2 | C(Me)2 | S | bromo |
| 1.1205 | H | CH2CH2 | CH2 | CH2 | SO | bromo |
| 1.1206 | H | CH2CH2 | CH(Me) | CH2 | SO | bromo |
| 1.1207 | H | CH2CH2 | C(Me)2 | CH2 | SO | bromo |
| 1.1208 | H | CH2CH2 | C(Me)2 | C(Me)2 | SO | bromo |
| 1.1209 | Me | CH2CH2 | CH2 | CH2 | SO | bromo |
| 1.1210 | Me | CH2CH2 | CH(Me) | CH2 | SO | bromo |
| 1.1211 | Me | CH2CH2 | C(Me)2 | CH2 | SO | bromo |
| 1.1212 | Me | CH2CH2 | C(Me)2 | C(Me)2 | SO | bromo |
| 1.1213 | H | CH2CH2 | CH2 | CH2 | SO2 | bromo |
| 1.1214 | H | CH2CH2 | CH(Me) | CH2 | SO2 | bromo |
| 1.1215 | H | CH2CH2 | C(Me)2 | CH2 | SO2 | bromo |
| 1.1216 | H | CH2CH2 | C(Me)2 | C(Me)2 | SO2 | bromo |
| 1.1217 | Me | CH2CH2 | CH2 | CH2 | SO2 | bromo |
| 1.1218 | Me | CH2CH2 | CH(Me) | CH2 | SO2 | bromo |
| 1.1219 | Me | CH2CH2 | C(Me)2 | CH2 | SO2 | bromo |
| 1.1220 | Me | CH2CH2 | C(Me)2 | C(Me)2 | SO2 | bromo |
| 1.1221 | H | CH2CH2 | CH2 | CH2 | S | cyano |
| 1.1222 | H | CH2CH2 | CH(Me) | CH2 | S | cyano |
| 1.1223 | H | CH2CH2 | C(Me)2 | CH2 | S | cyano |
| 1.1224 | H | CH2CH2 | C(Me)2 | C(Me)2 | S | cyano |
| 1.1225 | Me | CH2CH2 | CH2 | CH2 | S | cyano |
| 1.1226 | Me | CH2CH2 | CH(Me) | CH2 | S | cyano |
| 1.1227 | Me | CH2CH2 | C(Me)2 | CH2 | S | cyano |
| 1.1228 | Me | CH2CH2 | C(Me)2 | C(Me)2 | S | cyano |
| 1.1229 | H | CH2CH2 | CH2 | CH2 | SO | cyano |
| 1.1230 | H | CH2CH2 | CH(Me) | CH2 | SO | cyano |
| 1.1231 | H | CH2CH2 | C(Me)2 | CH2 | SO | cyano |
| 1.1232 | H | CH2CH2 | C(Me)2 | C(Me)2 | SO | cyano |
| 1.1233 | Me | CH2CH2 | CH2 | CH2 | SO | cyano |
| 1.1234 | Me | CH2CH2 | CH(Me) | CH2 | SO | cyano |
| 1.1235 | Me | CH2CH2 | C(Me)2 | CH2 | SO | cyano |
| 1.1236 | Me | CH2CH2 | C(Me)2 | C(Me)2 | SO | cyano |
| 1.1237 | H | CH2CH2 | CH2 | CH2 | SO2 | cyano |
| 1.1238 | H | CH2CH2 | CH(Me) | CH2 | SO2 | cyano |
| 1.1239 | H | CH2CH2 | C(Me)2 | CH2 | SO2 | cyano |
| 1.1240 | H | CH2CH2 | C(Me)2 | C(Me)2 | SO2 | cyano |
| 1.1241 | Me | CH2CH2 | CH2 | CH2 | SO2 | cyano |
| 1.1242 | Me | CH2CH2 | CH(Me) | CH2 | SO2 | cyano |
| 1.1243 | Me | CH2CH2 | C(Me)2 | CH2 | SO2 | cyano |
| 1.1244 | Me | CH2CH2 | C(Me)2 | C(Me)2 | SO2 | cyano |
| 1.1245 | H | CH2CH2 | CH2 | CH2 | S | methyl |
| 1.1246 | H | CH2CH2 | CH(Me) | CH2 | S | methyl |
| 1.1247 | H | CH2CH2 | C(Me)2 | CH2 | S | methyl |
| 1.1248 | H | CH2CH2 | C(Me)2 | C(Me)2 | S | methyl |
| 1.1249 | Me | CH2CH2 | CH2 | CH2 | S | methyl |
| 1.1250 | Me | CH2CH2 | CH(Me) | CH2 | S | methyl |

TABLE 1-continued

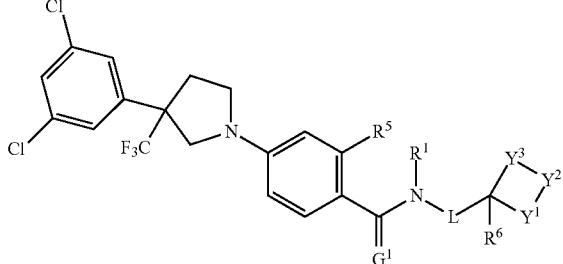

(I-A)

| Compound numbers | R6 | L | Y1 | Y3 | Y2 | R5 |
|---|---|---|---|---|---|---|
| 1.1251 | Me | CH2CH2 | C(Me)2 | CH2 | S | methyl |
| 1.1252 | Me | CH2CH2 | C(Me)2 | C(Me)2 | S | methyl |
| 1.1253 | H | CH2CH2 | CH2 | CH2 | SO | methyl |
| 1.1254 | H | CH2CH2 | CH(Me) | CH2 | SO | methyl |
| 1.1255 | H | CH2CH2 | C(Me)2 | CH2 | SO | methyl |
| 1.1256 | H | CH2CH2 | C(Me)2 | C(Me)2 | SO | methyl |
| 1.1257 | Me | CH2CH2 | CH2 | CH2 | SO | methyl |
| 1.1258 | Me | CH2CH2 | CH(Me) | CH2 | SO | methyl |
| 1.1259 | Me | CH2CH2 | C(Me)2 | CH2 | SO | methyl |
| 1.1260 | Me | CH2CH2 | C(Me)2 | C(Me)2 | SO | methyl |
| 1.1261 | H | CH2CH2 | CH2 | CH2 | SO2 | methyl |
| 1.1262 | H | CH2CH2 | CH(Me) | CH2 | SO2 | methyl |
| 1.1263 | H | CH2CH2 | C(Me)2 | CH2 | SO2 | methyl |
| 1.1264 | H | CH2CH2 | C(Me)2 | C(Me)2 | SO2 | methyl |
| 1.1265 | Me | CH2CH2 | CH2 | CH2 | SO2 | methyl |
| 1.1266 | Me | CH2CH2 | CH(Me) | CH2 | SO2 | methyl |
| 1.1267 | Me | CH2CH2 | C(Me)2 | CH2 | SO2 | methyl |
| 1.1268 | Me | CH2CH2 | C(Me)2 | C(Me)2 | SO2 | methyl |
| 1.1269 | H | CH2CH2 | CH2 | CH2 | S | trifluoromethyl |
| 1.1270 | H | CH2CH2 | CH(Me) | CH2 | S | trifluoromethyl |
| 1.1271 | H | CH2CH2 | C(Me)2 | CH2 | S | trifluoromethyl |
| 1.1272 | H | CH2CH2 | C(Me)2 | C(Me)2 | S | trifluoromethyl |
| 1.1273 | Me | CH2CH2 | CH2 | CH2 | S | trifluoromethyl |
| 1.1274 | Me | CH2CH2 | CH(Me) | CH2 | S | trifluoromethyl |
| 1.1275 | Me | CH2CH2 | C(Me)2 | CH2 | S | trifluoromethyl |
| 1.1276 | Me | CH2CH2 | C(Me)2 | C(Me)2 | S | trifluoromethyl |
| 1.1277 | H | CH2CH2 | CH2 | CH2 | SO | trifluoromethyl |
| 1.1278 | H | CH2CH2 | CH(Me) | CH2 | SO | trifluoromethyl |
| 1.1279 | H | CH2CH2 | C(Me)2 | CH2 | SO | trifluoromethyl |
| 1.1280 | H | CH2CH2 | C(Me)2 | C(Me)2 | SO | trifluoromethyl |
| 1.1281 | Me | CH2CH2 | CH2 | CH2 | SO | trifluoromethyl |
| 1.1282 | Me | CH2CH2 | CH(Me) | CH2 | SO | trifluoromethyl |
| 1.1283 | Me | CH2CH2 | C(Me)2 | CH2 | SO | trifluoromethyl |
| 1.1284 | Me | CH2CH2 | C(Me)2 | C(Me)2 | SO | trifluoromethyl |
| 1.1285 | H | CH2CH2 | CH2 | CH2 | SO2 | trifluoromethyl |
| 1.1286 | H | CH2CH2 | CH(Me) | CH2 | SO2 | trifluoromethyl |
| 1.1287 | H | CH2CH2 | C(Me)2 | CH2 | SO2 | trifluoromethyl |
| 1.1288 | H | CH2CH2 | C(Me)2 | C(Me)2 | SO2 | trifluoromethyl |
| 1.1289 | Me | CH2CH2 | CH2 | CH2 | SO2 | trifluoromethyl |
| 1.1290 | Me | CH2CH2 | CH(Me) | CH2 | SO2 | trifluoromethyl |
| 1.1291 | Me | CH2CH2 | C(Me)2 | CH2 | SO2 | trifluoromethyl |
| 1.1292 | Me | CH2CH2 | C(Me)2 | C(Me)2 | SO2 | trifluoromethyl |
| 1.1293 | H | CH2CH2 | CH2 | CH2 | S | fluoro |
| 1.1294 | H | CH2CH2 | CH(Me) | CH2 | S | fluoro |
| 1.1295 | H | CH2CH2 | C(Me)2 | CH2 | S | fluoro |
| 1.1296 | H | CH2CH2 | C(Me)2 | C(Me)2 | S | fluoro |
| 1.1297 | Me | CH2CH2 | CH2 | CH2 | S | fluoro |
| 1.1298 | Me | CH2CH2 | CH(Me) | CH2 | S | fluoro |
| 1.1299 | Me | CH2CH2 | C(Me)2 | CH2 | S | fluoro |
| 1.1300 | Me | CH2CH2 | C(Me)2 | C(Me)2 | S | fluoro |
| 1.1301 | H | CH2CH2 | CH2 | CH2 | SO | fluoro |
| 1.1302 | H | CH2CH2 | CH(Me) | CH2 | SO | fluoro |
| 1.1303 | H | CH2CH2 | C(Me)2 | CH2 | SO | fluoro |
| 1.1304 | H | CH2CH2 | C(Me)2 | C(Me)2 | SO | fluoro |
| 1.1305 | Me | CH2CH2 | CH2 | CH2 | SO | fluoro |
| 1.1306 | Me | CH2CH2 | CH(Me) | CH2 | SO | fluoro |
| 1.1307 | Me | CH2CH2 | C(Me)2 | CH2 | SO | fluoro |
| 1.1308 | Me | CH2CH2 | C(Me)2 | C(Me)2 | SO | fluoro |
| 1.1309 | H | CH2CH2 | CH2 | CH2 | SO2 | fluoro |
| 1.1310 | H | CH2CH2 | CH(Me) | CH2 | SO2 | fluoro |
| 1.1311 | H | CH2CH2 | C(Me)2 | CH2 | SO2 | fluoro |
| 1.1312 | H | CH2CH2 | C(Me)2 | C(Me)2 | SO2 | fluoro |

TABLE 1-continued

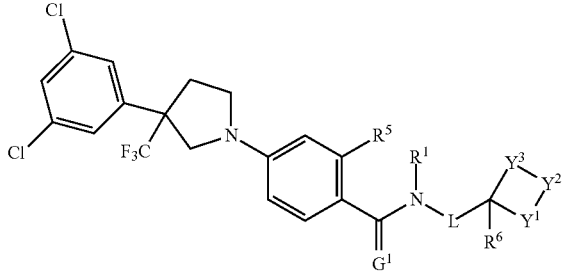

(I-A)

| Compound numbers | $R^6$ | L | $Y^1$ | $Y^3$ | $Y^2$ | $R^5$ |
|---|---|---|---|---|---|---|
| 1.1313 | Me | CH2CH2 | CH2 | CH2 | SO2 | fluoro |
| 1.1314 | Me | CH2CH2 | CH(Me) | CH2 | SO2 | fluoro |
| 1.1315 | Me | CH2CH2 | C(Me)2 | CH2 | SO2 | fluoro |
| 1.1316 | Me | CH2CH2 | C(Me)2 | C(Me)2 | SO2 | fluoro |
| 1.1317 | H | CH2CH2 | CH2 | CH2 | S | chloro |
| 1.1318 | H | CH2CH2 | CH(Me) | CH2 | S | chloro |
| 1.1319 | H | CH2CH2 | C(Me)2 | CH2 | S | chloro |
| 1.1320 | H | CH2CH2 | C(Me)2 | C(Me)2 | S | chloro |
| 1.1321 | Me | CH2CH2 | CH2 | CH2 | S | chloro |
| 1.1322 | Me | CH2CH2 | CH(Me) | CH2 | S | chloro |
| 1.1323 | Me | CH2CH2 | C(Me)2 | CH2 | S | chloro |
| 1.1324 | Me | CH2CH2 | C(Me)2 | C(Me)2 | S | chloro |
| 1.1325 | H | CH2CH2 | CH2 | CH2 | SO | chloro |
| 1.1326 | H | CH2CH2 | CH(Me) | CH2 | SO | chloro |
| 1.1327 | H | CH2CH2 | C(Me)2 | CH2 | SO | chloro |
| 1.1328 | H | CH2CH2 | C(Me)2 | C(Me)2 | SO | chloro |
| 1.1329 | Me | CH2CH2 | CH2 | CH2 | SO | chloro |
| 1.1330 | Me | CH2CH2 | CH(Me) | CH2 | SO | chloro |
| 1.1331 | Me | CH2CH2 | C(Me)2 | CH2 | SO | chloro |
| 1.1332 | Me | CH2CH2 | C(Me)2 | C(Me)2 | SO | chloro |
| 1.1333 | H | CH2CH2 | CH2 | CH2 | SO2 | chloro |
| 1.1334 | H | CH2CH2 | CH(Me) | CH2 | SO2 | chloro |
| 1.1335 | H | CH2CH2 | C(Me)2 | CH2 | SO2 | chloro |
| 1.1336 | H | CH2CH2 | C(Me)2 | C(Me)2 | SO2 | chloro |
| 1.1337 | Me | CH2CH2 | CH2 | CH2 | SO2 | chloro |
| 1.1338 | Me | CH2CH2 | CH(Me) | CH2 | SO2 | chloro |
| 1.1339 | Me | CH2CH2 | C(Me)2 | CH2 | SO2 | chloro |
| 1.1340 | Me | CH2CH2 | C(Me)2 | C(Me)2 | SO2 | chloro |

Table 1 provides 1340 compounds of formula (I-A) wherein $G^1$ is oxygen, $R^1$ is hydrogen, L, $R^5$, $Y^2$, $R^6$, $Y^1$ and $Y^3$ have the values listed in the table below.

Table 2:

Table 2 provides 1340 compounds of formula (I-B) wherein $G^1$ is oxygen, $R^1$ is hydrogen, L, $R^5$, $Y^2$, $R^6$, $Y^1$ and $Y^3$ have the values listed in Table 1.

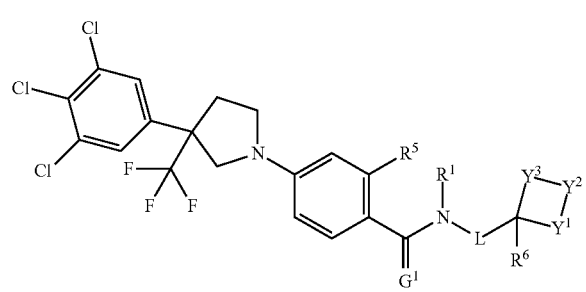

(I-B)

Table 3:

Table 3 provides 1340 compounds of formula (I-C) wherein $G^1$ is oxygen, $R^1$ is hydrogen, L, $R^5$, $Y^2$, $R^6$, $Y^1$ and $Y^3$ have the values listed in Table 1.

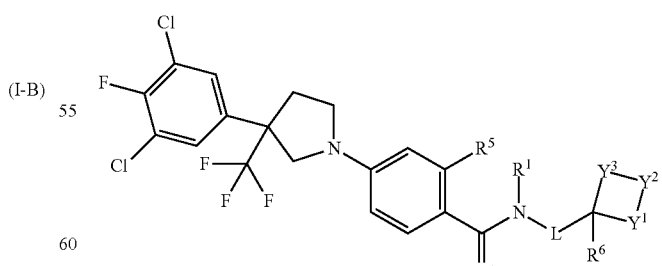

(I-C)

Table 4:

Table 4 provides 1340 compounds of formula (I-D) wherein $G^1$ is oxygen, $R^1$ is hydrogen, L, $R^5$, $Y^2$, $R^6$, $Y^1$ and $Y^3$ have the values listed in Table 1.

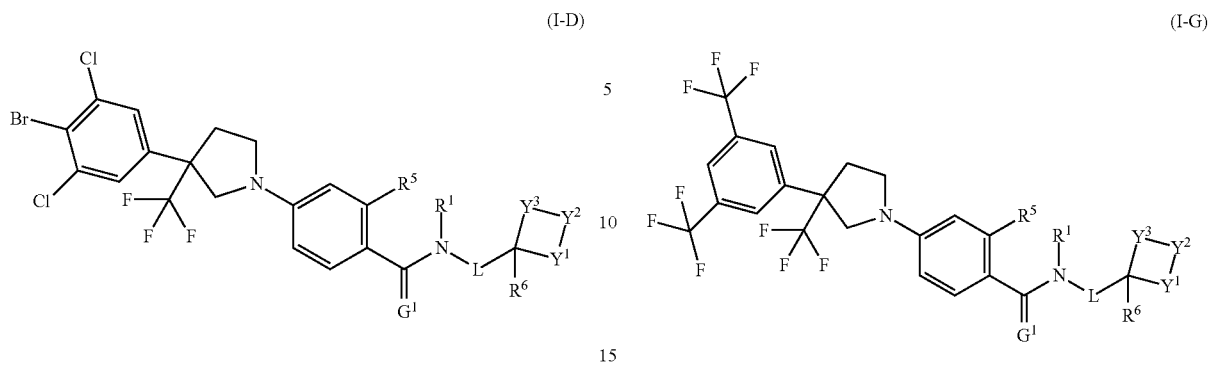

Table 5:

Table 5 provides 1340 compounds of formula (I-E) wherein $G^1$ is oxygen, $R^1$ is hydrogen, L, $R^5$, $Y^2$, $R^6$, $Y^1$ and $Y^3$ have the values listed in Table 1.

Table 8:

Table 8 provides 1340 compounds of formula (I—H) wherein $G^1$ is oxygen, $R^1$ is hydrogen, L, $R^5$, $Y^2$, $R^6$, $Y^1$ and $Y^3$ have the values listed in Table 1.

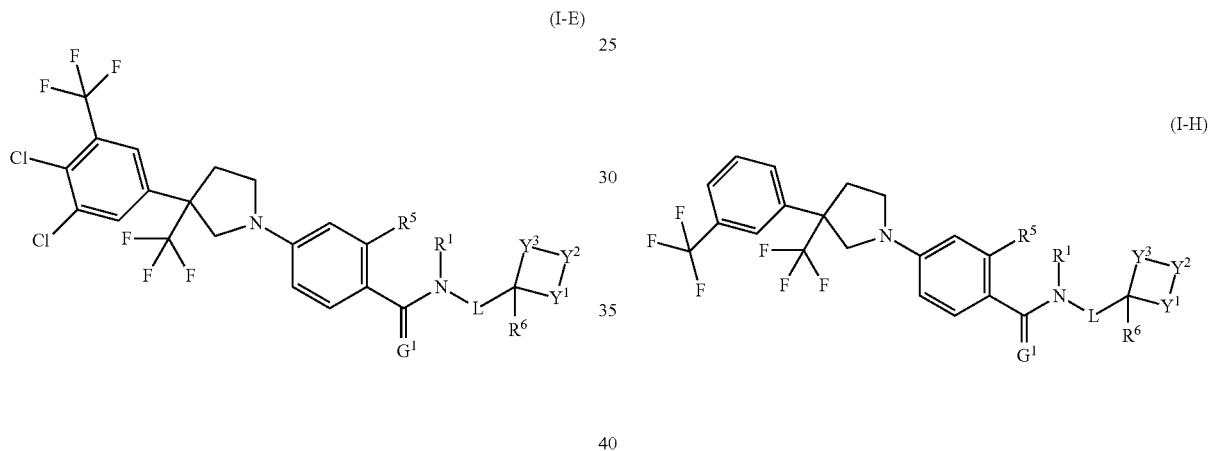

Table 6:

Table 6 provides 1340 compounds of formula (I-F) wherein $G^1$ is oxygen, $R^1$ is hydrogen, L, $R^5$, $Y^2$, $R^6$, $Y^1$ and $Y^3$ have the values listed in Table 1.

Table 9:

Table 9 provides 1340 compounds of formula (I-I) wherein $G^1$ is oxygen, $R^1$ is hydrogen, L, $R^5$, $Y^2$, $R^6$, $Y^1$ and $Y^3$ have the values listed in Table 1.

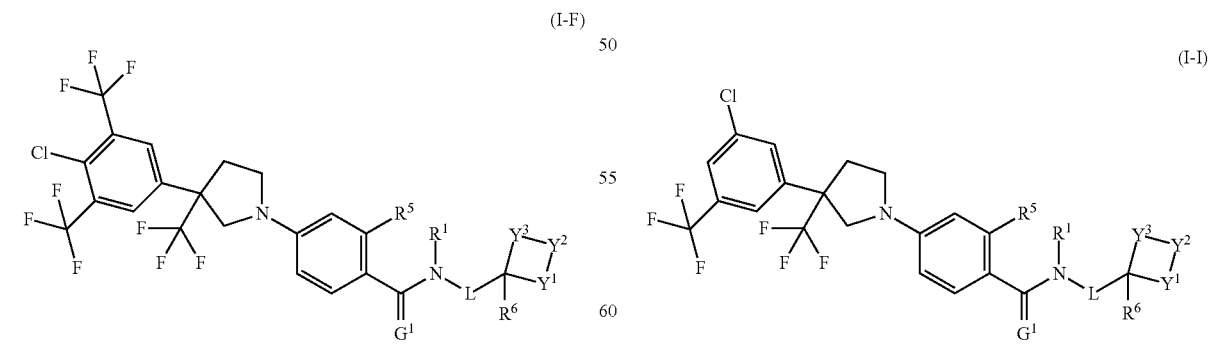

Table 7:

Table 7 provides 1340 compounds of formula (I-G) wherein $G^1$ is oxygen, $R^1$ is hydrogen, L, $R^5$, $Y^2$, $R^6$, $Y^1$ and $Y^3$ have the values listed in Table 1.

Table 10:

Table 10 provides 1340 compounds of formula (I-J) wherein $G^1$ is oxygen, $R^1$ is hydrogen, L, $R^5$, $Y^2$, $R^6$, $Y^1$ and $Y^3$ have the values listed in Table 1.

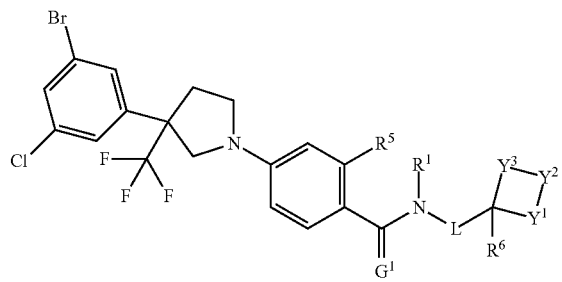
(I-J)

Table 11:
Table 11 provides 1340 compounds of formula (I-K) wherein G¹ is oxygen, R¹ is hydrogen, L, R⁵, Y², R⁶, Y¹ and Y³ have the values listed in Table 1.

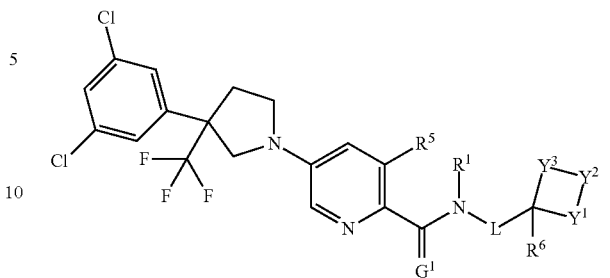
(I-A1)

Table 14:
Table 14 provides 1340 compounds of formula (I-B1) wherein G¹ is oxygen, R¹ is hydrogen, L, R⁵, Y², R⁶, Y¹ and Y³ have the values listed in Table 1.

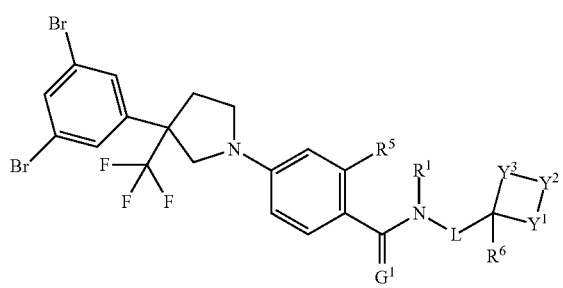
(I-J)

Table 12:
Table 12 provides 1340 compounds of formula (I-L) wherein G¹ is oxygen, R¹ is hydrogen, L, R⁵, Y², R⁶, Y¹ and Y³ have the values listed in Table 1.

Table 15:
Table 15 provides 1340 compounds of formula (I-C1) wherein G¹ is oxygen, R¹ is hydrogen, L, R⁵, Y², R⁶, Y¹ and Y³ have the values listed in Table 1.

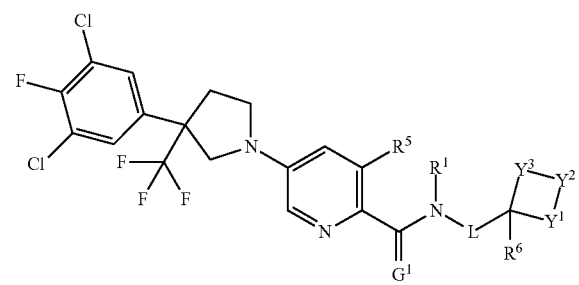
(I-C1)

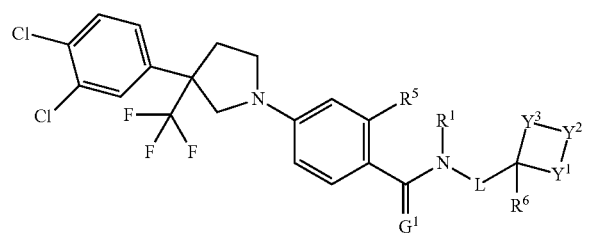
(I-L)

Table 13:
Table 13 provides 1340 compounds of formula (I-A1) wherein G¹ is oxygen, R¹ is hydrogen, L, R⁵, Y², R⁶, Y¹ and Y³ have the values listed in Table 1.

Table 16:
Table 16 provides 1340 compounds of formula (I-D1) wherein G¹ is oxygen, R¹ is hydrogen, L, R⁵, Y², R⁶, Y¹ and Y³ have the values listed in Table 1.

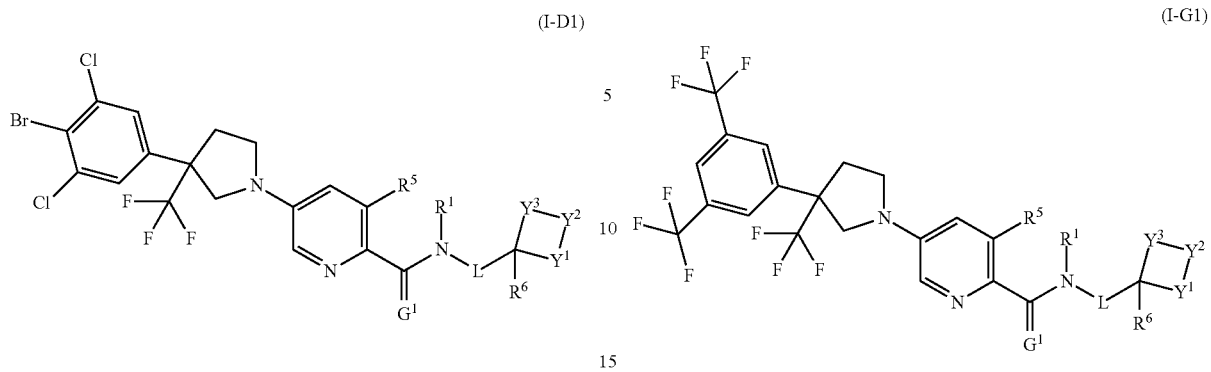

(I-D1)

(I-G1)

Table 17:

Table 17 provides 1340 compounds of formula (I-E1) wherein $G^1$ is oxygen, $R^1$ is hydrogen, L, $R^5$, $Y^2$, $R^6$, $Y^1$ and $Y^3$ have the values listed in Table 1.

Table 19:

Table 19 provides 1340 compounds of formula (I-H1) wherein $G^1$ is oxygen, $R^1$ is hydrogen, L, $R^5$, $Y^2$, $R^6$, $Y^1$ and $Y^3$ have the values listed in Table 1.

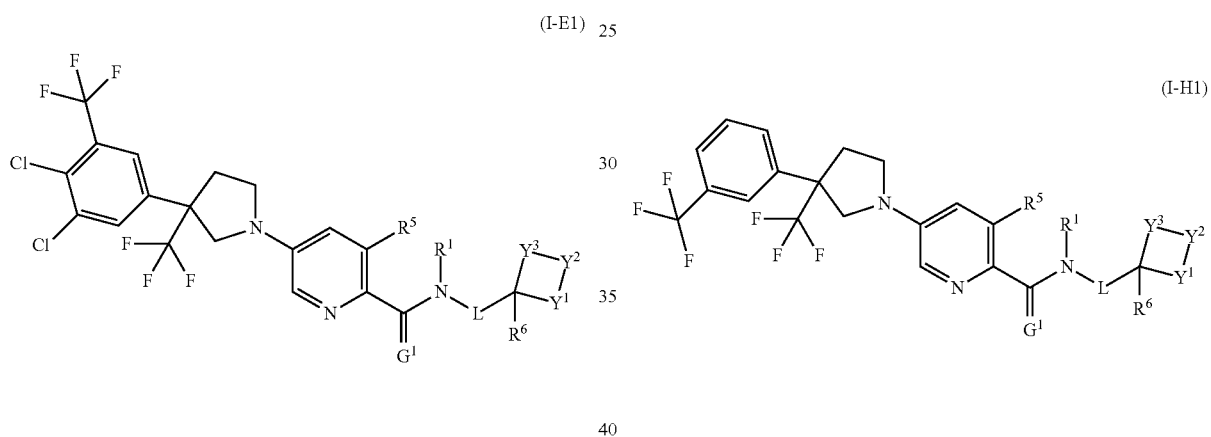

(I-E1)

(I-H1)

Table 18:

Table 18 provides 1340 compounds of formula (I-F1) wherein $G^1$ is oxygen, $R^1$ is hydrogen, L, $R^5$, $Y^2$, $R^6$, $Y^1$ and $Y^3$ have the values listed in Table 1.

Table 20:

Table 20 provides 1340 compounds of formula (I-I1) wherein $G^1$ is oxygen, $R^1$ is hydrogen, L, $R^5$, $Y^2$, $R^6$, $Y^1$ and $Y^3$ have the values listed in Table 1.

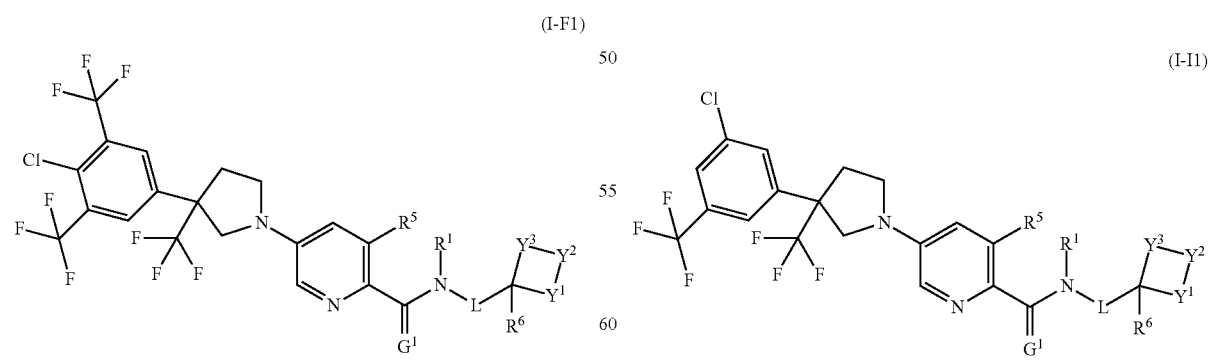

(I-F1)

(I-I1)

Table 19:

Table 19 provides 1340 compounds of formula (I-G1) wherein $G^1$ is oxygen, $R^1$ is hydrogen, L, $R^5$, $Y^2$, $R^6$, $Y^1$ and $Y^3$ have the values listed in Table 1.

Table 21:

Table 21 provides 1340 compounds of formula (I-J1) wherein $G^1$ is oxygen, $R^1$ is hydrogen, L, $R^5$, $Y^2$, $R^6$, $Y^1$ and $Y^3$ have the values listed in Table 1.

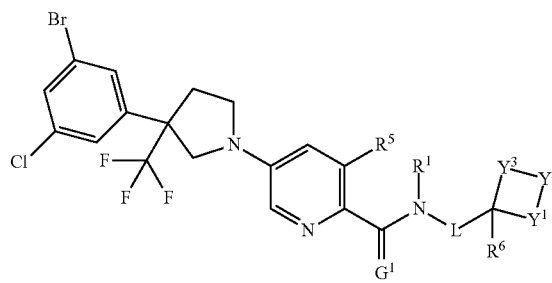
(I-J1)

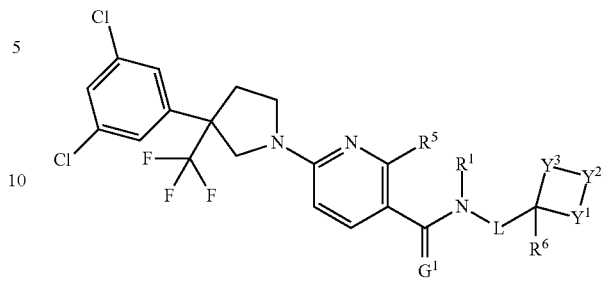
(I-A2)

Table 22:

Table 22 provides 1340 compounds of formula (I-K1) wherein $G^1$ is oxygen, $R^1$ is hydrogen, L, $R^5$, $Y^2$, $R^6$, $Y^1$ and $Y^3$ have the values listed in Table 1.

Table 25:

Table 25 provides 1340 compounds of formula (I-B2) wherein $G^1$ is oxygen, $R^1$ is hydrogen, L, $R^5$, $Y^2$, $R^6$, $Y^1$ and $Y^3$ have the values listed in Table 1.

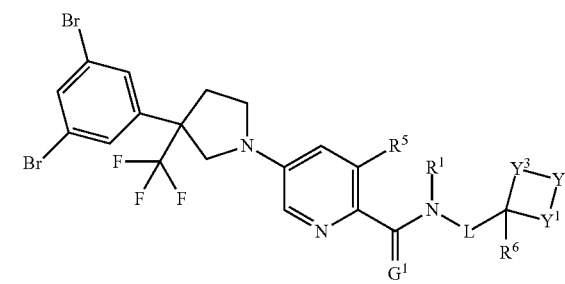
(I-K1)

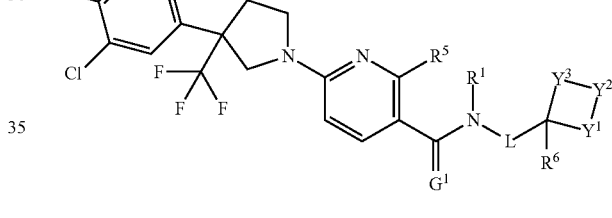
(I-B2)

Table 23:

Table 23 provides 1340 compounds of formula (I-L1) wherein $G^1$ is oxygen, $R^1$ is hydrogen, L, $R^5$, $Y^2$, $R^6$, $Y^1$ and $Y^3$ have the values listed in Table 1.

Table 26:

Table 26 provides 1340 compounds of formula (I-C2) wherein $G^1$ is oxygen, $R^1$ is hydrogen, L, $R^5$, $Y^2$, $R^6$, $Y^1$ and $Y^3$ have the values listed in Table 1.

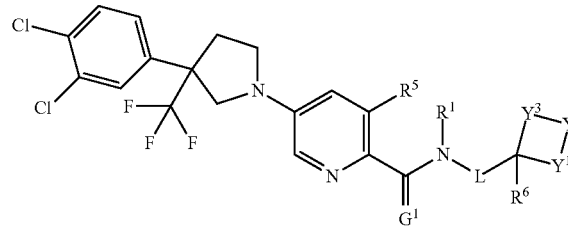
(I-L1)

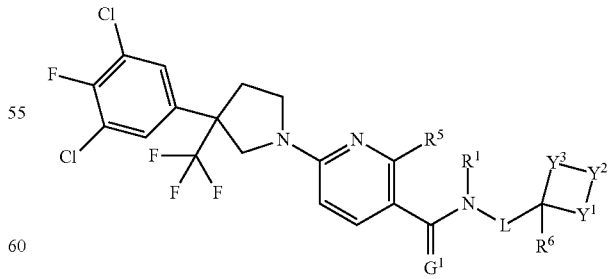
(I-C2)

Table 24:

Table 24 provides 1340 compounds of formula (I-A2) wherein $G^1$ is oxygen, $R^1$ is hydrogen, L, $R^5$, $Y^2$, $R^6$, $Y^1$ and $Y^3$ have the values listed in Table 1.

Table 27:

Table 27 provides 1340 compounds of formula (I-D2) wherein $G^1$ is oxygen, $R^1$ is hydrogen, L, $R^5$, $Y^2$, $R^6$, $Y^1$ and $Y^3$ have the values listed in Table 1.

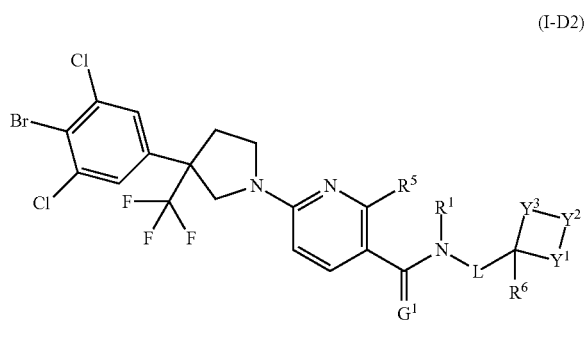

(I-D2)

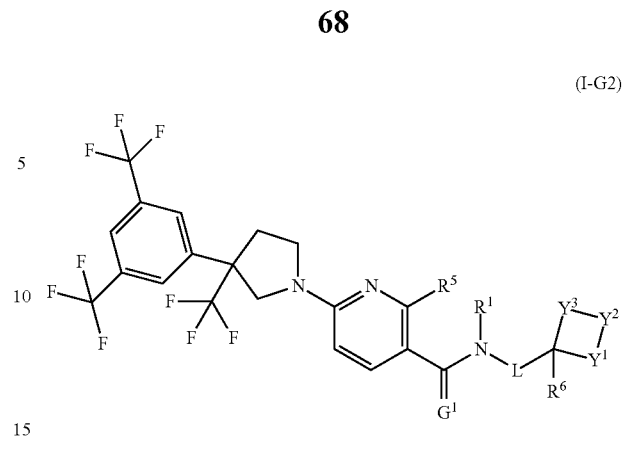

(I-G2)

Table 28:

Table 28 provides 1340 compounds of formula (I-E2) wherein $G^1$ is oxygen, $R^1$ is hydrogen, L, $R^5$, $Y^2$, $R^6$, $Y^1$ and $Y^3$ have the values listed in Table 1.

Table 31:

Table 31 provides 1340 compounds of formula (I-H2) wherein $G^1$ is oxygen, $R^1$ is hydrogen, L, $R^5$, $Y^2$, $R^6$, $Y^1$ and $Y^3$ have the values listed in Table 1.

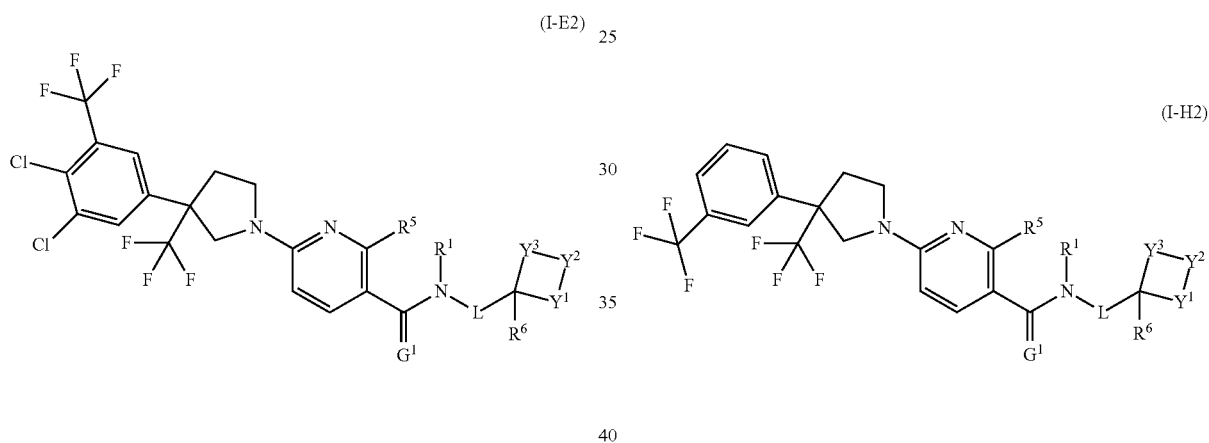

(I-E2)

(I-H2)

Table 29:

Table 29 provides 1340 compounds of formula (I-F2) wherein $G^1$ is oxygen, $R^1$ is hydrogen, L, $R^5$, $Y^2$, $R^6$, $Y^1$ and $Y^3$ have the values listed in Table 1.

Table 32:

Table 32 provides 1340 compounds of formula (I-I2) wherein $G^1$ is oxygen, $R^1$ is hydrogen, L, $R^5$, $Y^2$, $R^6$, $Y^1$ and $Y^3$ have the values listed in Table 1.

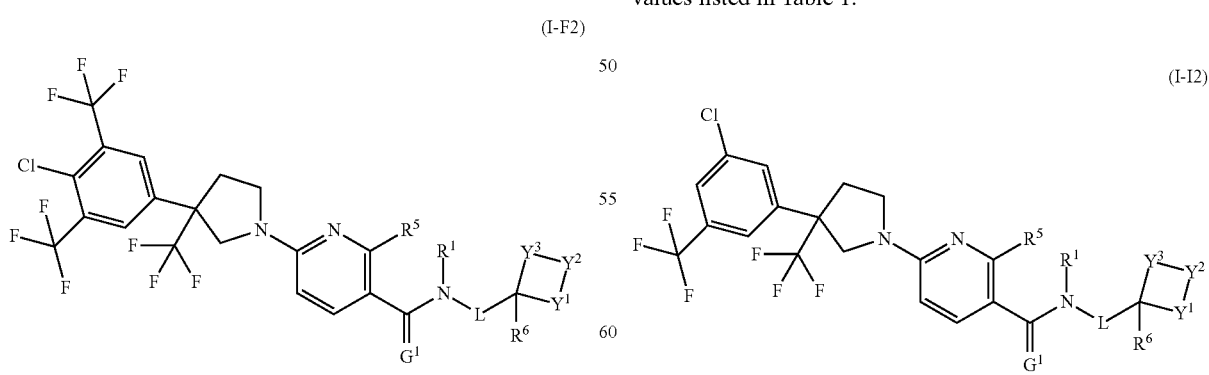

(I-F2)

(I-I2)

Table 30:

Table 30 provides 1340 compounds of formula (I-G2) wherein $G^1$ is oxygen, $R^1$ is hydrogen, L, $R^5$, $Y^2$, $R^6$, $Y^1$ and $Y^3$ have the values listed in Table 1.

Table 33:

Table 33 provides 1340 compounds of formula (I-J2) wherein $G^1$ is oxygen, $R^1$ is hydrogen, L, $R^5$, $Y^2$, $R^6$, $Y^1$ and $Y^3$ have the values listed in Table 1.

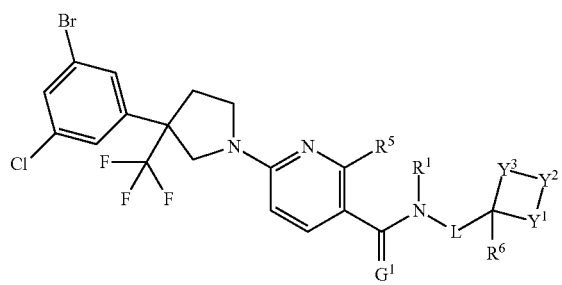
(I-J2)

Table 34:

Table 34 provides 1340 compounds of formula (I-K2) wherein $G^1$ is oxygen, $R^1$ is hydrogen, L, $R^5$, $Y^2$, $R^6$, $Y^1$ and $Y^3$ have the values listed in Table 1.

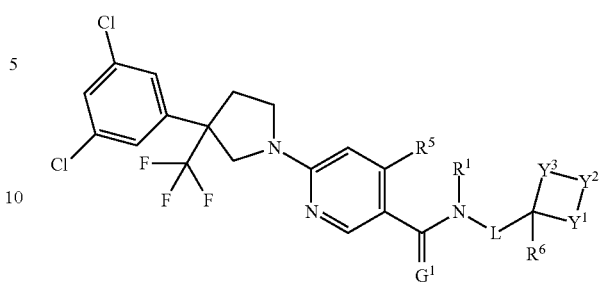
(I-A3)

Table 37:

Table 37 provides 1340 compounds of formula (I-B3) wherein $G^1$ is oxygen, $R^1$ is hydrogen, L, $R^5$, $Y^2$, $R^6$, $Y^1$ and $Y^3$ have the values listed in Table 1.

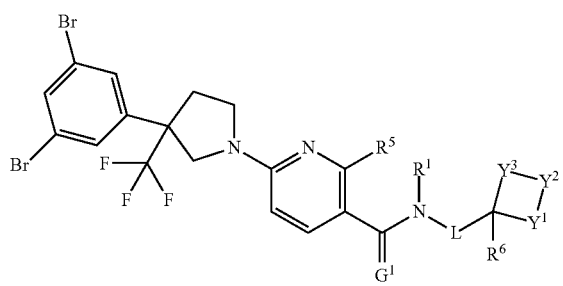
(I-K2)

Table 35:

Table 35 provides 1340 compounds of formula (I-L2) wherein $G^1$ is oxygen, $R^1$ is hydrogen, L, $R^5$, $Y^2$, $R^6$, $Y^1$ and $Y^3$ have the values listed in Table 1.

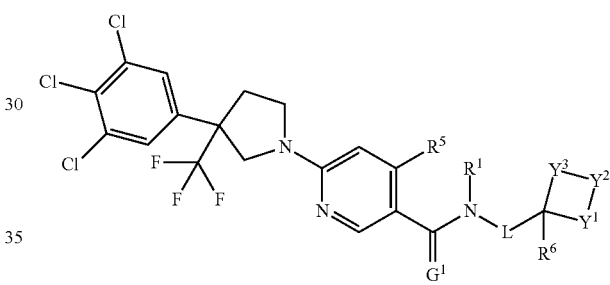
(I-B3)

Table 38:

Table 38 provides 1340 compounds of formula (I-C3) wherein $G^1$ is oxygen, $R^1$ is hydrogen, L, $R^5$, $Y^2$, $R^6$, $Y^1$ and $Y^3$ have the values listed in Table 1.

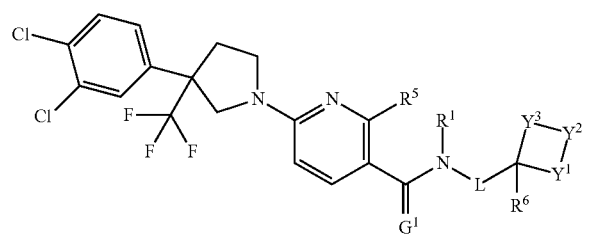
(I-L2)

Table 36:

Table 36 provides 1340 compounds of formula (I-A3) wherein $G^1$ is oxygen, $R^1$ is hydrogen, L, $R^5$, $Y^2$, $R^6$, $Y^1$ and $Y^3$ have the values listed in Table 1.

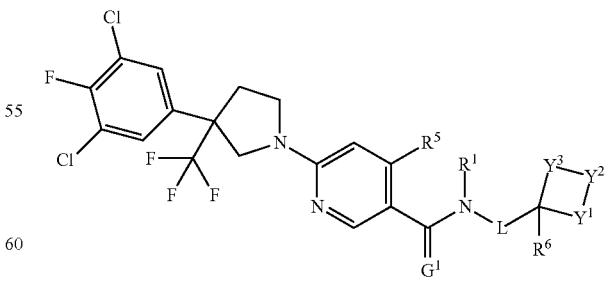
(I-C3)

Table 39:

Table 39 provides 1340 compounds of formula (I-D3) wherein $G^1$ is oxygen, $R^1$ is hydrogen, L, $R^5$, $Y^2$, $R^6$, $Y^1$ and $Y^3$ have the values listed in Table 1.

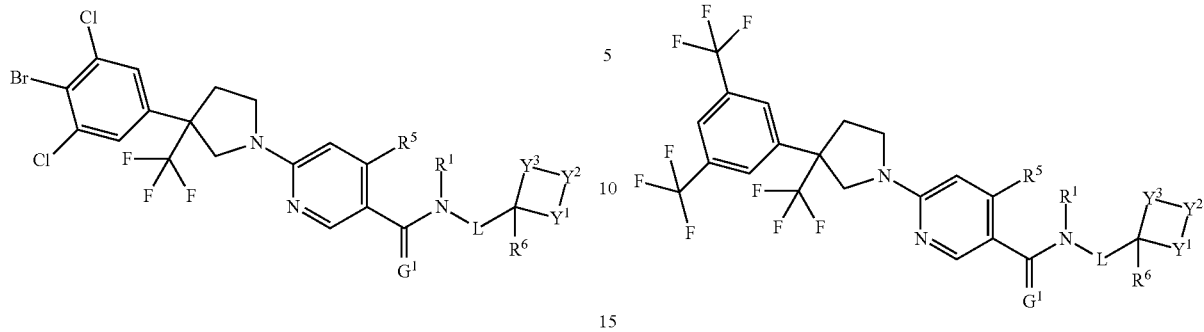

(I-D3)

(I-G3)

Table 40:

Table 40 provides 1340 compounds of formula (I-E3) wherein $G^1$ is oxygen, $R^1$ is hydrogen, L, $R^5$, $Y^2$, $R^6$, $Y^1$ and $Y^3$ have the values listed in Table 1.

Table 43:

Table 43 provides 1340 compounds of formula (I-H3) wherein $G^1$ is oxygen, $R^1$ is hydrogen, L, $R^5$, $Y^2$, $R^6$, $Y^1$ and $Y^3$ have the values listed in Table 1.

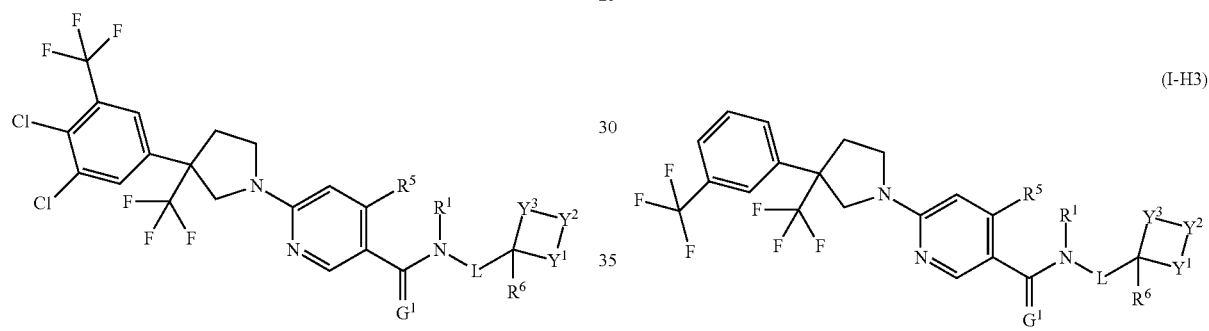

(I-E3)

(I-H3)

Table 41:

Table 41 provides 1340 compounds of formula (I-F3) wherein $G^1$ is oxygen, $R^1$ is hydrogen, L, $R^5$, $Y^2$, $R^6$, $Y^1$ and $Y^3$ have the values listed in Table 1.

Table 44:

Table 44 provides 1340 compounds of formula (I-I3) wherein $G^1$ is oxygen, $R^1$ is hydrogen, L, $R^5$, $Y^2$, $R^6$, $Y^1$ and $Y^3$ have the values listed in Table 1.

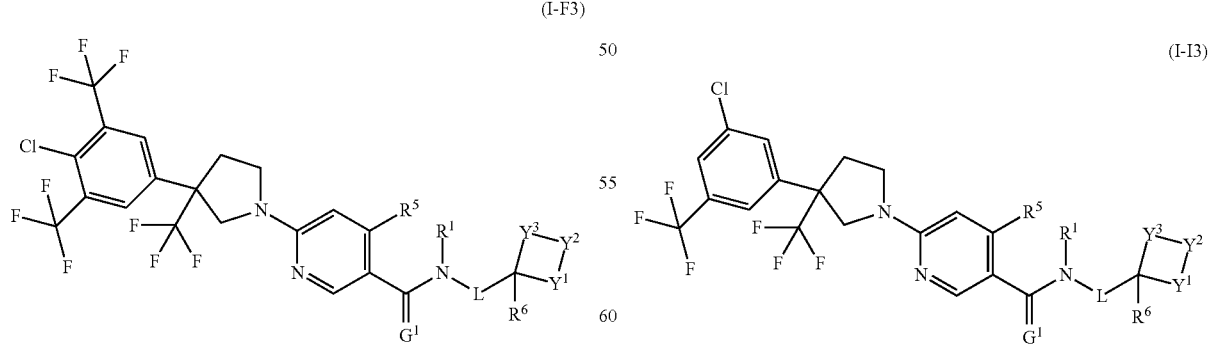

(I-F3)

(I-I3)

Table 42:

Table 42 provides 1340 compounds of formula (I-G3) wherein $G^1$ is oxygen, $R^1$ is hydrogen, L, $R^5$, $Y^2$, $R^6$, $Y^1$ and $Y^3$ have the values listed in Table 1.

Table 45:

Table 45 provides 1340 compounds of formula (I-J3) wherein $G^1$ is oxygen, $R^1$ is hydrogen, L, $R^5$, $Y^2$, $R^6$, $Y^1$ and $Y^3$ have the values listed in Table 1.

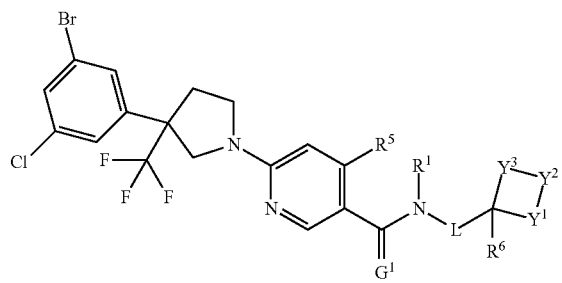

(I-J3)

Table 46:

Table 46 provides 1340 compounds of formula (I-K3) wherein $G^1$ is oxygen, $R^1$ is hydrogen, L, $R^5$, $Y^2$, $R^6$, $Y^1$ and $Y^3$ have the values listed in Table 1.

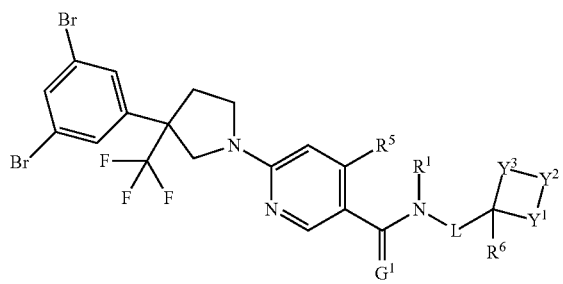

(I-K3)

Table 47:

Table 47 provides 1340 compounds of formula (I-L3) wherein $G^1$ is oxygen, $R^1$ is hydrogen, L, $R^5$, $Y^2$, $R^6$, $Y^1$ and $Y^3$ have the values listed in Table 1.

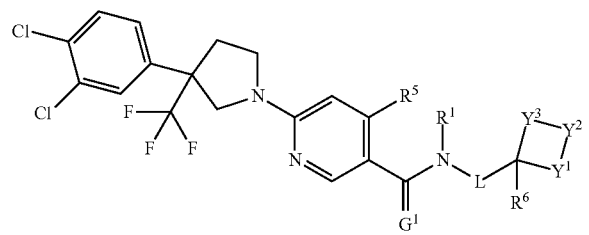

(I-L3)

Table 48:

Table 48 provides 1340 compounds of formula (I-A4) wherein $G^1$ is oxygen, $R^1$ is hydrogen, L, $R^5$, $Y^2$, $R^6$, $Y^1$ and $Y^3$ have the values listed in Table 1.

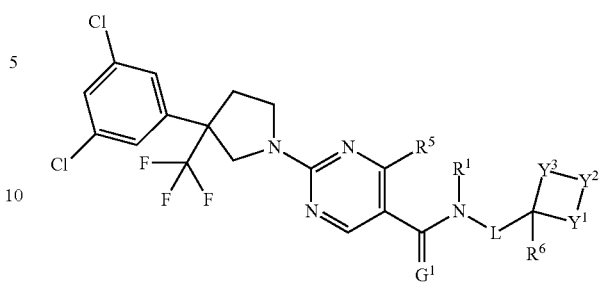

(I-A4)

Table 49:

Table 49 provides 1340 compounds of formula (I-B4) wherein $G^1$ is oxygen, $R^1$ is hydrogen, L, $R^5$, $Y^2$, $R^6$, $Y^1$ and $Y^3$ have the values listed in Table 1.

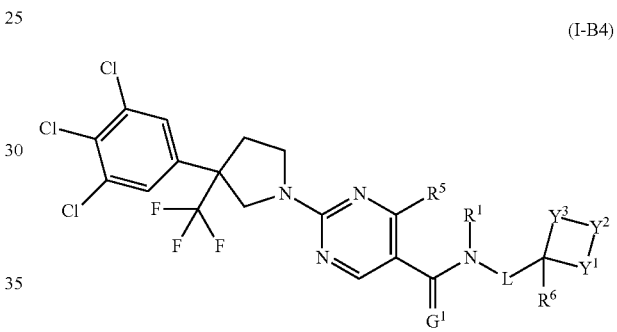

(I-B4)

Table 50:

Table 50 provides 1340 compounds of formula (I-C4) wherein $G^1$ is oxygen, $R^1$ is hydrogen, L, $R^5$, $Y^2$, $R^6$, $Y^1$ and $Y^3$ have the values listed in Table 1.

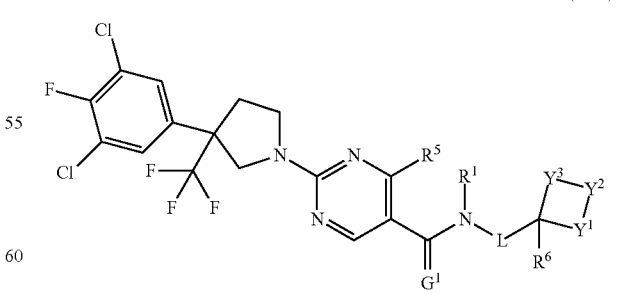

(I-C4)

Table 51:

Table 51 provides 1340 compounds of formula (I-D4) wherein $G^1$ is oxygen, $R^1$ is hydrogen, L, $R^5$, $Y^2$, $R^6$, $Y^1$ and $Y^3$ have the values listed in Table 1.

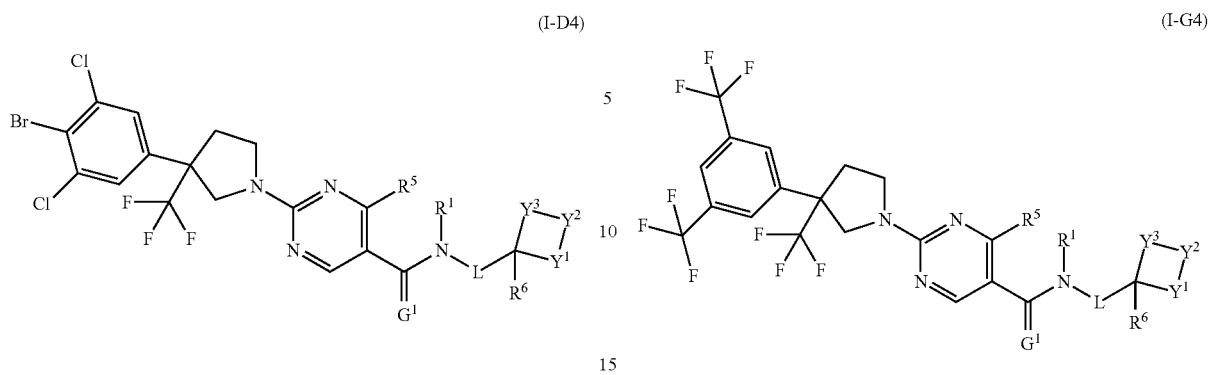

(I-D4)

(I-G4)

Table 52:

Table 52 provides 1340 compounds of formula (I-E4) wherein $G^1$ is oxygen, $R^1$ is hydrogen, L, $R^5$, $Y^2$, $R^6$, $Y^1$ and $Y^3$ have the values listed in Table 1.

Table 55:

Table 55 provides 1340 compounds of formula (I-H4) wherein $G^1$ is oxygen, $R^1$ is hydrogen, L, $R^5$, $Y^2$, $R^6$, $Y^1$ and $Y^3$ have the values listed in Table 1.

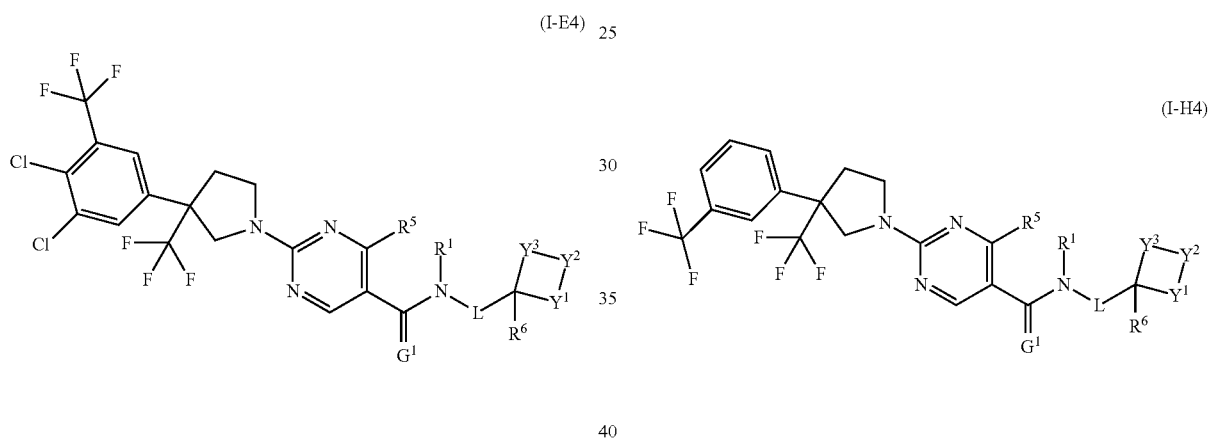

(I-E4)

(I-H4)

Table 53:

Table 53 provides 1340 compounds of formula (I-F4) wherein $G^1$ is oxygen, $R^1$ is hydrogen, L, $R^5$, $Y^2$, $R^6$, $Y^1$ and $Y^3$ have the values listed in Table 1.

Table 56:

Table 56 provides 1340 compounds of formula (I-I4) wherein $G^1$ is oxygen, $R^1$ is hydrogen, L, $R^5$, $Y^2$, $R^6$, $Y^1$ and $Y^3$ have the values listed in Table 1.

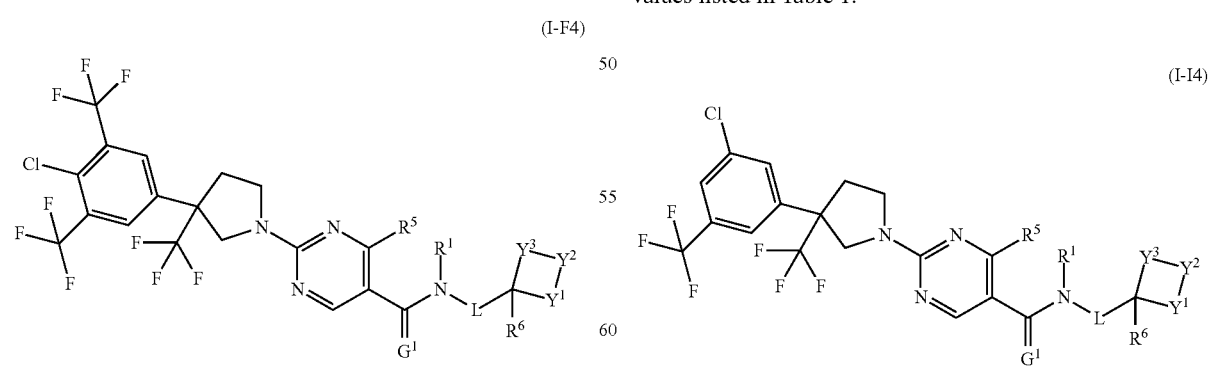

(I-F4)

(I-I4)

Table 54:

Table 54 provides 1340 compounds of formula (I-G4) wherein $G^1$ is oxygen, $R^1$ is hydrogen, L, $R^5$, $Y^2$, $R^6$, $Y^1$ and $Y^3$ have the values listed in Table 1.

Table 57:

Table 57 provides 1340 compounds of formula (I-J4) wherein $G^1$ is oxygen, $R^1$ is hydrogen, L, $R^5$, $Y^2$, $R^6$, $Y^1$ and $Y^3$ have the values listed in Table 1.

(I-J4)

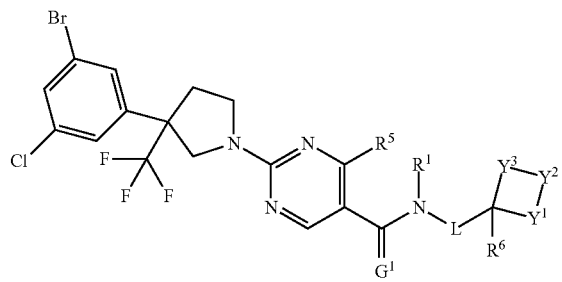

Table 58:

Table 58 provides 1340 compounds of formula (I-K4) wherein $G^1$ is oxygen, $R^1$ is hydrogen, L, $R^5$, $Y^2$, $R^6$, $Y^1$ and $Y^3$ have the values listed in Table 1.

(I-K4)

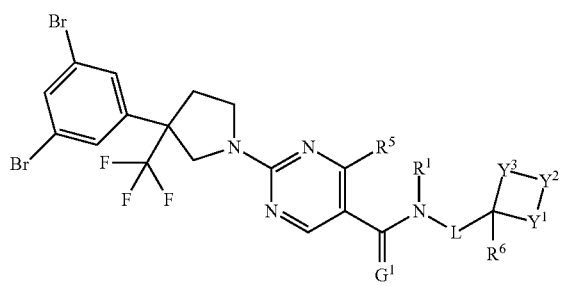

Table 59:

Table 59 provides 1340 compounds of formula (I-L4) wherein $G^1$ is oxygen, $R^1$ is hydrogen, L, $R^5$, $Y^2$, $R^6$, $Y^1$ and $Y^3$ have the values listed in Table 1.

(I-L4)

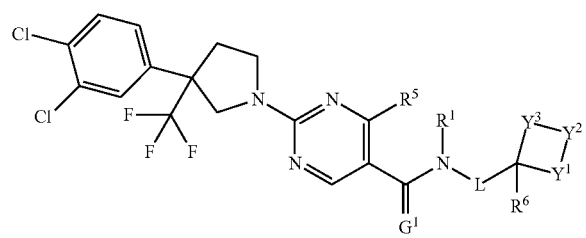

Compounds of formula I include at least one chiral centre and may exist as compounds of formula I* or compounds of formula I**.

(I*)

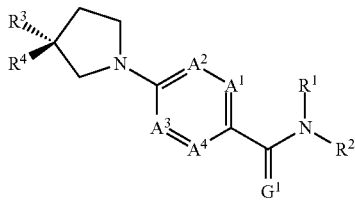

(I**)

The invention includes mixtures of compounds I* and I** in any ratio e.g. in a molar ratio of 1:99 to 99:1, e.g. 10:1 to 1:10, e.g. a substantially 50:50 molar ratio.

In an enantiomerically enriched mixture of formula I, the molar proportion of compound I compared to the total amount of both enantiomers is for example greater than 50%, e.g. at least 55, 60, 65, 70, 75, 80, 85, 90, 95, 96, 97, 98, or at least 99%. Likewise, in enantiomerically enriched mixture of formula I*, the molar proportion of the compound of formula I* compared to the total amount of both enantiomers is for example greater than 50%, e.g. at least 55, 60, 65, 70, 75, 80, 85, 90, 95, 96, 97, 98, or at least 99%.

Where $Y^1$, $Y^2$ or $Y^3$ is SO, the invention includes mixtures of the cis and trans isomer in any ratio, e.g. in a molar ratio of 1:99 to 99:1, e.g. 10:1 to 1:10, e.g. a substantially 50:50 molar ratio, e.g. in some cases the mixture may be cis enriched, in other cases the mixture may be trans enriched. For example, in trans enriched mixtures of formula I, e.g. when $Y^1$, $Y^2$ or V is SO, the molar proportion of the trans compound in the mixture compared to the total amount of both cis and trans is for example greater than 50%, e.g. at least 55, 60, 65, 70, 75, 80, 85, 90, 95, 96, 97, 98, or at least 99%. Likewise, in cis enriched mixtures of formula I, e.g. when $Y^1$, $Y^2$ or $Y^3$ is SO, the molar proportion of the cis compound in the mixture compared to the total amount of both cis and trans is for example greater than 50%, e.g. at least 55, 60, 65, 70, 75, 80, 85, 90, 95, 96, 97, 98, or at least 99%. The same applies to trans and cis enriched mixtures of formula I* respectively. Furthermore, enantiomerically enriched mixtures, e.g. enriched for the compound of formula I, may be also be enriched for the trans sulphoxide. Likewise, enantiomerically enriched mixtures, e.g. enriched for the compound of formula I, may be also be enriched for the cis sulphoxide. Reference herein to compounds of formula (I) also includes reference to enantiomerically enriched mixtures of formula (I)

Enantiomerically enriched mixtures of compounds of formula (I*) or (I**) may be prepared, for example, according to schemes 4 or 5 by formation of enantiomerically enriched mixtures of intermediates VI, X and XII to XXI. The preparation of enantioenriched compounds XII to XIV, XVI to XVIII, XX and XXI can be achieved via an asymmetric reaction, using methods known to a person skilled in the art, see for example in Organic Letters (2008), 10(7), 1389-1391 or following methods as shown in Schemes 1 to 15.

The compounds of the invention may be made by a variety of methods as shown in Schemes 1 to 15.

In all the following schemes, $A^1$, $A^2$, $A^3$ and $A^4$ are as described for compounds of formula (I), and Q can be a leaving group, for example a halogen, such as bromo, iodo, chloro or described by one of the two groups:

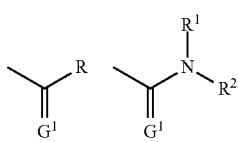

wherein $G^1$ is oxygen and R is OH, $C_1$-$C_6$alkoxy or Cl, F or Br, and $R^1$ and $R^2$ are as described for compounds of formula (I).

(Hunig's base). Preferred solvents are N,N-dimethylacetamide, tetrahydrofuran, dioxane, 1,2-dimethoxyethane, ethyl acetate and toluene. The reaction is carried out at a temperature of from 0° C. to 100° C., preferably from 15° C. to 30° C., in particular at ambient temperature. Amines of formula (III) are known in the literature or can be prepared using methods known to a person skilled in the art.

2) Acid halides of formula (II), wherein $G^1$ is oxygen and R is Cl, F or Br, may be made from carboxylic acids of formula (II), wherein $G^1$ is oxygen and R is OH, under standard

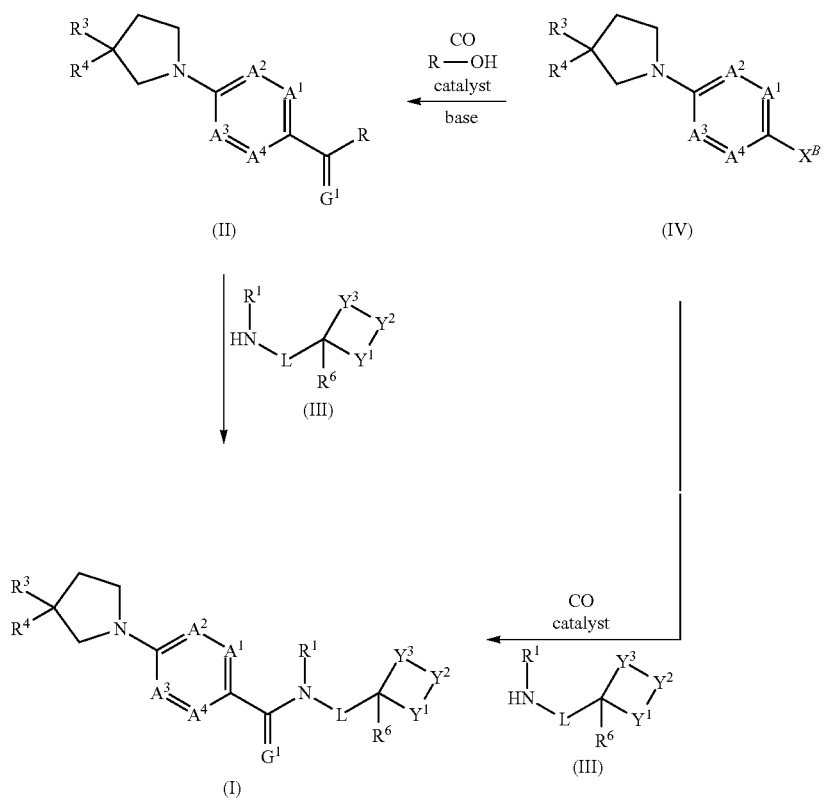

Scheme 1

1) Compounds of formula (I) wherein $G^1$ is oxygen, can be prepared by reacting a compound of formula (II) wherein $G^1$ is oxygen and R is OH, $C_1$-$C_6$alkoxy or Cl, F or Br, with an amine of formula (III) as shown in Scheme 1. When R is OH such reactions are usually carried out in the presence of a coupling reagent, such as N,N'-dicyclohexylcarbodiimide ("DCC"), 1-ethyl-3-(3-dimethylamino-propyl)carbodiimide hydrochloride ("EDC") or bis(2-oxo-3-oxazolidinyl)phosphonic chloride ("BOP—Cl"), in the presence of a base, and optionally in the presence of a nucleophilic catalyst, such as hydroxybenzotriazole ("HOBT"). When R is Cl, such reactions are usually carried out in the presence of a base, and optionally in the presence of a nucleophilic catalyst. Alternatively, it is possible to conduct the reaction in a biphasic system comprising an organic solvent, preferably ethyl acetate, and an aqueous solvent, preferably a solution of sodium hydrogen carbonate. When R is $C_1$-$C_6$alkoxy it is sometimes possible to convert the ester directly to the amide by heating the ester and amine together in a thermal process. Suitable bases include pyridine, triethylamine, 4-(dimethylamino)-pyridine ("DMAP") or diisopropylethylamine conditions, such as treatment with thionyl chloride or oxalyl chloride. A preferred solvent is dichloromethane. The reaction is carried out at a temperature of from 0° C. to 100° C., preferably from 15° C. to 30° C., in particular at ambient temperature.

3) Carboxylic acids of formula (II), wherein $G^1$ is oxygen and R is OH, may be formed from esters of formula (II), wherein $G^1$ is oxygen and R is $C_1$-$C_6$alkoxy. It is known to a person skilled in the art that there are many methods for the hydrolysis of such esters depending on the nature of the alkoxy group. One widely used method to achieve such a transformation is the treatment of the ester with an alkali hydroxide, such as lithium hydroxide, sodium hydroxide or potassium hydroxide, in a solvent, such as ethanol or tetrahydrofuran, in the presence of water. Another is the treatment of the ester with an acid, such as trifluoroacetic acid, in a solvent, such as dichloromethane, followed by addition of water. The reaction is carried out at a temperature of from 0° C. to 150° C., preferably from 15° C. to 100° C., in particular at 50° C.

4) Compounds of formula (II) wherein $G^1$ is oxygen and R is $C_1$-$C_6$alkoxy, can be prepared by reacting a compound of formula (IV) wherein $X^B$ is a leaving group, for example a halogen, such as bromo, with carbon monoxide and an alcohol of formula R—OH, such as ethanol, in the presence of a catalyst, such as bis(triphenylphosphine)palladium(II) dichloride, and a base, such as pyridine, triethylamine, 4-(dimethylamino)-pyridine ("DMAP") or diisopropylethylamine (Hunig's base). The reaction is carried out at a temperature of from 50° C. to 200° C., preferably from 100° C. to 150° C., in particular at 115° C. The reaction is carried out at a pressure of from 50 to 200 bar, preferably from 100 to 150 bar, in particular at 120 bar. Alternatively, Compounds of formula (II) wherein $G^1$ is oxygen and R is $C_1$-$C_6$alkoxy, can be made as described in the literature (e.g.: Journal of Medicinal Chemistry (1970), 13(5), 794-800).

5) Alternatively, compounds of formula (I) wherein $G^1$ is oxygen, can be prepared by reacting a compound of formula (IV) wherein $X^B$ is a leaving group, for example a halogen, such as bromo, with carbon monoxide and an amine of formula (III), in the presence of a catalyst, such as palladium(II) acetate or bis(triphenylphosphine)palladium(II) dichloride, optionally in the presence of a ligand, such as triphenylphosphine, and a base, such as sodium carbonate, pyridine, triethylamine, 4-(dimethylamino)-pyridine ("DMAP") or diisopropylethylamine (Hunig's base), in a solvent, such as water, N,N-dimethylformamide or tetrahydrofuran. The reaction is carried out at a temperature of from 50° C. to 200° C., preferably from 100° C. to 150° C. The reaction is carried out at a pressure of from 50 to 200 bar, preferably from 100 to 150 bar.

6) Compounds of formula (IV) wherein $X^B$ is a leaving group, for example a halogen, such as bromo, can be made as described in the literature (e.g.: Journal of Medicinal Chemistry (1970), 13(5), 794-800).

Scheme 2

(V)

(VI)

(I)

7) Alternatively, compounds of formula (I) wherein $G^1$ is oxygen, can be prepared by reaction of compound of formula (V) wherein $G^1$ is oxygen and wherein $X^B$ is a leaving group, for example a halogen, such as bromo, with an amine compound of formula (VI) as shown in Scheme 2 in the absence or the presence of a catalyst, such as palladium(II) acetate or bis-(triphenylphosphine)palladium(II) dichloride, optionally in the presence of a ligand, such as triphenylphosphine, and a base, such as sodium carbonate, pyridine, triethylamine, 4-(dimethylamino)-pyridine ("DMAP") or diisopropylethylamine (Hunig's base), in a solvent, such as water, N,N-dimethylformamide or tetrahydrofuran. The reaction is carried out at a temperature of from 50° C. to 200° C., preferably from 100° C. to 150° C. The reaction is carried out at a pressure of from 50 to 200 bar, preferably from 100 to 150 bar.

Compounds of formula (VI) can be prepared according to a method developed in the literature: Tetrahedron (1996), 52, (1), 59-70 and Tetrahedron Letters (1993), 34, (20), 3279-82.

8) Compounds of formula (V) wherein $G^1$ is oxygen and $X^B$ is a leaving group, for example a halogen, such as bromo, can be prepared as described in WO09080250.

Scheme 3

(VII)

(IX)

(Ia)

(VIII)

(IX)

9) Compounds of formula (Ia) can be prepared by reaction of compound of formula (VIII) wherein $R^{1'}$, $R^{2'}$ and $R^{3'}$ are independently of each other optionally substituted alkyl or optionally substituted phenyl groups, with styrene of formula (IX) according to a method developed in the literature: Journal of Medicinal Chemistry (1990), 33(2), 849-54.

10) Compounds of formula (Ia) can be prepared by reaction of compound of formula (VII) wherein $R^{4'}$ is optionally substituted alkyl group, $R^{1'}$, $R^{2'}$ and $R^{3'}$ are independently of each other optionally substituted alkyl or optionally substituted phenyl groups, with styrene of formula (IX) according to a method developed in the literature: Tetrahedron (1996), 52, (1), 59-70 and Tetrahedron Letters (1993), 34, (20), 3279-82.

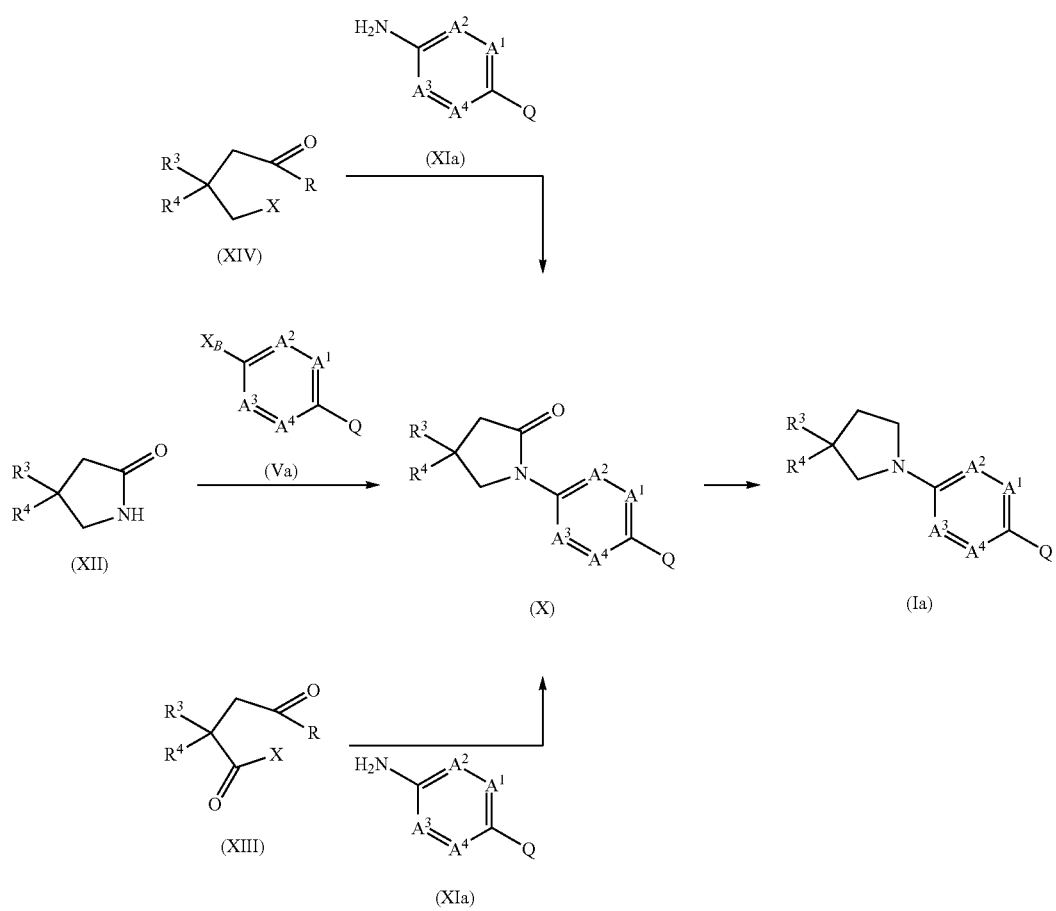

Scheme 4

11) Compounds of formula (Ia) can be prepared by reduction of compounds of formula (X) with a metal hydride, for instance according to a method developed in the literature: Journal of Pharmaceutical Sciences (1978), 67(7), 953-6.

12) Compounds of formula (X) can be prepared by reaction of compound of formula (XII) with a compound of formula (Va) wherein $X^B$ is a leaving group, for example a halogen, such as bromo, as described in 7).

Compounds of formula (XII) can be prepared by many methods as described in the literature (Bioorganic & Medicinal Chemistry Letters (2010), 20(1), 362-365).

13) Compounds of formula (X) can be prepared by reaction of compound of formula (XIII) wherein R is OH, $C_1$-$C_6$alkoxy or Cl, F or Br, with a compound of formula (XIa) under standard reductive amination conditions.

Compounds of formula (XIII) can be prepared by many methods as described in the literature (US patent US 2005148792).

14) Compounds of formula (X) can be prepared by reaction of compound of formula (XIV) wherein R is OH, $C_1$-$C_6$alkoxy or Cl, F or Br, and X is a leaving group, such as a mesylate, a tosylate or an halogen with a compound of formula (XIa) under standard substitution reaction conditions.

Scheme 5

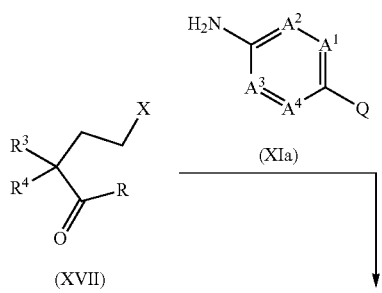

-continued

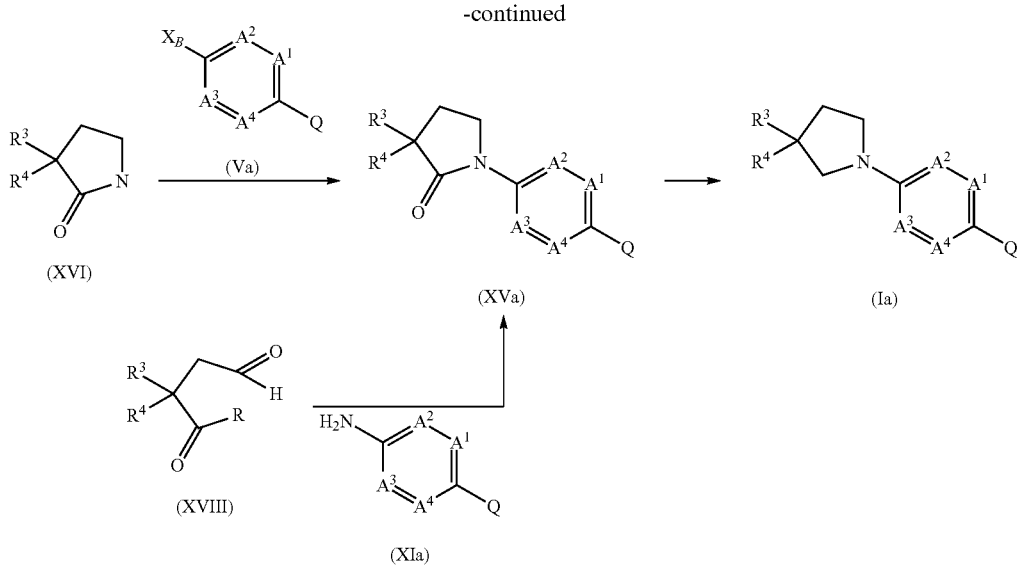

15) Compounds of formula (Ia) can be prepared by reduction of compounds of formula (XVa) with a metal hydride, for instance according to a method developed in the literature: Tetrahedron: Asymmetry (1999), 10(20), 3877-3881

16) Compounds of formula (XVa) can be prepared by reaction of compound of formula (XVI) with a compound of formula (Va) wherein $X^B$ is a leaving group, for example a halogen, such as bromo, as described in 7).

Compounds of formula (XVI) can be prepared by many methods as described in the literature (Tetrahedron: Asymmetry (1999), 10(20), 3877-3881).

17) Compounds of formula (XVa) can be prepared by reaction of compound of formula (XVIII) wherein R is OH, $C_1$-$C_6$alkoxy or Cl, F or Br, with a compound of formula (XIa) under standard reductive amination conditions.

Compounds of formula (XVIII) can be prepared by many methods as described in the literature.

18) Compounds of formula (XVa) can be prepared by reaction of compound of formula (XVII) wherein R is OH, $C_1$-$C_6$alkoxy or Cl, F or Br, and X is a leaving group, such as a mesylate, a tosylate or an halogen with a compound of formula (XIa) under standard substitution reaction conditions.

Scheme 6

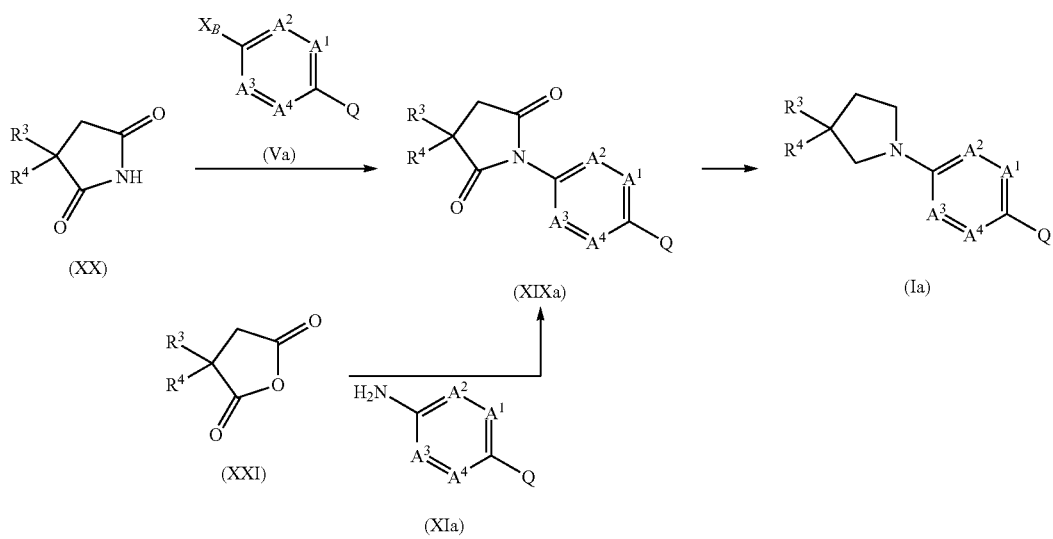

19) Compounds of formula (Ia) can be prepared by reduction of compounds of formula (XIXa) with a metal hydride, for instance according to a method developed in the literature (ARKIVOC, 2003, 5, And U.S. Pat. No. 4,524,206).

20) Compounds of formula (XIXa) can be prepared by reaction of compound of formula (XX) with a compound of formula (Va) wherein $X^B$ is a leaving group, for example a halogen, such as bromo, as described in 7).

21) Compounds of formula (XIXa) can be prepared by reaction of compound of formula (XXI) with a compound of formula (XIa) under standard substitution reaction conditions.

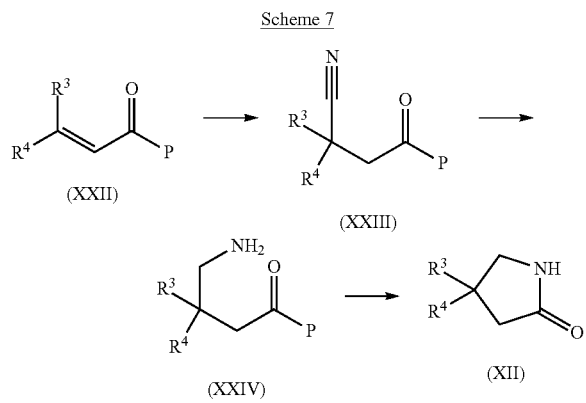

Scheme 7

(XXII) → (XXIII)

(XXIV) → (XII)

22) Compounds of formula (XII) can be prepared by cyclization of compound (XXIV) wherein P is $C_1$-$C_6$alkoxy, N-pyrrolyl, N-azolyl (N-imidazolyl, N-1,2-4-triazolyl, N-benzotriazolyl, $C_1$-$C_6$alkylsulfinyl under standard acidic or basic conditions.

23) Compounds of formula (XXIV) wherein P is $C_1$-$C_6$alkoxy, N-pyrrolyl, N-imidazolyl, N-1,2-4-triazolyl, N-benzotriazolyl, $C_1$-$C_6$alkylsulfinyl can be prepared by selective reduction of compounds of formula (XXIII) wherein P is $C_1$-$C_6$alkoxy, N-pyrrolyl, N-imidazolyl, N-1,2-4-triazolyl, N-benzotriazolyl, $C_1$-$C_6$alkylsulfinyl. Suitable reducing agents include iron and zinc in the presence of a strong acid, Raney nickel under the atmosphere of hydrogen or a mixture of titanium (IV) chloride with zinc or titanium (III) chloride. A reduction with Raney nickel is performed in suitable alcoholic solvents, such as methanol or ethanol at dilution between 0.1 M to 1 M and in most cases it is advantageous to conduct the reaction preferably 0.3 M to 0.5 M, at temperatures from 20° C. to 60° C. Hydrogen pressure used is from 1 bar to 20 bars and the amount of catalyst used is between 5 and 20 weight percent. The reaction time is usually between 10 min and 6 hours, preferably between 30 min and 2 hours. The extent of reduction could potentially be controlled by varying temperature and pressure of hydrogen. A reduction with zinc and acid is carried out in suitable polar solvents, such as dimethylformamide, which are miscible with water. The pH of a solution is kept at 1-2 and the amount of zinc powder used is between 2 and 10 molar equivalents, preferably between 2 and 4 molar equivalents. The reaction time is usually between 30 min and 4 hours, preferably between 30 min and 1 hour.

24) Alternatively Compounds of formula (XII) can be obtained by a reductive cyclization of compound of formula (XXIII) under the conditions described in 23).

25) Compounds of formula (XXIII) wherein P is $C_1$-$C_6$alkoxy, N-pyrrolyl, N-imidazolyl, N-1,2-4-triazolyl, N-benzotriazolyl, $C_1$-$C_6$alkylsulfinyl can be prepared by reaction of compound of formula (XXII) wherein P is $C_1$-$C_6$alkoxy, N-pyrrolyl, N-imidazolyl, N-1,2-4-triazolyl, N-benzotriazolyl, $C_1$-$C_6$alkylsulfinyl with a source of cyanide. Suitable cyanide sources include, but are not limited to alkali metal cyanides, trimethylsilyl and tert-butyldimethylsilyl cyanides, hydrogen cyanide, $CNCO_2Et$ and acetone cyanohydrin. This reaction can be done in the presence of a chiral catalyst to obtain enantioenriched compounds of formula (XXIII).

Depending from the catalyst used, suitable solvents include dioxane, tetrahydrofuran, dichloromethane, t-butylmethyl ether, 1,2-dichloroethane, dimethoxyethane, xylenes and toluene. In certain cases additives such as cesium fluoride, cesium chloride, lithium phenolate or 2,6-dimethylphenol are often required. In most cases it is advantageous to conduct the reaction in a suitable solvent at dilution between 0.1 M to 1 M, preferably 0.3 M to 0.5 M. The reaction temperature could be from −40° C. to 100° C., preferably between −20° C. and 50° C. The reaction time is usually between 1 hour and 96 hours, preferably between 6 hours and 24 hours. The amount of catalyst is usually between 0.02 and 0.2 molar equivalents, preferably between 0.05 and 0.1 molar equivalents.

Suitable conditions for this asymmetric reaction are disclosed in the literature: (a) Sammis, G. M.; Jacobsen, E. N. J. Am. Chem. Soc. 2003, 125, 4442. (b) Sammis, G. M.; Danjo, H.; Jacobsen, E. N. J. Am. Chem. Soc. 2004, 126, 9928. (c) Mazet, C.; Jacobsen, E. N. Angew. Chem., Int. Ed. 2008, 47, 1762. (d) Madhavana, N.; Weck, M. Adv. Synth. Catal. 2008, 350, 419. (e) Mita, T.; Sasaki, K.; Kanai, M.; Shibasaki, M. J. Am. Chem. Soc. 2005, 127, 514. (f) Fujimori, I.; Mita, T.; Maki, K.; Shiro, M.; Sato, A.; Furusho, S.; Kanaia, M.; Shibasaki, M. Tetrahedron 2007, 63, 5820. (g) Tanaka, Y.; Kanai, M.; Shibasaki, M. J. Am. Chem. Soc. 2008, 130, 6072. (h) Bernardi, L.; Fini, F.; Fochi, M.; Ricci, A. Synlett 2008, 1857. (i) Jun Wang, Wei Li, Yanling Liu, Yangyang Chu, Lili Lin, Xiaohua Liu, and Xiaoming Feng Organic Letters (2010), 12, (6), 1280-1283. (j) anaka, Yuta; Kanai, Motomu; Shibasaki, Masakatsu, Journal of the American Chemical Society 2010, 132, (26), 8862-8863. (k) Brian A. Provencher, Keith J. Bartelson, Yan Liu, Bruce M. Foxman, Li Deng, Angewandte Chemie International Edition.

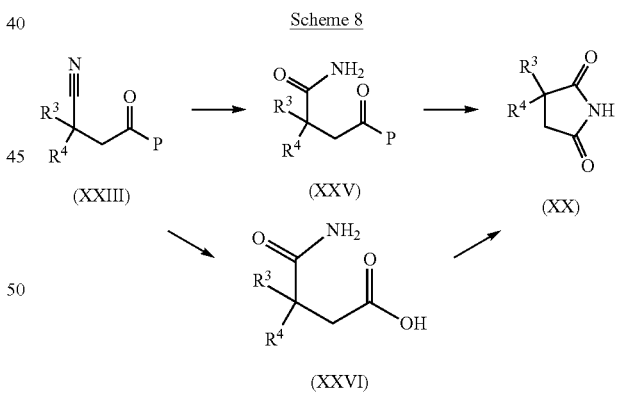

Scheme 8

(XXIII) → (XXV) → (XX)

(XXVI)

26) Compounds of formula (XX) can be obtained by a cyclization of compound of formula (XXV) wherein P is $C_1$-$C_6$alkoxy, N-pyrrolyl, N-imidazolyl, N-1,2-4-triazolyl, N-benzotriazolyl, $C_1$-$C_6$alkylsulfinyl under basic conditions such as those described in Tetrahedron, 39(19), 3055-7; 1983.

27) Compounds of formula (XXV) can be obtained by a selective hydrolysis of the nitrile function in compounds of formula (XXIII) by acidic or basic hydrolysis.

28) Alternatively, compounds of formula (XX) can be obtained by a cyclization of compounds of formula (XXVI) by a dehydrating reaction such as those described in Chemistry—A European Journal, 9(14), 3270-3281; 2003.

29) Compounds of formula (XXVI) can be obtained by complete hydrolysis of compound of formula (XXIII) under basic aqueous conditions.

Scheme 9

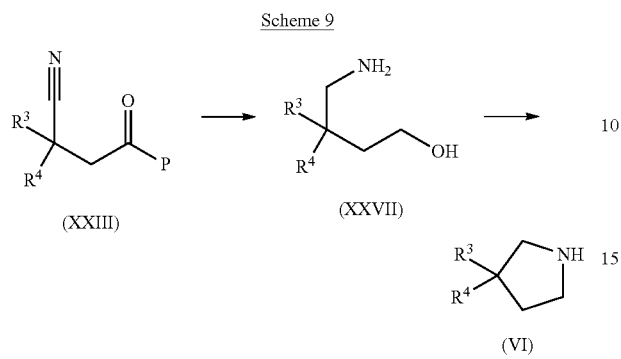

30) Compounds of formula (VI) can be obtained by treating a compound of formula (XXVII) with an activating agent such as thionyl chloride (SOCl$_2$) under the conditions described in J. Org. Chem. 2008, 73, 312-315.

31) Compounds of formula (XXVII) can be obtained by complete reduction of compounds of formula (XXIII) for example with a metal hydride such as lithium aluminum hydride (LiAlH$_4$). For instance according to a method developed in the literature in Journal of Medicinal Chemistry, 51(22), 7144-7153; 2008. Alternatively, suitable conditions involve the treatment of compounds of formula (XXIII) under an atmosphere of hydrogen gas in the presence of a metal catalyst, such as those described in the literature in Bioorganic Chemistry, 36(5), 241-251; 2008.

Scheme 10

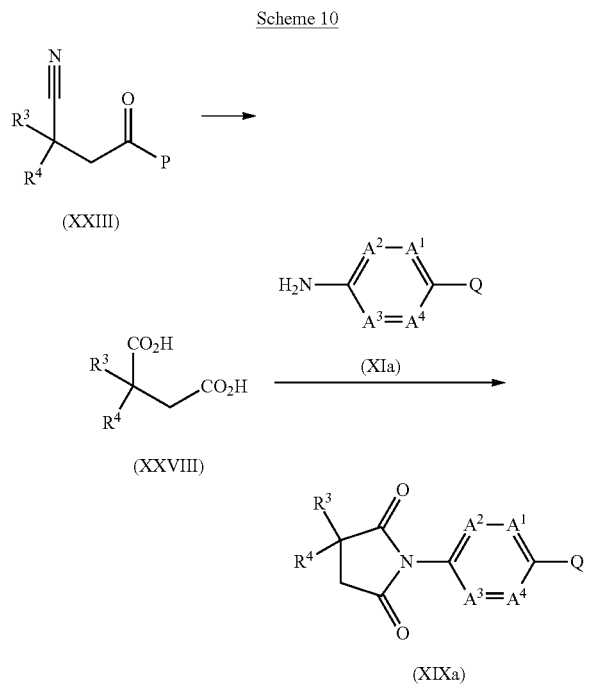

32) Compounds of formula (XIXa) can be obtained by reacting a compound of formula (XIa) and a compound of formula (XXVIII) in the presence of a suitable dehydrating agent such as thionyl chloride (SOCl$_2$). For instance according to a method described in Asian Journal of Chemistry, 19(6), 4939-4941; 2007.

33) Compounds of formula (XXVIII) can be obtained by hydrolysis of a compound of formula (XXIII) in the presence of aqueous mineral acid, such as aqueous sulphuric acid between 1% and 100% weight/weight, or hydrochloric acid between 1% and 100% weight/weight between 0.1 M to 5 M. In most cases it is advantageous to conduct the reaction preferably 0.3 M to 0.5 M, at temperatures from 20° C. to 120° C.

Scheme 11

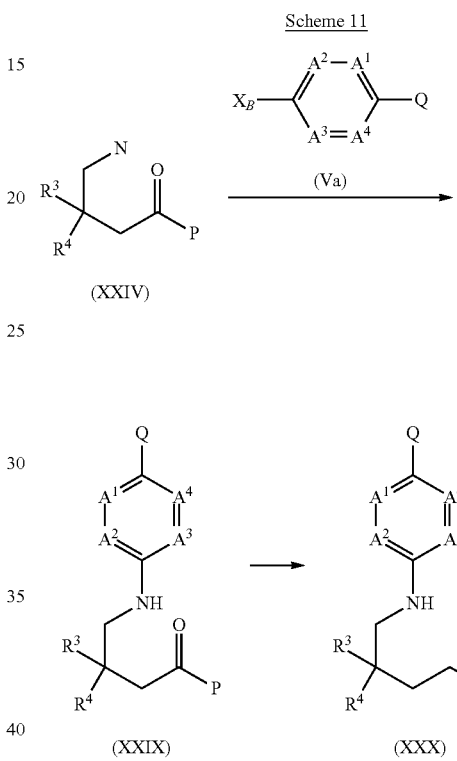

34) Compounds of formula (Ia) can be obtained by treating a compound of formula (XXX) with an activating agent such as thionyl chloride (SOCl$_2$) under the conditions described in the literature, such as in J. Org. Chem. 2008, 73, 312-315.

35) Compounds of formula (XXX) can be obtained by reducing a compound of formula (XXIX) with a suitable metal hydride such as Lithium aluminum hydride, for instance according to a method described in the literature in Journal of Medicinal Chemistry, 49(1), 399-406; 2006.

36) Compounds of formula (XXIX) can be obtained by reacting a compound of formula (XXIV) and a compound of formula (Va) in the presence of a metal catalyst and a base. Suitable conditions can be found in the literature in Organic Letters, 11(6), 1449-1452; 2009 and in Journal of the American Chemical Society, 132(1), 413-426; 2010.

Scheme 12

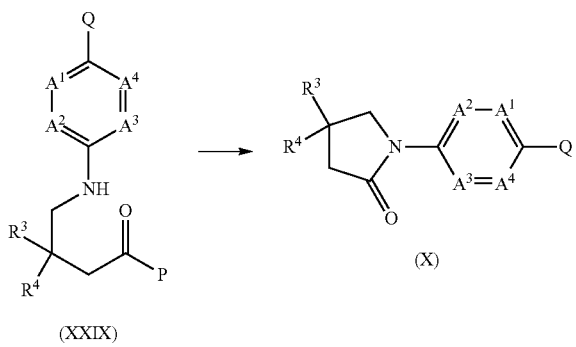

(XXIX) → (X)

37) Compounds of formula (X) can be obtained by cyclising a compound of formula (XXIX) under neutral conditions, such as those described in the literature in Bioorganic & Medicinal Chemistry Letters, 19(16), 4733-4739; 2009, or under basic conditions such as those described in Synlett, (4), 591-594; 2006.

Scheme 13.

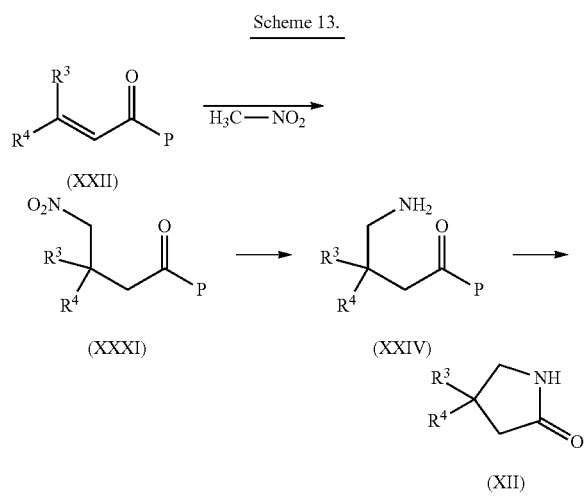

(XXII), (XXXI), (XXIV), (XII)

38) Compounds of formula (XII) can be prepared by cyclization of a compound of formula (XXIV) under basic, acidic or neutral conditions.

39) Compounds of formula (XXIV) can be prepared by reducing a compound of formula (XXXI). Suitable reducing agents include iron and zinc in the presence of a strong acid, a mixture of titanium (IV) chloride with zinc or titanium (III) chloride, or a late transition metal selected from Pd, Pt, Ni and Co and a source of hydride such as hydrogen gas, a silane, formic acid, a formate salt, or a borohydride salt. A reduction with Raney nickel is performed in suitable alcoholic solvents, such as methanol or ethanol, at temperatures from 20° C. to 60° C. Hydrogen pressure used is from 1 bar to 20 bar and the amount of catalyst used is between 5 and 20 weight percent. The reaction time is usually between 10 min and 6 hours, preferably between 30 min and 2 hours. The extent of reduction could potentially be controlled by varying temperature and pressure of hydrogen. A reduction with zinc and acid is carried out in suitable polar solvents, such as dimethylformamide, which are miscible with water. The pH of a solution is kept at 1-2 and the amount of zinc powder used is between 2 and 10 molar equivalents, preferably between 2 and 4 molar equivalents. The reaction time is usually between 30 min and 4 hours, preferably between 30 min and 2 hours.

Alternatively, the reduction can be carried out in the presence of a silane, such as triethylsilane, in the presence of a source of palladium, such as palladium supported on charcoal, in a suitable alcoholic solvent, such as methanol or ethanol, according to the conditions described in the literature in Journal of Organic Chemistry, 72(17), 6599-6601; 2007.

Alternatively, the reduction can be carried out in the presence of formic acid or a formate salt, such as ammonium formate, in the presence of a source of palladium, such as palladium supported on charcoal, in a suitable alcoholic solvent, such as methanol or ethanol, according to the conditions described in the literature in Synthesis (1986), (2), 133-5 and in Organic Letters, 3, 3153-3155; (2001).

Alternatively, the reduction can be carried out in the presence of a borohydride salt, such as sodium borohydride, in the presence of a nickel salt, such as nickel(II) dichloride hexahydrate, in a suitable alcoholic solvent, such as methanol or ethanol, according to the conditions described in the literature in Organic Letters, 3, 1825-1827; (2001).

Alternatively, the reduction can be carried out in the presence of a borohydride salt, such as sodium borohydride, in the presence of a cobalt salt, such as cobalt(II) dichloride, in a suitable alcoholic solvent, such as methanol or ethanol, according to the conditions described in the literature in Journal of Organic Chemistry, 62(24), 8565-8568; 1997.

40) Alternatively compounds of formula (XII) can be prepared by reducing and cyclizing compounds of formula (XXXI) under the reduction conditions described in 39).

41) Compounds of formula (XXXI) can be prepared by reacting a compound of formula (XXII) with nitromethane. In most other cases, however, it is necessary or useful to add a base to the reaction media. Suitable bases include amines, such as triethylamine, 2,5-dimethylpiperazine, tetramethylpiperidine, 4-dimethylamino pyridine, 1,8-Diazabicyclo[5.4.0]undeca-7-ene, metal alkoxides, such as sodium t-butoxide, metal carbonates, such as potassium carbonate or metal fluorides, such as cesium fluoride or cesium chloride and tetrabutylammonium fluoride. In most cases it is advantageous to conduct the reaction using nitromethane as a solvent at dilution between 0.1 M to 1 M, preferably 0.3 M to 0.5 M. Alternatively suitable organic solvents could be used, for example toluene, 1,2-dichloroethane, dichloromethane, tetrahydrofuran, methanol or ethyl acetate at a temperature from 0° C. to 100° C., preferably between 40 and 100° C., and at dilution of e.g. between 0.1 M to 1 M. The reaction time is usually between 12 and 96 hours, preferably between 24 and 72 hours. If a solvent other than nitromethane is used, the amount of nitromethane added is between 1.5 and 20 molar equivalents, preferably between 1.5 and 5 molar equivalents. The reaction can also be performed in a asymmetric fashion, usually in the presence of a chiral catalyst. Reaction with some chiral catalysts, notably bifunctional thiourea or urea catalysts, do not require any additives. The amount of catalyst is usually between 0.02 and 0.2 molar equivalents, preferably between 0.05 and 0.1 molar equivalents. In some instances an additional proton source such as 4-nitrophenol or t-butanol is needed or useful. Such methods have been described in the literature:

(a) Benedek Vakulya, Szilárd Varga and Tibor Soós, Journal of Organic Chemistry (2008), 73, (9), 3475-3480. (b) Tetrahedron Letters (2008), 49, (35), 5220-5223. (c) Roberto Ballini, Giovanna Bosica, Dennis Fiorini, Alessandro Palmieri, and Marino Petrini, Chem Rev 2005, 105, 933.

Scheme 14

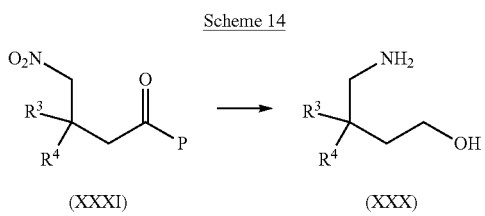

(XXXI) (XXX)

42) Compounds of formula (XXX) can be obtained by reduction of compound of formula (XXXI) using conditions described in 31).

Scheme 15

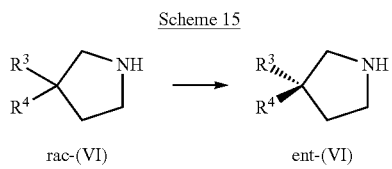

rac-(VI) ent-(VI)

43) Enantioenriched compounds of formula (VI) can be obtained by optical resolution of racemic compound (VI) in presence of a chiral acid through formation of a diastereoisomeric salt. The isolated diastereoisomeric salt is then separatively extracted in presence of a base to obtain compound (VI) as an enantiomericaly enriched mixture.

Suitable chiral acid for the formation of diastereoisomeric salt of compound (VI) can be for example, but not exclusively, (+)-mandelic acid, (−)-mandelic acid, (+)-camphorsulfonic acid, (−)-camphorsulfonic acid, (+)-tartric acid, (−)-tartric acid, (+)-dibenzoyltartaric acid, (−)-dibenzoyltartaric acid (−)-malic acid, (+)-lactic acid. Preferably the chiral acid is (−)-tartric acid or (+)-tartric acid. Alternatively, a preferred chiral acid can be (+)-dibenzoyltartaric acid or (−)-dibenzoyltartaric acid.

The amount of chiral acid is usually between 0.1 and 5 molar equivalent of compound (VI). Preferably the amount of chiral acid is between 0.5 and 1 molar equivalent of compound (VI).

Suitable organic solvents for the formation of the diastereoisomeric salt are for example toluene, dichloromethane, tetrahydrofuran, $C_1$-$C_6$ alcoholic solvents, acetone, ethyl acetate. Alternatively, binary or ternary mixtures of organic solvent can be used. The solvent is usually a $C_1$-$C_6$ alcoholic solvent. Preferably the solvent is methanol, ethanol, or 2-propanol.

The temperature of precipitation of the diastereoisomeric salt can be −30° C. and 150° C., is usually between −10° C. and 80° C. The preferred temperature for salt formation is between 0° C. and 50° C. The compounds according to the present invention show a potential insecticidal action and can therefore be used as an insecticide. Furthermore, the compounds according to the present invention can exhibit a strong control effect against harmful insects, without substantially imposing any harmful side effects to cultivated plants. The compounds of the present invention can thus be used for the control of a wide range of pest species, for example, harmful sucking insects, chewing insects, as well as other plant parasitic pests, storage insects, hygiene pests and the like, and can be applied for the purpose of disinfestations and extermination thereof.

Harmful animal pest are for example:

As for insects, coleopterans, for example, *Callosobruchus chinensis, Sitophilus zeamais, Tribolium castaneum, Epilachna vigintioctomaculata, Agriotes fuscicollis, Anomala rufocuprea, Leptinotarsa decemlineata, Diabrotica* spp., *Monochamus alternatus, Lissorhoptrus oryzophilus, Lyctus bruneus, Aulacophora femoralis*; lepidopterans, for example, *Lymantria dispar, Malacosoma neustria), Pieris rapae, Spodoptera litura, Mamestra brassicae, Chilo suppressalis), Pyrausta nubilalis, Ephestia cautella, Adoxophyes orana, Carpocapsa pomonella, Agrotisfucosa, Galleria mellonella, Plutella maculipennis, Heliothis virescens, Phyllocnistis citrella*; hemipterans, for example, *Nephotettix cincticeps, Nilaparvata lugens, Pseudococcus comstocki, Unaspis yanonensis, Myzus persicas, Aphis pomi, Aphis gossypii, Rhopalosiphum pseudobrassicas, Stephanitis nashi, Nezara* spp., *Trialeurodes vaporariorm, Psylla* spp.; thysanopterans, for example, *Thrips palmi, Franklinella occidental*; orthopterans, for example, *Blatella germanica, Periplaneta americana, Gryllotalpa Africana, Locusta migratoria migratoriodes*; isopterans, for example, *Reticulitermes speratus, Coptotermes formosanus*; dipterans, for example, *Musca domestica, Aedes aegypti, Hylemia platura, Culex pipiens, Anopheles sinensis, Culex tritaeniorhynchus, Liriomyza trifolii.*

As for acari, for example, *Tetranychus cinnabarinus, Tetranychus urticae, Panonychus citri, Aculops pelekassi, Tarsonemus* spp.

As for nematodes, for example, *Meloidogyne incognita, Bursaphelenchus lignicolus Mamiya et Kiyohara, Aphelenchoides besseyi, Heterodera glycines, Pratylenchus* spp.

Additionally, the compounds according to the present invention may show a good plant tolerance and favourable toxicity to warm-blooded animals and being tolerated well by the environment, and thus are suitable for protecting plants and plant parts. Application of the compounds of the invention may result in increasing the harvest yields, improving the quality of the harvested material.

Additionally, the compounds can be used for controlling animal pests, in particular insects, arachnids, helminths, nematodes and molluscs, which are encountered in agriculture, in horticulture, the field of veterinary medicine, in forests, in gardens and leisure facilities, in the protection of stored products and of materials, and in the hygiene sector. They may preferably be employed as plant protection agents. They may be active against normally sensitive and resistant species and against all or some stages of development.

These pests include inter alia:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscehdes obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp.,

*Atomaria* spp., *Attagenus* spp., *Bruchidius obtectus*, *Bruchus* spp., *Ceuthorhynchus* spp., *Cleonus mendicus*, *Conoderus* spp., *Cosmopolites* spp., *Costelytra zealandica*, *Curculio* spp., *Cryptorhynchus lapathi*, *Dermestes* spp., *Diabrotica* spp., *Epilachna* spp., *Faustinus cubae*, *Gibbium psylloides*, *Heteronychus arator*, *Hylamorpha elegans*, *Hylotrupes bajulus*, *Hypera postica*, *Hypothenemus* spp., *Lachnosterna consanguinea*, *Leptinotarsa decemlineata*, *Lissorhoptrus oryzophilus*, *Lixus* spp., *Lyctus* spp., *Meligethes aeneus*, *Melolontha melolontha*, *Migdolus* spp., *Monochamus* spp., *Naupactus xanthographus*, *Niptus hololeucus*, *Oryctes rhinoceros*, *Oryzaephilus surinamensis*, *Otiorrhynchus sulcatus*, *Oxycetonia jucunda*, *Phaedon cochleariae*, *Phyllophaga* spp., *Popillia japonica*, *Premnotrypes* spp., *Psylliodes chrysocephala*, *Ptinus* spp., *Rhizobius ventralis*, *Rhizopertha dominica*, *Sitophilus* spp., *Sphenophorus* spp., *Sternechus* spp., *Symphyletes* spp., *Tenebrio molitor*, *Tribolium* spp., *Trogoderma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus*.

From the order of the Diptera, for example, *Aedes* spp., *Anopheles* spp., *Bibio hortulanus*, *Calliphora erythrocephala*, *Ceratitis capitata*, *Chrysomyia* spp., *Cochliomyia* spp., *Cordylobia anthropophaga*, *Culex* spp., *Cuterebra* spp., *Dacus oleae*, *Dermatobia hominis*, *Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit*, *Pegomyia hyoscyami*, *Phorbia* spp., *Stomoxys* spp., *Tabanus* spp., *Tannia* spp., *Tipula paludosa*, *Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale*, *Ancylostoma ceylanicum*, *Acylostoma braziliensis*, *Ancylostoma* spp., *Ascaris lubricoides*, *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.

It may be furthermore possible to control protozoa, such as *Eimeria*.

From the order of the Heteroptera, for example, *Anasa tristis*, *Antestiopsis* spp., *Blissus* spp., *Calocoris* spp., *Campylomma livida*, *Cavelerius* spp., *Cimex* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Nezara* spp., *Oebalus* spp., Pentomidae, *Piesma quadrata*, *Piezodorus* spp., *Psallus seriatus*, *Pseudacysta persea*, *Rhodnius* spp., *Sahlbergella singularis*, *Scotinophora* spp., *Stephanitis nashi*, *Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus*, *Geococcus coffeae*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva fimbriolata*, *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*.

From the order of the Hymenoptera, for example, *Diprion* spp., *Hoplocampa* spp., *Lasius* spp., *Mono-morium pharaonis*, *Vespa* spp.

From the order of the Isopoda, for example, *Armadillidium vulgare*, *Oniscus asellus*, *Porcellio scaber*.

From the order of the Isoptera, for example, *Reticulitermes* spp., *Odontotermes* spp.

From the order of the Lepidoptera, for example, *Acronicta major*, *Aedia leucomelas*, *Agrotis* spp., *Alabama argillacea*, *Anticarsia* spp., *Barathra brassicae*, *Bucculatrix thurberiella*, *Bupalus piniarius*, *Cacoecia podana*, *Capua reticulana*, *Carpocapsa pomonella*, *Chematobia brumata*, *Chilo* spp., *Choristoneura fumiferana*, *Clysia ambiguella*, *Cnaphalocerus* spp., *Earias insulana*, *Ephestia kuehniella*, *Euproctis chrysorrhoea*, *Euxoa* spp., *Feltia* spp., *Galleria mellonella*, *Helicoverpa* spp., *Heliothis* spp., *Hofmannophila pseudospretella*, *Homona magnanima*, *Hyponomeuta padella*, *Laphygma* spp., *Lithocolletis blancardella*, *Lithophane antennata*, *Loxagrotis albicosta*, *Lymantria* spp., *Malacosoma neustria*, *Mamestra brassicae*, *Mocis repanda*, *Mythimna separata*, *Oria* spp., *Oulema oryzae*, *Panolis flammea*, *Pectinophora gossypiella*, *Phyllocnistis citrella*, *Pieris* spp., *Plutella xylostella*, *Prodenia* spp., *Pseudaletia* spp., *Pseudoplusia includens*, *Pyrausta nubilalis*, *Spodoptera* spp., *Thermesia gemmatalis*, *Tinea pellionella*, *Tineola bisselliella*, *Tortrix viridana*, *Trichoplusia* spp.

From the order of the Orthoptera, for example, *Acheta domesticus*, *Blatta orientalis*, *Blattella germanica*, *Gryllotalpa* spp., *Leucophaea maderae*, *Locusta* spp., *Melanoplus* spp., *Periplaneta americana*, *Schistocerca gregaria*.

From the order of the Siphonaptera, for example, *Ceratophyllus* spp., *Xenopsylla cheopis*. From the order of the Symphyla, for example, *Scutigerella immaculata*.

From the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.

From the order of the Thysanura, for example, *Lepisma saccharina*.

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

All plants and plant parts can be treated in accordance with the invention.

Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights.

Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds. Treatment according to the invention of the plants and plant parts with the active compounds is carried out directly or by allowing the compounds to act on their surroundings, habitat or storage space by the customary treatment methods, for example by immersion, spraying, evaporation, fogging, scattering, painting on, injecting and, in the case of propagation material, in particular in the case of seed, also by applying one or more coats.

In a preferred embodiment, wild plant species and plant cultivars, or those obtained by conventional biological breeding methods, such as crossing or protoplast fusion, and parts thereof, are treated.

In a further preferred embodiment, transgenic plants and plant cultivars obtained by genetic engineering methods, if appropriate in combination with conventional methods (Genetically Modified Organisms), and parts thereof, are treated. Particularly preferably, plants of the plant cultivars which are in each case commercially available or in use are treated according to the invention. Plant cultivars are understood as meaning plants having novel properties ("traits") which have been obtained by conventional breeding, by mutagenesis or by recombinant DNA techniques. These can be cultivars, bio- or genotypes. Depending on the plant species or plant cultivars, their location and growth conditions (soils, climate, vegetation period, diet), the treatment according to the invention may also result in superadditive "synergistic" effects.

Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The preferred transgenic plants or plant cultivars (obtained by genetic engineering) which are to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products.

Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape.

Traits that are emphasized in particular are the increased defense of the plants against insects, arachnids, nematodes and slugs and snails by virtue of toxins formed in the plants, in particular those formed in the plants by the genetic material from *Bacillus thuringiensis* (for example by the genes Cry1A (a), Cry1A(b), Cry1A(c), Cry11A, Cry111A, CryIIIB2, Cry9c, Cry2Ab, Cry3Bb and Cry1F and also combinations thereof) (referred to hereinbelow as "Bt plants").

Traits that are also particularly emphasized are the increased defense of the plants against fungi, bacteria and viruses by systemic acquired resistance (SAR), systemin, phytoalexins, elicitors and resistance genes and correspondingly expressed proteins and toxins.

Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants.

Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya beans), Liberty Link® (tolerance to phosphinotricin, for example oilseed rape), IMI® (tolerance to imidazolinones) and STS® (tolerance to sulphonylureas, for example maize).

Herbicide-resistant plants (plants bred in a conventional manner for herbicide tolerance) which may be mentioned include the varieties sold under the name Clearfield® (for example maize).

These statements also apply to plant cultivars having these genetic traits or genetic traits still to be developed, which plant cultivars will be developed and/or marketed in the future.

The plants listed can be treated according to the invention in a particularly advantageous manner with the compounds according to the invention at a suitable concentration.

Furthermore, in the field of veterinary medicine, the novel compounds of the present invention can be effectively used against various harmful animal parasitic pests (endoparasites and ectoparasites), for example, insects and helminthes.

Examples of such animal parasitic pests include the pests as described below. Examples of the insects include *Gasterophilus* spp., *Stomoxys* spp., *Trichodectes* spp., *Rhodnius* spp., *Ctenocephalides canis*, *Cimx lecturius*, *Ctenocephalides felis*, *Lucilia cuprina*, and the like. Examples of acari include *Ornithodoros* spp., *Ixodes* spp., *Boophilus* spp., and the like. In the veterinary fields, e.g. in the field of veterinary medicine, the active compounds according to the present invention are active against animal parasites, in particular ectoparasites or endoparasites.

The term endoparasites includes in particular helminths, such as cestodes, nematodes or trematodes, and protozoae, such as coccidia.

Ectoparasites are typically and preferably arthropods, in particular insects such as flies (stinging and licking), parasitic fly larvae, lice, hair lice, bird lice, fleas and the like; or acarids, such as ticks, for examples hard ticks or soft ticks, or mites, such as scab mites, harvest mites, bird mites and the like.

These parasites include:

From the order of the Anoplurida, for example *Haematopinus* spp., *Linognathus* spp., *Pediculus* spp., *Phtirus* spp., *Solenopotes* spp.; particular examples are: *Linognathus setosus*, *Linognathus vituli*, *Linognathus ovillus*, *Linognathus oviformis*, *Linognathus pedalis*, *Linognathus stereopsis*, *Haematopinus asini macrocephalus*, *Haematopinus eurysternus*, *Haematopinus suis*, *Pediculus humanus capitis*, *Pediculus humanus corporis*, *Phylloera vastatrix*, *Phthirus pubis*, *Solenopotes capillatus*; from the order of the Mallophagida and the suborders Amblycerina and Ischnocerina, for example *Trimenopon* spp., *Menopon* spp., *Trinoton* spp., *Bovicola* spp., *Wemeckiella* spp., *Lepikentron* spp., *Damalina* spp., *Trichodectes* spp., *Felicola* spp.; particular examples are: *Bovicola bovis*, *Bovicola ovis*, *Bovicola limbata*, *Damalina bovis*, *Trichodectes canis*, *Felicola subrostratus*, *Bovicola caprae*, *Lepikentron ovis*, *Werneckiella equi*; from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Phihpomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; particular examples are: *Aedes aegypti*, *Aedes albopictus*, *Aedes taeniorhynchus*, *Anopheles gambiae*, *Anopheles macuhpennis*, *Calliphora erythrocephala*, *Chrysozona pluvialis*, *Culex quinquefasciatus*, *Culex pipiens*, *Culex tarsalis*, *Fannia canicularis*, *Sarcophaga camaria*, *Stomoxys calcitrans*, *Tipula paludosa*, *Lucilia cuprina*, *Lucilia sericata*, *Simulium reptans*, *Phlebotomus papatasi*, *Phlebotomus longipalpis*, *Odagmia ornata*, *Wilhelmia equina*, *Boophthora erythrocephala*, *Tabanus bromius*, *Tabanus spodopterus*, *Tabanus atratus*, *Tabanus sudeticus*, *Hybomitra ciurea*, *Chrysops caecutiens*, *Chrysops relictus*, *Haematopota pluvialis*, *Haematopota italica*, *Musca autumnalis*, *Musca domestica*, *Haematobia irritans irritans*, *Haematobia irritans exigua*, *Haematobia stimulans*, *Hydrotaea irritans*, *Hydrotaea albipuncta*, *Chrysomya chloropyga*, *Chrysomya bezziana*, *Oestrus ovis*, *Hypoderma bovis*, *Hypoderma lineatum*, *Przhevalskiana silenus*, *Dermatobia hominis*, *Melophagus ovinus*, *Lipoptena capreoli*, *Lipoptena cervi*, *Hippobosca variegata*, *Hippobosca equina*, *Gasterophilus intestinalis*, *Gasterophilus haemorroidalis*, *Gasterophilus inermis*, *Gasterophilus nasalis*, *Gasterophilus nigricornis*, *Gasterophilus pecorum*, *Braula coeca*; from the order of the Siphonapterida, for example *Pulex* spp., *Ctenocephalides* spp., *Tunga* spp., *Xenopsylla* spp., *Ceratophyllus* spp.; particular examples are: *Ctenocephalides canis*, *Ctenocephalides felis*, *Pulex irritans*, *Tunga penetrans*, *Xenopsylla cheopis*; from the order of the Heteropterida, for example *Cimex* spp., *Triatoma* spp., *Rhodnius* spp., *Panstrongylus* spp.

From the order of the Blattarida, for example *Blatta orientalis*, *Periplaneta americana*, *Blattela germanica*, *Supella* spp. (e.g. *Suppella longipalpa*);

From the subclass of the Acari (Acarina) and the orders of the Meta- and Mesostigmata, for example *Argas* spp., *Ornithodorus* spp., *Otobius* spp., *Ixodes* spp., *Amblyomma* spp., *Rhipicephalus* (*Boophilus*) spp *Dermacentor* spp., *Haemophysalis* spp., *Hyalomma* spp., *Dermanyssus* spp., *Rhipicephalus* spp. (the original genus of multi host ticks) *Ornithonyssus* spp., *Pneumonyssus* spp., *Raillietia* spp., *Pneumonyssus* spp., *Sternostoma* spp., *Varroa* spp., *Acarapis* spp.; particular examples are: *Argas persicus*, *Argas reflexus*, *Ornithodorus moubata*, *Otobius megnini*, *Rhipicephalus* (*Boophilus*) *microplus*, *Rhipicephalus* (*Boophilus*) *decoloratus*, *Rhipicephalus* (*Boophilus*) *annulatus*, *Rhipicephalus* (*Boophilus*) *calceratus*, *Hyalomma anatolicum*, *Hyalomma aegypticum*, *Hyalomma marginatum*, *Hyalomma transiens*, *Rhipicephalus evertsi*, *Ixodes ricinus*, *Ixodes hexagonus*, *Ixodes canisuga*, *Ixodes pilosus*, *Ixodes rubicundus*, *Ixodes scapularis*, *Ixodes holocyclus*, *Haemaphysalis concinna*, *Haemaphysalis punctata*, *Haemaphysalis cinnabarina*, *Haemaphysalis otophila*, *Haemaphysalis leachi*, *Haemaphysalis longicorni*, *Dermacentor marginatus*, *Dermacentor reticulatus*, *Dermacentor pictus*, *Dermacentor albipictus*, *Dermacentor andersoni*, *Dermacentor variabilis*, *Hyalomma mauritanicum*, *Rhipicephalus sanguineus*, *Rhipicephalus bursa*, *Rhipicephalus appendiculatus*, *Rhipicephalus capensis*, *Rhipicephalus turanicus*, *Rhipicephalus zambeziensis*, *Amblyomma americanum*, *Amblyomma variegatum*, *Amblyomma maculatum*, *Amblyomma hebraeum*, *Amblyomma cajennense*, *Dermanyssus gallinae*, *Ornithonyssus bursa*, *Ornithonyssus sylviarum*, *Varroa jacobsoni*; from the order of the Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.; particular examples are: *Cheyletiella yasguri*, *Cheyletiella blakei*, *Demodex canis*, *Demodex bovis*, *Demodex ovis*, *Demodex caprae*, *Demodex equi*, *Demodex caballi*, *Demodex suis*, *Neotrombicula autumnalis*, *Neotrombicula desaleri*, *Neoschongastia xerothermobia*, *Trombicula akamushi*, *Otodectes cynotis*, *Notoedres cati*, *Sarcoptis canis*, *Sarcoptes bovis*, *Sarcoptes ovis*, *Sarcoptes rupicaprae* (*S. caprae*), *Sarcoptes equi*, *Sarcoptes suis*, *Psoroptes ovis*, *Pso-

*roptes cuniculi, Psoroptes equi, Chorioptes bovis, Psoergates ovis, Pneumonyssoidic mange, Pneumonyssoides caninum, Acarapis woodi.*

The active compounds according to the invention are also suitable for controlling arthropods, helminths and protozoae, which attack animals.

Animals include agricultural livestock such as, for example, cattle, sheep, goats, horses, pigs, donkeys, camels, buffaloes, rabbits, chickens, turkeys, ducks, geese, cultured fish, honeybees.

Moreover, animals include domestic animals—also referred to as companion animals—such as, for example, dogs, cats, cage birds, aquarium fish and what are known as experimental animals such as, for example, hamsters, guinea pigs, rats and mice.

By controlling these arthropods, helminths and/or protozoae, it is intended to reduce deaths and improve performance (in the case of meat, milk, wool, hides, eggs, honey and the like) and health of the host animal, so that more economical and simpler animal keeping is made possible by the use of the active compounds according to the invention.

For example, it may be desirable to prevent or interrupt the uptake of blood by the parasites from the hosts.

Also, controlling the parasites may help to prevent the transmittance of infectious agents.

The term "controlling" as used herein with regard to the veterinary field, means that the active compounds are effective in reducing the incidence of the respective parasite in an animal infected with such parasites to innocuous levels.

More specifically, "controlling", as used herein, means that the active compound is effective in killing the respective parasite, inhibiting its growth, or inhibiting its proliferation. Generally, when used for the treatment of animals the active compounds according to the invention can be applied directly.

Preferably they are applied as pharmaceutical compositions which may contain pharmaceutically acceptable excipients and/or auxiliaries which are known in the art.

In the veterinary field and in animal keeping, the active compounds are applied (e.g. administered) in the known manner by enteral administration in the form of, for example, tablets, capsules, drinks, drenches, granules, pastes, boluses, the feed-through method, suppositories; by parenteral administration, such as, for example, by injections (intramuscular, subcutaneous, intravenous, intraperitoneal and the like), implants, by nasal application, by dermal application in the form of, for example, bathing or dipping, spraying, pouring-on and spotting-on, washing, dusting, and with the aid of active-compound-comprising shaped articles such as collars, ear tags, tail tags, limb bands, halters, marking devices and the like.

The active compounds may be formulated as shampoo or as suitable formulations usable in aerosols, unpressurized sprays, for example pump sprays and atomizer sprays.

When used for livestock, poultry, domestic animals and the like, the active compounds according to the invention can be applied as formulations (for example powders, wettable powders ["WP"], emulsions, emulsifiable concentrates ["EC"], flowables, homogeneous solutions, and suspension concentrates ["SC"]) which comprise the active compounds in an amount of from 1 to 80 percent by weight, either directly or after dilution (e.g. 100- to 10 000-fold dilution), or else as a chemical bath.

When used in the veterinary field the active compounds according to the invention may be used in combination with suitable synergists or other active compounds, such as for example, acaricides, insecticides, anthelmintics, anti-protozoal drugs.

In the present invention, a substance having an insecticidal action against pests including all of these is referred to as an insecticide.

An active compound of the present invention can be prepared in conventional formulation forms, when used as an insecticide.

Examples of the formulation forms include solutions, emulsions, wettable powders, water dispersible granules, suspensions, powders, foams, pastes, tablets, granules, aerosols, active compound-infiltrated natural and synthetic materials, microcapsules, seed coating agents, formulations used with a combustion apparatus (for example, fumigation and smoking cartridges, cans, coils or the like as the combustion apparatus), ULV (cold mist, warm mist), and the like. These formulations can be produced by methods that are known per se.

For example, a formulation can be produced by mixing the active compound with a developer, that is, a liquid diluent or carrier; a liquefied gas diluent or carrier; a solid diluent or carrier, and optionally with a surfactant, that is, an emulsifier and/or dispersant and/or foaming agent. In the case where water is used as the developer, for example, an organic solvent can also be used as an auxiliary solvent.

Examples of the liquid diluent or carrier include aromatic hydrocarbons (for example, xylene, toluene, alkylnaphthalene and the like), chlorinated aromatic or chlorinated aliphatic hydrocarbons (for example, chlorobenzenes, ethylene chlorides, methylene chlorides), aliphatic hydrocarbons (for example, cyclohexanes), paraffins (for example, mineral oil fractions), alcohols (for example, butanol, glycols and their ethers, esters and the like), ketones (for example, acetone, methyl ethyl ketone, methyl isobutyl ketone, cyclohexanone and the like), strongly polar solvents (for example, dimethylformamide, dimethylsulfoxide and the like), water and the like. The liquefied gas diluent or carrier may be those which are gaseous at normal temperature and normal pressure, for example, aerosol propellants such as butane, propane, nitrogen gas, carbon dioxide and halogenated hydrocarbons. Examples of the solid diluent include pulverized natural minerals (for example, kaolin, clay, talc, chalk, quartz, attapulgite, montmorillonite, diatomaceous earth, and the like), pulverized synthetic minerals (for example, highly dispersed silicic acid, alumina, silicates and the like), and the like. Examples of the solid carrier for granules include pulverized and screened rocks (for example, calcite, marble, pumice, sepiolite, dolomite and the like), synthetic granules of inorganic and organic powder, fine particles of organic materials (for example, sawdust, coconut shells, maize cobs, tobacco stalk and the like), and the like. Examples of the emulsifier and/or foaming agent include nonionic and anionic emulsifiers [for example, polyoxyethylene fatty acid esters, polyoxyethylene fatty acid alcohol ethers (for example, alkylaryl polyglycol ether), alkylsulfonates, alkylsulfates, arylsulfonates and the like], albumin hydro lyzate, and the like. Examples of the dispersant include lignin sulfite waste liquor and methylcellulose.

Fixing agents can also be used in the formulations (powders, granules, emulsions), and examples of the fixing agent include carboxymethylcellulose, natural and synthetic polymers (for example, gum arabic, polyvinyl alcohol, polyvinyl acetate, and the like) and the like. Colorants can also be used, and examples of the colorants include inorganic pigments (for example, iron oxide, titanium oxide, Prussian Blue and the like), organic dyes such as alizarin dyes, azo dyes or metal phthalocyanine dyes, and in addition, trace elements such as the salts of iron, manganese, boron, copper, cobalt, molybdenum and zinc. The formulations in general can contain the active ingredient in an amount ranging from 0.1 to 95 percent by weight, and preferably 0.5 to 90 percent> by weight. The compound according to the present invention can also exist as an admixture with other active compounds, for example, insecticides, poisonous baits, bactericides, miticides, nematicides, fungicides, growth regulators, herbicides and the like, in the form of their commercially useful formulation forms and in the application forms prepared from those formulations.

The content of the compound according to the present invention in a commercially useful application form can be varied within a wide range.

The concentration of the active compound according to the present invention in actual usage can be, for example, in the range of 0.0000001 to 100 percent by weight, and preferably 0.00001 to 1 percent by weight.

The compounds according to the present invention can be used through conventional methods that are appropriate for the usage form.

The active compound of the present invention have, when used against hygiene pests and pests associated with stored products, stability effective against alkali on lime materials, and also shows excellent residual effectiveness on wood and soil. The compounds of the invention may have favourable properties with respect to amount applied, residue formulation, selectivity, toxicity, production methodology, high activity, wide spectrum of control, safety, control of resistant organisms, e.g. pests that are resistant to organic phosphorus agents and/or carbamate agents. Further embodiments of the invention are described below. The compounds of formula (I) can be used to control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be controlled by the use of the invention compounds include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

The compounds of the invention may be used for example on turf, ornamentals, such as flowers, shrubs, broad-leaved trees or evergreens, for example conifers, as well as for tree injection, pest management and the like.

In a further aspect the invention provides a method of protecting an animal from a parasitic invertebrate pest comprising administering to the animal a pesticidally effective amount of a compound of the invention. In a further aspect the invention provides a compound for use in protecting an animal from a parasitic invertebrate pest. In a further aspect the invention provides use of a compound in the manufacture of a medicament for protecting an animal from a parasitic invertebrate pest.

In a further aspect the invention provides a method of treating an animal suffering from a parasitic invertebrate pest comprising administering to the animal a pesticidally effective amount of a compound of the invention. In a further aspect the invention provides a compound for use in treating an animal suffering from a parasitic invertebrate pest. In a further aspect the invention provides use of a compound in the manufacture of a medicament for treating an animal suffering from a parasitic invertebrate pest.

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (*thrips*), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the *Mastotermitidae* (for example *Mastotermes* spp.), the *Kalotermitidae* (for example *Neotermes* spp.), the *Rhinotermitidae* (for example *Coptotermes formosanus, Reticulitermes flavipes, R. speratu, R. virginicus, R. hesperus,* and *R. santonensis*) and the *Termitidae* (for example *Globitermes sulfureus*), *Solenopsis geminata* (fire ant), *Monomorium pharaonic* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The compounds of the invention may be used for pest control on various plants, including soybean (e.g. in some cases 10-70 g/ha), corn (e.g. in some cases 10-70 g/ha), sugarcane (e.g. in some cases 20-200 g/ha), alfalfa (e.g. in some cases 10-70 g/ha), brassicas (e.g. in some cases 10-50 g/ha), oilseed rape (e.g. canola) (e.g. in some cases 20-70 g/ha), potatoes (including sweet potatoes) (e.g. in some cases 10-70 g/ha), cotton (e.g. in some cases 10-70 g/ha), rice (e.g. in some cases 10-70 g/ha), coffee (e.g. in some cases 30-150 g/ha), citrus (e.g. in some cases 60-200 g/ha), almonds (e.g. in some cases 40-180 g/ha), fruiting vegetables (e.g. tomatoes, pepper, chili, eggplant, cucumber, squash etc.) (e.g. in some cases 10-80 g/ha), tea (e.g. in some cases 20-150 g/ha), bulb vegetables (e.g. onion, leek etc.) (e.g. in some cases 30-90 g/ha), grapes (e.g. in some cases 30-180 g/ha), pome fruit (e.g. apples, pears etc.) (e.g. in some cases 30-180 g/ha), and stone fruit (e.g. pears, plums etc.) (e.g. in some cases 30-180 g/ha).

The compounds of the invention may be used on soybean to control, for example, *Elasmopalpus lignosellus, Diloboderus abderus, Diabrotica speciosa, Sternechus subsignatus*, Formicidae, *Agrotis ypsilon, Julus* ssp., *Anticarsia gemmatalis, Megascelis* ssp., *Procornitermes* ssp., Gryllotalpidae, *Nezara*

*viridula, Piezodorus* spp., *Acrosternum* spp., *Neomegalotomus* spp., *Cerotoma trifurcata, Popillia japonica, Edessa* spp., *Liogenys fuscus, Euchistus heros*, stalk borer, *Scaptocoris castanea, phyllophaga* spp., *Pseudoplusia includens, Spodoptera* spp., *Bemisia tabaci, Agriotes* spp. The compounds of the invention are preferably used on soybean to control *Diloboderus abderus, Diabrotica speciosa, Nezara viridula, Piezodorus* spp., *Acrosternum* spp., *Cerotoma trifurcata, Popillia japonica, Euchistus heros, phyllophaga* spp., *Agriotes* spp.

The compounds of the invention may be used on corn to control, for example, *Euchistus heros, Dichelops furcatus, Diloboderus abderus, Elasmopalpus lignosellus, Spodoptera frugiperda, Nezara viridula, Cerotoma trifurcata, Popillia japonica, Agrotis ypsilon, Diabrotica speciosa, Heteroptera, Procornitermes* ssp., *Scaptocoris castanea, Formicidae, Julus* ssp., *Dalbulus maidis, Diabrotica virgifera, Mocis latipes, Bemisia tabaci, heliothis* spp., *Tetranychus* spp., *thrips* spp., *phyllophaga* spp., *scaptocoris* spp., *Liogenys fuscus, Spodoptera* spp., *Ostrinia* spp., *Sesamia* spp., *Agriotes* spp. The compounds of the invention are preferably used on corn to control *Euchistus heros, Dichelops furcatus, Diloboderus abderus, Nezara viridula, Cerotoma trifurcata, Popillia japonica, Diabrotica speciosa, Diabrotica virgifera, Tetranychus* spp., *thrips* spp., *phyllophaga* spp., *scaptocoris* spp., *Agriotes* spp.

The compounds of the invention may be used on sugar cane to control, for example, *Sphenophorus* spp., termites, *Mahanarva* spp. The compounds of the invention are preferably used on sugar cane to control termites, *Mahanarva* spp.

The compounds of the invention may be used on alfalfa to control, for example, *Hypera brunneipennis, Hypera postica, Colias eurytheme, Collops* spp., *Empoasca solana, Epitrix, Geocoris* spp., *Lygus hesperus, Lygus lineolaris, Spissistilus* spp, *Spodoptera* spp., *Trichoplusia ni*. The compounds of the invention are preferably used on alfalfa to control *Hypera brunneipennis, Hypera postica, Empoasca solana, Epitrix, Lygus hesperus, Lygus lineolaris, Trichoplusia ni*.

The compounds of the invention may be used on brassicas to control, for example, *Plutella xylostella, Pieris* spp., *Mamestra* spp., *Plusia* spp., *Trichoplusia ni, Phyllotreta* spp., *Spodoptera* spp., *Empoasca solana*, thrips spp., *Spodoptera* spp., *Delia* spp. The compounds of the invention are preferably used on brassicas to control *Plutella xylostella Pieris* spp., *Plusia* spp., *Trichoplusia ni, Phyllotreta* spp., *thrips* spp.

The compounds of the invention may be used on oil seed rape, e.g. canola, to control, for example, *Meligethes* sp, *Ceutorhynchus napi, Psylloides* sp.

The compounds of the invention may be used on potatoes, including sweet potatoes, to control, for example, *Empoasca* sp, *Leptinotarsa* sp, *Diabrotica speciosa, Phthorimaea* sp, *Paratrioza* sp, *Maladera matrida, Agriotes* sp. The compounds of the invention are preferably used on potatoes, including sweet potatoes, to control *Empoasca* sp, *Leptinotarsa* sp, *Diabrotica speciosa, Phthorimaea* sp, *Paratrioza* sp, *Agriotes* sp.

The compounds of the invention may be used on cotton to control, for example, *Anthonomus grandis, Pectinophora* sp, *heliothis* sp, *Spodoptera* sp, *Tetranychus* sp, *Empoasca* sp, *thrips* sp, *Bemisia tabaci, Lygus* sp, *phyllophaga* sp, *Scaptocoris* sp. The compounds of the invention are preferably used on cotton to control *Anthonomus grandis, Tetranychus* sp, *Empoasca* sp, *thrips* sp, *Lygus* sp, *phyllophaga* sp, *Scaptocoris* sp.

The compounds of the invention may be used on rice to control, for example, *Leptocorisa* sp, *Cnaphalocrosis* sp, *Chilo* sp, *Scirpophaga* sp, *Lissorhoptrus* sp, *Oebalus pugnax*.

The compounds of the invention are preferably used on rice to control *Leptocorisa* sp, *Lissorhoptrus* sp, *Oebalus pugnax*.

The compounds of the invention may be used on coffee to control, for example, *Hypothenemus Hampei, Perileucoptera Coffeella, Tetranychus* sp. The compounds of the invention are preferably used on coffee to control *Hypothenemus Hampei, Perileucoptera Coffeella*.

The compounds of the invention may be used on citrus to control, for example, *Panonychus citri, Phyllocoptruta oleivora, Brevipalpus* sp, *Diaphorina citri, Scirtothrips* sp, *thrips* sp, *Unaspis* sp, *Ceratitis capitata, Phyllocnistis* sp. The compounds of the invention are preferably used on citrus to control *Panonychus citri, Phyllocoptruta oleivora, Brevipalpus* sp, *Diaphorina citri, Scirtothrips* sp, *thrips* sp, *Phyllocnistis* sp.

The compounds of the invention may be used on almonds to control, for example, *Amyelois transitella, Tetranychus* sp.

The compounds of the invention may be used on fruiting vegetable, including tomatoes, pepper, chili, eggplant, cucumber, squash etc, to control *thrips* sp, *Tetranychus* sp, *Polyphagotarsonemus* sp, *Aculops* sp, *Empoasca* sp, *Spodoptera* sp, *heliothis* sp, *Tuta absoluta, Liriomyza* sp, *Bemisia tabaci, Trialeurodes* sp, *Paratrioza* sp, *Frankliniella occidentalis, Frankliniella* sp, *Anthonomus* sp, *Phyllotreta* sp, *Amrasca* sp, *Epilachna* sp, *Halyomorpha* sp, *Scirtothrips* sp, *Leucinodes* sp, *Neoleucinodes* sp. The compounds of the invention are preferably used on fruiting vegetable, including tomatoes, pepper, chili, eggplant, cucumber, squash etc, to control, for example, *thrips* sp, *Tetranychus* sp, *Polyphagotarsonemus* sp, *Aculops* sp, *Empoasca* sp, *Spodoptera* sp, *heliothis* sp, *Tuta absoluta, Liriomyza* sp, *Paratrioza* sp, *Frankliniella occidentalis, Frankliniella* sp, *Amrasca* sp, *Scirtothrips* sp, *Leucinodes* sp, *Neoleucinodes* sp.

The compounds of the invention may be used on tea to control, for example, *Pseudaulacaspis* sp, *Empoasca* sp, *Scirtothrips* sp, *Caloptilia theivora*. The compounds of the invention are preferably used on tea to control *Empoasca* sp, *Scirtothrips* sp.

The compounds of the invention may be used on bulb vegetables, including onion, leek etc to control, for example, *thrips* sp, *Spodoptera* sp, *heliothis* sp. The compounds of the invention are preferably used on bulb vegetables, including onion, leek etc to control *thrips* sp.

The compounds of the invention may be used on grapes to control, for example, *Empoasca* sp, *Lobesia* sp, *Frankliniella* sp, *thrips* sp, *Tetranychus* sp, *Rhipiphorothrips Cruentatus, Eotetranychus Willamettei, Erythroneura Elegantula, Scaphoides* sp. The compounds of the invention are preferably used on grapes to control *Frankliniella* sp, *thrips* sp, *Tetranychus* sp, *Rhipiphorothrips Cruentatus, Scaphoides* sp.

The compounds of the invention may be used on pome fruit, including apples, pairs etc, to control, for example, *Cacopsylla* sp, *Psylla* sp, *Panonychus ulmi, Cydia pomonella*. The compounds of the invention are preferably used on pome fruit, including apples, pairs etc, to control *Cacopsylla* sp, *Psylla* sp, *Panonychus ulmi*.

The compounds of the invention may be used on stone fruit to control, for example, *Grapholita molesta, Scirtothrips* sp, *thrips* sp, *Frankliniella* sp, *Tetranychus* sp. The compounds of the invention are preferably used on stone fruit to control *Scirtothrips* sp, *thrips* sp, *Frankliniella* sp, *Tetranychus* sp.

The invention therefore provides a method of controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest. The compounds of formula (I) are preferably used against insects or acarines. The compounds of the invention may also be used for controlling insects that are resistant to known insecticides.

The term "plant" as used herein includes seedlings, bushes and trees.

Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®.

Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is generally used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and for example a suitable carrier or diluent therefor. The composition is preferably an insecticidal or acaricidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifiying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurized, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilizers (for example nitrogen-, potassium- or phosphorus-containing fertilizers). Suitable formulation types include granules of fertilizer. The mixtures preferably contain up to 25% by weight of the compound of formula (I).

The invention therefore also provides a fertilizer composition comprising a fertilizer and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition Examples of suitable pesticides include the following (where "Tx" means a compound of formula (I), and in particular a compound selected from Tables 1 to Table 59, which may result in a synergistic combination with the given active ingredient):

a) Pyrethroids, wherein suitable combinations include permethrin+Tx, cypermethrin+Tx, fenvalerate+Tx, esfenvalerate+Tx, deltamethrin+Tx, cyhalothrin+Tx (in particular lambda-cyhalothrin+Tx and gamma cyhalothrin+Tx), bifenthrin+Tx, fenpropathrin+Tx, cyfluthrin+Tx, tefluthrin+Tx, fish safe pyrethroids+Tx (for example ethofenprox+Tx), natural pyrethrin+Tx, tetramethrin+Tx, S-bioallethrin+Tx, fenfluthrin+Tx, prallethrin+Tx or 5-benzyl-3-furylmethyl-(E)-(1R,3S)-2,2-dimethyl-3-(2-oxothiolan-3-ylidenemethyl)cyclopropane carboxylate+Tx;

b) Organophosphates, wherein suitable combinations include profenofos+Tx, sulprofos+Tx, acephate+Tx, methyl parathion+Tx, azinphos-methyl+Tx, demeton-s-methyl+Tx, heptenophos+Tx, thiometon+Tx, fenamiphos+Tx, monocrotophos+Tx, profenofos+Tx, triazophos+Tx, methamidophos+Tx, dimethoate+Tx, phosphamidon+Tx, malathion+Tx, chlorpyrifos+Tx, phosalone+Tx, terbufos+Tx, fensulfothion+Tx, fonofos+Tx, phorate+Tx, phoxim+Tx, pirimiphos-methyl+Tx, pirimiphos-ethyl+Tx, fenitrothion+Tx, fosthiazate+Tx or diazinon+Tx;

c) Carbamates (including aryl carbamates), wherein suitable combinations include pirimicarb+Tx, triazamate+Tx, cloethocarb+Tx, carbofuran+Tx, furathiocarb+Tx, ethiofencarb+Tx, aldicarb+Tx, thiofurox+Tx, carbosulfan+Tx, bendiocarb+Tx, fenobucarb+Tx, propoxur+Tx, methomyl+Tx or oxamyl+Tx;

d) Benzoyl ureas, wherein suitable combinations include diflubenzuron+Tx, triflumuron+Tx, hexaflumuron+Tx, flufenoxuron+Tx, lufeneron+Tx or chlorfluazuron+Tx;

e) Organic tin compounds, wherein suitable combinations include cyhexatin+Tx, fenbutatin oxide+Tx or azocyclotin+Tx;

f) Pyrazoles, wherein suitable combinations include tebufenpyrad+Tx and fenpyroximate+Tx;

g) Macrolides, such as avermectins or milbemycins, wherein suitable combinations include for example abamectin+Tx, emamectin benzoate+Tx, ivermectin+Tx, milbemycin+Tx, spinosad+Tx, azadirachtin+Tx or spinetoram+Tx;

h) Hormones or pheromones;

i) Organochlorine compounds, wherein suitable combinations include endosulfan+Tx (in particular alpha-endosulfan+Tx), benzene hexachloride+Tx, DDT+Tx, chlordane+Tx or dieldrin+Tx;

j) Amidines, wherein suitable combinations include chlordimeform+Tx or amitraz+Tx;

k) Fumigant agents, wherein suitable combinations include chloropicrin+Tx, dichloropropane+Tx, methyl bromide+Tx or metam+Tx;

l) Neonicotinoid compounds, wherein suitable combinations include imidacloprid+Tx, thiacloprid+Tx, ace tamiprid+Tx, nitenpyram+Tx, dinotefuran+Tx, thiamethoxam+Tx, clothianidin+Tx or nithiazine+Tx;

m) Diacylhydrazines, wherein suitable combinations include tebufenozide+Tx, chromafenozide+Tx or methoxyfenozide+Tx;

n) Diphenyl ethers, wherein suitable combinations include diofenolan+Tx or pyriproxifen+Tx;

o) Indoxacarb+Tx;

p) Chlorfenapyr+Tx;

q) Pymetrozine+Tx or flonicamid+Tx;

r) Spirotetramat+Tx, spirodiclofen+Tx or spiromesifen+Tx;

s) Diamides, wherein suitable combinations include flubendiamide+Tx, chlorantraniliprole (Rynaxypyr®)+Tx or cyantraniliprole+Tx;

t) Sulfoxaflor+Tx; or u) Metaflumizone+Tx;

v) Fipronil+Tx and Ethiprole+Tx;
w) Pyrifluqinazon+Tx;
x) buprofezin+Tx; or
y) 4-[(6-Chloro-pyridin-3-ylmethyl)-(2,2-difluoro-ethyl)-amino]-5H-furan-2-one (DE 102006015467)+Tx.

In addition to the major chemical classes of pesticide listed above, other pesticides having particular targets may be employed in the composition, if appropriate for the intended utility of the composition. For instance, selective insecticides for particular crops, for example stemborer specific insecticide (combinations such as cartap+Tx) or hopper specific insecticides (combinations such as buprofezin+Tx) for use in rice may be employed. Alternatively insecticides or acaricides specific for particular insect species/stages may also be included in the compositions (for example acaricidal ovolarvicides, to give combinations such as clofentezine+Tx, flubenzimine+Tx, hexythiazox+Tx or tetradifon+Tx; acaricidal motilicides, to give combinations such as dicofol+Tx or propargite+Tx; acaricides, to give combinations such as bromopropylate+Tx or chlorobenzilate+Tx; or growth regulators, such as hydramethylnon+Tx, cyromazine+Tx, methoprene+Tx, chlorfluazuron+Tx or diflubenzuron+Tx).

Examples of fungicidal compounds and combinations which may be included in the composition of the invention are (E)-N-methyl-2-[2-(2,5-dimethylphenoxymethyl)phenyl]-2-methoxy-iminoacetamide (SSF-129)+Tx, 4-bromo-2-cyano-N,N-dimethyl-6-trifluoromethyl-benzimidazole-1-sulfonamide+Tx, α-[N-(3-chloro-2,6-xylyl)-2-methoxyacetamido]-γ-butyrolactone+Tx, 4-chloro-2-cyano-N,N-dimethyl-5-p-tolylimidazole-1-sulfonamide (IKF-916, cyamidazosulfamid)+Tx, 3-5-dichloro-N-(3-chloro-1-ethyl-1-methyl-2-oxopropyl)-4-methylbenzamide (RH-7281, zoxamide)+Tx, N-allyl-4,5,-dimethyl-2-trimethylsilylthiophene-3-carboxamide (MON65500)+Tx, N-(1-cyano-1,2-dimethylpropyl)-2-(2,4-dichlorophenoxy)-propionamide (AC382042)+Tx, N-(2-methoxy-5-pyridyl)-cyclopropane carboxamide+Tx, acibenzolar (CGA245704) (e.g. acibenzolar-5-methyl)+Tx, alanycarb+Tx, aldimorph+Tx, anilazine+Tx, azaconazole+Tx, azoxystrobin+Tx, benalaxyl+Tx, benomyl+Tx, benthiavalicarb+Tx, biloxazol+Tx, bitertanol+Tx, bixafen+Tx, blasticidin S+Tx, boscalid+Tx, bromuconazole+Tx, bupirimate+Tx, captafol+Tx, captan+Tx, carbendazim+Tx, carbendazim+Tx, chlorhydrate+Tx, carboxin+Tx, carpropamid+Tx, carvone+Tx, CGA41396+Tx, CGA41397+Tx, chinomethionate+Tx, chlorothalonil+Tx, chlorozolinate+Tx, clozylacon+Tx, copper containing compounds to give combintations such as copper oxychloride+Tx, copper oxyquinolate+Tx, copper sulfate+Tx, copper tallate+Tx and Bordeaux mixture+Tx, cyclufenamid+Tx, cymoxanil+Tx, cyproconazole+Tx, cyprodinil+Tx, debacarb+Tx, di-2-pyridyl disulfide 1,1'-dioxide+Tx, dichlofluanid+Tx, diclomezine+Tx, dicloran+Tx, diethofencarb+Tx, difenoconazole+Tx, difenzoquat+Tx, diflumetorim+Tx, O,O-di-iso-propyl-5-benzyl thiophosphate+Tx, dimefluazole+Tx, dimetconazole+Tx, dimethomorph+Tx, dimethirimol+Tx, diniconazole+Tx, dinocap+Tx, dithianon+Tx, dodecyl dimethyl ammonium chloride+Tx, dodemorph+Tx, dodine+Tx, doguadine+Tx, edifenphos+Tx, epoxiconazole+Tx, ethirimo+Tx 1, ethyl-(Z)-N-benzyl-N-([methyl(methyl-thioethylideneamino-oxycarbonyl)amino]thio)-β-alaninate+Tx, etridiazole+Tx, famoxadone+Tx, fenamidone (RPA407213)+Tx, fenarimol+Tx, fenbuconazole+Tx, fenfuram+Tx, fenhexamid (KBR2738)+Tx, fenpiclonil+Tx, fenpropidin+Tx, fenpropimorph+Tx, fentin acetate+Tx, fentin hydroxide+Tx, ferbam+Tx, ferimzone+Tx, fluazinam+Tx, fludioxonil+Tx, flumetover+Tx, fluopyram+Tx, fluoxastrobin+Tx, fluoroimide+Tx, fluquinconazole+Tx, flusilazole+Tx, flutolanil+Tx, flutriafol+Tx, fluxapyroxad+Tx, folpet+Tx, fuberidazole+Tx, furalaxyl+Tx, furametpyr+Tx, guazatine, +Tx hexaconazole+Tx, hydroxyisoxazole+Tx, hymexazole+Tx, imazalil+Tx, imibenconazole+Tx, iminoctadine+Tx, iminoctadine triacetate+Tx, ipconazole+Tx, iprobenfos+Tx, iprodione+Tx, iprovalicarb (SZX0722)+Tx, isopropanyl butyl carbamate+Tx, isoprothiolane+Tx, isopyrazam+Tx, kasugamycin+Tx, kresoxim-methyl+Tx, LY186054+Tx, LY211795+Tx, LY248908+Tx, mancozeb+Tx, mandipropamid+Tx, maneb+Tx, mefenoxam+Tx, metalaxyl+Tx, mepanipyrim+Tx, mepronil+Tx, metalaxyl+Tx, metconazole+Tx, metiram+Tx, metiram-zinc+Tx, metominostrobin+Tx, myclobutanil+Tx, neoasozin+Tx, nickel dimethyldithiocarbamate+Tx, nitrothal-isopropyl+Tx, nuarimol+Tx, ofurace+Tx, organomercury compounds, +Tx oxadixyl+Tx, oxasulfuron+Tx, oxolinic acid+Tx, oxpoconazole+Tx, oxycarboxin+Tx, pefurazoate+Tx, penconazole+Tx, pencycuron+Tx, penflufen+Tx, penthiopyrad+Tx, phenazin oxide+Tx, phosetyl-Al+Tx, phosphorus acids+Tx, phthalide+Tx, picoxystrobin (ZA1963)+Tx, polyoxinD+Tx, polyram+Tx, probenazole+Tx, prochloraz+Tx, procymidone+Tx, propamocarb+Tx, propiconazole+Tx, propineb+Tx, propionic acid+Tx, prothioconazole+Tx, pyrazophos+Tx, pyrifenox+Tx, pyrimethanil+Tx, pyraclostrobin+Tx, pyroquilon+Tx, pyroxyfur+Tx, pyrrolnitrin+Tx, quaternary ammonium compounds+Tx, quinomethionate+Tx, quinoxyfen+Tx, quintozene+Tx, sedaxane+Tx, sipconazole (F-155)+Tx, sodium pentachlorophenate+Tx, spiroxamine+Tx, streptomycin+Tx, sulfur+Tx, tebuconazole+Tx, tecloftalam+Tx, tecnazene+Tx, tetraconazole+Tx, thiabendazole+Tx, thifluzamid+Tx, 2-(thiocyanomethylthio)benzothiazole+Tx, thiophanate-methyl+Tx, thiram+Tx, timibenconazole+Tx, tolclofos-methyl+Tx, tolylfluanid+Tx, triadimefon+Tx, triadimenol+Tx, triazbutil+Tx, triazoxide+Tx, tricyclazole+Tx, tridemorph+Tx, trifloxystrobin (CGA279202)+Tx, triforine+Tx, triflumizole+Tx, triticonazole+Tx, validamycin A+Tx, vapam+Tx, vinclozolin+Tx, zineb+Tx and ziram+Tx, N-[9-(dichloromethylene)-1,2,3,4-tetrahydro-1,4-methanonaphthalen-5-yl]-3-(difluoromethyl)-1-methyl-1H-pyrazole-4-carboxamide [1072957-71-1]+Tx, 1-methyl-3-difluoromethyl-1H-pyrazole-4-carboxylic acid (2-dichloromethylene-3-ethyl-1-methyl-indan-4-yl)-amide+Tx, and 1-methyl-3-difluoromethyl-4H-pyrazole-4-carboxylic acid [2-(2,4-dichloro-phenyl)-2-methoxy-1-methyl-ethyl]-amide+Tx.

The active ingredients combinations described above comprising a compound selected of the invention, in particularly from Tables 1 to Table 59 and an active ingredient as described above are preferably combined in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The compounds of the invention are also useful in the field of animal health, e.g. they may be used against parasitic invertebrate pests, more preferably against parasitic invertebrate pests in or on an animal. Examples of pests include nematodes, trematodes, cestodes, flies, mites, tricks, lice, fleas, true bugs and maggots. The animal may be a non-human animal, e.g. an animal associated with agriculture, e.g. a cow, a pig, a sheep, a goat, a horse, or a donkey, or a companion animal, e.g. a dog or a cat.

In a further aspect the invention provides a compound of the invention for use in a method of therapeutic treatment.

In a further aspect the invention relates to a method of controlling parasitic invertebrate pests in or on an animal comprising administering a pesticidally effective amount of a compound of the invention. The administration may be for example oral administration, parenteral administration or external administration, e.g. to the surface of the animal body. In a further aspect the invention relates to a compound of the invention for controlling parasitic invertebrate pests in or on an animal. In a further aspect the invention relates to use of a compound of the invention in the manufacture of a medicament for controlling parasitic invertebrate pests in or on an animal In a further aspect, the invention relates to a method of controlling parasitic invertebrate pests comprising administering a pesticidally effective amount of a compound of the invention to the environment in which an animal resides.

In a further aspect the invention relates to a method of protecting an animal from a parasitic invertebrate pest comprising administering to the animal a pesticidally effective amount of a compound of the invention. In a further aspect the invention relates to a compound of the invention for use in protecting an animal from a parasitic invertebrate pest. In a further aspect the invention relates to use of a compound of the invention in the manufacture of a medicament for protecting an animal from a parasitic invertebrate pest.

In a further aspect the invention provides a method of treating an animal suffering from a parasitic invertebrate pest comprising administering to the animal a pesticidally effective amount of a compound of the invention. In a further aspect the invention relates to a compound of the invention for use in treating an animal suffering from a parasitic invertebrate pest. In a further aspect the invention relates to use of a compound of the invention in the manufacture of a medicament for treating an animal suffering from a parasitic invertebrate pest.

In a further aspect, the invention provides a pharmaceutical composition comprising a compound of the invention and a pharmaceutically suitable excipient.

The compounds of the invention may be used alone or in combination with one or more other biologically active ingredients.

In one aspect the invention provides a combination product comprising a pesticidally effective amount of a component A and a pesticidally effective amount of component B wherein component A is a compound of the invention and component B is a compound as described below.

The compounds of the invention may be used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in U.S. Pat. No. 5,015,630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epsiprantel.

The compounds of the invention may be used in combination with derivatives and analogues of the paraherquamide/marcfortine class of anthelmintic agents, as well as the antiparasitic oxazolines such as those disclosed in U.S. Pat. No. 5,478,855, U.S. Pat. No. 4,639,771 and DE-19520936.

The compounds of the invention may be used in combination with derivatives and analogues of the general class of dioxomorpholine antiparasitic agents as described in WO-9615121 and also with anthelmintic active cyclic depsipeptides such as those described in WO-9611945, WO-9319053, WO-9325543, EP-626375, EP-382173, WO-9419334, EP-382173, and EP-503538.

The compounds of the invention may be used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

The compounds of the invention may be used in combination with terpene alkaloids, for example those described in International Patent Application Publication Numbers WO95/19363 or WO04/72086, particularly the compounds disclosed therein.

Other examples of such biologically active compounds that the compounds of the invention may be used in combination with include but are not restricted to the following:

Organophosphates: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717.

Pyrethroids: acrinathin, allethrin, alphametrin, 5-benzyl-3-furylmethyl(E)-(1R)-cis-2,2-dimethyl-3-(2-oxothiolan-3-ylidenemethyl)cyclopropanecarboxylate, bifenthrin, beta-cyfluthrin, cyfluthrin, a-cypermethrin, beta-cypermethrin, bioallethrin, bioallethrin((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, lambda-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene (including S-methoprene), fenoxycarb; d) lipid biosynthesis inhibitors: spirodiclofen.

Other antiparasitics: acequinocyl, amitraz, AKD-1022, ANS-118, azadirachtin, *Bacillus thuringiensis*, bensultap, bifenazate, binapacryl, bromopropylate, BTG-504, BTG-505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, pyrimidifen, NC-1111, R-195, RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301.

Fungicides: acibenzolar, aldimorph, ampropylfos, andoprim, azaconazole, azoxystrobin, benalaxyl, benomyl, bialaphos, blasticidin-S, Bordeaux mixture, bromuconazole, bupirimate, carpropamid, captafol, captan, carbendazim, chlorfenazole, chloroneb, chloropicrin, chlorothalonil, chlozolinate, copper oxychloride, copper salts, cyflufenamid, cymoxanil, cyproconazole, cyprodinil, cyprofuram, RH-7281, diclocymet, diclobutrazole, diclomezine, dicloran, difenoconazole, RP-407213, dimethomorph, domoxystrobin, diniconazole, diniconazole-M, dodine, edifenphos, epoxiconazole, famoxadone, fenamidone, fenarimol, fenbuconazole, fencaramid, fenpiclonil, fenpropidin, fenpropimorph, fentin acetate, fluazinam, fludioxonil, flumetover, flumorf/flumorlin, fentin hydroxide, fluoxastrobin, fluquinconazole, flusilazole, flutolanil, flutriafol, folpet, fosetyl-aluminium, furalaxyl, furametapyr, hexaconazole, ipconazole, iprobenfos, iprodione, isoprothiolane, kasugamycin, krsoxim-methyl, mancozeb, maneb, mefenoxam, mepronil, metalaxyl, metconazole, metominostrobin/fenominostrobin, metrafenone, myclobutanil, neo-asozin, nicobifen, orysastrobin, oxadixyl, penconazole, pencycuron, probenazole, prochloraz, propamocarb, propioconazole, proquinazid, prothioconazole, pyrifenox, pyraclostrobin, pyrimethanil, pyroquilon, quinoxyfen, spiroxamine, sulfur, tebuconazole, tetrconazole, thiabendazole, thifluzamide, thiophanate-methyl, thiram, tiadinil, triadimefon, triadimenol, tricyclazole, trifloxystrobin, triticonazole, validamycin, vinclozin.

Biological agents: *Bacillus thuringiensis* ssp *aizawai, kurstaki, Bacillus thuringiensis* delta endotoxin, baculovirus, entomopathogenic bacteria, virus and fungi.

Bactericides: chlortetracycline, oxytetracycline, streptomycin.

Other biological agents: enrofloxacin, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, carprofen, metaflumizone, praziquarantel, triclabendazole.

When used in combination with other active ingredients, the compounds of the invention are preferably used in combination with the following (where "Tx" means a compound of formula (I), and in particular a compound selected from Tables 1 to Table 120, which may result in a synergistic combination with the given active ingredient): imidacloprid+Tx, enrofloxacin+Tx, praziquantel+Tx, pyrantel embonate+Tx, febantel+Tx, penethamate+Tx, moloxicam+Tx, cefalexin+Tx, kanamycin+Tx, pimobendan+Tx, clenbuterol+Tx, fipronil+Tx, ivermectin+Tx, omeprazole+Tx, tiamulin+Tx, benazepril+Tx, milbemycin+Tx, cyromazine+Tx, thiamethoxam+Tx, pyriprole+Tx, deltamethrin+Tx, cefquinome+Tx, florfenicol+Tx, buserelin+Tx, cefovecin+Tx, tulathromycin+Tx, ceftiour+Tx, selamectin+Tx, carprofen+Tx, metaflumizone+Tx, moxidectin+Tx, methoprene (including S-methoprene)+Tx, clorsulon+Tx, pyrantel+Tx, amitraz+Tx, triclabendazole+Tx, avermectin+Tx, abamectin+Tx, emamectin+Tx, eprinomectin+Tx, doramectin+Tx, selamectin+Tx, nemadectin+Tx, albendazole+Tx, cambendazole+Tx, fenbendazole+Tx, flubendazole+Tx, mebendazole+Tx, oxfendazole+Tx, oxibendazole+Tx, parbendazole+Tx, tetramisole+Tx, levamisole+Tx, pyrantel pamoate+Tx, oxantel+Tx, morantel+Tx, triclabendazole+Tx, epsiprantel+Tx, fipronil+Tx, lufenuron+Tx, ecdysone+Tx or tebufenozide+Tx; more preferably, enrofloxacin+Tx, praziquantel+Tx, pyrantel embonate+Tx, febantel+Tx, penethamate+Tx, moloxicam+Tx, cefalexin+Tx, kanamycin+Tx, pimobendan+Tx, clenbuterol+Tx, omeprazole+Tx, tiamulin+Tx, benazepril+Tx, pyriprole+Tx, cefquinome+Tx, florfenicol+Tx, buserelin+Tx, cefovecin+Tx, tulathromycin+Tx, ceftiour+Tx, selamectin+Tx, carprofen+Tx, moxidectin+Tx, clorsulon+Tx, pyrantel+Tx, eprinomectin+Tx, doramectin+Tx, selamectin+Tx, nemadectin+Tx, albendazole+Tx, cambendazole+Tx, fenbendazole+Tx, flubendazole+Tx, mebendazole+Tx, oxfendazole+Tx, oxibendazole+Tx, parbendazole+Tx, tetramisole+Tx, levamisole+Tx, pyrantel pamoate+Tx, oxantel+Tx, morantel+Tx, triclabendazole+Tx, epsiprantel+Tx, lufenuron+Tx or ecdysone+Tx; even more preferably enrofloxacin+Tx, praziquantel+Tx, pyrantel embonate+Tx, febantel+Tx, penethamate+Tx, moloxicam+Tx, cefalexin+Tx, kanamycin+Tx, pimobendan+Tx, clenbuterol+Tx, omeprazole+Tx, tiamulin+Tx, benazepril+Tx, pyriprole+Tx, cefquinome+Tx, florfenicol+Tx, buserelin+Tx, cefovecin+Tx, tulathromycin+Tx, ceftiour+Tx, selamectin+Tx, carprofen+Tx, moxidectin+Tx, clorsulon+Tx or pyrantel+Tx.

Examples of ratios include 100:1 to 1:6000, 50:1 to 1:50, 20:1 to 1:20, even more especially from 10:1 to 1:10, 5:1 to 1:5, 2:1 to 1:2, 4:1 to 2:1, 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

Of particular note is a combination where the additional active ingredient has a different site of action from the compound of formula I. In certain instances, a combination with at least one other parasitic invertebrate pest control active ingredient having a similar spectrum of control but a different site of action will be particularly advantageous for resistance management. Thus, a combination product of the invention may comprise a pesticidally effective amount of a compound of formula I and pesticidally effective amount of at least one additional parasitic invertebrate pest control active ingredient having a similar spectrum of control but a different site of action.

One skilled in the art recognizes that because in the environment and under physiological conditions salts of chemical compounds are in equilibrium with their corresponding non salt forms, salts share the biological utility of the non salt forms.

Thus a wide variety of salts of compounds of the invention (and active ingredients used in combination with the active ingredients of the invention) may be useful for control of invertebrate pests and animal parasites. Salts include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The compounds of the invention also include N-oxides. Accordingly, the invention comprises combinations of compounds of the invention including N-oxides and salts thereof and an additional active ingredient including N-oxides and salts thereof.

The compositions for use in animal health may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in McCutcheon's Volume 2: Functional Materials, annual International and North American editions published by McCutcheon's Division, The Manufacturing Confectioner Publishing Co.; and PCT Publication WO 03/024222.

The compounds of the invention can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of the combination products. Compositions with spray oils, spray oil concentrations, spreader stickers, adjuvants, other solvents, and synergists such as piperonyl butoxide often enhance compound efficacy. Such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as the case may be. Of note is a spray composition comprising a pesticidally effective amount of a compound of the invention and a carrier. One embodiment of such a spray composition comprises a pesticidally effective amount of a compound of the invention and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one parasitic invertebrate pest selected from the group consisting of mosquitoes, black flies, stable flies, deer flies, horse flies, wasps, yellow jackets, hornets, ticks, spiders, ants, gnats, and the like, including individually or in combinations.

The controlling of animal parasites includes controlling external parasites that are parasitic to the surface of the body of the host animal (e.g., shoulders, armpits, abdomen, inner part of the thighs) and internal parasites that are parasitic to the inside of the body of the host animal (e.g., stomach, intestine, lung, veins, under the skin, lymphatic tissue). External parasitic or disease transmitting pests include, for example, chiggers, ticks, lice, mosquitoes, flies, mites and fleas. Internal parasites include heartworms, hookworms and helminths. The compounds of the invention may be particularly suitable for combating external parasitic pests. The compounds of the invention may be suitable for systemic and/or non-systemic control of infestation or infection by parasites on animals.

The compounds of the invention may be suitable for combating parasitic invertebrate pests that infest animal subjects including those in the wild, livestock and agricultural working animals. Livestock is the term used to refer (singularly or plurally) to a domesticated animal intentionally reared in an agricultural setting to make produce such as food or fiber, or for its labor; examples of livestock include cattle, sheep, goats, horses, pigs, donkeys, camels, buffalo, rabbits, hens, turkeys, ducks and geese (e.g., raised for meat, milk, butter, eggs, fur, leather, feathers and/or wool). By combating parasites, fatalities and performance reduction (in terms of meat, milk, wool, skins, eggs, etc.) are reduced, so that applying the compounds of the invention allows more economic and simple husbandry of animals.

The compounds of the invention may be suitable for combating parasitic invertebrate pests that infest companion animals and pets (e.g., dogs, cats, pet birds and aquarium fish), research and experimental animals (e.g., hamsters, guinea pigs, rats and mice), as well as animals raised for/in zoos, wild habitats and/or circuses.

In an embodiment of this invention, the animal is preferably a vertebrate, and more preferably a mammal, avian or fish. In a particular embodiment, the animal subject is a mammal (including great apes, such as humans). Other mammalian subjects include primates (e.g., monkeys), bovine (e.g., cattle or dairy cows), porcine (e.g., hogs or pigs), ovine (e.g., goats or sheep), equine (e.g., horses), canine (e.g., dogs), feline (e.g., house cats), camels, deer, donkeys, buffalos, antelopes, rabbits, and rodents (e.g., guinea pigs, squirrels, rats, mice, gerbils, and hamsters). Avians include Anatidae (swans, ducks and geese), Columbidae (e.g., doves and pigeons), Phasianidae (e.g., partridges, grouse and turkeys), Thesienidae (e.g., domestic chickens), Psittacines (e.g., parakeets, macaws, and parrots), game birds, and ratites (e.g., ostriches).

Birds treated or protected by the compounds of the invention can be associated with either commercial or noncommercial aviculture. These include Anatidae, such as swans, geese, and ducks, Columbidae, such as doves and domestic pigeons, Phasianidae, such as partridge, grouse and turkeys, Thesienidae, such as domestic chickens, and Psittacines, such as parakeets, macaws and parrots raised for the pet or collector market, among others.

For purposes of the present invention, the term "fish" is understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping. Examples of potential fish recipients include the Salmonidae, Serranidae, Sparidae, Cichlidae, and Centrarchidae, among others.

Other animals are also contemplated to benefit from the inventive methods, including marsupials (such as kangaroos), reptiles (such as farmed turtles), and other economically important domestic animals for which the inventive methods are safe and effective in treating or preventing parasite infection or infestation.

Examples of parasitic invertebrate pests controlled by administering a pesticidally effective amount of the compounds of the invention to an animal to be protected include ectoparasites (arthropods, acarines, etc.) and endoparasites (helminths, e.g., nematodes, trematodes, cestodes, acanthocephalans, etc.).

The disease or group of diseases described generally as helminthiasis is due to infection of an animal host with parasitic worms known as helminths. The term 'helminths' is meant to include nematodes, trematodes, cestodes and acanthocephalans. Helminthiasis is a prevalent and serious economic problem with domesticated animals such as swine, sheep, horses, cattle, goats, dogs, cats and poultry.

Among the helminths, the group of worms described as nematodes causes widespread and at times serious infection in various species of animals.

Nematodes that are contemplated to be treated by the compounds of the invention include, without limitation, the following genera: *Acanthocheilonema, Aelurostrongylus, Ancylostoma, Angiostrongylus, Ascaridia, Ascaris, Brugia, Bunostomum, Capillaria, Chabertia, Cooperia, Crenosoma, Dictyocaulus, Dioctophyme, Dipetalonema, Diphyllobothrium, Dirofilaria, Dracunculus, Enterobius, Filaroides, Haemonchus, Heterakis, Lagochilascaris, Loa, Mansonella, Muellerius, Necator, Nematodirus, Oesophagostomum, Ostertagia, Oxyuris, Parafilaria, Parascaris, Physaloptera, Protostrongylus, Setaria, Spirocerca, Stephanofilaria, Strongyloides, Strongylus, Thelazia, Toxascaris, Toxocara, Trichinella, Trichonema, Trichostrongylus, Trichuris, Uncinaria* and *Wuchereria*.

Of the above, the most common genera of nematodes infecting the animals referred to above are *Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris*. Certain of these, such as *Nematodirus, Cooperia* and *Oesophagostomum* attack primarily the intestinal tract while others, such as *Haemonchus* and *Ostertagia*, are more prevalent in the stomach while others such as *Dictyocaulus* are found in the lungs. Still other parasites may be located in other tissues such as the heart and blood vessels, subcutaneous and lymphatic tissue and the like.

Trematodes that are contemplated to be treated by the invention and by the inventive methods include, without limitation, the following genera: *Alaria, Fasciola, Nanophyetus, Opisthorchis, Paragonimus* and *Schistosoma*.

Cestodes that are contemplated to be treated by the invention and by the inventive methods include, without limitation, the following genera: *Diphyllobothrium, Diplydium, Spirometra* and *Taenia*.

The most common genera of parasites of the gastrointestinal tract of humans are *Ancylostoma, Necator, Ascaris, Strongy hides, Trichinella, Capillaria, Trichuris* and *Enterobius*. Other medically important genera of parasites which are found in the blood or other tissues and organs outside the gastrointestinal tract are the filarial worms such as *Wuchereria, Brugia, Onchocerca* and *Loa*, as well as *Dracunculus* and extra intestinal stages of the intestinal worms *Strongyloides* and *Trichinella*.

Numerous other helminth genera and species are known to the art, and are also contemplated to be treated by the compounds of the invention. These are enumerated in great detail in Textbook of Veterinary Clinical Parasitology, Volume 1, Helminths, E. J. L. Soulsby, F. A. Davis Co., Philadelphia, Pa.; Helminths, Arthropods and Protozoa, ($6^{th}$ Edition of Monnig's Veterinary Helminthology and Entomology), E. J. L. Soulsby, Williams and Wilkins Co., Baltimore, Md.

The compounds of the invention may be effective against a number of animal ectoparasites (e.g., arthropod ectoparasites of mammals and birds).

Insect and acarine pests include, e.g., biting insects such as flies and mosquitoes, mites, ticks, lice, fleas, true bugs, parasitic maggots, and the like.

Adult flies include, e.g., the horn fly or *Haematobia irritans*, the horse fly or *Tabanus* spp., the stable fly or *Stomoxys calcitrans*, the black fly or *Simulium* spp., the deer fly or *Chrysops* spp., the louse fly or *Melophagus ovinus*, and the tsetse fly or *Glossina* spp. Parasitic fly maggots include, e.g., the bot fly (*Oestrus ovis* and *Cuterebra* spp.), the blow fly or *Phaenicia* spp., the screwworm or *Cochliomyia hominivorax*, the cattle grub or *Hypoderma* spp., the fleeceworm and the *Gastrophilus* of horses. Mosquitoes include, for example, *Culex* spp., *Anopheles* spp. and *Aedes* spp.

Mites include *Mesostigmalphatalpha* spp. e.g., mesostigmatids such as the chicken mite, *Dermalphanyssus galphallinalphae*; itch or scab mites such as *Sarcoptidae* spp. for example, *Salpharcoptes scalphabiei*; mange mites such as *Psoroptidae* spp. including *Chorioptes bovis* and *Psoroptes ovis*; chiggers e.g., *Trombiculidae* spp. for example the North American chigger, *Trombiculalpha alphalfreddugesi*.

Ticks include, e.g., soft-bodied ticks including *Argasidae* spp. for example *Argalphas* spp. and *Ornithodoros* spp.;

hard-bodied ticks including *Ixodidae* spp., for example *Rhipicephalphalus sanguineus, Dermacentor variabilis, Dermacentor andersoni, Amblyomma americanum, Ixodes scapularis* and other *Rhipicephalus* spp. (including the former *Boophilus* genera).

Lice include, e.g., sucking lice, e.g., *Menopon* spp. and *Bovicola* spp.; biting lice, e.g., *Haematopinus* spp., *Linognathus* spp. and *Solenopotes* spp.

Fleas include, e.g., *Ctenocephalides* spp., such as dog flea (*Ctenocephalides canis*) and cat flea (*Ctenocephalides felis*); *Xenopsylla* spp. such as oriental rat flea (*Xenopsylla cheopis*); and *Pulex* spp. such as human flea (*Pulex irritans*).

True bugs include, e.g., *Cimicidae* or e.g., the common bed bug (*Cimex lectularius*); *Triatominae* spp. including triatomid bugs also known as kissing bugs; for example *Rhodnius prolixus* and *Triatoma* spp.

Generally, flies, fleas, lice, mosquitoes, gnats, mites, ticks and helminths cause tremendous losses to the livestock and companion animal sectors. Arthropod parasites also are a nuisance to humans and can vector disease-causing organisms in humans and animals.

Numerous other parasitic invertebrate pests are known to the art, and are also contemplated to be treated by the compounds of the invention. These are enumerated in great detail in Medical and Veterinary Entomology, D. S. Kettle, John Wiley AND Sons, New York and Toronto; Control of Arthropod Pests of Livestock: A Review of Technology, R. O. Drummand, J. E. George, and S. E. Kunz, CRC Press, Boca Raton, Fla.

The compounds of the invention may also be effective against ectoparasites including: flies such as *Haematobia (Lyperosia) irritans* (horn fly), *Simulium* spp. (blackfly), *Glossina* spp. (tsetse flies), *Hydrotaea irritans* (head fly), *Musca autumnalis* (face fly), *Musca domestica* (house fly), *Morellia simplex* (sweat fly), *Tabanus* spp. (horse fly), *Hypoderma bovis, Hypoderma lineatum, Lucilia sericata, Lucilia cuprina* (green blowfly), *Calliphora* spp. (blowfly), *Protophormia* spp., *Oestrus ovis* (nasal botfly), *Culicoides* spp. (midges), *Hippobosca equine, Gastrophilus intestinalis, Gastrophilus haemorrhoidalis* and *Gastrophilus nasalis*; lice such as *Bovicola* (Damalinia) *bovis, Bovicola equi, Haematopinus asini, Felicola subrostratus, Heterodoxus spiniger, Lignonathus setosus* and *Trichodectes canis*; keds such as *Melophagus ovinus*; and mites such as *Psoroptes* spp., *Sarcoptes scabei, Chorioptes bovis, Demodex equi, Cheyletiella* spp., *Notoedres cati, Trombicula* spp. and *Otodectes cyanotis* (ear mites).

Treatments of the invention are by conventional means such as by enteral administration in the form of, for example, tablets, capsules, drinks, drenching preparations, granulates, pastes, boli, feed-through procedures, or suppositories; or by parenteral administration, such as, for example, by injection (including intramuscular, subcutaneous, intravenous, intraperitoneal) or implants; or by nasal administration.

When compounds of the invention are applied in combination with an additional biologically active ingredient, they may be administered separately e.g. as separate compositions. In this case, the biologically active ingredients may be administered simultaneously or sequentially. Alternatively, the biologically active ingredients may be components of one composition.

The compounds of the invention may be administered in a controlled release form, for example in subcutaneous or orally adminstered slow release formulations.

Typically a parasiticidal composition according to the present invention comprises a compound of the invention, optionally in combination with an additional biologically active ingredient, or N-oxides or salts thereof, with one or more pharmaceutically or veterinarily acceptable carriers comprising excipients and auxiliaries selected with regard to the intended route of administration (e.g., oral or parenteral administration such as injection) and in accordance with standard practice. In addition, a suitable carrier is selected on the basis of compatibility with the one or more active ingredients in the composition, including such considerations as stability relative to pH and moisture content. Therefore of note are compounds of the invention for protecting an animal from an invertebrate parasitic pest comprising a parasitically effective amount of a compound of the invention, optionally in combination with an additional biologically active ingredient and at least one carrier.

For parenteral administration including intravenous, intramuscular and subcutaneous injection, the compounds of the invention can be formulated in suspension, solution or emulsion in oily or aqueous vehicles, and may contain adjuncts such as suspending, stabilizing and/or dispersing agents.

The compounds of the invention may also be formulated for bolus injection or continuous infusion. Pharmaceutical compositions for injection include aqueous solutions of water-soluble forms of active ingredients (e.g., a salt of an active compound), preferably in physiologically compatible buffers containing other excipients or auxiliaries as are known in the art of pharmaceutical formulation. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes.

Aqueous injection suspensions may contain substances that increase the viscosity of the suspension, such as sodium carboxymethyl cellulose, sorbitol, or dextran. Formulations for injection may be presented in unit dosage form, e.g., in ampoules or in multi-dose containers. Alternatively, the active ingredient may be in powder form for constitution with a suitable vehicle, e.g., sterile, pyrogen-free water, before use.

In addition to the formulations described supra, the compounds of the invention may also be formulated as a depot preparation. Such long acting formulations may be administered by implantation (for example, subcutaneously or intramuscularly) or by intramuscular or subcutaneous injection. The compounds of the invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

For administration by inhalation, the compounds of the invention can be delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount.

Capsules and cartridges of, for example, gelatin for use in an inhaler or insufflator may be formulated containing a powder mix of the compound and a suitable powder base such as lactose or starch.

The compounds of the invention may have favourable pharmacokinetic and pharmacodynamic properties providing systemic availability from oral administration and ingestion. Therefore after ingestion by the animal to be protected, parasiticidally effective concentrations of a compound of the invention in the bloodstream may protect the treated animal from blood-sucking pests such as fleas, ticks and lice. Therefore of note is a composition for protecting an animal from an invertebrate parasite pest in a form for oral administration (i.e. comprising, in addition to a parasiticidally effective amount of a compound of the invention, one or more carriers selected from binders and fillers suitable for oral administration and feed concentrate carriers).

For oral administration in the form of solutions (the most readily available form for absorption), emulsions, suspensions, pastes, gels, capsules, tablets, boluses, powders, granules, rumen-retention and feed/water/lick blocks, the compounds of the invention can be formulated with binders/fillers known in the art to be suitable for oral administration compositions, such as sugars and sugar derivatives (e.g., lactose, sucrose, mannitol, sorbitol), starch (e.g., maize starch, wheat starch, rice starch, potato starch), cellulose and derivatives (e.g., methylcellulose, carboxymethylcellulose, ethylhydroxycellulose), protein derivatives (e.g., zein, gelatin), and synthetic polymers (e.g., polyvinyl alcohol, polyvinylpyrrolidone). If desired, lubricants (e.g., magnesium stearate), disintegrating agents (e.g., cross-linked polyvinylpyrrolidinone, agar, alginic acid) and dyes or pigments can be added. Pastes and gels often also contain adhesives (e.g., acacia, alginic acid, bentonite, cellulose, xanthan gum, colloidal magnesium aluminum silicate) to aid in keeping the composition in contact with the oral cavity and not being easily ejected.

In one embodiment a composition of the present invention is formulated into a chewable and/or edible product (e.g., a chewable treat or edible tablet). Such a product would ideally have a taste, texture and/or aroma favored by the animal to be protected so as to facilitate oral administration of the compounds of the invention.

If the parasiticidal compositions are in the form of feed concentrates, the carrier is typically selected from high-performance feed, feed cereals or protein concentrates. Such feed concentrate-containing compositions can, in addition to the parasiticidal active ingredients, comprise additives promoting animal health or growth, improving quality of meat from animals for slaughter or otherwise useful to animal husbandry. These additives can include, for example, vitamins, antibiotics, chemotherapeutics, bacteriostats, fungistats, coccidiostats and hormones.

The compound of the invention may also be formulated in rectal compositions such as suppositories or retention enemas, using, e.g., conventional suppository bases such as cocoa butter or other glycerides.

The formulations for the method of this invention may include an antioxidant, such asBHT (butylated hydroxytoluene). The antioxidant is generally present in amounts of at 0.1-5 percent (wt/vol). Some of the formulations require a solubilizer, such as oleic acid, to dissolve the active agent, particularly if spinosad is included. Common spreading agents used in these pour-on formulations include isopropyl myristate, isopropyl palmitate, caprylic/capric acid esters of saturated $C_{12}$-$C_{18}$ fatty alcohols, oleic acid, oleyl ester, ethyl oleate, triglycerides, silicone oils and dipropylene glycol methyl ether. The pour-on formulations for the method of this invention are prepared according to known techniques. Where the pour-on is a solution, the parasiticide/insecticide is mixed with the carrier or vehicle, using heat and stirring if required. Auxiliary or additional ingredients can be added to the mixture of active agent and carrier, or they can be mixed with the active agent prior to the addition of the carrier. Pour-on formulations in the form of emulsions or suspensions are similarly prepared using known techniques.

Other delivery systems for relatively hydrophobic pharmaceutical compounds may be employed. Liposomes and emulsions are well-known examples of delivery vehicles or carriers for hydrophobic drugs. In addition, organic solvents such as dimethylsulfoxide may be used, if needed.

The rate of application required for effective parasitic invertebrate pest control (e.g. "pesticidally effective amount") will depend on such factors as the species of parasitic invertebrate pest to be controlled, the pest's life cycle, life stage, its size, location, time of year, host crop or animal, feeding behavior, mating behavior, ambient moisture, temperature, and the like. One skilled in the art can easily determine the pesticidally effective amount necessary for the desired level of parasitic invertebrate pest control.

In general for veterinary use, the compounds of the invention are administered in a pesticidally effective amount to an animal, particularly a homeothermic animal, to be protected from parasitic invertebrate pests.

A pesticidally effective amount is the amount of active ingredient needed to achieve an observable effect diminishing the occurrence or activity of the target parasitic invertebrate pest. One skilled in the art will appreciate that the pesticidally effective dose can vary for the various compounds and compositions useful for the method of the present invention, the desired pesticidal effect and duration, the target parasitic invertebrate pest species, the animal to be protected, the mode of application and the like, and the amount needed to achieve a particular result can be determined through simple experimentation.

For oral or parenteral administration to animals, a dose of the compositions of the present invention administered at suitable intervals typically ranges from about 0.01 mg/kg to about 100 mg/kg, and preferably from about 0.01 mg/kg to about 30 mg/kg of animal body weight.

Suitable intervals for the administration of the compositions of the present invention to animals range from about daily to about yearly. Of note are administration intervals ranging from about weekly to about once every 6 months. Of particular note are monthly administration intervals (i.e. administering the compounds to the animal once every month).

The following Examples illustrate, but do not limit, the invention.

PREPARATION EXAMPLES

The following abbreviations were used in this section: s=singlet; bs=broad singlet; d=doublet; dd=double doublet; dt=double triplet; t=triplet; tt=triple triplet, q=quartet, sept=septet; m=multiplet; Me=methyl; Et=ethyl; Pr=propyl; Bu=butyl; M.p.=melting point; RT=retention time, [M+H]$^+$ =molecular mass of the molecular cation, [M−H]$^-$=molecular mass of the molecular anion.

The following LC-MS methods were used to characterize the compounds:
Method C

| | |
|---|---|
| MS | ZQ Mass Spectrometer from Waters (single quadrupole mass spectrometer), ionization method: electrospray, polarity: positive ionization, capillary (kV) 3.00, cone (V) 30.00, extractor (V) 3.00, source temperature (° C.) 100, desolvation temperature (° C.) 200, cone gas flow (L/Hr) 200, desolvation gas flow (L/Hr) 250, mass range: 150 to 800 Da. |

| LC | 1100er Series HPLC from Agilent: quaternary pump, heated column compartment and diode-array detector. |
|---|---|
| | Column: Waters Atlantis dc18, length (mm) 20, internal diameter (mm) 3, particle size (μm) 3, temperature (° C.) 40, DAD wavelength range (nm): 200 to 500, solvent gradient: A = 0.1% v/v formic acid in water and B = 0.1% v/v formic acid in acetonitrile. |

| Time (min) | A % | B % | Flow (ml/min) |
|---|---|---|---|
| 0.0 | 90 | 10 | 1.7 |
| 5.5 | 0.0 | 100 | 1.7 |
| 5.8 | 0.0 | 100 | 1.7 |
| 5.9 | 90 | 10 | 1.7 |

Method D

| MS | ZMD Mass Spectrometer from Waters (single quadrupole mass spectrometer), ionization method: electrospray, polarity: positive ionization, capillary (kV) 3.00, cone (V) 30.00, extractor (V) 3.00, source temperature (° C.) 150, desolvation temperature (° C.) 320, cone gas flow (L/Hr) 50, desolvation gas flow (L/Hr) 400, mass range: 150 to 800 Da. |
|---|---|
| LC | Alliance 2795 LC HPLC from Waters: quaternary pump, heated column compartment and diode-array detector. |
| | Column: Waters Atlantis dc18, length (mm) 20, internal diameter (mm) 3, particle size (μm) 3, temperature (° C.) 40, DAD wavelength range (nm): 200 to 500, solvent gradient: A = 0.1% v/v formic acid in water and B = 0.1% v/v formic acid in acetonitrile. |

| Time (min) | A % | B % | Flow (ml/min) |
|---|---|---|---|
| 0.0 | 80 | 20 | 1.7 |
| 2.5 | 0.0 | 100 | 1.7 |
| 2.8 | 0.0 | 100 | 1.7 |
| 2.9 | 80 | 20 | 1.7 |

Method F

| MS | ZQ Mass Spectrometer from Waters (single quadrupole mass spectrometer), ionization method: electrospray, polarity: negative ionization, capillary (kV) 3.00, cone (V) 45.00, source temperature (° C.) 100, desolvation temperature (° C.) 250, cone gas flow (L/Hr) 50, desolvation gas flow (L/Hr) 400, mass range: 150 to 1000 Da. |
|---|---|
| LC | HP 1100 HPLC from Agilent: solvent degasser, binary pump, heated column compartment and diode-array detector. |
| | Column: Phenomenex Gemini C18, length (mm) 30, internal diameter (mm) 3, particle size (μm) 3, temperature (° C.) 60, DAD wavelength range (nm): 200 to 500, solvent gradient: A = 0.05% v/v formic acid in water and B = 0.04% v/v formic acid in acetonitrile/methanol (4:1). |

| Time (min) | A % | B % | Flow (ml/min) |
|---|---|---|---|
| 0.0 | 95 | 5.0 | 1.7 |
| 2.0 | 0.0 | 100 | 1.7 |
| 2.8 | 0.0 | 100 | 1.7 |
| 2.9 | 95 | 5.0 | 1.7 |
| 3.1 | 95 | 5 | 1.7 |

Example 1a

Separation of the Enantiomers of 3-(3,5-dichlorophenyl)-3-(trifluoromethyl)pyrrolidine by Diastereomeric Crystallization with L-Tartric Acid Chiral HPLC method:
HPLC Waters Alliance 2695
UV detector Waters 996 DAD
Column: Daicel CHIRALPAK® IA, 0.46 cm×25 cm
Mobile phase: Heptan/2-Propanol 70/30
Flow rate: 1 mL/min
Detection: DAD
Sample concentration: 1 mg/mL in Heptan/2-Propanol 70/30
Injection: 1 μL A mixture of rac-3-(3,5-dichlorophenyl)-3-(trifluoromethyl)pyrrolidine (1 g) and L-tartaric acid (530 mg) was completely dissolved in methanol (40 mL) and allowed to stand at room temperature after the removal of ca 10 mL of methanol Crystallization of the salts was allowed to occur overnight. After filtration, the solid (840 mg) was recrystallised one more time in methanol to obtained new crystals (200 mg). The mother liquors were evaporated to give a colorless solid (640 mg).

The crystals obtained and the mother liquors were separately extracted between ethyl acetate and a saturated solution of sodium carbonate to release the amine. After extraction, the crystals yielded a white solid (110 mg) which was analysed by chiral HPLC and proved to contain an enriched mixture of the enantiomers of 3-(3,5-dichlorophenyl)-3-(trifluoromethyl)pyrrolidine:

First eluting enantiomer: 4.04 min; 8.6%
Second eluting enantiomer: 5.42 min; 91.4%

Example 1b

Separation of the Enantiomers of 3-(3,5-dichlorophenyl)-3-(trifluoromethyl)pyrrolidine by Diastereomeric Crystallization with (+)-Dibenzoyl-D-Tartaric Acid A mixture of rac-3-(3,5-dichlorophenyl)-3-(trifluoromethyl)pyrrolidine (284 mg) was dissolved in 2-propanol (8 mL) and to this mixture was added a solution of (+)-dibenzoyl-D-tartaric acid (358 mg) in 2-propanol (8 mL). A white precipitate formed instantly. The solution was heated to 70° C. until a clear solution was obtained and the solution was left to cool slowly to room temperature. After 16 h the solid was filtered and washed thrice with 2-propanol (4 mL) and dried to furnish 400 mg of a white solid. The solid obtained was separately extracted between ethyl acetate and a saturated solution of sodium carbonate to release the amine. After extraction, the white solid (104 mg) obtained was analysed by chiral HPLC and proved to contain an enriched mixture of the enantiomers of 3-(3,5-dichlorophenyl)-3-(trifluoromethyl)pyrrolidine:

First eluting enantiomer: 4.04 min; 38.0
Second eluting enantiomer: 5.42 min; 62.0%

Example 2

Method for Preparing the Compounds of the Invention from a Carboxylic Acid

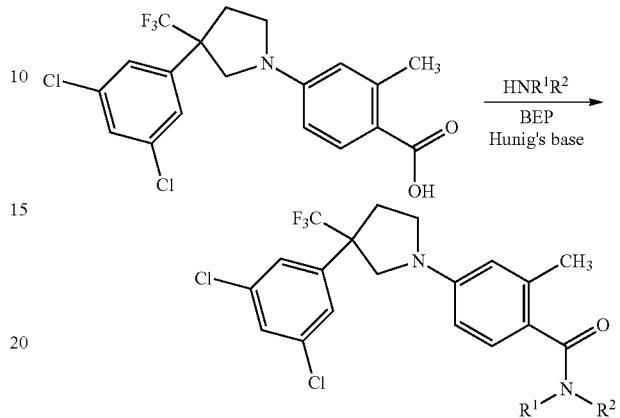

To a solution of the appropriate carboxylic acid (25 μmol), for example 4-[3-(3,5-Dichloro-phenyl)-3-trifluoromethyl-pyrrolidin-1-yl]-2-methyl-benzoic acid (preparation described in JP 2008110971) in dichloromethane (0.5 ml) was added an amine of formula $HNR^1R^2$ (30 mmol), for example 1-oxo-thietan-3-ylamine (preparation described in, for example, WO 2007/080131) in the case of compound No. A1 of Table A, diisopropylethylamine (Hunig's Base) (0.020 ml), followed by 2-bromo-1-ethyl pyridinium tetrafluoroborate (BEP) (12 mg). The reaction mixture was stirred at ambient temperature for 16 hours. Then dichlormethane was evaporated and the residue was dissolved in acetonitrile/dimethylacetamide (4:1) (0.8 ml) and purified by HPLC.

TABLE A (A)

| Compound No. | $R^1$ | $R^2$ | R | RT (min) | [M + H]$^+$ | LC-MS method |
|---|---|---|---|---|---|---|
| A1 | H | 1-oxo-thietan-3-yl- | H | 3.35 | 505 | C |
| A2 | H | 1,1-Dioxo-thietan-3-yl- | OCH3 | * | | |
| A3 | H | 1,1-Dioxo-thietan-3-yl- | F | * | | |
| A4 | H | thietan-3-yl- | H | 2.01 | 489 | D |
| A5 | H | 1,1-Dioxo-thietan-3-yl- | H | 1.82 | 521 | D |
| A6 | H | 3-Methyl-thietan-3-yl- | H | 2.11 | 503 | D |
| A7 | H | thietan-3-ylmethyl- | H | 2.02 | 503 | D |
| A8 | H | thietan-2-ylmethyl- | H | 2.04 | 503 | D |
| A9 | H | (1-oxothietan-2-yl)methyl- | H | 1.76 | 519 | D |
| A10 | H | (1,1-dioxothietan-2-yl)methyl- | H | 1.82 | 535 | D |
| A11 | H | 2-(thietan-3-yl)ethanyl | H | 2.07 | 517 | D |
| A12 | H | 2-(1,1-dioxothietan-3-yl)ethanyl | H | 1.81 | 549 | D |
| A13 | H | 3-(2,2,2-trifluoroethoxyimino)cyclobutyl | H | 2.09 | 582 | D |

*: NMR analysis:

Table A provides compounds of formula (A) where $G^1$ is oxygen, $R^3$ is trifluoromethyl, $R^5$ is methyl, and $R^1$ and $R^2$ have the values listed in the table below.

A2: $^1$H NMR (CDCl$_3$, 400 MHz): δ=7.39 (d, 1H), 7.34 (m, 2H), 6.33-6.45 (m, 2H), 4.80-4.91 (m, 2H), 4.54-4.68 (m, 2H), 3.98-4.13 (m, 2H), 3.93 (s, 2H), 3.79 (d, 2H), 3.58 (d, 2H), 3.50 (m, 2H), 2.81-2.92 (m, 2H), 2.44-2.59 (m, 2H) ppm

TABLE B

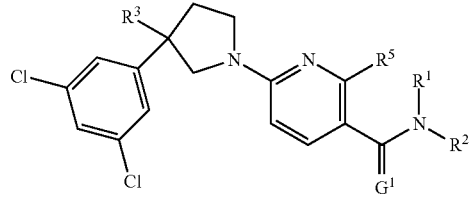

(B)

| Compound No. | $R^1$ | $R^2$ | RT (min) | [M + H]$^+$ | LC-MS method |
|---|---|---|---|---|---|
| B1 | H | thietan-3-yl- | 2.02 | 490/492 | D |
| B2 | H | 1-oxo-thietan-3-yl- | 1.45 | 506 | D |
| B3 | H | 1,1-Dioxo-thietan-3-yl- | 1.59 | 522 | D |
| B4 | H | 3-Methyl-thietan-3-yl- | 1.85 | 504 | D |
| B5 | H | thietan-3-ylmethyl- | 1.76 | 504 | D |
| B6 | H | 3-(2,2,2-trifluoroethoxy-imino)cyclobutyl | 1.9 | 583 | D |
| B7 | H | thietan-2-ylmethyl- | 1.77 | 504 | D |
| B8 | H | (1-oxothietan-2-yl)methyl- | 1.46 | 520 | D |
| B9 | H | (1,1-dioxothietan-2-yl)methyl- | 1.54 | 536 | D |
| B10 | H | 2-(thietan-3-yl)ethanyl | 1.8 | 518 | D |
| B11 | H | 2-(1,1-dioxothietan-3-yl)ethanyl | 1.52 | 550 | D |

Table B provides compounds of formula (B) where $G^1$ is oxygen, $R^3$ is trifluoromethyl, $R^5$ is methyl, and $R^1$ and $R^2$ have the values listed in the table below.

TABLE C

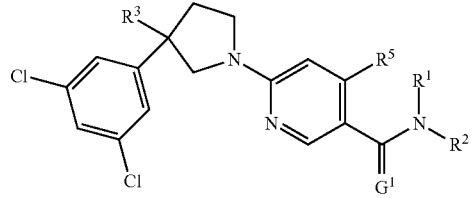

(C)

| Compound No. | $R^1$ | $R^2$ | RT (min) | [M + H]$^+$ | LC-MS method |
|---|---|---|---|---|---|
| C1 | H | thietan-3-yl- | 1.98 | [M − H]$^-$ 488/490 | F |
| C2 | H | 1-oxo-thietan-3-yl- | 1.4 | 506 | D |
| C3 | H | 1,1-Dioxo-thietan-3-yl- | 1.52 | 522 | D |
| C4 | H | 3-Methyl-thietan-3-yl- | 1.75 | 504 | D |
| C5 | H | thietan-3-ylmethyl- | 1.67 | 504 | D |
| C6 | H | 3-(2,2,2-trifluoroethoxy-imino)cyclobuty | 1.82 | 583 | D |
| C7 | H | thietan-2-ylmethyl- | 1.68 | 504 | D |
| C8 | H | (1-oxothietan-2-yl)methyl- | 1.39 | 520 | D |
| C9 | H | (1,1-dioxothietan-2-yl)methyl- | 1.48 | 536 | D |
| C10 | H | 2-(thietan-3-yl)ethanyl | 1.72 | 518 | D |
| C11 | H | 2-(1,1-dioxothietan-3-yl)ethanyl | 1.46 | 551 | D |

Table C provides compounds of formula (B) where $G^1$ is oxygen, $R^3$ is trifluoromethyl, $R^5$ is methyl, and $R^1$ and $R^2$ have the values listed in the table below.

TABLE D

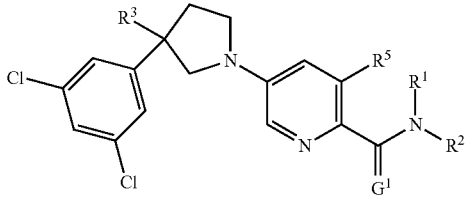

(D)

| Compound No. | $R^1$ | $R^2$ | RT (min) | [M + H]$^+$ | LC-MS method |
|---|---|---|---|---|---|
| D1 | H | thietan-3-yl- | 2.15 | 488/490 | F |

Table D provides compounds of formula (D) where $G^1$ is oxygen, $R^3$ is trifluoromethyl, $R^5$ is methyl, and $R^1$ and $R^2$ have the values listed in the table below.

Biological Examples

This Example illustrates the insecticidal and acaricidal properties of compounds of formula (I). The tests were performed as follows:

*Spodoptera littoralis* (Egyptian Cotton Leafworm):

Cotton leaf discs were placed on agar in a 24-well microtiter plate and sprayed with test solutions at an application rate of 200 ppm. After drying, the leaf discs were infested with 5 L1 larvae. The samples were checked for mortality, feeding behavior, and growth regulation 3 days after treatment (DAT).

The following compound gave at least 80% control of *Spodoptera littoralis*:

A1, A9, A10, A11, A12, A13, A2, A3, A4, A5, A6, A7, A8, B1, B8, B9, B10, B11, B2, B3, B4, B5, B6, B7, C1, C2, C3, C4, C5, C6, C7, D1.

*Heliothis virescens* (Tobacco Budworm):

Eggs (0-24 h old) were placed in 24-well microtiter plate on artificial diet and treated with test solutions at an application rate of 200 ppm (concentration in well 18 ppm) by pipetting. After an incubation period of 4 days, samples were checked for egg mortality, larval mortality, and growth regulation.

The following compound gave at least 80% control of *Heliothis virescens*:

A1, A9, A10, A11, A12, A13, A2, A3, A4, A5, A6, A7, A8, B1, B8, B9, B10, B11, B2, B3, B4, B5, B6, B7, C1, C2, C3, C4, C5, C6, D1.

*Plutella xylostella* (Diamond Back Moth):

24-well microtiter plate (MTP) with artificial diet was treated with test solutions at an application rate of 200 ppm (concentration in well 18 ppm) by pipetting. After drying, the MTP's were infested with L2 larvae (7-12 per well). After an incubation period of 6 days, samples were checked for larval mortality and growth regulation.

The following compound gave at least 80% control of *Plutella xylostella*:

A1, A9, A10, A11, A12, A13, A2, A3, A4, A5, A6, A7, A8, B1, B8, B10, B2, B3, B4, B5, B6, B7, C1, C8, C2, C3, C4, C5, C6, C7, D1.

*Diabrotica balteata* (Corn Root Worm):

A 24-well microtiter plate (MTP) with artificial diet was treated with test solutions at an application rate of 200 ppm (concentration in well 18 ppm) by pipetting. After drying, the MTP's were infested with L2 larvae (6-10 per well). After an incubation period of 5 days, samples were checked for larval mortality and growth regulation.

The following compound gave at least 80% control of *Diabrotica balteata*:
A1, A9, A10, A11, A12, A13, A2, A3, A4, A5, A6, A7, A8, B1, B9, B10, B11, B2, B3, B4, B5, B6, B7, C1, C2, C3, C4, C5, C6, C7, D1.

*Thrips tabaci* (Onion Thrips):

Sunflower leaf discs were placed on agar in a 24-well microtiter plate and sprayed with test solutions at an application rate of 200 ppm. After drying, the leaf discs were infested with a *thrip* population of mixed ages. After an incubation period of 7 days, samples were checked for mortality.

The following compounds gave at least 80% control of *Thrips tabaci*:
A1, A2, A3, A4, A5, A6, A7, B1, B2, B3, B4, B5, C1, C5.

*Tetranychus urticae* (Two-Spotted Spider Mite):

Bean leaf discs on agar in 24-well microtiter plates were sprayed with test solutions at an application rate of 200 ppm. After drying, the leaf discs are infested with mite populations of mixed ages. 8 days later, discs are checked for egg mortality, larval mortality, and adult mortality.

The following compound gave at least 80% control of *Tetranychus urticae*: A1, A9, A10, A11, A12, A13, A2, A3, A4, A5, A6, A7, A8, B1, B8, B9, B10, B11, B2, B3, B4, B5, B6, B7, C1, C9, C2, C3, C4, C5, C7.

Comparative Examples

In the comparative test Tables the tests were performed as described above with the application rates indicated in the Tables.

Comparative test Table 1

Compound 1-4 of WO08128711

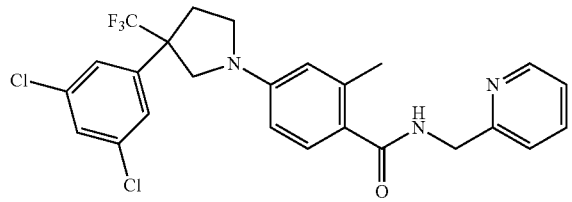 [SMILES: Cc1cc(N2CCC(c3cc(Cl)cc(Cl)c3)(C(F)(F)F)C2)ccc1C(=O)NCc1ccccn1]

Compound A1 of the present invention

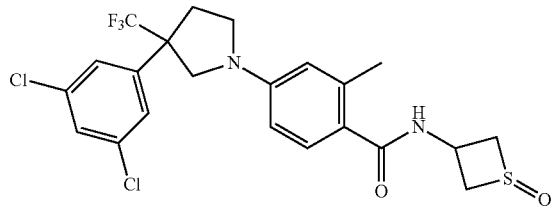 [SMILES: Cc1cc(N2CCC(c3cc(Cl)cc(Cl)c3)(C(F)(F)F)C2)ccc1C(=O)NC1CS(=O)C1]

| Compound | Test | Application rate | Control |
|---|---|---|---|
| Compound 1-4 of WO08128711 | *Heliothis virescens* (Tobacco budworm) | 0.8 ppm | 0% |
| Compound A1 of the present invention | *Heliothis virescens* (Tobacco budworm) | 0.8 ppm | 100% |
| Compound 1-4 of WO08128711 | *Diabrotica balteata* (Corn root worm): | 12 ppm | 0% |
| Compound A1 of the present invention | *Diabrotica balteata* (Corn root worm): | 12 ppm | 80% |
| Compound 1-4 of WO08128711 | *Tetranychus urticae* (Two-spotted spider mite) | 12 ppm | 0% |

Comparative test Table 1 -continued

Compound 1-4 of WO08128711

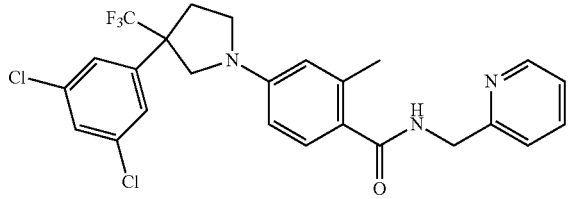 [SMILES: Cc1cc(N2CCC(c3cc(Cl)cc(Cl)c3)(C(F)(F)F)C2)ccc1C(=O)NCc1ccccn1]

Compound A1 of the present invention

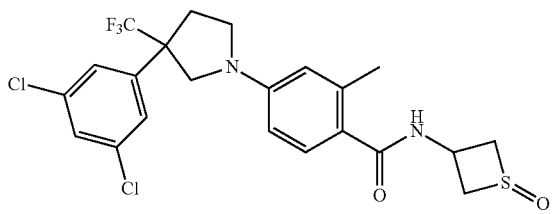

| Compound | Test | Application rate | Control |
|---|---|---|---|
| Compound A1 of the present invention | *Tetranychus urticae* (Two-spotted spider mite) | 12 ppm | 100% |

Comparative data Table 2

Compound 1-4 of WO08128711

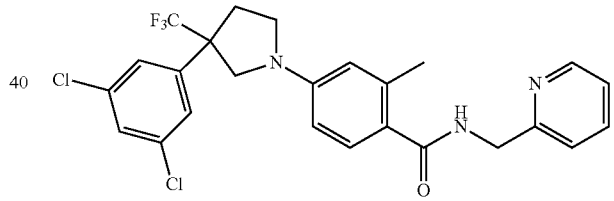

Compound A4 of the present invention

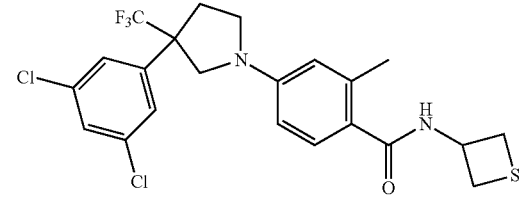 [SMILES: Cc1cc(N2CCC(c3cc(Cl)cc(Cl)c3)(C(F)(F)F)C2)ccc1C(=O)NC1CSC1]

| Compound | Test | Application rate | Control |
|---|---|---|---|
| Compound 1-4 of WO08128711 | *Heliothis virescens* (Tobacco budworm) | 3 ppm | 50% |
| Compound A4 of the present invention | *Heliothis virescens* (Tobacco budworm) | 3 ppm | 80% |
| Compound 1-4 of WO08128711 | *Diabrotica balteata* (Corn root worm): | 12 ppm | 0% |
| Compound A4 of the present invention | *Diabrotica balteata* (Corn root worm): | 12 ppm | 100% |
| Compound 1-4 of WO08128711 | *Tetranychus urticae* (Two-spotted spider mite) | 12 ppm | 0% |

Comparative data Table 2

Compound 1-4 of WO08128711

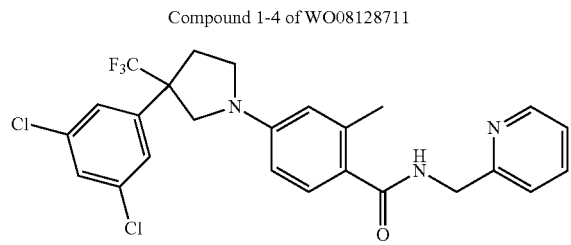

Compound A4 of the present invention

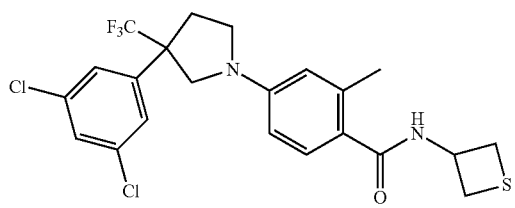

| Compound | Test | Application rate | Control |
|---|---|---|---|
| Compound A4 of the present invention | *Tetranychus urticae* (Two-spotted spider mite) | 12 ppm | 100% |

Comparative data Table 3

Compound 1-4 of WO08128711

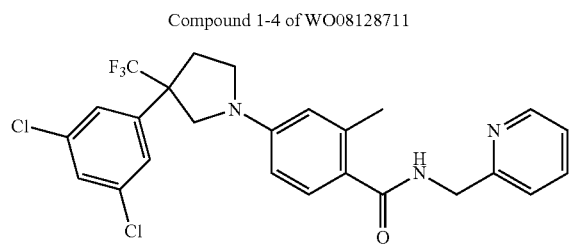

Compound A5 of the present invention

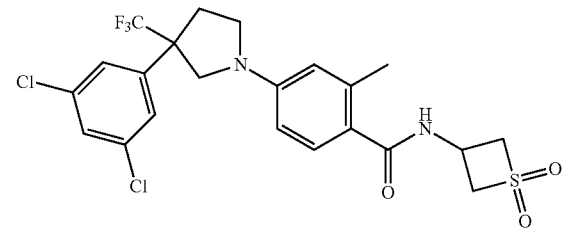

| Compound | Test | Application rate | Control |
|---|---|---|---|
| Compound 1-4 of WO08128711 | *Heliothis virescens* (Tobacco budworm) | 3 ppm | 50% |
| Compound A5 of the present invention | *Heliothis virescens* (Tobacco budworm) | 3 ppm | 80% |
| Compound 1-4 of WO08128711 | *Diabrotica balteata* (Corn root worm): | 12 ppm | 0% |
| Compound A5 of the present invention | *Diabrotica balteata* (Corn root worm): | 12 ppm | 100% |
| Compound 1-4 of WO08128711 | *Tetranychus urticae* (Two-spotted spider mite) | 12 ppm | 0% |

Comparative data Table 3

Compound 1-4 of WO08128711

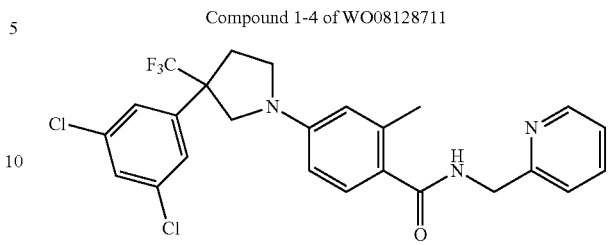

Compound A5 of the present invention

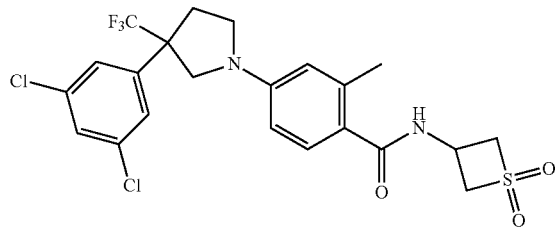 [SMILES: Cc1cc(N2CCC(c3cc(Cl)cc(Cl)c3)(C(F)(F)F)C2)ccc1C(=O)NC1CS(=O)(=O)C1]

| Compound | Test | Application rate | Control |
|---|---|---|---|
| Compound A5 of the present invention | *Tetranychus urticae* (Two-spotted spider mite) | 12 ppm | 100% |

The enantioenriched compounds can be obtained by chiral separation on preparative HPLC, which was conducted on compound A5 according to the following procedure:

Analytical HPLC Method:

HPLC from Waters: allianceHT, 996 Waters UV/Visible Detector, 2795 Separation Module Column: Daicel CHIRALPAK® IA-3, 0.46 cm×10 cm Mobile phase: Heptan/2-Propanol/0.1DEA 70/30

Flow rate: 1 ml/min

Detection: UV 270 nm

Temperature: 25° C.

Preparative HPLC Method:

Autopurification System from Waters: 2767 sample Manager, 2489 UV/Visible Detector, 2545 Quaternary Gradient Module.

Column: Daicel CHIRALPAK® IA 1.0 cm×25 cm

Mobile phase: Heptan/2-Propanol/0.1DEA 70/30

Flow rate: 5 ml/min

Detection: UV 270 nm

Temperature: 25° C.

Results:

From 75 mg crude material (plus ca ~40 mg of impure material), 2 compounds could be isolated:

| First eluting enantiomer A5a | Second eluting enantiomer A5b |
|---|---|
| Retention time (min) ~5.6 | Retention time (min) ~8.5 |
| Quantity (mg) 39.5 | Quantity (mg) 34.5 |
| Chemical purity (area % at 270 nm) 95 | Chemical purity (area % at 270 nm) 99 |
| Enantiomeric excess (%) >98 | Enantiomeric excess (%) >98 |

Biological Examples of Enantiomers

These examples illustrate the comparative insecticidal and acaricidal properties of compounds A5a and A5b. The tests were performed as follows:

*Spodoptera littoralis* (Systemic) (Egyptian Cotton Leaf Worm)

Test compounds were applied by pipette into 24 well plates and mixed with agar. Salad seeds were placed on the agar and the multi well plate is closed by another plate which contains also agar. After 7 days the roots have absorbed the compound and the salad has grown into the lid plate. The salad leafs were now cut off into the lid plate. *Spodoptera* eggs were pipette through a plastic stencil on a humid gel blotting paper and the plate closed with it. The samples are checked for mortality, repellent effect, feeding behavior, and growth regulation 5 days after infestation.

| Insects: Spodoptera littoralis | % Control at 200 ppm | % Control at 12.5 ppm |
|---|---|---|
| Compound A5a | 100 | 100 |
| Compound A5b | 100 | 0 |

*Heliothis virescens* (Tobacco Budworm):

Eggs (0-24 h old) were placed in 24-well microtiter plate on artificial diet and treated with test solutions at an application rate starting at 200 ppm (concentration in well 18 ppm) by pipetting. After an incubation period of 4 days, samples were checked for egg mortality, larval mortality, and growth regulation.

| Insects: Heliothis virescens | % Control at 200 ppm | % Control at 12.5 ppm |
|---|---|---|
| Compound A5a | 100 | 100 |
| Compound A5b | 100 | 0 |

*Plutella xylostella* (Diamond Back Moth):

24-well microtiter plate (MTP) with artificial diet was treated with test solutions at an application rate of 200 ppm (concentration in well 18 ppm) by pipetting. After drying, the MTPs were infested with L2 larvae (7-12 per well). After an incubation period of 6 days, samples were checked for larval mortality and growth regulation.

| Insects: Plutella xylostella | % Control at 200 ppm | % Control at 12.5 ppm |
|---|---|---|
| Compound A5a | 100 | 100 |
| Compound A5b | 100 | 0 |

*Diabrotica balteata* (Corn Root Worm):

A 24-well microtiter plate (MTP) with artificial diet was treated with test solutions at an application rate of 12.5 ppm (concentration in well 18 ppm) by pipetting. After drying, the MTP's were infested with L2 larvae (6-10 per well). After an incubation period of 5 days, samples were checked for larval mortality and growth regulation.

| Insects: Diabrotica balteata | % Control at 200 ppm | % Control at 12.5 ppm |
|---|---|---|
| Compound A5a | 100 | 100 |
| Compound A5b | 0 | 0 |

*Thrips tabaci* (Onion Thrips):

Sunflower leaf discs were placed on agar in a 24-well microtiter plate and sprayed with test solutions at an application rate of 50 ppm. After drying, the leaf discs were infested with a thrip population of mixed ages. After an incubation period of 7 days, samples were checked for mortality.

| Insects: Thrips tabaci | % Control at 200 ppm |
|---|---|
| Compound A5a | 90 |
| Compound A5b | 0 |

*Tetranychus urticae* (Two-Spotted Spider Mite):

Bean leaf discs on agar in 24-well microtiter plates were sprayed with test solutions at an application rate of 200 ppm. After drying, the leaf discs are infested with mite populations of mixed ages. 8 days later, discs are checked for egg mortality, larval mortality, and adult mortality.

| Insects: Tetranychus urticae | % Control at 200 ppm | % Control at 12.5 ppm |
|---|---|---|
| Compound A5a | 100 | 100 |
| Compound A5b | 0 | 0 |

The invention claimed is:

1. A compound of formula (I)

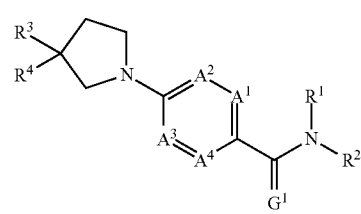

where
$A^1$, $A^2$, $A^3$ and $A^4$ are independently of each other C—H, C—$R^5$ or nitrogen;
$G^1$ is oxygen or sulfur;
$R^1$ is hydrogen, $C_1$-$C_8$alkyl, $C_1$-$C_8$alkoxy-, $C_1$-$C_8$alkylcarbonyl-, $C_1$-$C_8$alkoxycarbonyl- or $C_1$-$C_8$haloalkoxycarbonyl-;
$R^2$ is a group of formula (II)

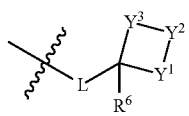

where
L is a single bond or $C_1$-$C_6$alkylene; and
$Y^1$, $Y^2$ and $Y^3$ are independently of another $CR^8R^9$, C=O, C=N—$OR^{10}$, N—$R^{10}$, S, SO, $SO_2$, S=N—$R^{10}$ or SO=N—R$^{10}$, provided that at least one of Y$^1$, Y$^2$ or Y$^3$ is not CR$^8$R$^9$, C=O or C=N—OR$^{10}$;

R$^3$ is C$_1$-C$_8$haloalkyl;

R$^4$ is aryl or aryl substituted by one to five R$^7$, or heteroaryl or heteroaryl substituted by one to five R$^7$;

each R$^5$ is independently halogen, cyano, nitro, C$_1$-C$_8$alkyl, C$_1$-C$_8$haloalkyl, C$_2$-C$_8$alkenyl, C$_2$-C$_8$haloalkenyl, C$_2$-C$_8$alkynyl, C$_2$-C$_8$haloalkynyl, C$_3$-C$_{10}$cycloalkyl, C$_1$-C$_8$alkoxy-, C$_1$-C$_8$haloalkoxy-, C$_1$-C$_8$alkylthio-, C$_1$-C$_8$haloalkylthio-, C$_1$-C$_8$alkylsulfinyl-, C$_1$-C$_8$haloalkyl-sulfinyl-, C$_1$-C$_8$alkylsulfonyl- or C$_1$-C$_8$haloalkylsulfonyl-, or two R$^5$ on adjacent carbon atoms together form a —CH=CH—CH=CH— bridge;

R$^6$ is hydrogen, C$_1$-C$_8$haloalkyl or C$_1$-C$_8$alkyl;

each R$^7$ is independently halogen, cyano, nitro, C$_1$-C$_8$alkyl, C$_1$-C$_8$haloalkyl, C$_2$-C$_8$alkenyl, C$_2$-C$_8$haloalkenyl, C$_2$-C$_8$alkynyl, C$_2$-C$_8$haloalkynyl, hydroxy, C$_1$-C$_8$alkoxy-, C$_1$-C$_8$haloalkoxy-, mercapto, C$_1$-C$_8$alkylthio-, C$_1$-C$_8$haloalkylthio-, C$_1$-C$_8$alkylsulfinyl-, C$_1$-C$_8$haloalkylsulfinyl-, C$_1$-C$_8$alkylsulfonyl-, C$_1$-C$_8$haloalkylsulfonyl-, C$_1$-C$_8$alkylcarbonyl-, C$_1$-C$_8$alkoxycarbonyl-, aryl or aryl substituted by one to five R$^{11}$, or heterocyclyl or heterocyclyl substituted by one to five R$^{11}$;

each R$^8$ and R$^9$ is independently hydrogen, halogen, C$_1$-C$_8$alkyl or C$_1$-C$_8$haloalkyl;

each R$^{10}$ is independently hydrogen, cyano, C$_1$-C$_8$alkyl, C$_1$-C$_8$haloalkyl, C$_1$-C$_8$alkylcarbonyl-, C$_1$-C$_8$haloalkylcarbonyl-, C$_1$-C$_8$alkoxycarbonyl-, C$_1$-C$_8$haloalkoxycarbonyl-, C$_1$-C$_8$alkylsulfonyl-, C$_1$-C$_8$haloalkylsulfonyl-, aryl-C$_1$-C$_4$alkylene- or aryl-C$_1$-C$_4$alkylene- where the aryl moiety is substituted by one to three R$^{12}$, or heteroaryl-C$_1$-C$_4$alkylene- or heteroaryl-C$_1$-C$_4$alkylene- where the heteroaryl moiety is substituted by one to three R$^{12}$;

each R$^{11}$ and R$^{12}$ is independently halogen, cyano, nitro, C$_1$-C$_8$alkyl, C$_1$-C$_8$haloalkyl, C$_1$-C$_8$alkoxy-, C$_1$-C$_8$haloalkoxy- or C$_1$-C$_8$alkoxycarbonyl-;

or a salt or N-oxide thereof.

2. A compound according to claim 1 where A$^1$ is C—R$^5$, A$^2$ is C—H, A$^3$ is C—H or nitrogen and A$^4$ is C—H or nitrogen.

3. A compound according to claim 1 where G is oxygen.

4. A compound according to claim 1 where R$^1$ is hydrogen, methyl, ethyl, methylcarbonyl-, or methoxycarbonyl-.

5. A compound according to claim 1 where R$^2$ is a group of formula (IIc)

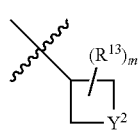

where

R$^{13}$ is C$_1$-C$_8$alkyl, m is 0, 1, 2, 3, 4, or 5, and

Y$^2$ is S, SO, SO$_2$, S=N—R$^{10}$, SO=N—R$^{10}$ or C=N—OR$^{10}$.

6. A compound according to claim 1 where R$^2$ is thietan-3-yl-, 1-oxo-thietan-3-yl-, or 1,1-dioxo-thietan-3-yl-.

7. A compound according to claim 1 where R$^3$ is chlorodifluoromethyl or trifluoromethyl.

8. A compound according to claim 1 where R$^4$ is phenyl or phenyl substituted by one to five R$^7$.

9. A compound according to claim 1 wherein

A$^1$, A$^2$, A$^3$ and A$^4$ are independently of each other C—H or C—R$^5$;

G$^1$ is oxygen;

R$^1$ is hydrogen, methyl or ethyl;

R$^2$ is a group of formula (IIb)

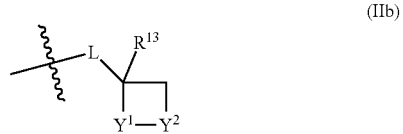

where

L is a single bond, methylene, ethylene or propylene;

one of Y$^1$ and Y$^2$ is S, SO, SO$_2$, S=N—R$^{10}$, SO=N—R$^{10}$ or C=N—OR$^{10}$ and the other is CH$_2$;

R$^3$ is chlorodifluoromethyl or trifluoromethyl;

R$^4$ is 3-chloro-5-trifluoromethyl-phenyl-, 3,5-dichloro-phenyl-, 3,5-bis-(trifluoromethyl)-phenyl-, 3,5-dichloro-4-fluoro-phenyl-, 3,4,5-trichloro-phenyl- or 3-trifluoromethyl-phenyl-;

each R$^5$ is independently bromo, chloro, fluoro, methyl, trifluoromethyl or vinyl, or two R$^5$ on adjacent carbon atoms together form a —CH=CH—CH=CH— bridge;

each R$^{10}$ is independently methyl, 2,2,2-trifluoro-ethyl or hydrogen;

R$^{13}$ is hydrogen or C$_1$-C$_8$alkyl.

10. A compound according to claim 1 wherein

A$^1$, A$^2$, A$^3$ and A$^4$ are independently of each other C—H or C—R$^5$;

G$^1$ is oxygen;

R$^1$ is hydrogen;

R$^2$ is a group of formula (IIc)

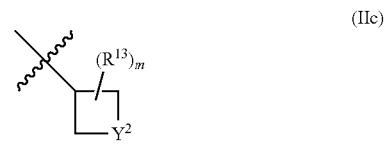

where m is 0, 1, 2, 3, 4, or 5, and

Y$^2$ is S, SO, SO$_2$, or C=N—OR$^{10}$;

R$^3$ is chlorodifluoromethyl or trifluoromethyl;

R$^4$ is 3-chloro-5-trifluoromethyl-phenyl-, 3,5-dichloro-phenyl-, 3,5-bis-(trifluoromethyl)-phenyl-, 3,5-dichloro-4-fluoro-phenyl-, 3,4,5-trichloro-phenyl- or 3-trifluoromethyl-phenyl-;

each R$^5$ is independently bromo, chloro, fluoro, methyl, trifluoromethyl or vinyl, or two R$^5$ on adjacent carbon atoms together form a —CH=CH—CH=CH— bridge;

each R$^{10}$ is independently methyl, 2,2,2-trifluoro-ethyl or hydrogen;

R$^{13}$ is methyl.

11. A compound of formula (Int-III)

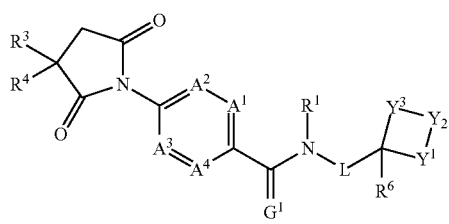
(Int-III)

wherein $A^1, A^2, A^3, A^4, G^1, L, R^1, R^3, R^4, R^6, Y^1, Y^2$ and $Y^3$ are as defined for a compound of formula (I) in claim 1; or a compound of formula (Int-IV);

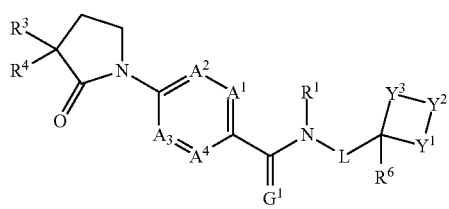
(Int-IV)

wherein $A^1, A^2, A^3, A^4, G^1, L, R^1, R^6, R^3, R^4, R^6, Y^1, Y^2$ and $Y^3$ are as defined for a compound of formula (I) in claim 1; or a compound of formula (Int-V)

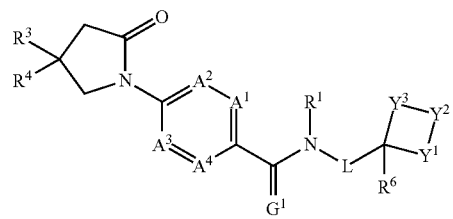
(Int-V)

wherein $A^1, A^2, A^3, A^4, G^1, L, R^1, R^3, R^4, R^6, Y^1, Y^2$ and $Y^3$ are as defined for a compound of formula (I) in claim 1; or a compound of formula (Int-VI)

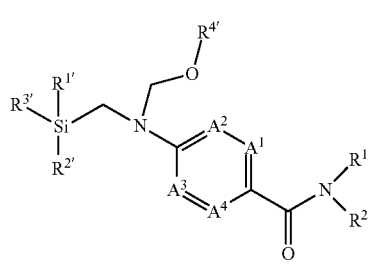
(Int-VI)

wherein $A^1, A^2, A^3, A^4, R^1$ and $R^2$ are as defined for a compound of formula (I) in claim 1, $R^{1'}, R^{2'}$ and $R^{3'}$ are each independently optionally substituted alkyl or optionally substituted phenyl, $R^{4'}$ is optionally substituted phenyl or optionally substituted alkyl; or a compound of formula (Int-VII)

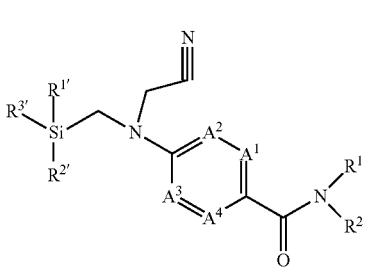
(Int-VII)

wherein $A^1, A^2, A^3, A^4, R^1$ and $R^2$ are as defined for a compound of formula (I) in claim 1, $R^{1'}, R^{2'}$ and $R^{3'}$ are each independently optionally substituted alkyl or optionally substituted phenyl.

12. A method of controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I) as defined in claim 1.

13. An insecticidal, acaricidal, nematicidal or molluscicidal composition comprising an insecticidally, acaricidally, nematicidally or molluscicidally effective amount of a compound of formula (I) as defined in claim 1.

14. An insecticidal, acaricidal, nematicidal or molluscicidal composition according to claim 13 comprising an additional compound having biological activity.

15. A method of treatment of insect pests in or on animals, comprising administering an effective amount of a compound as defined in claim 1, or a composition comprising said compound, to an animal.

16. A compound according to claim 1, or a composition comprising said compound, for use in treatment of insect pests in or on animals.

17. A combination product comprising a pesticidally effective amount of a component A and a pesticidally effective amount of component B, wherein component A is a compound of formula (I) as defined in claim 1, and compound B is imidacloprid, enrofloxacin, praziquantel, pyrantel embonate, febantel, penethamate, moloxicam, cefalexin, kanamycin, pimobendan, clenbuterol, fipronil, ivermectin, omeprazole, tiamulin, benazepril, milbemycin, cyromazine, thiamethoxam, pyriprole, deltamethrin, cefquinome, florfenicol, buserelin, cefovecin, tulathromycin, ceftiour, selamectin, carprofen, metaflumizone, moxidectin, methoprene (including S-methoprene), clorsulon, pyrantel, amitraz, triclabendazole, avermectin, abamectin, emamectin, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, fipronil, lufenuron, ecdysone or tebufenozide.

* * * * *